US011117952B2

(12) United States Patent
Kapp et al.

(10) Patent No.: US 11,117,952 B2
(45) Date of Patent: Sep. 14, 2021

(54) POLYMERIC FORMS OF H-NOX PROTEINS

(71) Applicant: Omniox, Inc., San Carlos, CA (US)

(72) Inventors: Gregory Kapp, San Francisco, CA (US); Laura Serwer, Brisbane, CA (US); Natacha Le Moan, San Francisco, CA (US); Stephen P. L. Cary, San Mateo, CA (US)

(73) Assignee: OMNIOX, INC., San Carlos, CA (US)

( * ) Notice: Subject to any disclaimer, the term of this patent is extended or adjusted under 35 U.S.C. 154(b) by 0 days.

(21) Appl. No.: 16/931,736

(22) Filed: Jul. 17, 2020

(65) Prior Publication Data

US 2021/0002351 A1    Jan. 7, 2021

Related U.S. Application Data

(60) Division of application No. 16/450,913, filed on Jun. 24, 2019, now Pat. No. 10,766,947, which is a continuation of application No. 14/759,635, filed as application No. PCT/US2013/020602 on Jan. 7, 2013, now Pat. No. 10,385,116.

(51) Int. Cl.
| C07H 21/00 | (2006.01) |
| C07K 14/795 | (2006.01) |
| A61K 38/41 | (2006.01) |
| A61N 5/10 | (2006.01) |
| G01N 33/53 | (2006.01) |
| G01N 33/574 | (2006.01) |
| A61K 38/16 | (2006.01) |
| A61K 45/06 | (2006.01) |
| A61K 38/00 | (2006.01) |

(52) U.S. Cl.
CPC .......... *C07K 14/795* (2013.01); *A61K 38/164* (2013.01); *A61K 38/41* (2013.01); *A61K 45/06* (2013.01); *A61N 5/10* (2013.01); *G01N 33/53* (2013.01); *G01N 33/57407* (2013.01); *A61K 38/00* (2013.01); *A61N 2005/1098* (2013.01); *C07K 2319/21* (2013.01); *G01N 2800/52* (2013.01); *Y02A 50/30* (2018.01)

(58) Field of Classification Search
None
See application file for complete search history.

(56) References Cited

U.S. PATENT DOCUMENTS

| 4,873,192 | A | 10/1989 | Kunkel |
| 5,248,766 | A | 9/1993 | Nelson et al. |
| 5,679,638 | A | 10/1997 | Teicher et al. |
| 5,776,898 | A | 7/1998 | Teicher et al. |
| 5,981,710 | A | 11/1999 | Hai et al. |
| 6,432,918 | B1 | 8/2002 | Winslow |
| 6,974,795 | B2 | 12/2005 | Winslow et al. |
| 7,989,593 | B1 | 8/2011 | Wong et al. |
| 8,106,011 | B1 | 1/2012 | Wong et al. |
| 8,404,631 | B2 | 3/2013 | Cary et al. |
| 8,404,632 | B2 | 3/2013 | Cary et al. |
| 8,742,073 | B2 | 6/2014 | Wong et al. |
| 9,493,526 | B2 | 11/2016 | Cary et al. |
| 9,493,527 | B2 | 11/2016 | Cary et al. |
| 2011/0243849 | A1 | 10/2011 | Marletta et al. |
| 2013/0052232 | A1 | 2/2013 | Wong et al. |
| 2013/0177641 | A1 | 7/2013 | Ghoroghchian |
| 2014/0255477 | A1 | 9/2014 | Ghoroghchian |
| 2014/0363496 | A1 | 12/2014 | Ghoroghchian |
| 2015/0273024 | A1 | 10/2015 | Cary et al. |
| 2017/0267732 | A1 | 9/2017 | Cary et al. |
| 2017/0360706 | A1 | 12/2017 | Ghoroghchian |
| 2017/0361126 | A1 | 12/2017 | Ghoroghchian |

FOREIGN PATENT DOCUMENTS

| JP | 2009537145 A | 10/2009 |
| JP | 2009538134 A | 11/2009 |
| JP | 2010503418 A | 2/2010 |
| JP | 2010513405 A | 4/2010 |
| JP | 2012235793 A | 12/2012 |
| WO | WO 1992020369 A1 | 11/1992 |
| WO | WO 1999003484 A1 | 1/1999 |
| WO | WO 2006091542 A2 | 8/2006 |
| WO | WO 2007079096 A2 | 7/2007 |
| WO | WO 2007079096 A3 | 7/2007 |
| WO | WO 2007133811 A2 | 11/2007 |
| WO | WO 2007133811 A3 | 11/2007 |
| WO | WO 2007139767 A2 | 12/2007 |
| WO | WO 2007139791 A2 | 12/2007 |
| WO | WO 2008034608 A1 | 3/2008 |
| WO | WO 2008074865 A1 | 6/2008 |
| WO | WO 2011149602 A1 | 12/2011 |
| WO | WO 2013032828 A2 | 3/2013 |
| WO | WO 2014107171 A1 | 7/2014 |
| WO | WO 2016090111 A1 | 6/2016 |

OTHER PUBLICATIONS

U.S. Appl. No. 62/088,199, filed Dec. 5, 2014, Ghoroghchian.
U.S. Appl. No. 62/127,557, filed Mar. 3, 2015, Ghoroghchian.
Arora et al., 2012, "Nitric oxide regulated two-component signaling in Pseudoalteromonas atlantica," Biochem Biophys Res Commun., 421(3):521-526.
Behrends et al., 2001, "Abstract No. 165: The beta2 subunit is the first example of a mammalian homodimeric nitric oxide-sensitive guanylyl cyclase," Naunyn-Schmiedeberg's Archives of Pharmacology, 363(4 Supplement):R45.
Bhardwaj et al., 2007, "Domain Organization and Polarity of Tail Needle GP26 in the Portal Vertex Structure of Bacteriophage P22," J Mol Biol, 371:374-387.

(Continued)

*Primary Examiner* — Fred H Reynolds
(74) *Attorney, Agent, or Firm* — Mintz, Levin, Cohn, Ferris, Glovsky and Popeo, P.C.

(57) ABSTRACT

The invention provides polymeric H-NOX proteins for the delivery of oxygen with longer circulation half-lives compared to monomeric H-NOX proteins. Polymeric H-NOX proteins extravasate into and preferentially accumulate in tumor tissue for sustained delivery of oxygen. The invention also provides the use of H-NOX proteins as radiosensitizers for the treatment of brain cancers.

25 Claims, 53 Drawing Sheets

Specification includes a Sequence Listing.

(56) References Cited

OTHER PUBLICATIONS

Bhardwaj et al., 2008, "Foldon-guided Self-assembly of Ultrastable Protein Fibers," Protein Sci, 17:1475-1485.
Bobofchak et al., 2003, "A Recombinant Polymeric Hemoglobin with Conformational, Functional, and Physiological Characteristics of an in Vivo O2 Transporter," Am. J. Physiol Heart Circ., 285(2):H549-H561.
Boon et al., 2005, "A Molecular Basis for NO Selectivity in Soluble Guanylate Cyclase," Nature Chemical Biology 1(1):53-59.
Boon et al., 2005, "Ligand Discrimination in Soluble Guanylate Cyclase and the H-NOX Family of Heme Sensor Proteins," Curr. Opin. Chem. Biol., 9(5):441-446.
Boon et al., 2005, "Ligand Specificity of H-NOX Domains: From sGC to Bacterial NO Sensors," J. Inorg. Biochem., 99(4):892-902.
Boon et al., 2006, "Nitric Oxide Binding to Prokaryotic Homologs of the Soluble Guanylate Cyclase {b1 H-NOX Domain," J. Biol. Chem., 281 (31):21892-21902.
Boon et al., 2006, "Sensitive and selective detection of nitric oxide using an H-NOX domain," J Am Chem Soc., 128(31):10022-10023.
Borlongan et al, 1988, "Transplantation of Cryopreserved Human Embryonal Carcinoma-Derived Neuron (NT2N Cells) Promotes Functional Recovery in Ischemic Rats," Experimental Neurology, 149:310-321.
Boudko et al., 2002, "Domain Organization, Folding and Stability of Bacteriophage T4 Fibritin, A Segmented Coiled-Coil Protein," Eur J. Biochem., 269:833-841.
Brown et al., 2010, "Stereotactic Ablative Radiotherapy Should be Combined with a Hypoxic Cell Radiosensitizer," Int J Radiat Oncol Biol Phys, 78:323-327.
Capece et al., 2008, "Dynamical characterization of the heme NO oxygen binding (HNOX) domain. Insight into soluble guanylate cyclase allosteric transition", Biochemistry, 47(36):9416-9427.
Cary et al., 2005, "Tonic and Acute Nitric Oxide Signaling Through Soluble Guanylate Cyclase is Mediated by Nonheme Nitric Oxide, ATP, and GTP," Proc. Natl. Acad. Sci. USA, 102(37):13064-13069.
Cary et al., 2006, "Nitric Oxide Signaling: No Longer Simply On or Off," Trends Bio. Sci., 31(4):231-239.
Cary et al., 2011, "H-Nox: A nitric-oxide neutral, tunable oxygen delivery technology," Artificial Cells, Blood Substitutes and Biotechnology 40.3 (Abstracts from XIII International Symposium on Blood Substitutes and Oxygen Therapeutics):206.
Cary, 2012, Project No. 1R43NS076272-01A1 "Reducing Brain Injury After Focal Ischemia Using a Nitric Oxide-nuetral Oxygen CA," retrieved from www.sbir.gov/print/sbirsearch/detail/400994 on Nov. 14, 2018 (3 pages).
Choi et al., 2007, "Renal clearance of quantum dots," Nat Biotechnol., 25(10):1165-1170.
Dente, et al., 1985, "Chapter 5: The pEMBL Family of Single-stranded Vectors" DNA Cloning, vol. 1—A Prractical Approach, Glover, Ed. IRL Press, pp. 101-107.
Derbyshire et al., 2011, "Probing Domain Interactions in Soluable Guanylate Cyclase," Biochemistry 50(20):4281-4290.
Dmochowski et al., 2000, "Enantiomeric Discrimination of Ru-Substrates by Cytochrome P540cam," Journal of Inorganic Biochemistry, 81:221-228.
Dreher et al., 2006, "Tumor vascular permeability, accumulation, and penetration of macromolecular drug carriers," J Natl Cancer Inst., 98(5):335-344.
Du et al., 2008, "Improvement of Thermostability ofRecombinant Collagen-like Protein by Incorporating a Foldon Sequence," Appl Microbiol Biotechnol, 79:195-202.
Efimov et al., 1994 "Fibritin Encoded by Bacteriophage T4 Gene wac has a Parallel Triple-Stranded α-Helical Coiled-coil Structure," J. Mol. Biol., 242:470-486.
Extended European Search Report and Search Opinion dated May 17, 2016, for European Patent Application No. 13870254.3 (8 pages).
Guarnone et al., 1995, "Performance Characteristics of Hemox-Analyzer for Assessment of the Hemoglobin Dissociation Curve," Haematologica, 80(5):426-430.
Guthe et al., 2004, "Very Fast Folding and Association of a Trimerization Domain from bacteriophage T4 Fibritin," J. Mol. Biol., 337:905-915.
Heller et al., 1999, "Conformational Stability of Lyophilized PEGylated Proteins in a Phase-Separating System," Journal of Pharmaceutical Sciences, 88(1):58-64.
Hu et al., 2008, "Allostery in recombinant soluble guanylyl cyclase from Manduca sexta," J. Biol. Chem., 283(30):20968-20977.
Huang et al., 2007, "Ligand Binding and Inhibition of an Oxygen-Sensitive Soluble Guanylate Cyclase, Gyc-88E, from Drosphila," Biochemistry, 46:15115-15122.
International Search Report dated Mar. 14, 2013, for International Application No. PCT/US2013/020602, filed on Jan. 7, 2013 (4 pages).
Irwin et al., 2008, "Polymerized bovine hemoglobin decreases oxygen delivery during normoxia," Am. J. Physiol. Heart Circ. Physiol., 295:H1090-H1099.
Ito et al, 2011, "Trimerization of murine TNF ligand family member LIGHT increases the cytotoxic activity against the FM3A mammary carcinoma cell line," Appl Microbiol Biotechnol., 90(5):1691-1699.
Iyer et al., 2003, "Ancient Conserved Domains Shared by Animal Soluble Guanylyl Cyclases and Bacterial Signaling Proteins," BMC Genomics 4(1):5 (8 pages).
Jones et al., 1990, "A Rapid Method for Site-Specific Mutagenesis and Directional Subcloning by Using the Polymerase Chain Reaction to Generate Recombinant Circles," Biotechniques, 8(2):178-183.
Jones et al., 1991 "A Rapid Method for Recombination and Site-Specific Mutagenesis by Placing Homologous Ends on DNA Using Polymerase Chain Reaction," Biotechniques, 10(1):62-66.
Karow et al., 2004, "Spectroscopic Characterization of the Soluble Guanylate Cyclase-Like Heme Domains From Vibrio cholera and Thermoanaerobacter Tengcongensis," Biochemistry 43(31):10203-10211.
Karow et al., 2005, "Characterization of Functional Heme Domains from Soluble Guanylate cyclase," Biochemistry, 44(49):16266-16274.
Keating et al., 2015, "Epigenetics and Metabolism," Circulation Research, 116:715-736.
Koglin et al., 2001, "Nitric oxide activates the beta 2 subunit of soluble guanylyl cyclase in the absence of a second subunit," J Biol Chem., 276(33):30737-30743.
Krtolica et al., 2014, "Abstract No. ET-31: Radiosensitization by OMX-4.80p, A Pegylated H-Nox Oxygen Carrier That Penetrates and Oxygenates Hypoxic Tumors, in Preclinical Models of Glioblastoma and Other Hypoxic Cancers," Neuro-Oncology 16 (suppl. 5): v86.
Krtolica et al., 2014, "Abstract No. O2.04: Treatment With OMX-4.80, A Tumor-Penetrating Tunable Oxygen Carrier, Reduces Tumor Hypoxia and Dramatically Enhances Radiation Therapy in Intracranial Models of Glioblastoma," Neuro-Oncology 16 (suppl. 2):ii3-ii4.
Krtolica, 2013, Project 1R43CA165629-01A1 "Improving Chemotherapy with a Novel Oxygen-delivery Protein" National Institute of Health (1 page).
Kunkel, 1985, "Rapid and Efficient Site-Specific Mutagenesis Without Phenotypic Selection," Proc. Natl. Acad. Sci. USA, 82(2):488-492.
Kunkel, 1987, "Rapid and Efficient Site-Specific Mutagenesis Without Phenotypic Selection," Methods Enzymol, 154:367-382.
Laquintana et al., 2009, "New strategies to deliver anticancer drugs to brain tumors," Expert Opin Drug Deliv., (10):1017-1032.
Le Moan et al., 2013, "Abstract No: ET-055: Targeting Hypoxia in Glioblastoma Multiforme with a Novel Oxygen Carrier Protein," Neuro-Oncology 15 iii37-iii61.
Le Moan et al., 2013, "Targeting Hypoxia in Glioblastoma Multiforme with a Novel Oxygen Carrier Protein," Neuro-Oncology 15 (suppl. 3):iii50—Poster.
Le Moan et al., 2017, "A new paradigm in protecting ischemic brain: preserving the neurovascular unit before reperfusion," in Book titled Neuroprotective Therapy for Stroke and Ischemic

(56) References Cited

OTHER PUBLICATIONS

Disease, Chapter 27, Lapchak & Zhang (des.), Springer International Publishing Switzerland, pp. 641-664.
Letarov et al., 1999, "The Carboxy-Terminal Domain Initiates Trimerization of Bacteriophage T4 Fibritin," Biochemistry (Mosc), 64:817-823.
Li et al., 1988, "Cloning of the *Escherichia coli* K-12 hemB Gene," Journal of Bacteriology, 170:1021-1025.
Ma et al., 2008, "PAS-mediated dimerization of soluble guanylyl cyclase revealed by signal transduction histidine kinase domain crystal structure," J. Biol. Chem., 283(2):1167-1178.
Mammen et al., 1998, "Polyvalent Interactions in Biological Systems: Implications for Design and Use of Multivalent Ligands and Inhibitors," Angew Chem Int Ed Engl., 37(20):2754-2794.
Migata et al., 1997, "Blood Volume and Cardiac Index in Rats After Exchange Transfusion with Hemoglobin-based Oxygen Carriers," J. Appl. Physiol., 82(6):1995-2002.
Moeller et al., 2007, "Hypoxia and Radiotherapy: Opportunities for Improved Outcomes in Cancer Treatment," Cancer and Metastasis Rev., 26:241-248.
Morton et al., 2003, "MsGC-beta3 forms active homodimers and inactive heterodimers with NO-sensitive soluble guanylyl cyclase subunits," The Journal of Experimental Biology, 206 (Pt 6):937-947.
Nakamaye et al., 1986, "Inhibition of Restriction Endonuclease Nci I Cleavage by Phosphorothioate Groups and its Application to Oligonucleotide-Directed Mutagenesis," Nucleic Acids Res., 14(24):9679-9698.
Nemoto et al., 2006, "Salvage of focal cerebral ischemic damage by transfusion of high O2-affinity recombinant hemoglobin polymers in mouse," J. Appl. Physiol., 100:1688-1691.
Noguchi et al., 1998, "Early phase tumor accumulation of macromolecules: a great difference in clearance rate between tumor and normal tissues," Jpn J Cancer Res., 89(3):307-314.
Office Action (final) dated Apr. 21, 2017 in connection with U.S. Appl. No. 14/530,569, filed Oct. 31, 2014 (10 pages).
Office Action (final) dated Mar. 3, 2016 in connection with U.S. Appl. No. 14/530,569, filed Oct. 31, 2014 (13 pages).
Office Action (mon-final) dated Aug. 17, 2015 in connection with U.S. Appl. No. 14/530,569, filed Oct. 31, 2014 (10 pages).
Office Action (non-final) dated Oct. 12, 2016 in connection with U.S. Appl. No. 14/530,569, filed Oct. 31, 2014 (10 pages).
Ouellet et al., 2002, "Truncated Hemoglobin HbN Protects Mycobacterium Bovis from Nitric Oxide," Proc. Natl. Acad. Sci. USA, 99(9):5902-5907.
Ozawa et al., 2010, "Establishing Intracranial Brain Tumor Xenografts with Subsequent Analysis of Tumor Growth and Response to Therapy Using Bioluminescence Imaging," J Vis Exp., 41:e1986.
Papanikolopoulou et al., 2004, "Adenovirus Fibre Shaft Sequences Fold into the Native Triple Beta-Spiral Fold when N-terminally Fused to the Bacteriophage T4 Fibritin Foldon Trimerisation Motif," J Mol Biol, 342:219-227.
Papanikolopoulou et al., 2004, "Formation of Highly Stable Chimeric Trimers by Fusion of an Adenovirus Fiber Shaft Fragment with the Foldon Domain of Bacteriophage T4 Fibritin," J. Bio. Chem., 279:8991-8998.
Pellicena et al., 2004, "Crystal Structure of an Oxygen-Binding Heme Domain Related to Soluble Guanylate Cyclases," Proc. Natl. Acad. Sci. USA, 101(35):12854-12859.
Phillips et al., 2006, "Molecular Subclasses of High-Grade Glioma Predict Prognosis, Delineate a Pattern of Disease Progression, and Resemble Stages in Neurogenesis," Cancer Cell, 9(3):157-173.
Rockwell et al., 2009, "Hypoxia and Radiation Therapy: Past History, Ongoing Research, and Future Promise," Curr Mol Med., 9(4):442-458.
Rohlfs et al., 1998, "Arterial Blood Pressure Responses to Cell-free hemoglobin Solutions and the Reaction with Nitric Oxide," J. Biol. Chem., 273(20):12128-12134.
Serwer et al., 2012, "Abstract No. 3301: Novel Oxygen Carrier Proteins, H-NOX, reduce Tumor Hypoxia and Act as Radiosensitizers in an Orthotopic Mouse Model of Human Cancer," International Journal of Radiation Oncology Biology Physics, 84(3S):S707.
Serwer et al., 2013, "Abstract No. ET-088: Preferential Accumulation of a multimeric H-Nox Oxygen Carrier Protein in Multiple Intracranial Glioblastoma Models," Neuro-Oncology, 15(suppl. 3):iii57-iii58.
Serwer et al., 2015, "Real-Time Pet Imaging Demonstrates Tumor Accumulation and Oxygenation by Omx-4.80p, an Oxygen Carrier Engineered for the Treatment of Glioblastoma." Neuro-Oncology, 17:v153-v171—Abstract No. NIMG-45.
Sissoeff et al. 2005, "Stable Trimerization of Recombinant Rabies Virus Glycoprotein Ectodomain is Required for Interaction with the p75NTR Receptor," J Gen Virol, 86:2543-2552.
Spence et al., 2008, "Regional Hypoxia in Glioblastoma Multiforme Quantified with [18F] Fluoromisonidazole Positron Emission Tomography before Radiotherapy: Correlation with Time to Progression and Survival," Clin Cancer Res, 14(9):2623-2630.
Stetefeld et al., 2003, "Collagen Stabilization at Atomic Level: Crystal Structure of Designed (GlyProPro)10foldon," Structure, 11:339-346.
Stojiljkovic et al., 2003, "Characterization of 9L Glioma Model of the Wistar Rat," J. Neurooncol, 63:1-7.
Tao et al., 1997, "Structure of Bacteriophage T4 Fibritin: A Segmented Coiled Coil and the Role of the C-Terminal Domain," Structure, 5:789-798.
Taylor et al., 1985, "The Rapid Generation of Oligonucleotide-Directed Mutations at High Frequency Using Phosphorothioate-Modified DNA," Nucleic Acids Res., 13(24):8765-8785.
Taylor et al., 1985, "The Use of Phosphorothioate-Modified DNA in Restriction Enzyme Reactions to Prepare Nicked DNA," Nucleic Acids Res., 13(24):8749-8764.
Uversky, 2013, "Unusual biophysics of intrinsically disordered proteins," Biochim Biophys Acta., 1834(5):932-951.
Vandegriff et al., 2004, "Kinetics of NO and O2 Binding to a Maleimide Poly(ethylene glycol)-Conjugated Human Haemoglobin," Biochem. J., 382(Pt1):183-189.
Varlotto et al., 2005, "Anemia, Tumor Hypoxemia, and the Cancer Patient," Int J Radiat Oncol Biol Phys, 63(1):25-36.
Vaupel, 2004, "Tumor Microenvironmental Physiology and its Implications for Radiation Oncology," Semin Radiat Oncol., 14(3):198-206.
Verhaak et al., 2010, "An Intergrated Genomic Analysis Identifies Clinically Relevant Subtypes of Glioblastoma Characterized by Abnormalities in PDGFRA, IDH1, EGFR, and NF1," Cancer Cell, 17(1):98-110.
Vijayachandra et al., 2000, "characterization of the intracellular domain of the human guanylyl cyclase C receptor provides evidence for a catalytically active homotrimer," Biochemistry, 39(51):16075-16083.
Villard et al., 2002, "Use of a Blood Substitute to Determine Instantaneous Murine Right Ventricular Thickening with Optical Coherence Tomography," Circulation, 105:1843-1849.
Winger et al., 2007, e-published in 2006, "Dissociation of Nitric Oxide from Soluble Guanylate Cyclase and Heme-Nitric Oxide/Oxygen Binding Domain Constructs," The Journal of Biological Chemistry, 282(2):897-907.
Written Opinion dated Mar. 14, 2013 for International Application No. PCT/US2013/020602 filed on Jan. 7, 2013 (4 pages).
Yang et al., 2002, "Highly Stable Trimers Formed by Human Immunodeficiency Virus Type 1 Envelope Glycoproteins Fused with the Trimeric Motif of T4 Bacteriophage Fibritin," J. Virol 76:4634-4642.
Yao et al., 1992, "Site-directed Mutagenesis of Herpesvirus Glycoprotein Phosphorylation Sites by Recombination Polymerase Chain Reaction," Genome Res., 1(3):205-207.
Yokoi et al., 2010, "Construction of Robust Bio-nanotubes Using the Controlled Self-Assembly of Component Proteins of Bacteriophage T4," Small, 6(17):1873-1879.
Zhang et al., 2009, "Purification and Characterization of a Transgenic Corn Grain-derived Recombinant Collagen Type 1 alpha 1," Biotechnol Prog, 25(6):1660-1668.
Zhao et al., 1997, "Localization of the Heme Binding Region in Soluble Guanylate Cyclase," Biochemistry, 36(50):15959-15964.

(56) References Cited

OTHER PUBLICATIONS

Zhao et al., 1999, "Characterization of the nitric oxide sensing domain of soluble guanylate cyclase," Dissertation Abstracts International, vol. 60, No. 7B. Order No. AAI9938578, ProQuest Dissertations & Theses (204 pages).

Zhong et al., 2011, "A novel insight into the heme and NO/CO binding mechanism of the alpha subunit of human soluble guanylate cyclase", J Biol Inorg Chem., 16(8):1227-1239.

FIG. 1

```
vac foldon sequence.ape
/Users/omnioxlab2/Desktop/vac foldon sequence.ape
from 1 to 81.
Translation 27 a.a.  MW=3081.5599999999995

```
pCW-Tt(L144F)+Foldon.gb
/Users/omnioxlab2/OmnioxLabData/100128-Sequencing/012810_GK/pCW-Tt(L144F)+Foldon.gb
From 2521 to 3210.
Translation 229 a.a.  MW=26677.05999999972

2521 ATG AAG GGG ACA ATC GTC GGG ACA TGG ATA AAG ACC CTG AGG GAC CTT TAC GGG AAT GAT 2580
   1  M   K   G   T   I   V   G   T   W   I   K   T   L   R   D   L   Y   G   N   D  20

2581 GTG GTT GAT GAA TCT TTA AAA AGT GTG GGT GAG TGG GAA CCA GAT AGG GTA ATT ACA CCT CTG 2640
  21  V   V   D   E   S   L   K   S   V   G   E   W   E   P   D   R   V   I   T   P   L  40

2641 GAG GAT ATT GAT GAC GAT GAT GAG GTT AGG AGA ATT TTT GCT AAG GTG AGT GAA ACT GGT 2700
  41  E   D   I   D   D   D   D   E   V   R   R   I   F   A   K   V   S   E   T   G  60

2701 AAA AAT GTC AAC GAA ATA TGG AGA GAG GTA AGG CAG AGG AAC ATA AAA ACT TTC AGC GAA 2760
  61  K   N   V   N   E   I   W   R   E   V   R   Q   R   N   I   K   T   F   S   E  80

2761 TGG TTT CCC TCC TAT TTT GCA GGG AGA AGG CTA GTG AAT TTT TTA ATG ATG CTT ATT GAG 2820
  81  W   F   P   S   Y   F   A   G   R   R   L   V   N   F   L   M   M   L   I   E  100

2821 GTA CAC CTA CAG ACC AAG ATG GAG GCC ACT GTT GTC TTC AAG AGG AAG ATT GCA AAG 2880
 101  V   H   L   Q   T   K   M   E   A   T   V   V   F   K   R   K   I   A   K  120

2881 CCT GTT GCA AAA GAT GCC ATT GAG ATG TAC TCT AAA TTT TCA AGG CTA AAA GTC AGG GAT 2940
 121  P   V   A   K   D   A   I   E   M   Y   S   K   F   S   R   L   K   V   R   D  140

2941 TTT TTA GGG TTT ATA GAG GGT AGT GGC TTT GGT AGA GAA ATT TCA ATA TTT CCT GAA GAG 3000
 141  F   L   G   F   I   E   G   S   G   F   G   R   E   I   S   I   F   P   E   E  160

3001 GTC GAA AGA GGC GAA AAA GAT GAT GGC TTT TCA AGG CTA AAA GTC AGG ATA AAA TTT AAA AAC 3060
 161  V   E   R   G   E   K   D   D   G   F   S   R   L   K   V   R   I   K   F   K   N  180

3061 CCC GTT GAG TAT TTT GAG TAT AAG CAG GCT TAC GTT CGT AAA AAT CTC GAG GGT TAT ATT CCT GAA GCT CCA 3120
 181  P   V   E   Y   F   E   Y   K   Q   A   Y   V   R   K   N   L   E   G   Y   I   P   E   A   P  200

3121 AGA GAT GGT TTA GGG CAG GCT TAC GTT CGT AAA AAT CTC GAG GAT GGC GAA TGG GTA TTA CTT TCT ACC TTT TTA 3180
 201  R   D   G   L   G   Q   A   Y   V   R   K   N   L   E   D   G   E   W   V   L   L   S   T   F   L  220

3181 AGA GGT AGT CAC CAT CAC CAT CAC CAT TGA 3210
 221  R   G   S   H   H   H   H   H   H   *  230
```

FIG. 2B

```
Thu Jan 03, 2013 12:16 PST
pCW-f002.5.gb
/Users/omnioxlab2/DNA/pCW-f002.5.gb
From 2521 to 3183.
Translation 220 a.a. MW=25553.8999999976

2521 ATG AAG GGC ACA ATC CTC AGG ATA AAG ACC CTC AGG GAC CTT TAC GGG AAT GAT     2580
   1  M   K   G   T   I   L   R   I   K   T   L   R   D   L   Y   G   N   D       20

2581 GTC CTT GAT GAA TCT TTA AAA GTT CGT TGG GAA CCA GAT AGG CCA ATT GAA CTC     2640
  21  V   L   D   E   S   L   K   V   R   W   E   P   D   R   P   I   E   L       40

2641 GAG GAT AAT GTC ATT GAT CAC GAT GAG CTT AGA ACA AGT AGG GTA ACT AGC GGT     2700
  41  E   D   N   V   I   D   H   D   E   L   R   T   S   R   V   T   S   G       60

2701 AAA AAT GTC CCC AAA GAA ATA CGG GCA CAC GAC CTA ACT ATC TTC ATG GAT GAA     2760
  61  K   N   V   P   K   E   I   R   A   H   D   L   T   I   F   M   D   E       80

2761 TGG TTT CCC TAC CTT TCT CTT GGT GCT CAG AAT TTT CCT AAA ATC ATG GCA GAG     2820
  81  W   F   P   Y   L   S   L   G   A   Q   N   F   P   K   I   M   A   E      100

2821 GTA CAC CTA CAG GCA AAA GAT ATA GAG AGG CTA ACC CCA AGA GAT TTA TCA AAC     2880
 101  V   H   L   Q   A   K   D   I   E   R   L   T   P   R   D   L   S   N      120

2881 CCT TTT GCA CTA CTT AAG TTT AGG GCA ATC ATG AAA GGA GAA TCT CCT TAT TTA     2940
 121  P   F   A   L   L   K   F   R   A   I   M   K   G   E   S   P   Y   L      140

2941 TTT TTA TTA GAA CGC CGG GAA GCT TCA CGC TTT ACC GTC AAA TGA GAG AAC CCA     3000
 141  F   L   L   E   R   R   E   A   S   R   F   T   V   K   *   E   N   P      160

3001 GTC GAA AGA CGC GAA ATA GAG GCT TAT AGG AGC TGG AAC ATC TAC GAG AAC CCA     3060
 161  V   E   R   R   E   I   E   A   Y   R   S   W   N   I   Y   E   N   P      180

3061 CCC GAT GAT CTT TTT CAG CAG TAT AAG AAA TAC GAG ATG TAT ATT TCT CTT CCA     3120
 181  P   D   D   L   F   Q   Q   Y   K   K   Y   E   M   Y   I   S   L   P      200

3121 AGA GAT GGG CAG CAG GCT CCT TAC TTT CGC AAA GGG GAA TTA CCT TAC TTA TTA     3180
 201  R   D   G   Q   Q   A   P   Y   F   R   K   G   E   L   P   Y   L   L      220

3181 tga 3183
 221  *   221
```

```
Thu Jan 28, 2010  9:56 PST
pCW-TtWT+Foldon.gb
Alignment to
3I-A_QB0135_2010-01-28_B01_013.seq--     Matches:1122; Mismatches:2; Gaps:121; Unattempted:0
from 2174 to 3332

*         *         *         *         *         *         *         *
2174  ----gcgc-a---acgc-a-att-a-at-g-t-----a--a--gtt------agc-----t---cactc-at-  2207
1211  ACTTTTTCCGAGCGCTATTACAATTGCACATTGGAAGATTTGCAACTTCTTTGGCAGACAGTTGAACTTGGAAGCGCCAGTTGAACGCACGCAATA  1112

*         *         *         *         *         *         *         *
2208  --------------gcaccccagGCTTTACACTTTATGCTTCCGGCTCGTATAATGTGTGGAA--TTGTGAGCGGATAACAATTCACACAGGAA  2289
1111  TGTAGTTACTTACTCATTTGCACCCCAGGCTTTACACTTTATGCTTCCGGCTCGTATAATGTGTGGAATTTGTGAGCGGATAACAATTTCACACAGGAA  1013

*         *         *         *         *         *         *         *
2290  ac--aggatcgatccatcgatgagcttactcccccatccccctgttgacaattaatcatcggctcgtataatgtgtggaattgtgagcggataacaatttc  2387
1012  ACCAAGGATCGATCCATCGATGAGCTCACTCCCCATCCCCCTGTTGACAATTAATCATCGGCTCGTATAATGTGTGGAATTGTGAGCGGATAACAATTTC  915

*         *         *         *         *         *         *         *
2388  acacaggaaacaggatcagctcgatcagtccatccagatcatcgcgatccgcatcatcgtcgtcgtataatgtgtggaattgtgagcggataacaatttcacaca  2487
914   ACACAGGAAACAGGATCAGCTCAGTCCATCCGATCATCGAAGGGACAATCGTCGGGACATGGATAAAGACCCTGAGGGACCTTTACGGAATGATGTGGTTG  815

*         *         *         *         *         *         *         *
2488  ggaaacaggatccatcgatgctggagaggtcatatGAAGGGACAATCGTCGGGACATGGATAAAGACCCTGAGGGACCTTTACGGAATGATGTGGTTG  2587
814   GGAAACAGGATCCATCGATGCTTAGGAGGTCATATGAAGAAGGGACAATCGTCGGGACATGGATAAAGACCCTGAGGGACCTTTACGGAATGATGTGGTTG  715

*         *         *         *         *         *         *         *
2588  ATGAATCTTTAAAAAGTGTGGGTTGGGAACCAGATAGGGTAATTACACCTCTGGAGGATATTGATGACCATGAGGTTAGGAGAATTTTGCTAAGGTGAG  2687
714   ATGAATCTTTAAAAAGTGTGGGTTGGGAACCAGATAGGGTAATTACACCTCTGGAGGATATTGATGACGATGAGGTTAGGAGAATTTTTGCTAAGGTGAG  615

MKGTIVGTWIKTLRDLYGNDVVDESLKSVGWEPDRVITPLEDID
DDEVRRIFAKVSEKTGKNVNEIWREVGRQNIKTFSEWFPSYFAG
RRLVNFLMMDEVHLQLTKMIKGATPPRLIAKPVAKDAIEMEYV
SKRKMYDYFLGLIEGSSKFFKEEISVEEVERGEKDGFSRLKVRI
KFKNPVFEYKKNLEGGSGGYIPEAPRDGQAYVRKDGEEWVLLST
FLRGSHHHHHH
(SEQ ID NO:10)

FIG. 3C

```
ATGAAGGGGACAATCGTCGGGACATGGATAAAGACCCTGAGGGA
CCTTTACGGGAATGATGTGGTTGATGAATCTTTAAAAGTGTGG
GTTGGGAACCAGATAGGGTAATTACACCTCTGGAGGATATTGAT
GACGATGAGGTTAGGAGAATTTTTGCTAAGGTGAGTGAAAAAC
TGGTAAAAATGTCAACGAAATATGGAGAGAGGTAGGAAGGCAGA
ACATAAAAAACTTTCAGCGAATGGTTTCCCCTATTTTGCAGGG
AGAAGGCTAGTGAATTTTTTAATGATGATGAGGTACACCT
ACAGCTTACCAAGATGATAAAAGGAGCCACTCCTCCAAGGCTTA
TTGCAAAGCCTGTTGCAAAAGATGCCATTGAAATGGAGTACGTT
TCTAAAAGAAAGATGTACGATTACTTTTTAGGGCTTATAGAGGG
TAGTTCTAAATTTTTCAAGGAAGAAATTTCAGTGGAAGAGGTCG
AAAGAGGCGAAAAAGATGGCTTTTTGAGTATAAGAAAAATCTCGAGGG
AAATTTAAAAACCCCGTTTTCCTGAAGCTCCAAGAGATGGGCAGCTT
CAGCGGCGGTTATATTCCGAAGCTCCAAGAGATGGGCAGCTT
ACGTTCGTAAAGATGGCGAATGGGTATTACTTTCTACCTTTTA
AGGGTAGT
(SEQ ID NO:11)

MKGTIVGTWIKTLRDLYGNDVVDESLKSVGWEPDRVITPLEDID
DDEVRRIFAKVSEKTGKNVNEIWREVGRQNIKTFSEWFPSYFAG
RRLVNFLMMDEVHLQLTKMIKGATPPRLIAKPVAKDAIEMEYV
SKRKMYDYFLGLIEGSSKFFKEEISVEEVERGEKDGFSRLKVRI
KFKNPVFEYKKNLEGGSGGYIPEAPRDGQAYVRKDGEEWVLLST
FL
(SEQ ID NO:12)
```

Monomer = Tt H-NOX L144F monomer

Trimer = Tt H-NOX L144F trimer

*hypoxia throughout tumor
**no hypoxia in tumor

OMX = H-NOX Tt trimer L144F
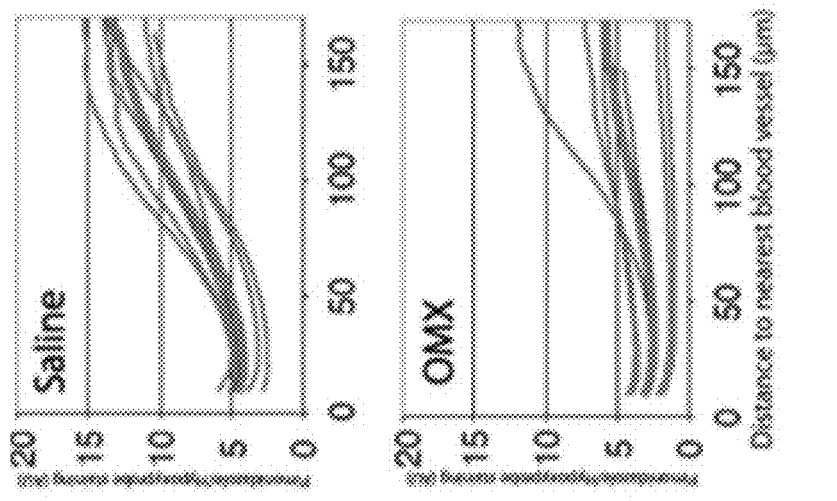
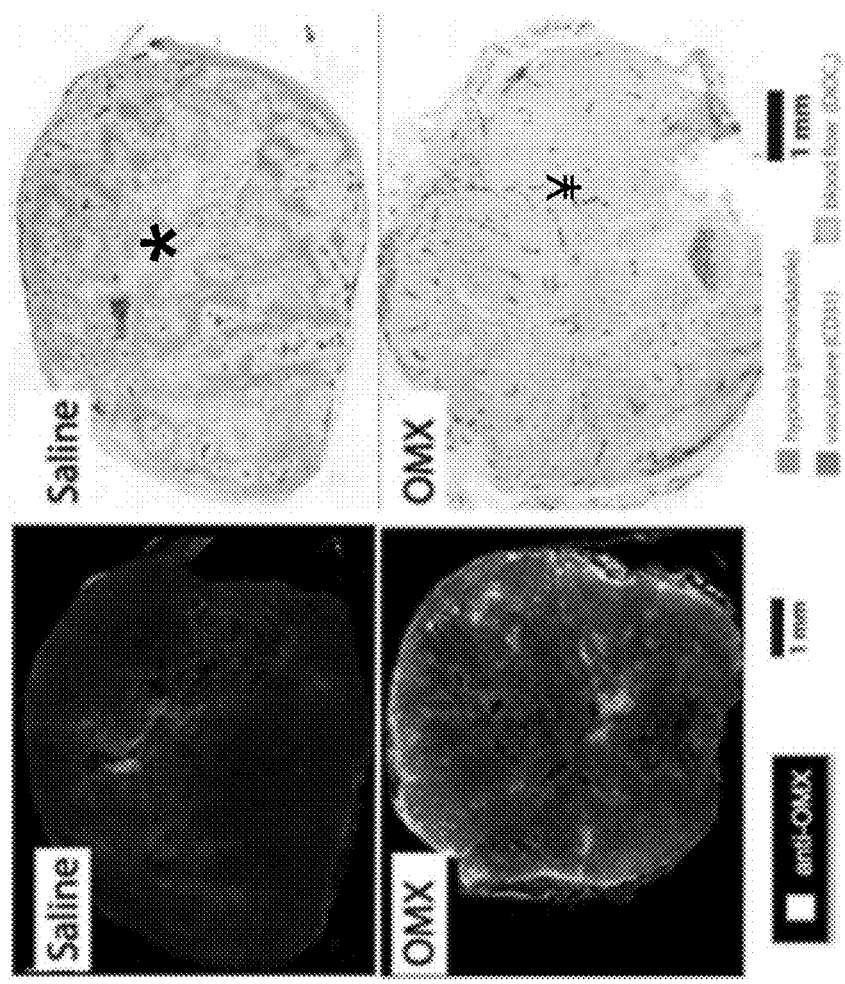
*hypoxia throughout tumor
✳no hypoxia in tumor

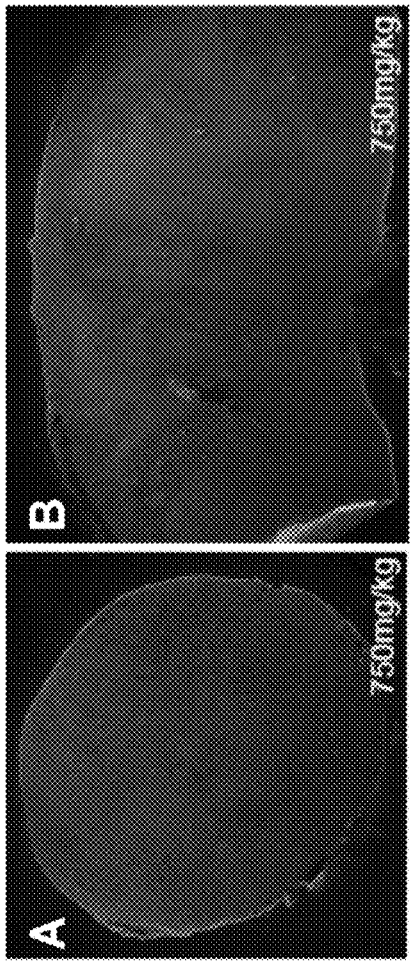
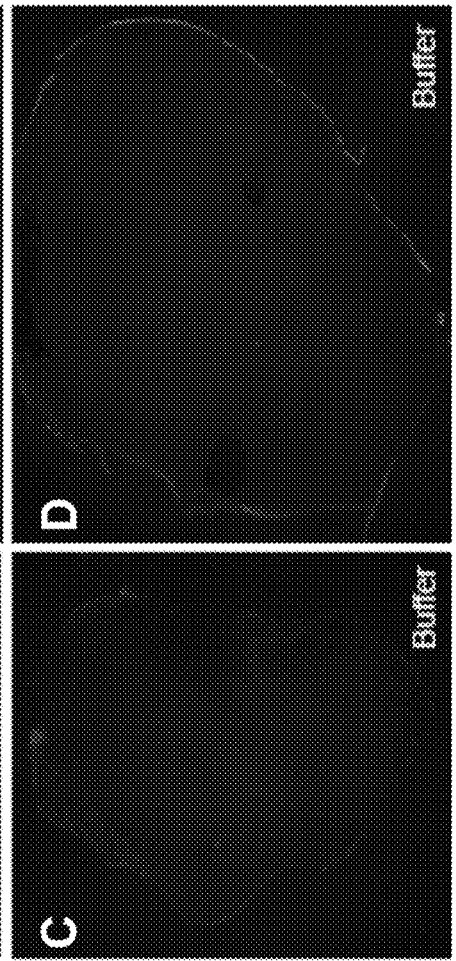
FIG 15A, FIG 15B, FIG 15C, FIG 15D
White stain = anti-H-NOX
RIF-1 tumor sizes
A, B = Tt H-NOX L144F trimer
C, D = vehicle buffer

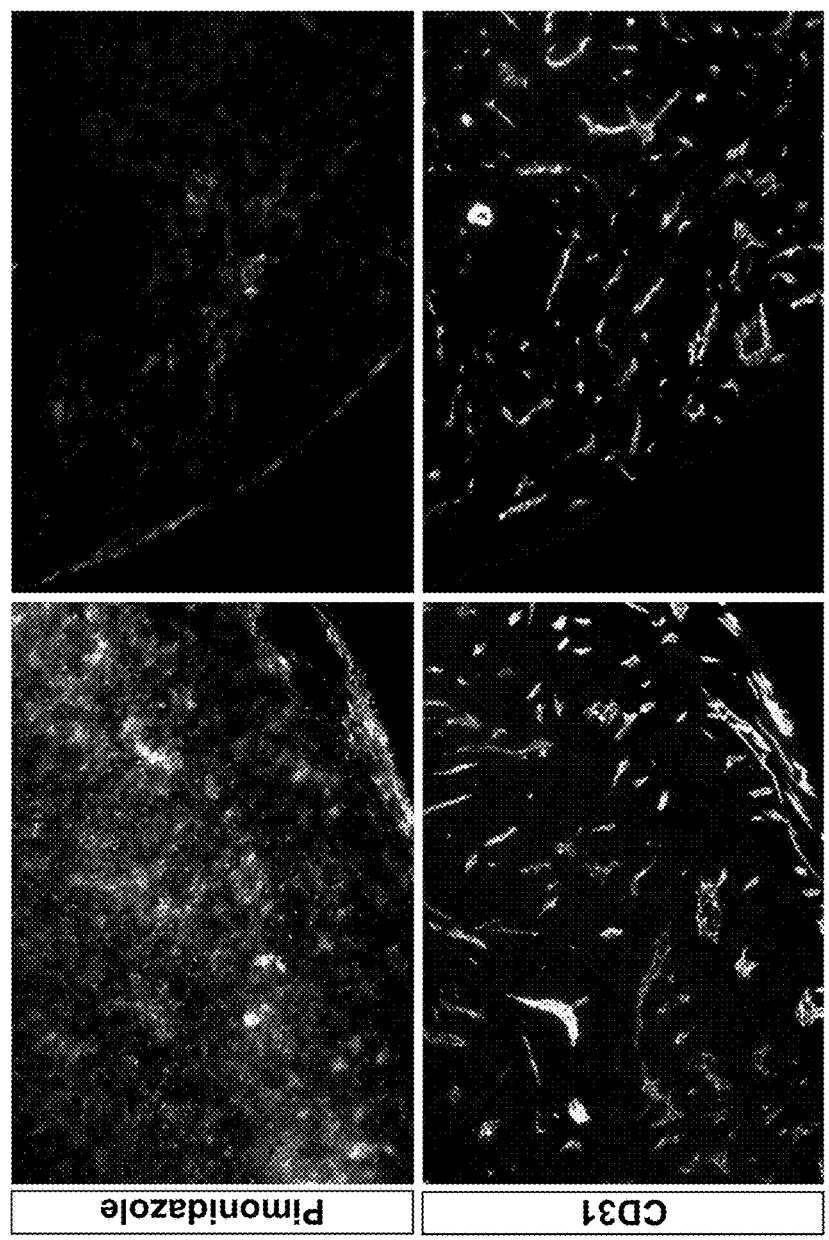
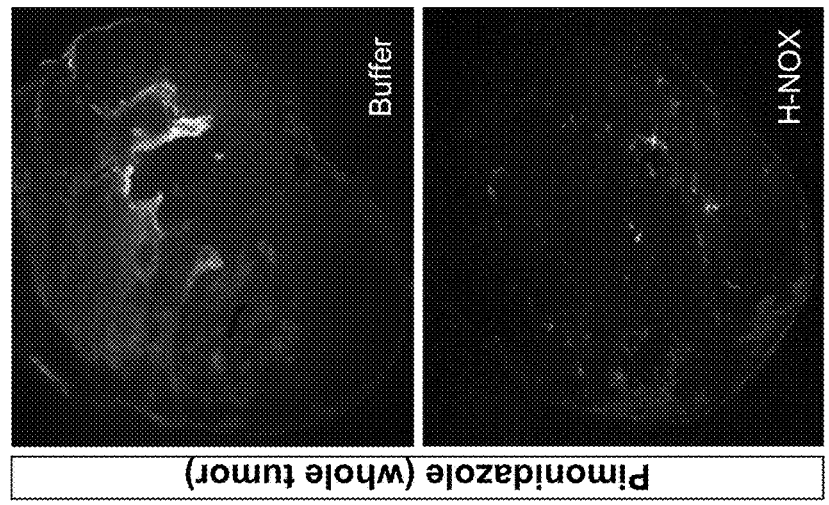
FIG. 15F
FIG. 15E

** $p < 0.01$, * $p < 0.05$ by unpaired Student's t test

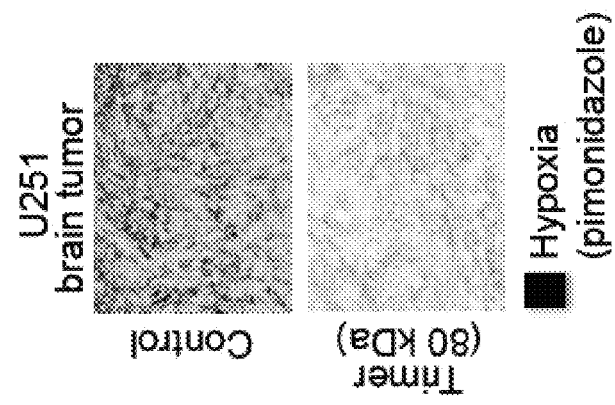
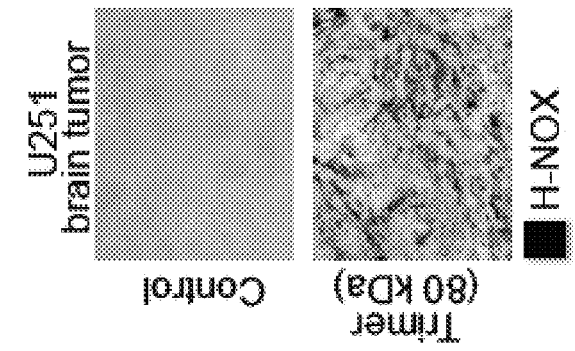

\* $p < 0.05$ by unpaired Student's t test

FIG. 19A  H-NOX
FIG. 19B  DAPI
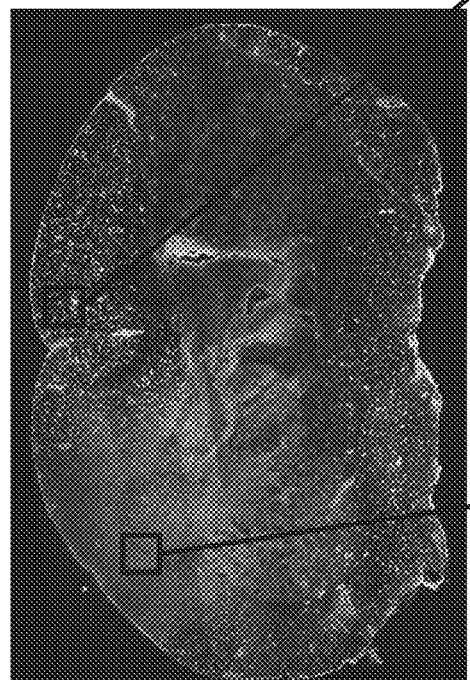
FIG. 19C  H-NOX (inside tumor)
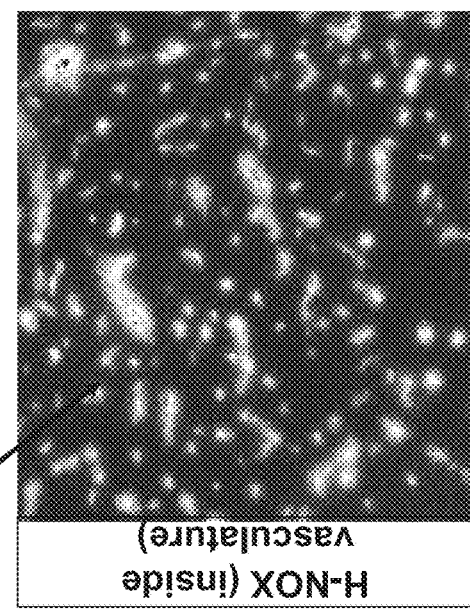
FIG. 19D  H-NOX (inside vasculature)
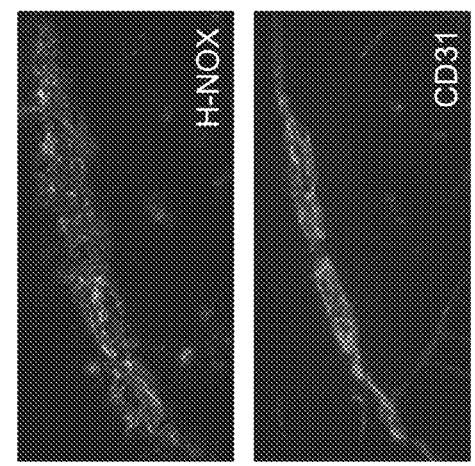
FIG. 19E  H-NOX / CD31

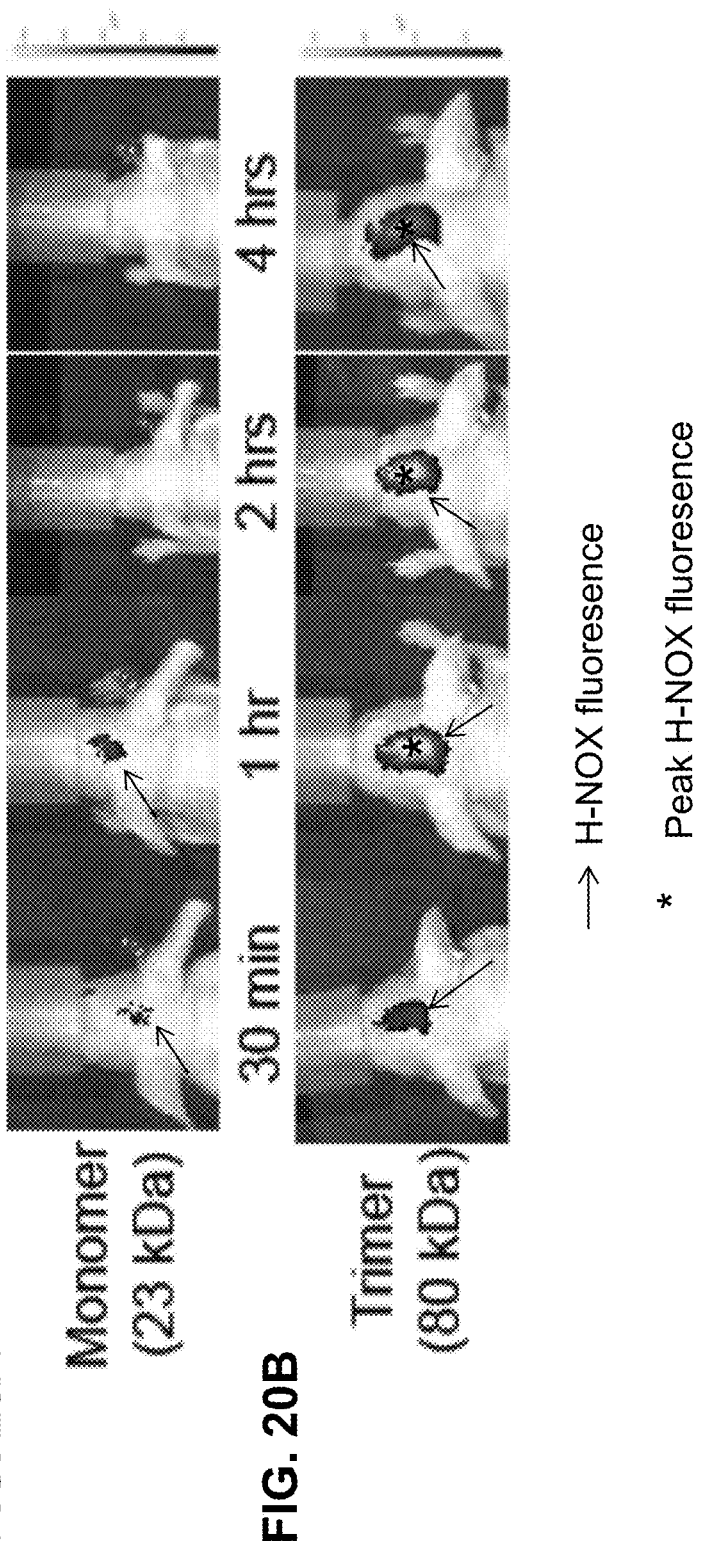

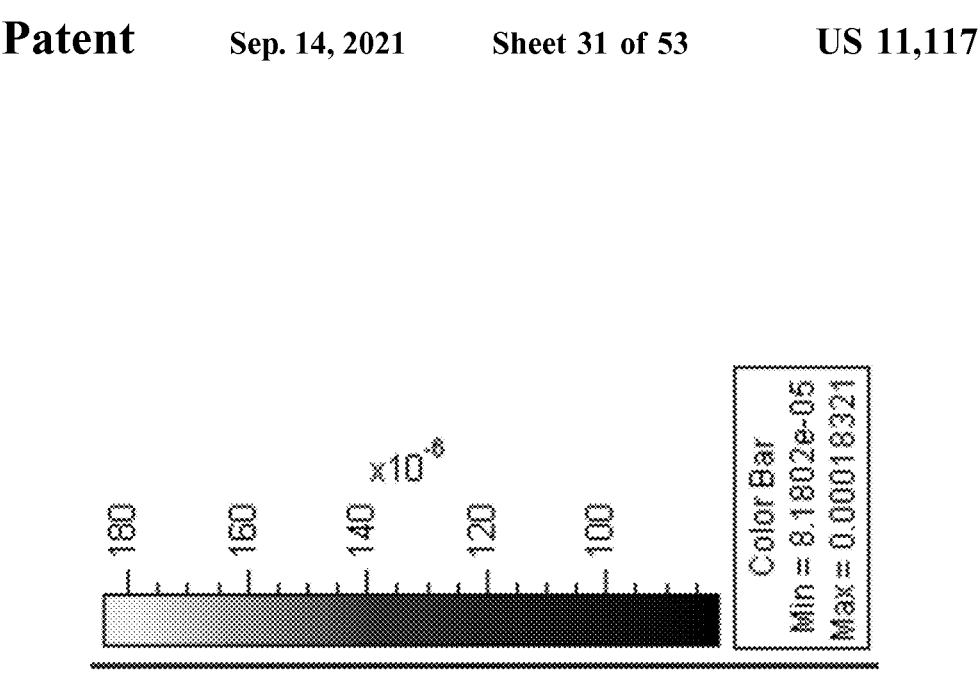
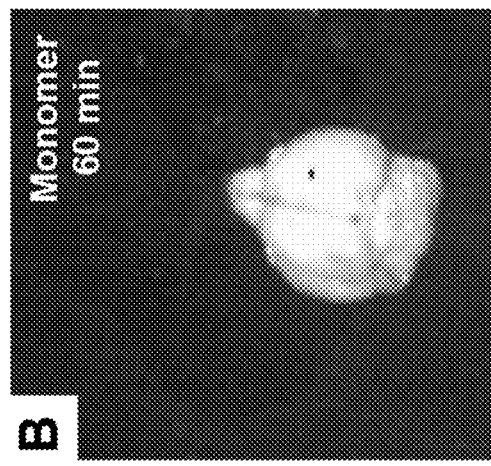
FIG. 21A
FIG. 21B
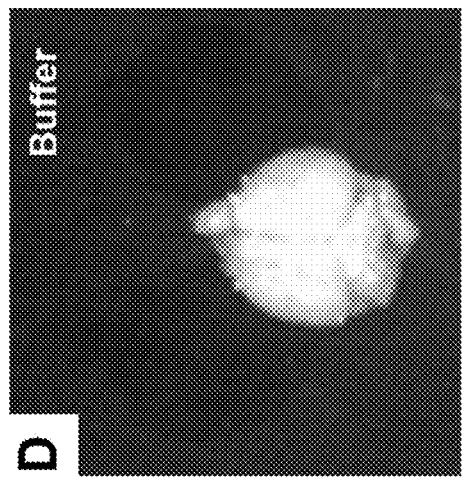
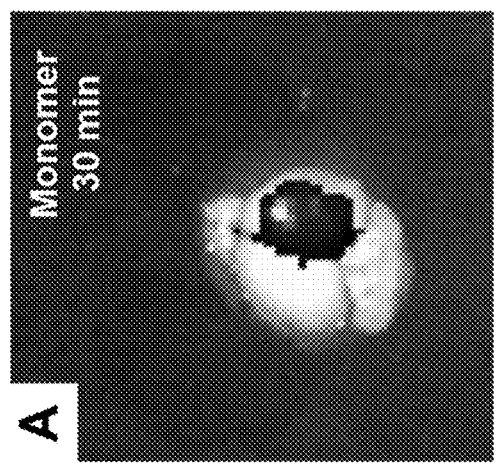
FIG. 21C
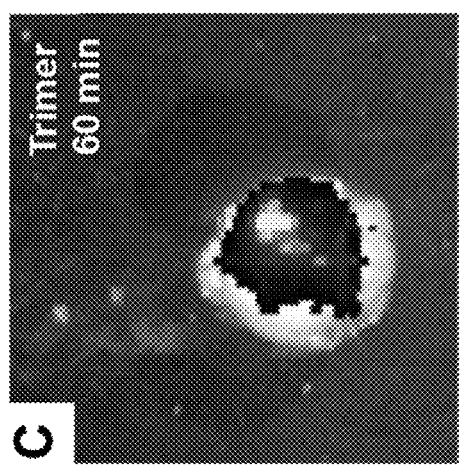
FIG. 21D

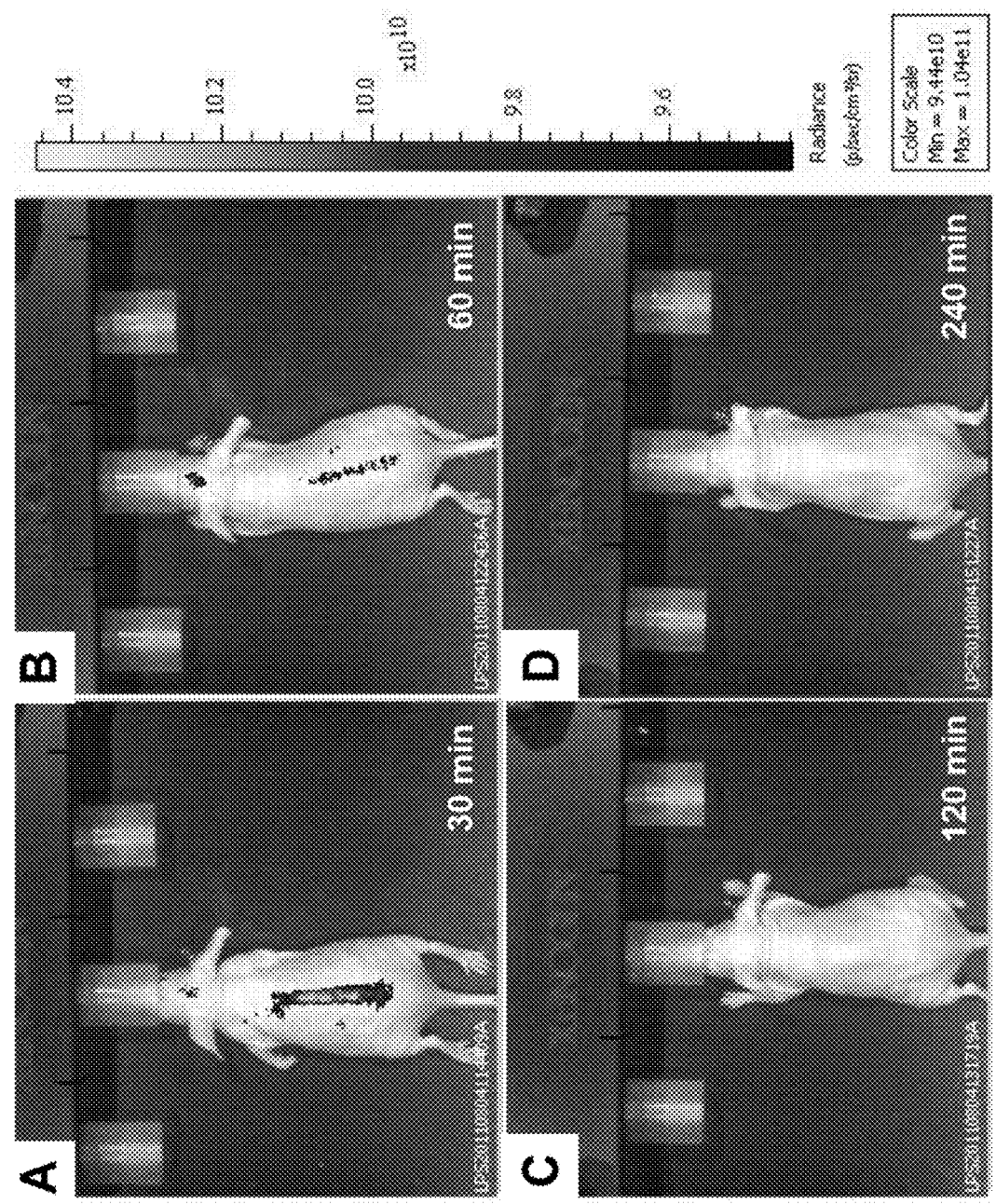

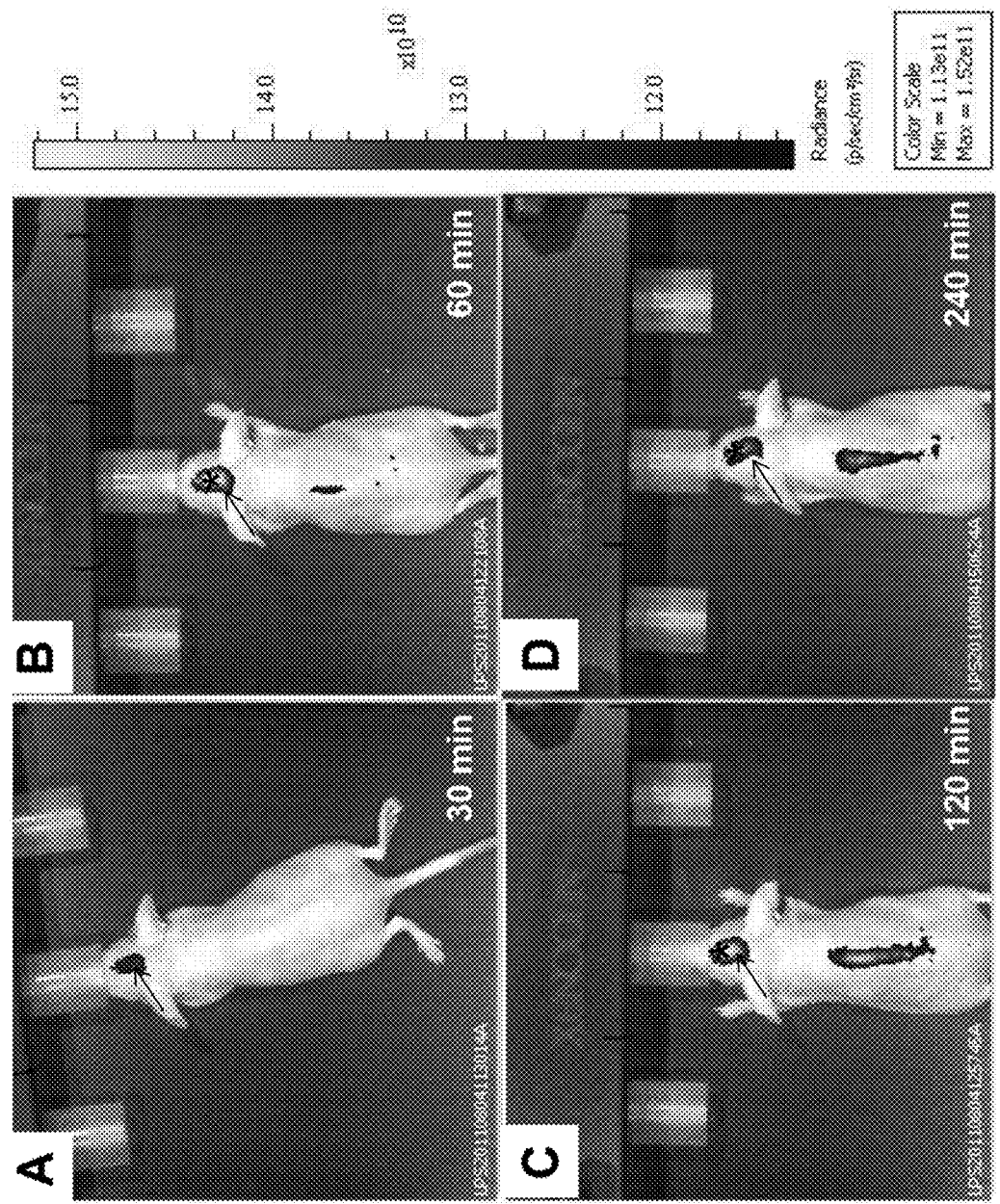

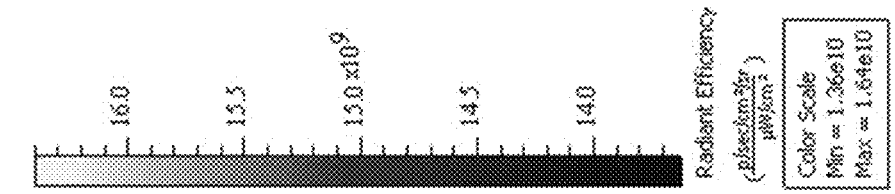
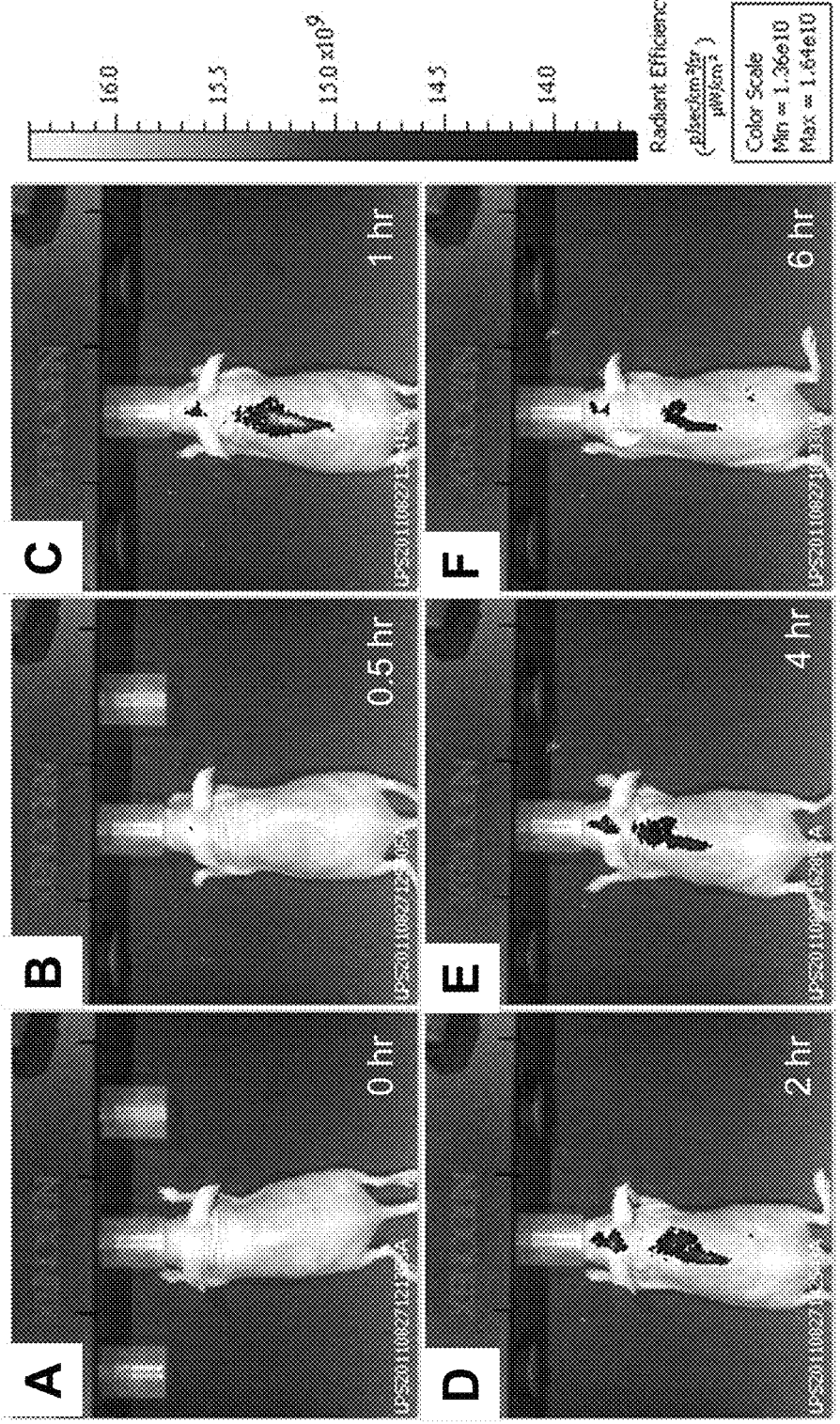
FIG. 25A  FIG. 25B  FIG. 25C
FIG. 25D  FIG. 25E  FIG. 25F

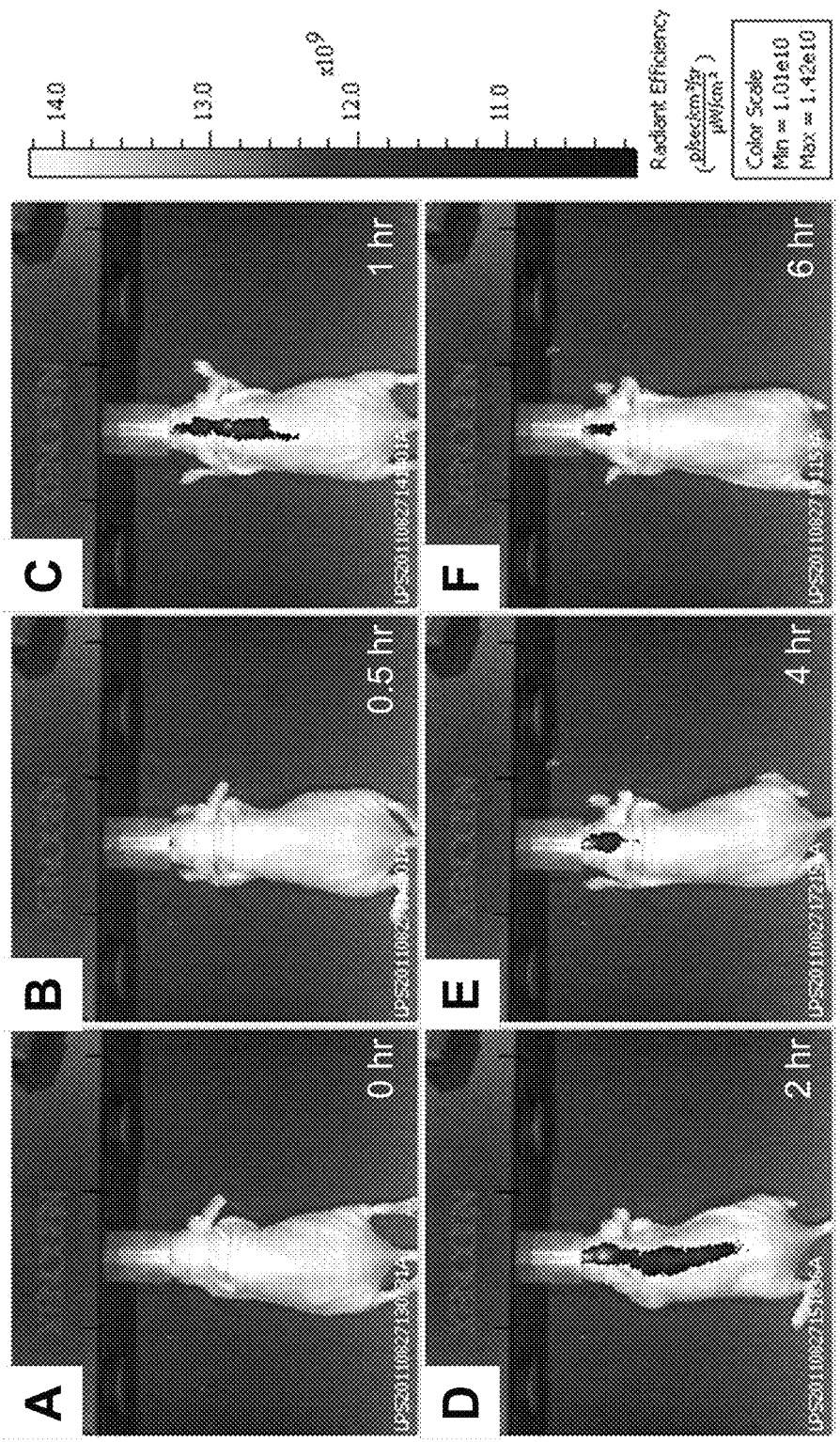

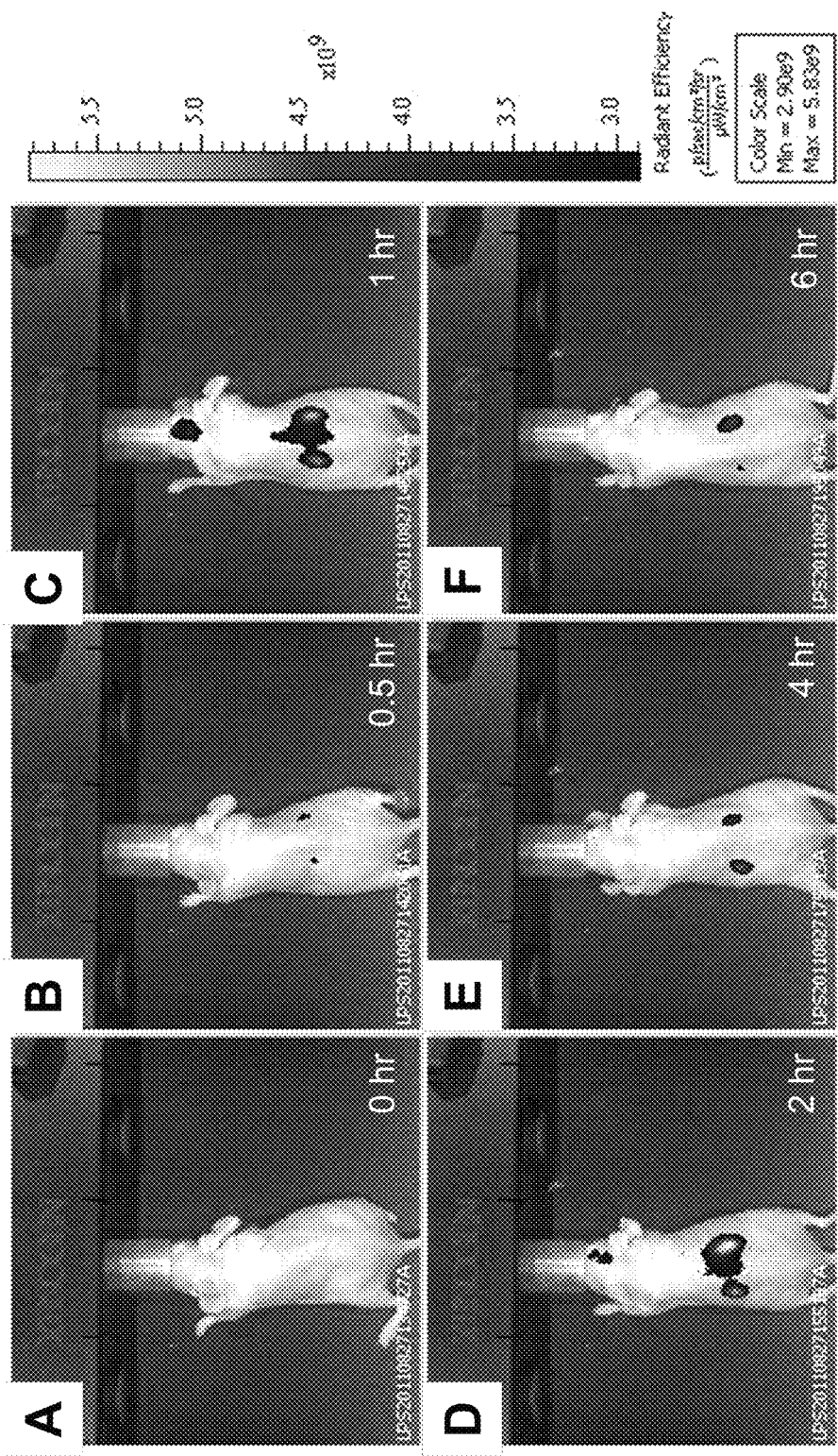

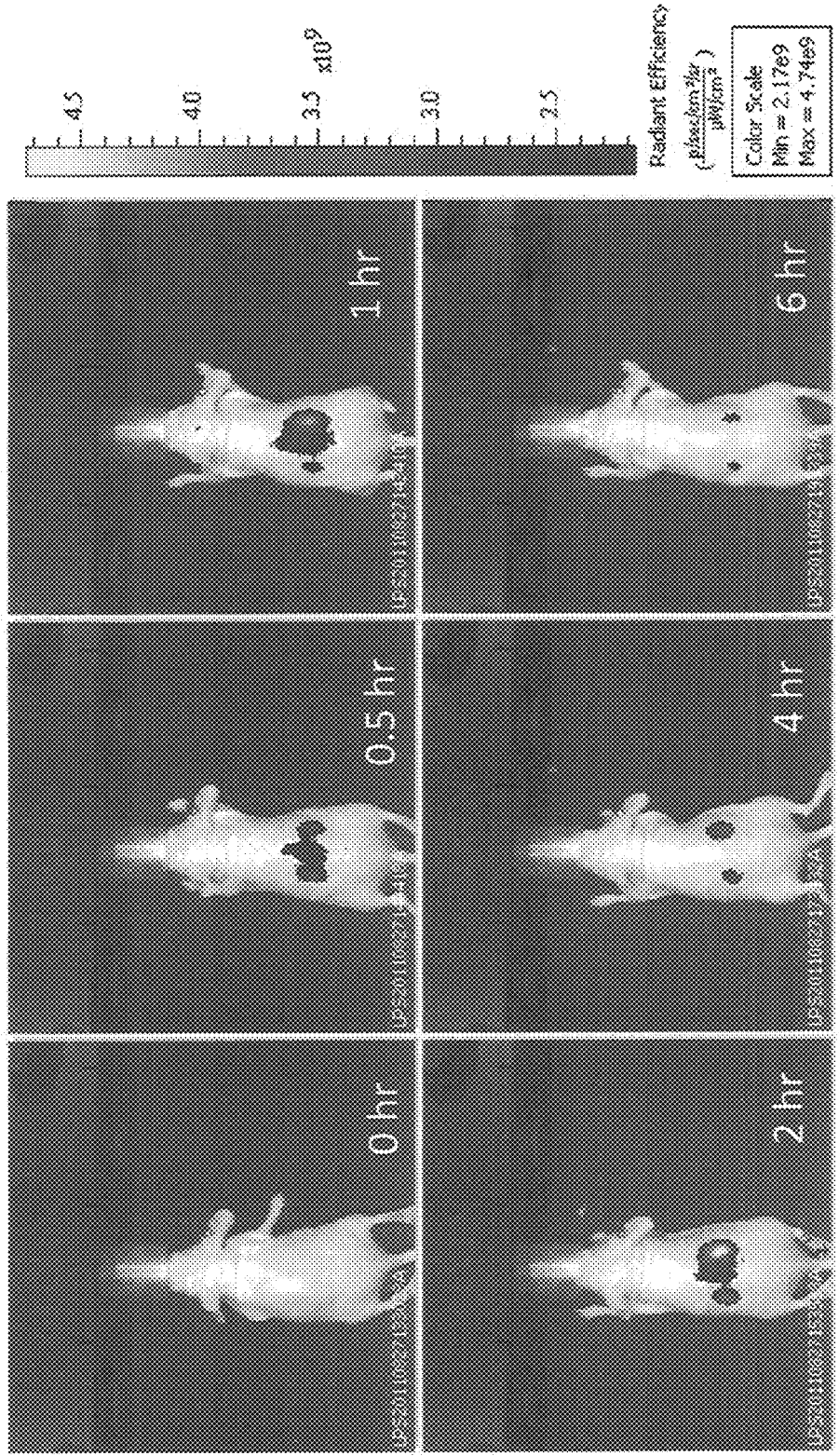

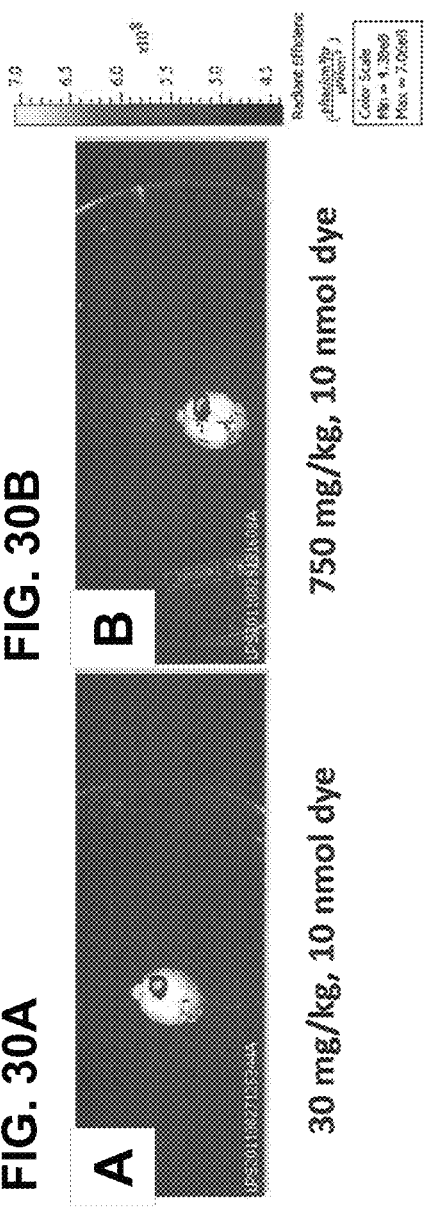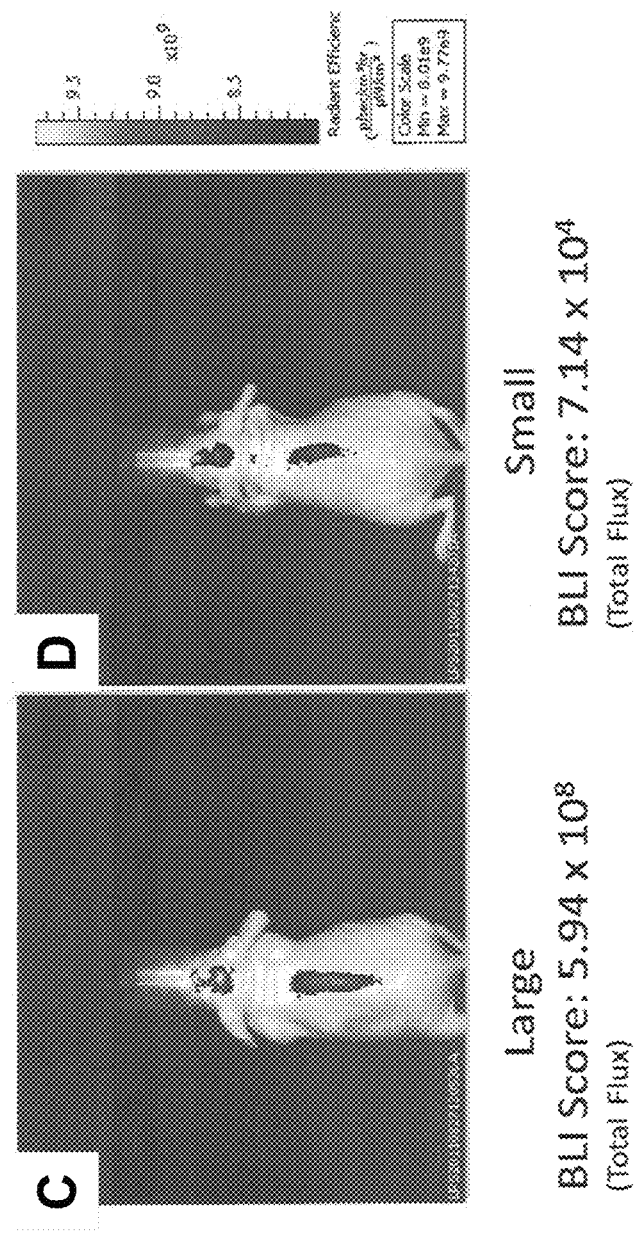

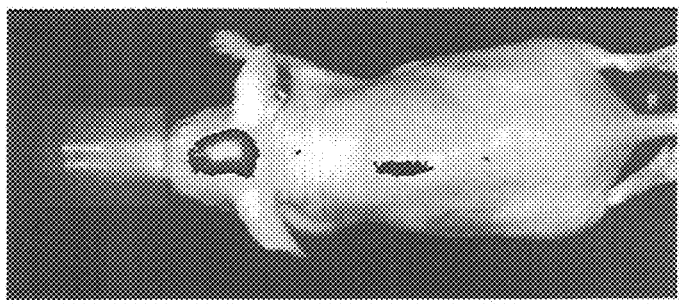
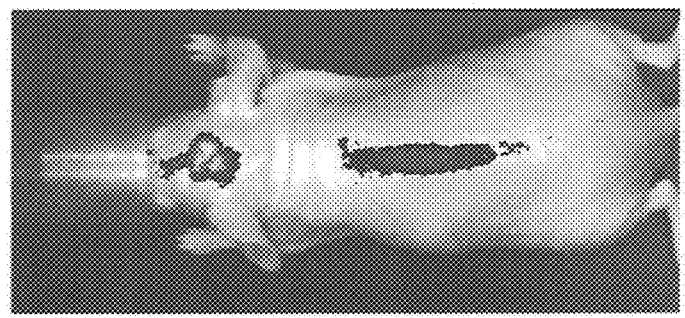
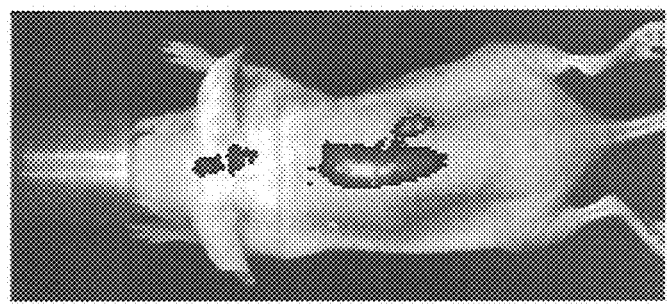
FIG. 31

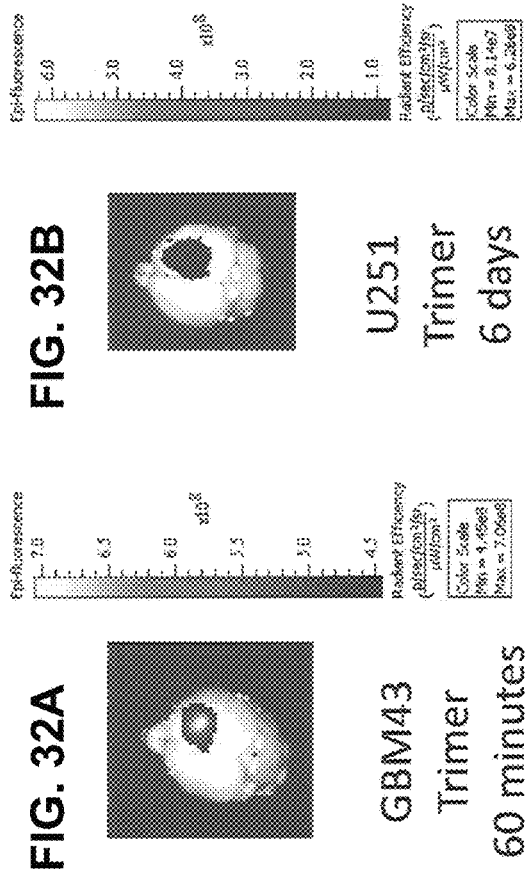
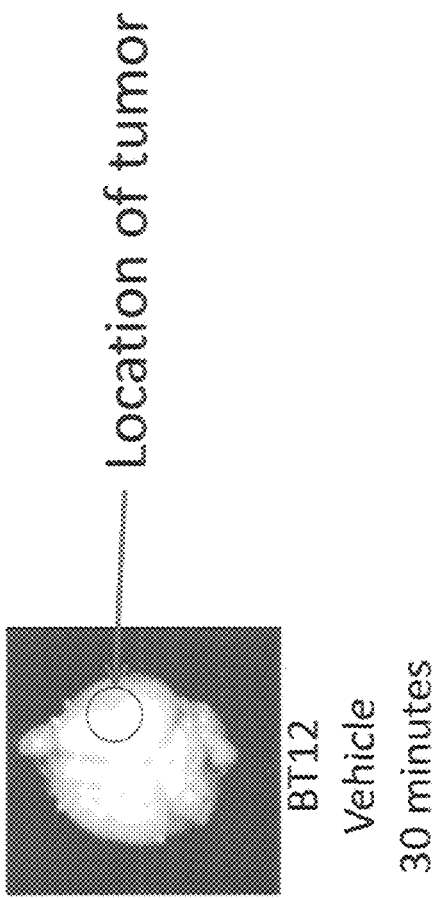
FIG. 32A GBM43 Trimer 60 minutes
FIG. 32B U251 Trimer 6 days
FIG. 32C BT-12 Monomer 30 minutes
FIG. 32D BT-12 Trimer 60 minutes
FIG. 32E BT12 Vehicle 30 minutes — Location of tumor

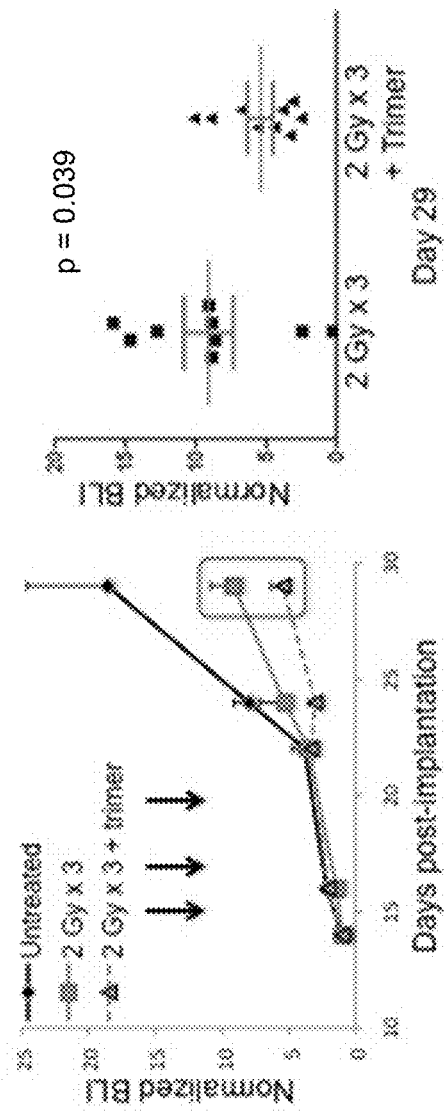
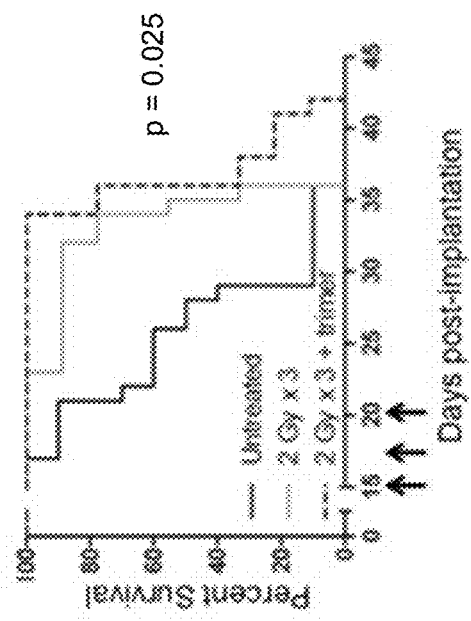
FIG. 35A
FIG. 35B
FIG. 35C

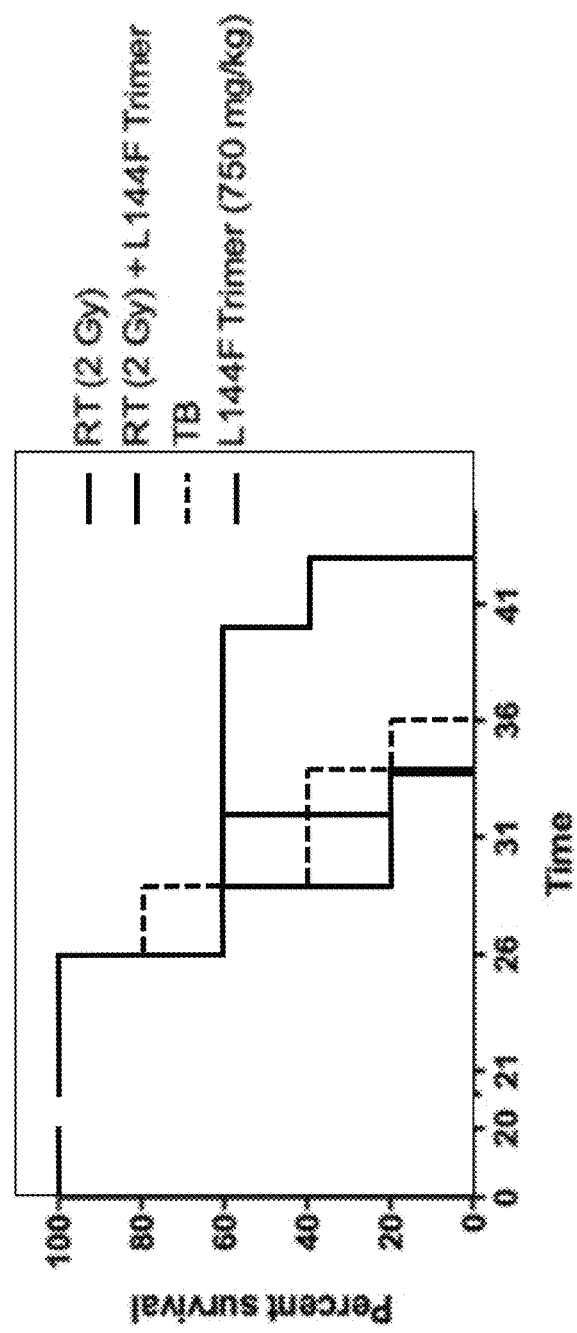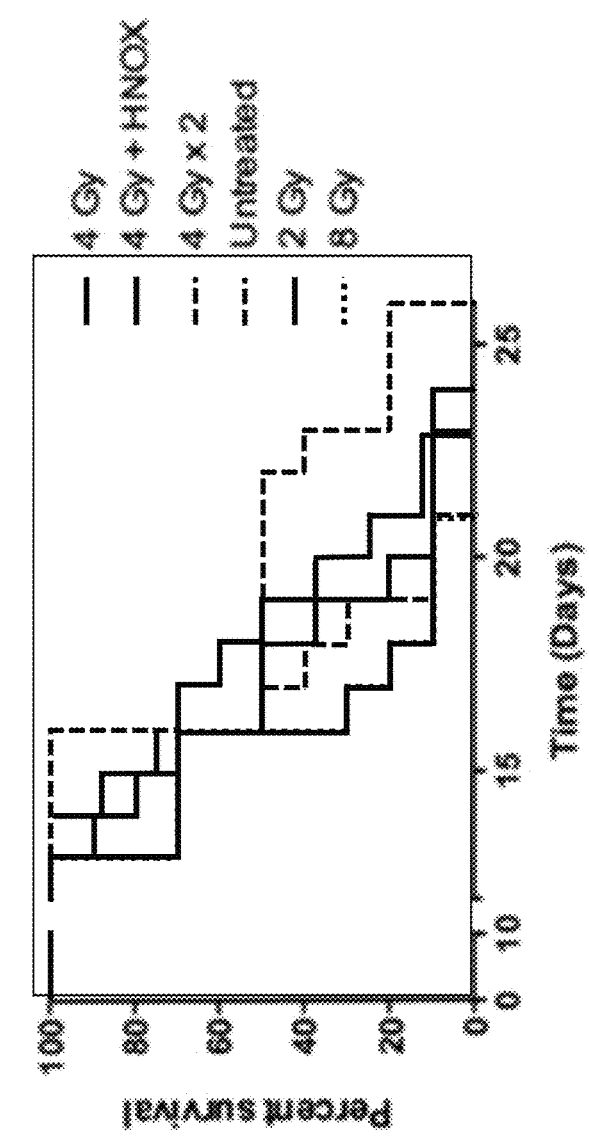
FIG. 36A
FIG. 36B

ATGAAGGGGACAATCGTCGGGACATGGATAAAGACCCTGAGGGACCTTTAC
GGGAATGATGTGGTTGATGAATCTTTAAAAAGTGTGGGTTGGGAACCAGAT
AGGGTAATTACACCTCTGGAGGATATTGATGACGATGAGGTTAGGAGAATT
TTTGCTAAGGTGAGTGAGAAAACTGGTAAAAATGTCAACGAAATATGGAGA
GAGGTAGGAAGCAGAACATAAAAACTTTCAGCGAATGGTTTCCCTCCTAT
TTTGCAGGGAGAAGGCTAGTGATGAATTTTTAATGATGATGAGGTACAC
CTACAGCTTACCAAGATGATAAAAGGAGCCACTCCTCCAAGGCTTATTGCA
AAGCCTGTTGCAAAAGATGCCATTGAAATGGAGTACGTTTCTAAAAGAAAG
ATGTACGATTACTTTTTAGGGCTTATAGAGGGTAGTTCTAAATTTTTCAAG
GAAGAAATTTCAGTGGAAGAGGTCGAAAAGAGGCGAAAAAGATGGCTTTTCA
AGGCTAAAAGTCAGGATAAAATTTAAAAACCCCGTTTTTGAGTGA (SEQ ID NO:1)

MKGTIVGTWIKTLRDLYGNDVVDESLKSVGWEPDRVITPLEDIDDDEVRRI
FAKVSEKTGKNVNEIWREVGRQNIKTFSEMFPSYFAGRRLVNFLMMMDEVH
LQLTKMIKGATPPRLIAKPVAKDAIEMEYVSKRKMYDYFLGLIEGSSKFFK
EEISVEEVERGEKDGFSRLKVRIKFKNPVFE (SEQ ID NO:2)

ATGATGTCTATGAAAGGAATCATATATTCAACGAATTTCTCAATTTTGTAGAA
AAAAGTGAATCCTACACCCTGGTAGATCAAATTATTATGGATAGTCATTTG
AAGTCCCATGGTGCCTACACGTCTATCGGTACATACTCTCCAAAGAATTA
TTTCAATTGGTTAAAGCGCTTGCTATGAAAAATGGCAAACCAACATCAGTG
ATTTTACAAGAATATGGTGAGTATTTGTTTGAGGTTTTGCAAAAAATAT
CCTCAATTTTTCAGGGAAAAAAAGTCGGTGTTTCAATTTTTGGAAGCGCTT
GAAACACACATATTCATTTCGAAGTGAAAAATTGTATGACTATACTGAACTA
CCCCATTTTGAATGCCAATATCACAGTCAAAATCAAAATGGAAATGATTTAC
ACTTCTTCCGCGTCCTTTGGCCGATTTGCGGAAGGTTTAATAAAAGGTTGT
ATTAAATATCATAAAGAAAACATGACTATTGTTCGTGAAAAATCTGCCTGCA
AAAACAGGCTTTAAGGTAAGATTTGTATTAACAAAAGGCGATCCTGATGAG
TGA
(SEQ ID NO:13)

MMSMKGIIFNEFLNFVEKSESYTLVDQIIMDSHLKSHGAYTSIGTYSPKEL
FQLVKALAMKNGKPTSVILQEYGEYLFEVFAKKYPQFFREKKSVFQFLEAL
ETHIHFEVKKLYDYTELPHFECQYHSQNQMEMIYTSSRPLADFAEGLIKGC
IKYHKENMTIVRENLPAKTGFKVRFVLTKGDPDE
(SEQ ID NO:14)

ATGAAAGGTATCGTTTTTACCTCCCTTAAATGACATGATTATAGAACAATTT
GGCATAGAAAACCTGGGACCAACTCGTATCCTCACTAGACCTTCCAAGTGGT
GGAAGTTATACAGCAGGCGGCACTTACTCGGATACAGAATTTCAGCAATTG
ATTAAGGCCATTGCGAAGAGGACCAATCAGCACGCTTCTGTTTTTTAGAG
GCCTTTGGTGAATACATGTTTCCTATCTTATCGAGTAAGTGCGCAATTTTT
TTAAAAAAGGACATGATAGAAAAGTTATACCCAGATGAAACATTACCTATT
AGCTATGAAGAGCCTGCTGCAAACCAATTGGTTATGGTGTATCGATCGCAT
AGAAGACTCTGTCATTTTGCAATTAAGCAGACTCACTGCATGTTAAAAAAGAT
TTTAAAAAGAAATTACCATTAAGCAGACTCACTGCATGTTAAAAAAGAT
GATCATTGTCGTTTGGAGATTACCTTTGAGTGA
(SEQ ID NO:15)

MKGIVFTSLNDMIIEQFGIETWDQLVSSLDLPSGGSYTAGGTYSDTEFQQL
IKAIAKRTNQHASVFLEAFGEYMFPILSSKCAIFLKKDMTLKEFLKSIDGT
IHVEVEKLYPDETLPTISYEEPAANQLVMVYRSHRRLCHFAMGLIQGAAQH
FKKKITIKQTHCMLKKDDHCRLEITFE
(SEQ ID NO:16)

FIG. 37D

*Homo sapiens* β1(1-385)

Hs. WT (1-385)

ATGTACGGATTTGTGAATCACGCCCTGGAGTTGCTGGTGATCCGCAATTACGGCCCCGAGGTGTGGGAAGACATC
AAAAAAGAGGCACAGTTAGATGAAGAAGGACACAGTTTCTTGTCAGAATAATATATGATGACTCCAAAACTTATGAT
TTGGTTGCTGCTGCAAGCAAAGTCCTCAATCTCAATGCTGGAGTGTCTCAAATGTTTGGGAAGATGTTTTTC
GTCTTTTTGCCAAGAATCTGGTTATGATACAATCTTGCGTGTGCTCACCCAGGAATGCGTGACAGGACTTCTACAGAAC
CTTGATGCTCTGCACGACCACCTCATTTTGCACTACTACTGCTGAAATAGACATGAAGGTTTATTCAGCAAAGATCATC
GAAAAGGGCAAAGGACTCATTTTGCACTACTACTCAGAAATAGACATGAAGGTTTATTCAGCAAAGATCTTGAAGAA
AAAACAGTGGCACAACAAATCCATGGCACTGAAATAGAGTCAAAAGAGGATTTTATGAAGATCTTGACAGATTTGAAGAA
CATACTCAATTTTAATTGAAGAAAAAGAGTCAAAAGAGGATTTTATGAAGATCTTGACAGATATATTTGACCGG
GACTTACCCAGGAATCACGCATCAGTGGCAATGCTATATACAGAGTTCTCCCCCCAGCTCCTGGAATTGCAGCCTT
CTGTCTGTCTTCTGCTGGTTCGTCTGTTCGTCTGCTGATATTAGTTTCCATGGGATCCTTTCTCACATCAATACTGTT
TTTGTATTGAGAAGCAAGAAGGATTGTTGATGTGGAGAAATTAGAATGTGAGGATGAACTGACTGGGACTGAG
ATCAGCTGCTTACGTCTCAAGGCTCAAATGATCTCATCTACCTGAAGCAGATAGCATCTAAGTGACATCCCTCTGCATGATGCCACGCC
AGTGTCATGAACCTGGACGATTTGACAAGGAGAGGGCTGTATCTAAGTGACATCCCTCTGCATGATGCCACGCC
GATCTTGTTCTTTTGGGAGAACAATTAGAGAGAGAGAGAGAGCCCTGAAGATTGA
CTACAGCTCACGTTAAGAGAGCCCTGGAAGATTGA (SEQ ID NO:17)

MYGFVNHALELLVIRNYGPEVWEDIKKEAQLDEEGQFLVRIIYDDSKTYDLVAAASKVLNLNAGEILQMFGKMFF
VFCQESGYDTILRVLGSNVREFLQNLDALHDHLATIYPGMRAPSFRCTDAEKGKGLILHYYSEREGLQDIVIGII
KTVAQQIHGTEIDMKVIQQRNEECDHTQFLIEEKESKEEDFYEDLDRFEENGTQESRISPYTFCKAFPFHIFDR
DLVVTQCGNAIYRVLPQLQPGNCSLLSVFSLVRPHIDISFHGILSHINTVFVLRSKEGLLDVEKLECEDELTGTE
ISCLRLKGQMIYLPEADSILFLCSPSVMNLDDLTRRGLYLSDIPLHDATRDLVLLGEQFREEYKLTQELEILTDR
LQLTLRALED (SEQ ID NO:18)

FIG. 37E

*Homo sapiens* β2 (1-217)

ATGTATGGATTCATCATCAACACCTGCCTGCAGTCTCTTGTGACAGAGAAATTT
GGTGAGGAGACATGGGAGAAGCTGAAGGCTCCTGCAGAAGTGCAAGATGTC
TTCATGACCTACACCGTGTATGATGACATTATCACCATTAAGCTCATCCAA
GAAGCCTGCAAGGTTCTGGATGTGTCCATGGAAGCCATTCTGAAGCTCTTT
GGCGAATACTTCTTTAAGTTCTGTAAGATGTCTGGCTATGACAGGATGCTG
CGGACACTTGGAGGAAATCTCACCGAGTTTATTGAAAACCTAGATGCACTC
CACAGTTACCTGGCACTGTCCTATCAGGAAATGAACGCACCATCCTTTCGA
GTGGAGGAAGGAGCTGACGGGGCGATGCTTCCACTACTACTCAGACAGA
CATGGTCTGTGTCACATTGTACCAGGTATCATTGAAGCTGTGGCCAAGGAC
TTCTTTGACACTGATGTGGCCATGAGTATCCTGGATATGAACGAAGAGGTG
GAAAGGACAGGGAAGAAAGAACATGTTGTGTTTCTGGTCGTGCAGAAGGCT
CACAGACAGATAAGAGGAGCAAAGGCCAGCCGGCCACAAGGCAGTGAGGAC
AGCCAGGCAGACCAGGAGGCTCTCCAGGGAACACTCCTT
(SEQ ID NO:19)

MYGFINTCLQSLVTEKFGEETWEKLKAPAEVQDVFMTYTVYDDIITIKLIQ
EACKVLDVSMEAILKLFGEYFFKFCKMSGYDRMLRTLGGNLTEFIENLDAL
HSYLALSYQEMNAPSFRVEEGADGAMLLHYYSDRHGLCHIVPGIIEAVAKD
FFDTDVAMSILDMNEEVERTGKKEHVVFLVVQKAHRQIRGAKASRPQGSED
SQADQEALQGTLL
(SEQ ID NO:20)

FIG. 37F

*Rattus norvegicus* β1(1-385)

Rn. WT (1-385)

(SEQ ID NO:21)
ATGTACGGTTTTGTGAACCATGCCCTGGAGCTGCTGGTGATCCGCAATTACGGTCCCGAGGTGTGGG
AAGACATCAAAAAAGAGGCCGCAGCTGGATGAAGAAGGCCAGTTTCTTGTGAGAATAATCTACGATGA
TTCCAAAACCTATGACTTGGTGGCTGCTGCGAGCAAAGTCCTCAACCTCAATGCTGGTGAAATCCTG
CAGATGTTTGGGAAGATGTTTTTCGTCTGTCAAGAGTCTGGCTATGATACCATCTTGCGTGTCC
TGGGATCTAATGTCAGGGAGTTTTTGCAGAACCTCGACGCCCTGCACGACCACCTGCCACCATCTA
CCCAGGGATGCGCGCAAACCTTCCTTCCGGTGTCAGGACATTGTGATCGGGATTATCAAGACTGTAGCTCAACATGA
TCCATGCACTGAGATAGACATGAAAGTTATTTATTCAGCAAAGAAGTGAAGAATGTGATCATACCCAATT
TTTAATTGAAGAAAAAGAATCAAAAGAGAGGATTTTTATGAAGATCTGGACAGTTTGAAGAGAAC
GGTACCCAGGACTCCCGTATCAGCCCGTACACCTTCTGCAAAGCGTTTCCTTTTCACATCATATTTG
ACCGGGACTAGTAGTCAGCCAGTGTGAAATGCTATCTACAGAGTGCTCCCCCAGCTCCCAGCCTGG
GAAGTGCAGCCTTCTGTCTGTCTTGTACTGAGAAGCAAGGAAGGGTTGCTGGATGTTGAGAAACTTG
CTTTCACACATCAATACCGTCTTTGTACTGAGAAGCAAGGAAGGGTTGCTGGATGTTGAGAAACTTG
AATGTGAGGATGAACTGACTGGGGCAGAGATTAGCTGCCTCCGTCTCAAAGGCCAAATGATCTATTT
ACCGGGAAGCAGATAGCATCCCTCCTCCTGTTCACCAAGTGTGATGAACTGGATGACCTAACAAGA
AGAGGCCTGTACCTGAGTGACATCCCTCCATGATGCTACACGAGACCTGGTCCTTTTGGAGAAC
AGTTCCGGGAGGAGTACAAACTGACAACTGGAAATCCTCACAGACAGGCTGCAGCTCACACT
GAGGGCTTTGGAGGATTGA (SEQ ID NO:22)
MYGFVNHALELLVIRNYGPEVWEDIKKEAQLDEEGQFLVRIIYDDSKTYDLVAAASKVLNLNAGEIL
QMFGKMFFVFCQESGYDTILRVLGSNVREFLQNLDALHDHLATIYPGMRAPSFRCTDAEKGKGLLLH
YYSEREGLQDIVIGIIKTVAQQIHGTEIDMKVIQQRSEECDHTQFLIEEKESKEEDFYEDLDRFEEN
GTQDSRISPYTFCKAFPFHIIFDRDLVVTQCGNAIYRVLPQLQPGKCSLLSVFSLVRPHIDISFHGI
LSHINTVFVLRSKEGLLDVEKLECEDELTGAEISCLRLKGQMIYLPEADSILFLCSPSVMNLDDLTR
RGLYLSDIPLHDATRDLVLLGEQFREEYKLTQELEILTDRLQLTLRALED

FIG. 37G

Rattus norvegicus β2

(SEQ ID NO:23)
ATGTATGGATTCATCAACACCTGCCTGCAGTCTCTTGTGACAGAGAAATTTGGTGAGGAGACATGGGAGAAGCTCCTGCAGAAGTGCAAGATGTCTT
CATGAGCTACACACCGTGTATGATGACATTCACCATTCACCACGAAGCCTGAAGTTCTGATGTTCTGAGGCCATTCTGAAGCTCTTTGGCG
AATACTTCTTTAAGTTCTGTAAGATGTCTGGCTATGACAGAATGCTGCGACACTTGGAGGACACAGTTATTGAAAACCTAGATGCACTCCACAGT
TACCTGGCACTGTCCTATCAGGAAATGAACGCACCATCCTTTCGAAGGAGCTGAGCGGGCGATGCTTCTCCACTACTACTCAGACAGACATGGTCT
GTGTCACATTGTACCAGGTATCATTGAAGCTGTCGTGCAGAAGACTTCTTTGACACTTGAGCAGTATCCTGGATATGAACGAAGAGGTGAAGGACAG
GAAGAGAACATGTTGTGTTTCTGTTCTGCAGAAGGCTCACAGATAAGAGAGCAAGCCAGTGAGGAGCCGGCCACACTGCCAGCCAGGCAGAC
CAGGAGGCTCTCCAGGAACACTCCTTCAGGGACACCTTCCAGCCCGTCATCCCGAGAGACATGGGTCCTGAAGAGGAGTGTCTGTGATGCTTTCCACATTG
CCTTTTTGAAAAGGCCCCTCAAGGCACTAAGGGTCAACAAGCTGAGGTCATGATCCTGAGAAGTATGTCCCTGAATTCTTAACCAGAAGTTTGCACTAGATGAGATATTTTTCCATC
TCTTTGATGAAGCACTAAGGGTCAACAACCATCCAGTACTTTCAACATCTCCGGGCTGCTCAAACTCCCGGGTCAGATGATCTCGATGGAGTGCATCGACACCAGAGATCTGAAGAGAGAAGCAAGCGCTGAAGAGAG
AGAGCAAGATGCATCTTCGATATCGCTCCGCACACCAGGATCTCAATGCTGGCCATGCAGAAGAAGAGACCTTGCTGTATGACATTTACCAACATCTGTGCCTGTGAAC
CTATCCAAATCGTGAACATGCTGAATTCAATGTACTCCAAGTTGACAGTTGCCATGATGTCTACAAAGTAGAAACATAGGGATGCTTACATG
GTGTGGGGTGAGTACCAGTACCCGTTGAAAGCCATGCTGAAGAGTCGGCCCAATTTGCTCTGGGATGAAGACAAGAGCCCTGAAAAACAAAGGTTTGAAATTGTCAGGAGA
TGGGAACCTATCCAGATCAGATGGAAGTCACGGGCTTCCAGCAAGTGCATCTGAGCCCACAGAACCTGAATGCCACCAGACCATCAGCAGCCCATCACCAGATGAGACAAGAGTC
ACAGCCCTCGAAGATGGAAAGTCACGGGCTTCCAGCAAGTGCATCTGAGCCCACAGAACCTGAATGCCACCAGACCATCAGCAACAGTCTACAAAGGAGACCCAGCAG
GCGAGATCGAAGTGAAGGGAAAGGAAAGATGACCAAGTGACCACATACTTTCAGGAAGTCCCCTGTCCCGAGGAGTCCAGAGATGGGGCGACCTTCAGCCCCGC
TGATGGAAGGAAGTATGTACTCCGGAAGCACACCACTTGCTCGGGAGCCCAGTGCAGGGCAGAGTCAGTCAATAACCAGTAGCTCACCAGATGAGACAAGAGACCAAGAAGTGTC
ACGCTTCTAATGAAGCTCACACACTTGCTGCTCAGGGAGCCCAGTGCAGGGCAGAGTCAGCAGTCAATAACCAGCCATCACCAGATGAGACAAGAGACCAAGAAGTGTC
GTTGCTAGTGGCCCTGCTGTGCTGCTTCTGCTTCTGTCTGTGTGCTGTGA (SEQ ID NO:24)
MYGFINTCLQSLVTEKFGEETWEKLKAPAEVQDVFMTYTVYDDIITIKLIQEACKVLDVSMEAILKLFGEYFFKFCKMSGYDRMLRTLGGNLTEFIENLDALHS
YLALSYQEMNAPSFRVEEGADGAMLLHYYSDRHGLCHIVPGIIEAVAKDFFDTDVAMSILDMNEEVERTGKKEHVVFLVVQKAHRQIRGAKASRPQGSEDSQAD
QEALQGTLLRMKERYLNIPVCPGEKSHSTAVRASVLFGKGPLRDTFQPVYPERLWVEEEVFCDAFPFHIVFDEALRVKQAGVNIQKYVPGILTQKFALDEYFSI
IHPQVTFNISSICKFINSQFVLKTRKEMMPKARKSQPMLKLRGQMIWMESLRCMIFMCSPNVRSLQELEESKMHLSDIAPHDTTRDLILLNQQRLAEMELSCQL
EKKEELRVLSNHLAIEKKKTETLLYAMLPEHVANQLKEGRKVAAGEFETCTILFSDVVTFTNICAACEPIQIVNMLNSMYSKFDRLTSVHDVYKVETIGDAYM
VVGGVPVPVESHAQRVANFALGMRISAKEVMNPVTGEPIQIRVGIHTGPVLAGVVGDKMPRYCLFGDTVNTASRMESHGLPSKVHLSPTAHRALKNKGFEIVRR
GEIEVKGKGKMTTYFLIQNLNATEDEIMGRPSAPADGKEVCTPGNQVRKSPAVPRNTDHQQQVYKGDPADASNEVTLAGSPVAGRNSTDAVNNQPSPDETKTSV
VASGPVLSAFCVVL

SEQUENCE LISTING

<160> NUMBER OF SEQ ID NOS: 28

<210> SEQ ID NO 1
<211> LENGTH: 555

```
<212> TYPE: DNA
<213> ORGANISM: Thermoanaerobacter tengcongensis

<400> SEQUENCE: 1
atgaagggga caatcgtcgg gacatggata agaccctga gggacccttta cgggaatgat    60 gtggttgatg aatctttaaa aagtgtgggt tgggaaccag atagggtaat tacacctctg   120
gaggatattg atgacgatga ggttaggaga attttttgcta aggtgagtga aaaaactggt   180
aaaaatgtca acgaaatatg gagagaggta ggaaggcaga acataaaaac tttcagcgaa   240
tggtttccct cctatttttgc agggagaagg ctagtgaatt ttttaatgat gatggatgag   300
gtacacctac agcttaccaa gatgataaaa ggagccactc ctccaaggct tattgcaaag   360
cctgttgcaa aagatgccat tgaaatggag tacgtttcta aaagaaagat gtacgattac   420
tttttagggc ttatagaggg tagttctaaa tttttcaagg aagaaatttc agtgaagag    480 gtcgaaagag gcgaaaaaga tggctttca aggctaaaag tcaggataaa atttaaaaac   540
cccgtttttg agtga                                                    555

<210> SEQ ID NO 2
<211> LENGTH: 184
<212> TYPE: PRT
<213> ORGANISM: Thermoanaerobacter tengcongensis

<400> SEQUENCE: 2

Met Lys Gly Thr Ile Val Gly Thr Trp Ile Lys Thr Leu Arg Asp Leu
  1               5                  10                  15

Tyr Gly Asn Asp Val Val Asp Glu Ser Leu Lys Ser Val Gly Trp Glu
             20                  25                  30

Pro Asp Arg Val Ile Thr Pro Leu Glu Asp Ile Asp Asp Asp Glu Val
         35                  40                  45

Arg Arg Ile Phe Ala Lys Val Ser Glu Lys Thr Gly Lys Asn Val Asn
     50                  55                  60

Glu Ile Trp Arg Glu Val Gly Arg Gln Asn Ile Lys Thr Phe Ser Glu
 65                  70                  75                  80

Trp Phe Pro Ser Tyr Phe Ala Gly Arg Arg Leu Val Asn Phe Leu Met
                 85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu
            180

<210> SEQ ID NO 3
<211> LENGTH: 81
<212> TYPE: DNA
<213> ORGANISM: Artificial Sequence
<220> FEATURE:
<223> OTHER INFORMATION: Synthetic Construct

<400> SEQUENCE: 3
```

```
ggttatattc ctgaagctcc aagagatggg caagcttacg ttcgtaaaga tggcgaatgg    60
gtattacttt ctacctttttt a                                              81
```

```
<210> SEQ ID NO 4
<211> LENGTH: 27
<212> TYPE: PRT
<213> ORGANISM: Artificial Sequence
<220> FEATURE:
<223> OTHER INFORMATION: Synthetic Construct

<400> SEQUENCE: 4
```

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

```
<210> SEQ ID NO 5
<211> LENGTH: 690
<212> TYPE: DNA
<213> ORGANISM: Artificial Sequence
<220> FEATURE:
<223> OTHER INFORMATION: Synthetic Construct

<400> SEQUENCE: 5
atgaagggga caatcgtcgg gacatggata agaccctga gggacctta cgggaatgat    60 gtggttgatg aatctttaaa aagtgtgggt tgggaaccag ataggataat tacacctctg   120
gaggatattg atgacgatga ggttaggaga attttttgcta aggtgagtga aaaaactggt   180
aaaaatgtca acgaaatatg gagagaggta ggaaggcaga acataaaaac tttcagcgaa   240 tggtttcccct cctattttgc agggagaagg ctagtgaatt ttttaatgat gatggatgag   300
gtacacctac agcttaccaa gatgataaaa ggagccactc ctccaaggct tattgcaaag   360
cctgttgcaa aagatgccat tgaaatggag tacgtttcta aaagaaagat gtacgattac   420 ttttagggt ttatagaggg tagttctaaa ttttcaagg aagaaatttc agtggaagag   480
gtcgaaagag gcgaaaaaga tggcttttca aggctaaaag tcaggataaa atttaaaaac   540 cccgttttg agtataagaa aaatctcgag ggcagcggcg ttatattcc tgaagctcca   600 agagatgggc aggcttacgt tcgtaaagat ggcgaatggg tattactttc tacctttta   660 agggtagtc accatcacca tcaccattga                                    690
```

```
<210> SEQ ID NO 6
<211> LENGTH: 229
<212> TYPE: PRT
<213> ORGANISM: Artificial Sequence
<220> FEATURE:
<223> OTHER INFORMATION: Synthetic Construct

<400> SEQUENCE: 6
```

Met Lys Gly Thr Ile Val Gly Thr Trp Ile Lys Thr Leu Arg Asp Leu
1               5                   10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

```
Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
        100                 105                 110

Thr Pro Pro Arg Leu Ile Ala Lys Pro Val Ala Lys Asp Ala Ile Glu
    115                 120                 125

Met Glu Tyr Val Ser Lys Arg Lys Met Tyr Asp Tyr Phe Leu Gly Phe
130                 135                 140

Ile Glu Gly Ser Ser Lys Phe Phe Lys Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn Leu Glu Gly Ser
            180                 185                 190

Gly Gly Tyr Ile Pro Glu Ala Pro Arg Asp Gly Gln Ala Tyr Val Arg
        195                 200                 205

Lys Asp Gly Glu Trp Val Leu Leu Ser Thr Phe Leu Arg Gly Ser His
210                 215                 220

His His His His His
225

<210> SEQ ID NO 7
<211> LENGTH: 663
<212> TYPE: DNA
<213> ORGANISM: Artificial Sequence
<220> FEATURE:
<223> OTHER INFORMATION: Synthetic Construct

<400> SEQUENCE: 7
atgaagggga caatcgtcgg gacatggata agaccctga gggaccttta cgggaatgat        60
gtggttgatg aatcttaaa agtgtgggt tgggaaccag atagggtaat tacacctctg       120
gaggatattg atgacgatga ggttaggaga attttttgcta aggtgagtga aaaaactggt      180
aaaaatgtca acgaaatatg gagagaggta ggaaggcaga acataaaaac tttcagcgaa      240
tggtttccct cctatttttgc agggagaagg ctagtgaatt tttaatgat gatggatgag      300 gtacacctac agcttaccaa gatgataaaa ggagccactc ctccaaggct tattgcaaag      360
cctgttgcaa aagatgccat tgaaatggag tacgttttcta aaagaaagat gtacgattac      420
tttttagggt ttatagaggg tagttctaaa tttttcaagg aagaaatttc agtggaagag      480
gtcgaaagag gcgaaaaaga tggctttca aggctaaaag tcaggataaa atttaaaaac      540
cccgtttttg agtataagaa aaatctcgag ggcagcggcg gttatattcc tgaagctcca      600
agagatgggc aggcttacgt tcgtaaagat ggcgaatggg tattacttc taccttttta      660 tga                                                                   663

<210> SEQ ID NO 8
<211> LENGTH: 220
<212> TYPE: PRT
<213> ORGANISM: Artificial Sequence
<220> FEATURE:
<223> OTHER INFORMATION: Synthetic Construct

<400> SEQUENCE: 8

Met Lys Gly Thr Ile Val Gly Thr Trp Ile Lys Thr Leu Arg Asp Leu
1               5                   10                  15

Tyr Gly Asn Asp Val Val Asp Glu Ser Leu Lys Ser Val Gly Trp Glu
                20                  25                  30
```

```
Pro Asp Arg Val Ile Thr Pro Leu Glu Asp Ile Asp Asp Glu Val
         35                  40                  45
Arg Arg Ile Phe Ala Lys Val Ser Glu Lys Thr Gly Lys Asn Val Asn
 50                  55                  60
Glu Ile Trp Arg Glu Val Gly Arg Gln Asn Ile Lys Thr Phe Ser Glu
 65                  70                  75                  80
Trp Phe Pro Ser Tyr Phe Ala Gly Arg Arg Leu Val Asn Phe Leu Met
                 85                  90                  95
Met Met Asp Glu Val His Leu Gln Leu Thr Lys Met Ile Lys Gly Ala
            100                 105                 110
Thr Pro Pro Arg Leu Ile Ala Lys Pro Val Ala Lys Asp Ala Ile Glu
            115                 120                 125
Met Glu Tyr Val Ser Lys Arg Lys Met Tyr Asp Tyr Phe Leu Gly Phe
130                 135                 140
Ile Glu Gly Ser Ser Lys Phe Phe Lys Glu Glu Ile Ser Val Glu Glu
145                 150                 155                 160
Val Glu Arg Gly Glu Lys Asp Gly Phe Ser Arg Leu Lys Val Arg Ile
                165                 170                 175
Lys Phe Lys Asn Pro Val Phe Glu Tyr Lys Lys Asn Leu Glu Gly Ser
            180                 185                 190
Gly Gly Tyr Ile Pro Glu Ala Pro Arg Asp Gly Gln Ala Tyr Val Arg
            195                 200                 205
Lys Asp Gly Glu Trp Val Leu Leu Ser Thr Phe Leu
210                 215                 220
```

<210> SEQ ID NO 9
<211> LENGTH: 1158
<212> TYPE: DNA
<213> ORGANISM: Artificial Sequence
<220> FEATURE:
<223> OTHER INFORMATION: Synthetic Construct

<400> SEQUENCE: 9

```
gcgcaacgca attaatgtaa gttagctcac tcattaggca ccccaggctt tacactttat    60
gcttccggct cgtataatgt gtggaattgt gagcggataa caatttcaca caggaaacag   120
gatcgatcca tcgatgagct tactccccat cccctgttg acaattaatc atcggctcgt    180
ataatgtgtg gaattgtgag cggataacaa tttcacacag gaaacaggat cagcttactc   240
cccatccccc tgttgacaat taatcatcgg ctcgtataat gtgtggaatt gtgagcggat   300
aacaatttca cacaggaaac aggatccatc gatgcttagg aggtcatatg aaggggacaa   360
tcgtcgggac atggataaag accctgaggg acctttacgg gaatgatgtg ttgatgaat   420
cttaaaaag tgtgggttgg gaaccagata gggtaattac acctctggag gatattgatg   480
acgatgaggt taggagaatt tttgctaagg tgagtgaaaa aactggtaaa aatgtcaacg   540
aaatatggag agaggtagga aggcagaaca taaaaacttt cagcgaatgg tttccctcct   600
attttgcagg gagaaggcta gtgaattttt aatgatgat ggatgaggta cacctacagc    660
ttaccaagat gataaaagga gccactcctc caaggcttat tgcaaagcct gttgcaaaag   720
atgccattga aatggagtac gtttctaaaa gaaagatgta cgattacttt ttaggctta    780
tagagggtag ttctaaattt ttcaaggaag aaatttcagt ggaagaggtc gaaagaggcg   840
aaaaagatgg cttttcaagg ctaaaagtca ggataaaatt taaaaccccc gtttttgagt   900
ataagaaaaa ctcgagggca gcggcggtta tattcctgaa gctccaagag atgggcaggc   960
```

```
ttacgttcgt aaagatggcg aatgggtatt actttctacc ttttaaggg gtagtcacca    1020 tcaccatcac cattgatcta gagtcgacct gcagcccaag cttatcgatg ataagctgtc    1080
aaacatgagc agatctgagc cgcctaatg agcgggcttt ttttcagat ctgcttgaag     1140 acgaaagggc ctcgtgat                                                  1158
```

<210> SEQ ID NO 10
<211> LENGTH: 231
<212> TYPE: PRT
<213> ORGANISM: Artificial Sequence
<220> FEATURE:
<223> OTHER INFORMATION: Synthetic Construct

<400> SEQUENCE: 10

```
Met Lys Gly Thr Ile Val Gly Thr Trp Ile Lys Thr Leu Arg Asp Leu
1               5                   10                  15

Tyr Gly Asn Asp Val Val Asp Glu Ser Leu Lys Ser Val Gly Trp Glu
                20                  25                  30

Pro Asp Arg Val Ile Thr Pro Leu Glu Asp Ile Asp Asp Glu Val
            35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn Leu Glu Gly Gly
            180                 185                 190

Ser Gly Gly Tyr Ile Pro Glu Ala Pro Arg Asp Gly Gln Ala Tyr Val
        195                 200                 205

Arg Lys Asp Gly Glu Glu Trp Val Leu Leu Ser Thr Phe Leu Arg Gly
    210                 215                 220

Ser His His His His His His
225                 230
```

<210> SEQ ID NO 11
<211> LENGTH: 669
<212> TYPE: DNA
<213> ORGANISM: Artificial Sequence
<220> FEATURE:
<223> OTHER INFORMATION: Synthetic Construct

<400> SEQUENCE: 11

```
atgaagggga caatcgtcgg gacatggata aagaccctga gggaccttta cgggaatgat    60
gtggttgatg aatctttaaa aagtgtgggt tggaaccag ataggggtaat tacacctctg    120 gaggatattg atgacgatga ggttaggaga attttttgcta aggtgagtga aaaaactggt    180
```

```
aaaaatgtca acgaaatatg gagagaggta ggaaggcaga acataaaaac tttcagcgaa    240
tggtttccct cctatttttgc agggagaagg ctagtgaatt ttttaatgat gatggatgag    300
gtacacctac agcttaccaa gatgataaaa ggagccactc ctccaaggct tattgcaaag    360
cctgttgcaa aagatgccat tgaaatggag tacgtttcta aaagaaagat gtacgattac    420 ttttttagggc ttatagaggg tagttctaaa tttttcaagg aagaaatttc agtggaagag    480
gtcgaaagag gcgaaaaaga tggcttttca aggctaaaag tcaggataaa atttaaaaac    540
cccgtttttg agtataagaa aaatctcgag ggcagcggcg ttatattcc tgaagctcca    600 agagatgggc aggcttacgt tcgtaaagat ggcgaatggg tattactttc tacctttta    660 aggggtagt                                                              669
```

```
<210> SEQ ID NO 12
<211> LENGTH: 222
<212> TYPE: PRT
<213> ORGANISM: Artificial Sequence
<220> FEATURE:
<223> OTHER INFORMATION: Synthetic Construct

<400> SEQUENCE: 12

Met Lys Gly Thr Ile Val Gly Thr Trp Ile Lys Thr Leu Arg Asp Leu
1               5                   10                  15

Tyr Gly Asn Asp Val Val Asp Glu Ser Leu Lys Ser Val Gly Trp Glu
            20                  25                  30

Pro Asp Arg Val Ile Thr Pro Leu Glu Asp Ile Asp Asp Glu Val
        35                  40                  45

Arg Arg Ile Phe Ala Lys Val Ser Glu Lys Thr Gly Lys Asn Val Asn
    50                  55                  60

Glu Ile Trp Arg Glu Val Gly Arg Gln Asn Ile Lys Thr Phe Ser Glu
65                  70                  75                  80

Trp Phe Pro Ser Tyr Phe Ala Gly Arg Arg Leu Val Asn Phe Leu Met
                85                  90                  95

Met Met Asp Glu Val His Leu Gln Leu Thr Lys Met Ile Lys Gly Ala
            100                 105                 110

Thr Pro Pro Arg Leu Ile Ala Lys Pro Val Ala Lys Asp Ala Ile Glu
        115                 120                 125

Met Glu Tyr Val Ser Lys Arg Lys Met Tyr Asp Tyr Phe Leu Gly Leu
    130                 135                 140

Ile Glu Gly Ser Ser Lys Phe Phe Lys Glu Glu Ile Ser Val Glu Glu
145                 150                 155                 160

Val Glu Arg Gly Glu Lys Asp Gly Phe Ser Arg Leu Lys Val Arg Ile
                165                 170                 175

Lys Phe Lys Asn Pro Val Phe Glu Tyr Lys Lys Asn Leu Glu Gly Gly
            180                 185                 190

Ser Gly Gly Tyr Ile Pro Glu Ala Pro Arg Asp Gly Gln Ala Tyr Val
        195                 200                 205

Arg Lys Asp Gly Glu Glu Trp Val Leu Leu Ser Thr Phe Leu
    210                 215                 220
```

```
<210> SEQ ID NO 13
<211> LENGTH: 564
<212> TYPE: DNA
<213> ORGANISM: Legionella pneumophilia

<400> SEQUENCE: 13
atgatgtcta tgaaaggaat cat

```
tcctacaccc tggtagatca aattattatg gatagtcatt tgaagtccca tggtgcctac    120
acgtctatcg gtacatactc tcccaaagaa ttatttcaat tggttaaagc gcttgctatg    180
aaaaatggca aaccaacatc agtgatttta caagaatatg gtgagtattt gtttgaggtt    240
tttgcaaaaa aatatcctca atttttcagg gaaaaaaagt cggtgtttca atttttggaa    300
gcgcttgaaa cacatattca tttcgaagtg aaaaaattgt atgactatac tgaactaccc    360
cattttgaat gccaatatca cagtcaaaat caaatggaaa tgatttacac ttcttcgcgt    420
cctttggccg attttgcgga aggtttaata aaaggttgta ttaaatatca taaagaaaac    480
atgactattg ttcgtgaaaa tctgcctgca aaaacaggct ttaaggtaag atttgtatta    540
acaaaaggcg atcctgatga gtga                                            564
```

```
<210> SEQ ID NO 14
<211> LENGTH: 187
<212> TYPE: PRT
<213> ORGANISM: Legionella pneumophilia

<400> SEQUENCE: 14

Met Met Ser Met Lys Gly Ile Ile Phe Asn Glu Phe Leu Asn Phe Val
1               5                   10                  15

Glu Lys Ser Glu Ser Tyr Thr Leu Val Asp Gln Ile Ile Met Asp Ser
            20                  25                  30

His Leu Lys Ser His Gly Ala Tyr Thr Ser Ile Gly Thr Tyr Ser Pro
        35                  40                  45

Lys Glu Leu Phe Gln Leu Val Lys Ala Leu Ala Met Lys Asn Gly Lys
    50                  55                  60

Pro Thr Ser Val Ile Leu Gln Glu Tyr Gly Glu Tyr Leu Phe Glu Val
65                  70                  75                  80

Phe Ala Lys Lys Tyr Pro Gln Phe Phe Arg Glu Lys Lys Ser Val Phe
                85                  90                  95

Gln Phe Leu Glu Ala Leu Glu Thr His Ile His Phe Glu Val Lys Lys
            100                 105                 110

Leu Tyr Asp Tyr Thr Glu Leu Pro His Phe Glu Cys Gln Tyr His Ser
        115                 120                 125

Gln Asn Gln Met Glu Met Ile Tyr Thr Ser Ser Arg Pro Leu Ala Asp
    130                 135                 140

Phe Ala Glu Gly Leu Ile Lys Gly Cys Ile Lys Tyr His Lys Glu Asn
145                 150                 155                 160

Met Thr Ile Val Arg Glu Asn Leu Pro Ala Lys Thr Gly Phe Lys Val
                165                 170                 175

Arg Phe Val Leu Thr Lys Gly Asp Pro Asp Glu
            180                 185
```

```
<210> SEQ ID NO 15
<211> LENGTH: 543
<212> TYPE: DNA
<213> ORGANISM: Legionella pneumophilia

<400> SEQUENCE: 15
atgaaaggta tcgtttttac ctccttaaat gacatgatta tagaacaatt tggcatagaa     60
acctgggacc aactcgtatc ctcactagac cttccaagtg gtggaagtta tacagcaggc    120
ggcacttact cggatacaga atttcagcaa ttgattaagg ccattgcgaa gaggaccaat    180
cagcacgctt ctgttttttt agaggccttt ggtgaataca tgtttcctat cttatcgagt    240
```
aagtgcgcaa ttttttaaa aaaggacatg acattaaaag aatttttaaa aagcattgat 300
ggaacaattc atgtggaagt agaaaagtta tacccagatg aaacattacc taccattagc 360
tatgaagagc ctgctgcaaa ccaattggtt atggtgtatc gatcgcatag aagactctgt 420
cattttgcaa tggggctcat ccagggagca gcgcaacatt ttaaaaagaa aattaccatt 480
aagcagactc actgcatgtt aaaaaaagat gatcattgtc gtttggagat tacctttgag 540
tga 543

<210> SEQ ID NO 16
<211> LENGTH: 180
<212> TYPE: PRT
<213> ORGANISM: Legionella pneumophilia

<400> SEQUENCE: 16

Met Lys Gly Ile Val Phe Thr Ser Leu Asn Asp Met Ile Ile Glu Gln
1 5 10 15

Phe Gly Ile Glu Thr Trp Asp Gln Leu Val Ser Ser Leu Asp Leu Pro
20 25 30

Ser Gly Gly Ser Tyr Thr Ala Gly Gly Thr Tyr Ser Asp Thr Glu Phe
35 40 45

Gln Gln Leu Ile Lys Ala Ile Ala Lys Arg Thr Asn Gln His Ala Ser
50 55 60

Val Phe Leu Glu Ala Phe Gly Glu Tyr Met Phe Pro Ile Leu Ser Ser
65 70 75 80

Lys Cys Ala Ile Phe Leu Lys Lys Asp Met Thr Leu Lys Glu Phe Leu
85 90 95

Lys Ser Ile Asp Gly Thr Ile His Val Glu Val Glu Lys Leu Tyr Pro
100 105 110

Asp Glu Thr Leu Pro Thr Ile Ser Tyr Glu Glu Pro Ala Ala Asn Gln
115 120 125

Leu Val Met Val Tyr Arg Ser His Arg Arg Leu Cys His Phe Ala Met
130 135 140

Gly Leu Ile Gln Gly Ala Ala Gln His Phe Lys Lys Lys Ile Thr Ile
145 150 155 160

Lys Gln Thr His Cys Met Leu Lys Lys Asp Asp His Cys Arg Leu Glu
165 170 175

Ile Thr Phe Glu
180

<210> SEQ ID NO 17
<211> LENGTH: 1158
<212> TYPE: DNA
<213> ORGANISM: Homo sapiens

<400> SEQUENCE: 17
atgtacggat ttgtgaatca cgccctggag ttgctggtga tccgcaatta cggccccgag 60
gtgtgggaag acatcaaaaa agaggcacag ttagatgaag aaggacagtt tcttgtcaga 120
ataatatatg atgactccaa aacttatgat ttggttgctg ctgcaagcaa agtcctcaat 180
ctcaatgctg gagaaatcct ccaaatgttt gggaagatgt tttcgtcttt ttgccaagaa 240
tctggttatg atacaatctt gcgtgtcctg ggctctaatg tcagagaatt tctacagaac 300
cttgatgctc tgcacgacca ccttgctacc atctacccag gaatgcgtgc accttccttt 360
aggtgcactg atgcagaaaa gggcaaagga ctcattttgc actactactc agagagagaa 420
ggacttcagg atattgtcat tggaatcatc aaaacagtgg cacaacaaat ccatggcact 480

```
gaaatagaca tgaaggttat tcagcaaaga aatgaagaat gtgatcatac tcaattttta      540
attgaagaaa aagagtcaaa agaagaggat ttttatgaag atcttgacag atttgaagaa      600
aatggtaccc aggaatcacg catcagccca tatacattct gcaaagcttt tcctttcat      660 ataatatttg accgggacct agtggtcact cagtgtggca atgctatata cagagttctc      720
ccccagctcc agcctgggaa ttgcagcctt ctgtctgtct tctcgctggt tcgtcctcat      780
attgatatta gtttccatgg gatcctttct cacatcaata ctgtttttgt attgagaagc      840
aaggaaggat tgttggatgt ggagaaatta gaatgtgagg atgaactgac tgggactgag      900
atcagctgct tacgtctcaa gggtcaaatg atctacttac ctgaagcaga tagcatactt      960
tttctatgtt caccaagtgt catgaacctg gacgatttga caaggagagg gctgtatcta     1020
agtgacatcc ctctgcatga tgccacgcgc gatcttgttc ttttgggaga acaatttaga     1080
gaggaataca aactcaccca agaactggaa atcctcactg acaggctaca gctcacgtta     1140
agagccctgg aagattga                                                   1158
```

<210> SEQ ID NO 18
<211> LENGTH: 385
<212> TYPE: PRT
<213> ORGANISM: Homo sapiens

<400> SEQUENCE: 18

```
Met Tyr Gly Phe Val Asn His Ala Leu Glu Leu Leu Val Ile Arg Asn
1               5                   10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Asp Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Lys Cys Ser Leu Leu Ser Val Phe Ser Leu
```

```
                    245                 250                 255
Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Ala Glu Ile Ser Cys Leu
    290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380

Asp
385

<210> SEQ ID NO 19
<211> LENGTH: 651
<212> TYPE: DNA
<213> ORGANISM: Homo sapiens

<400> SEQUENCE: 19
atgtatggat tcatcaacac ctgcctgcag tctcttgtga cagagaaatt tggtgaggag      60
acatgggaga agctgaaggc tcctgcagaa gtgcaagatg tcttcatgac ctacaccgtg     120
tatgatgaca tcatcaccat taagctcatc caagaagcct gcaaggttct ggatgtgtcc     180
atggaagcca ttctgaagct ctttggcgaa tacttcttta gttctgtaa gatgtctggc      240 tatgacagga tgctgcggac acttggagga aatctcaccg agtttattga aaacctagat     300
gcactccaca gttacctggc actgtcctat caggaaatga acgcaccatc ctttcgagtg     360
gaggaaggag ctgacggggc gatgcttctc cactactact cagacagaca tggtctgtgt     420
cacattgtac caggtatcat tgaagctgtg gccaaggact tctttgacac tgatgtggcc     480
atgagtatcc tggatatgaa cgaagaggtg gaaaggacag gaagaaaga acatgttgtg      540 tttctggtcg tgcagaaggc tcacagacag ataagaggag caaaggcaag ccggccacaa     600
ggcagtgagg acagccaggc agaccaggag gctctccagg gaacactcct t              651

<210> SEQ ID NO 20
<211> LENGTH: 217
<212> TYPE: PRT
<213> ORGANISM: Homo sapiens

<400> SEQUENCE: 20

Met Tyr Gly Phe Ile Asn Thr Cys Leu Gln Ser Leu Val Thr Glu Lys
1               5                   10                  15

Phe Gly Glu Glu Thr Trp Glu Lys Leu Lys Ala Pro Ala Glu Val Gln
            20                  25                  30

Asp Val Phe Met Thr Tyr Thr Val Tyr Asp Asp Ile Ile Thr Ile Lys
        35                  40                  45

Leu Ile Gln Glu Ala Cys Lys Val Leu Asp Val Ser Met Glu Ala Ile
    50                  55                  60
```

| | | | | | | | | | | | | | | | |
|---|---|---|---|---|---|---|---|---|---|---|---|---|---|---|---|
|Leu|Lys|Leu|Phe|Gly|Glu|Tyr|Phe|Phe|Lys|Phe|Cys|Lys|Met|Ser|Gly|
|65| | | | |70| | | |75| | | | |80| |

| | | | | | | | | | | | | |
|---|---|---|---|---|---|---|---|---|---|---|---|---|
|Tyr|Asp|Arg|Met|Leu|Arg|Thr|Leu|Gly|Gly|Asn|Leu|Thr|Glu|Phe|Ile|
| | | | |85| | | | |90| | | | |95| |

Glu Asn Leu Asp Ala Leu His Ser Tyr Leu Ala Leu Ser Tyr Gln Glu
            100                 105                 110

Met Asn Ala Pro Ser Phe Arg Val Glu Glu Gly Ala Asp Gly Ala Met
            115                 120                 125

Leu Leu His Tyr Tyr Ser Asp Arg His Gly Leu Cys His Ile Val Pro
            130                 135                 140

Gly Ile Ile Glu Ala Val Ala Lys Asp Phe Phe Asp Thr Asp Val Ala
145                 150                 155                 160

Met Ser Ile Leu Asp Met Asn Glu Glu Val Glu Arg Thr Gly Lys Lys
            165                 170                 175

Glu His Val Val Phe Leu Val Val Gln Lys Ala His Arg Gln Ile Arg
            180                 185                 190

Gly Ala Lys Ala Ser Arg Pro Gln Gly Ser Glu Asp Ser Gln Ala Asp
            195                 200                 205

Gln Glu Ala Leu Gln Gly Thr Leu Leu
            210                 215

<210> SEQ ID NO 21
<211> LENGTH: 1158
<212> TYPE: DNA
<213> ORGANISM: Rattus norvegicus

<400> SEQUENCE: 21

```
atgtacggtt ttgtgaacca tgccctggag ctgctggtga tccgcaatta cggtcccgag    60
gtgtgggaag acatcaaaaa agaggcgcag ctggatgaag aaggccagtt tcttgtgaga   120
ataatctacg atgattccaa acctatgact tggtggctg ctgcgagcaa agtcctcaac    180
ctcaatgctg gtgaaatcct gcagatgttt gggaagatgt ttttcgtctt ctgtcaagag   240
tctggctatg ataccatctt gcgtgtcctg ggatctaatg tcagggagtt tttgcagaac   300
ctcgacgccc tgcacgacca cctcgccacc atctacccag ggatgcgcgc accttccttc   360
cggtgcaccg atgcagaaaa aggcaaaggg ctcattctgc actactactc ggaaagagag   420
gggcttcagg acattgtgat cgggattatc aagactgtag ctcaacagat ccatggcact   480
gagatagaca tgaaggttat tcagcaaaga agtgaagaat gtgatcatac ccaattttta   540
attgaagaaa aagaatcaaa agaagaggat tttatgaag atctggacag gtttgaagag   600
aacggtaccc aggactcccg tatcagcccg tacaccttct gcaaagcgtt tccttttcac   660
atcatatttg accgggacct agtagtcacg cagtgtggaa atgctatcta cagagtgctc   720
ccccagctcc agcctgggaa gtgcagcctt ctgtctgtct tctctctggt ccgccctcat   780
attgacatca gtttccacgg gattctttca cacatcaata ccgtctttgt actgagaagc   840
aaggaagggt tgctggatgt tgagaaactt gaatgtgagg atgaactgac tggggcagag   900
attagctgcc tccgtctcaa aggccaaatg atctatttac cggaagcaga tagcatcctc   960
ttcctctgtt caccaagtgt gatgaacttg atgacctaa caagaagagg cctgtacctg  1020
agtgacatcc ctctccatga tgctacacga gacctggtcc ttttgggaga acagttccgg  1080
gaggagtaca aactgacaca agagctggaa atcctcacag acaggctgca gctcacactg  1140
agggctttgg aggattga                                                1158
```

```
<210> SEQ ID NO 22
<211> LENGTH: 385
<212> TYPE: PRT
<213> ORGANISM: Rattus norvegicus

<400> SEQUENCE: 22

Met Tyr Gly Phe Val Asn His Ala Leu Glu Leu Leu Val Ile Arg Asn
1               5                   10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ser Lys Val Leu Asn Leu Asn Ala Gly
    50                  55                  60

Glu Ile Leu Gln Met Phe Gly Lys Met Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp Leu Ala Thr Ile Tyr
                100                 105                 110

Pro Gly Met Arg Ala Pro Ser Phe Arg Cys Thr Asp Ala Glu Lys Gly
                115                 120                 125

Lys Gly Leu Ile Leu His Tyr Tyr Ser Glu Arg Glu Gly Leu Gln Asp
            130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Ser Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Asp Arg Phe Glu Glu Asn Gly Thr Gln Asp Ser Arg Ile
        195                 200                 205

Ser Pro Tyr Thr Phe Cys Lys Ala Phe Pro Phe His Ile Ile Phe Asp
    210                 215                 220

Arg Asp Leu Val Val Thr Gln Cys Gly Asn Ala Ile Tyr Arg Val Leu
225                 230                 235                 240

Pro Gln Leu Gln Pro Gly Lys Cys Ser Leu Leu Ser Val Phe Ser Leu
                245                 250                 255

Val Arg Pro His Ile Asp Ile Ser Phe His Gly Ile Leu Ser His Ile
                260                 265                 270

Asn Thr Val Phe Val Leu Arg Ser Lys Glu Gly Leu Leu Asp Val Glu
            275                 280                 285

Lys Leu Glu Cys Glu Asp Glu Leu Thr Gly Ala Glu Ile Ser Cys Leu
        290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
    370                 375                 380
```

Asp
385

<210> SEQ ID NO 23
<211> LENGTH: 2229
<212> TYPE: DNA
<213> ORGANISM: Rattus norvegicus

<400> SEQUENCE: 23

| | | | | | |
|---|---|---|---|---|---|
| atgtatggat | tcatcaacac | ctgcctgcag | tctcttgtga | cagagaaatt | tggtgaggag | 60 |
| acatgggaga | agctgaaggc | tcctgcagaa | gtgcaagatg | tcttcatgac | ctacaccgtg | 120 |
| tatgatgaca | tcatcaccat | taagctcatc | caagaagcct | gcaaggttct | ggatgtgtcc | 180 |
| atggaagcca | ttctgaagct | ctttggcgaa | tacttcttta | agttctgtaa | gatgtctggc | 240 |
| tatgacagga | tgctgcggac | acttggagga | aatctcaccg | agtttattga | aaacctagat | 300 |
| gcactccaca | gttacctggc | actgtcctat | caggaaatga | acgcaccatc | ctttcgagtg | 360 |
| gaggaaggag | ctgacggggc | gatgcttctc | cactactact | cagacagaca | tggtctgtgt | 420 |
| cacattgtac | caggtatcat | tgaagctgtg | gccaaggact | tctttgacac | tgatgtggcc | 480 |
| atgagtatcc | tggatatgaa | cgaagaggtg | gaaaggacag | ggaagaaaga | acatgttgtg | 540 |
| tttctggtcg | tgcagaaggc | tcacagacag | ataagaggag | caaaggcaag | ccggccacaa | 600 |
| ggcagtgagg | acagccaggc | agaccaggag | gctctccagg | gaacactcct | tcggatgaag | 660 |
| gagagatatt | taaacatccc | tgtttgccct | ggggagaaat | ctcactcaac | tgctgtgagg | 720 |
| gcatcggtcc | tttttggaaa | agggcccctc | agggacacct | tccagcccgt | ctatcctgag | 780 |
| agactatggg | tcgaagagga | ggtgttctgt | gatgcttttc | ctttccacat | tgtctttgat | 840 |
| gaagcactaa | gggtcaagca | agctggagtg | aatattcaga | agtatgtccc | tggaatctta | 900 |
| acccagaagt | ttgcactaga | tgagtatttt | tccatcatcc | accctcaagt | tactttcaac | 960 |
| atctccagca | tctgcaagtt | cattaacagt | cagtttgtct | tgaagacaag | aaaagaaatg | 1020 |
| atgcccaaag | caaggaagag | ccagccgatg | ctcaaactcc | ggggtcagat | gatctggatg | 1080 |
| gagtctctga | ggtgcatgat | cttcatgtgt | tccccaaacg | tccgcagcct | gcaagagctg | 1140 |
| gaagagagca | agatgcatct | ttctgatatc | gctccgcacg | acacgaccag | ggatctcatc | 1200 |
| ctcctcaacc | agcagaggct | ggcagagatg | gagctgtcct | gccaactgga | aaagaagaag | 1260 |
| gaggagttgc | gtgtcctttc | caatcacctg | gccatcgaga | agaagaagac | agagaccttg | 1320 |
| ctgtatgcca | tgctgcctga | acatgtggcc | aaccaactca | aggagggcag | aaaggtggct | 1380 |
| gcaggagaat | ttgaaacatg | tacaatcctt | ttcagcgatg | ttgtgacatt | taccaacatc | 1440 |
| tgtgcagcct | gtgaacctat | ccaaatcgtg | aacatgctga | attcaatgta | ctccaagttt | 1500 |
| gacaggttaa | ccagtgtcca | tgatgtctac | aaagtagaaa | caatagggga | tgcttacatg | 1560 |
| gtggtgggtg | gagtaccagt | acccgttgaa | agccatgctc | aaagagtcgc | caattttgct | 1620 |
| ctggggatga | gaatttctgc | aaaagaagtg | atgaatcctg | tcactgggga | acctatccag | 1680 |
| atcagagtgg | gaatccacac | tggaccagtc | ttagcaggtg | ttgtgggaga | caagatgcct | 1740 |
| cggtactgct | tgtttggtga | cactgtaaac | acagcctcta | ggatggaaag | tcacgggctt | 1800 |
| cccagcaaag | tgcatctgag | ccccacagcc | cacagagccc | tgaaaacaa | agggtttgaa | 1860 |
| attgtcagga | gaggcgagat | cgaagtgaag | gggaaaggaa | agatgaccac | atactttctg | 1920 |
| atccagaacc | tgaatgccac | cgaggatgag | ataatgggc | gaccttcagc | ccccgctgat | 1980 |
| gggaaggaag | tatgtactcc | cggaaaccaa | gtcaggaagt | cccctgctgt | cccgaggaac | 2040 |

```
acagaccatc agcaacaagt ctacaaagga gacccagcag acgcttctaa tgaagtcaca    2100
cttgctggga gcccagtggc agggcgaaac tccacagatg cagtcaataa ccagccatca    2160
ccagatgaga ccaagacaag tgtcgttgct agtggccctg tgctgtctgc tttctgtgtt    2220
gtgctgtga                                                           2229
```

<210> SEQ ID NO 24
<211> LENGTH: 742
<212> TYPE: PRT
<213> ORGANISM: Rattus norvegicus

<400> SEQUENCE: 24

```
Met Tyr Gly Phe Ile Asn Thr Cys Leu Gln Ser Leu Val Thr Glu Lys
1               5                   10                  15

Phe Gly Glu Thr Trp Glu Lys Leu Lys Ala Pro Ala Glu Val Gln
            20                  25                  30

Asp Val Phe Met Thr Tyr Thr Val Tyr Asp Asp Ile Ile Thr Ile Lys
            35                  40                  45

Leu Ile Gln Glu Ala Cys Lys Val Leu Asp Val Ser Met Glu Ala Ile
    50                  55                  60

Leu Lys Leu Phe Gly Glu Tyr Phe Phe Lys Phe Cys Lys Met Ser Gly
65                  70                  75                  80

Tyr Asp Arg Met Leu Arg Thr Leu Gly Gly Asn Leu Thr Glu Phe Ile
                85                  90                  95

Glu Asn Leu Asp Ala Leu His Ser Tyr Leu Ala Leu Ser Tyr Gln Glu
            100                 105                 110

Met Asn Ala Pro Ser Phe Arg Val Glu Glu Gly Ala Asp Gly Ala Met
        115                 120                 125

Leu Leu His Tyr Tyr Ser Asp Arg His Gly Leu Cys His Ile Val Pro
    130                 135                 140

Gly Ile Ile Glu Ala Val Ala Lys Asp Phe Phe Asp Thr Asp Val Ala
145                 150                 155                 160

Met Ser Ile Leu Asp Met Asn Glu Glu Val Glu Arg Thr Gly Lys Lys
                165                 170                 175

Glu His Val Val Phe Leu Val Val Gln Lys Ala His Arg Gln Ile Arg
            180                 185                 190

Gly Ala Lys Ala Ser Arg Pro Gln Gly Ser Glu Asp Ser Gln Ala Asp
        195                 200                 205

Gln Glu Ala Leu Gln Gly Thr Leu Leu Arg Met Lys Glu Arg Tyr Leu
    210                 215                 220

Asn Ile Pro Val Cys Pro Gly Glu Lys Ser His Ser Thr Ala Val Arg
225                 230                 235                 240

Ala Ser Val Leu Phe Gly Lys Gly Pro Leu Arg Asp Thr Phe Gln Pro
                245                 250                 255

Val Tyr Pro Glu Arg Leu Trp Val Glu Glu Val Phe Cys Asp Ala
            260                 265                 270

Phe Pro Phe His Ile Val Phe Asp Glu Ala Leu Arg Val Lys Gln Ala
        275                 280                 285

Gly Val Asn Ile Gln Lys Tyr Val Pro Gly Ile Leu Thr Gln Lys Phe
    290                 295                 300

Ala Leu Asp Glu Tyr Phe Ser Ile Ile His Pro Gln Val Thr Phe Asn
305                 310                 315                 320

Ile Ser Ser Ile Cys Lys Phe Ile Asn Ser Gln Phe Val Leu Lys Thr
                325                 330                 335
```

```
Arg Lys Glu Met Met Pro Lys Ala Arg Lys Ser Gln Pro Met Leu Lys
            340                 345                 350

Leu Arg Gly Gln Met Ile Trp Met Glu Ser Leu Arg Cys Met Ile Phe
        355                 360                 365

Met Cys Ser Pro Asn Val Arg Ser Leu Gln Glu Leu Glu Glu Ser Lys
    370                 375                 380

Met His Leu Ser Asp Ile Ala Pro His Asp Thr Thr Arg Asp Leu Ile
385                 390                 395                 400

Leu Leu Asn Gln Gln Arg Leu Ala Glu Met Glu Leu Ser Cys Gln Leu
                405                 410                 415

Glu Lys Lys Lys Glu Glu Leu Arg Val Leu Ser Asn His Leu Ala Ile
            420                 425                 430

Glu Lys Lys Lys Thr Glu Thr Leu Leu Tyr Ala Met Leu Pro Glu His
            435                 440                 445

Val Ala Asn Gln Leu Lys Glu Gly Arg Lys Val Ala Ala Gly Glu Phe
        450                 455                 460

Glu Thr Cys Thr Ile Leu Phe Ser Asp Val Val Thr Phe Thr Asn Ile
465                 470                 475                 480

Cys Ala Ala Cys Glu Pro Ile Gln Ile Val Asn Met Leu Asn Ser Met
                485                 490                 495

Tyr Ser Lys Phe Asp Arg Leu Thr Ser Val His Asp Val Tyr Lys Val
            500                 505                 510

Glu Thr Ile Gly Asp Ala Tyr Met Val Val Gly Val Pro Val Pro
        515                 520                 525

Val Glu Ser His Ala Gln Arg Val Ala Asn Phe Ala Leu Gly Met Arg
        530                 535                 540

Ile Ser Ala Lys Glu Val Met Asn Pro Val Thr Gly Glu Pro Ile Gln
545                 550                 555                 560

Ile Arg Val Gly Ile His Thr Gly Pro Val Leu Ala Gly Val Val Gly
                565                 570                 575

Asp Lys Met Pro Arg Tyr Cys Leu Phe Gly Asp Thr Val Asn Thr Ala
            580                 585                 590

Ser Arg Met Glu Ser His Gly Leu Pro Ser Lys Val His Leu Ser Pro
        595                 600                 605

Thr Ala His Arg Ala Leu Lys Asn Lys Gly Phe Glu Ile Val Arg Arg
    610                 615                 620

Gly Glu Ile Glu Val Lys Gly Lys Gly Lys Met Thr Thr Tyr Phe Leu
625                 630                 635                 640

Ile Gln Asn Leu Asn Ala Thr Glu Asp Glu Ile Met Gly Arg Pro Ser
                645                 650                 655

Ala Pro Ala Asp Gly Lys Glu Val Cys Thr Pro Gly Asn Gln Val Arg
            660                 665                 670

Lys Ser Pro Ala Val Pro Arg Asn Thr Asp His Gln Gln Val Tyr
        675                 680                 685

Lys Gly Asp Pro Ala Asp Ala Ser Asn Glu Val Thr Leu Ala Gly Ser
        690                 695                 700

Pro Val Ala Gly Arg Asn Ser Thr Asp Ala Val Asn Asn Gln Pro Ser
705                 710                 715                 720

Pro Asp Glu Thr Lys Thr Ser Val Val Ala Ser Gly Pro Val Leu Ser
            725                 730                 735

Ala Phe Cys Val Val Leu
            740
```

<210> SEQ ID NO 25
<211> LENGTH: 1254
<212> TYPE: DNA
<213> ORGANISM: Artificial Sequence
<220> FEATURE:
<223> OTHER INFORMATION: Synthetic Construct

<400> SEQUENCE: 25

```
atgtacggat tcgtgaatca cgcgctggag ctgctggtga tccgcaacta cggccccgag      60
gtgtgggaag acatcaaaaa agaggcacag ttagatgaag aaggacaatt tcttgtcaga     120
ataatatatg atgattccaa aacttatgat ttggtggctg ctgcaagcaa agtcctcaat     180
ctcaatgctg gggaaatcct ccaaatgttc gggaagatgt tttttgtctt ttgccaagag     240
tctggttatg atacaatctt gcgtgtcctg ggatctaatg tcagagaatt tctacagaac     300
cttgatgctc tacatgatca ccttgctacc atctacccag gcatgcgtgc tccttcgttt     360
aggtgcacgg atgcagaaaa gggcaaagga ctcattctgc actactactc cgagagagag     420
ggacttcagg atattgtcat cggaatcatc aaaactgttg ctcaacaaat acatggcacc     480
gaaatagaca tgaaggttat tcagcaaaga atgaagaat gtgatcatac tcaatttcta     540
attgaggaaa aagagtcaaa agaagaagat ttttatgaag atcttgatag atttgaagaa     600
aatggtaccc aggaatcacg catcagccca tataccttct gcaaagcttt tccttttcac     660
ataatatttg accgggacct agtggttact cagtgtggca acgccatata cagagtgctt     720
ccccagctcc agcctgggaa ctgcagccta ttgtctgtct tctctctcgt ccgtcctcat     780
atcgacatta gtttccatgg gatcctttca cacatcaata cggttttcgt attgagaagc     840
aaggaaggat tgttggacgt agagaaattg gaatgtgagg atgagctgac tggaactgag     900
atcagctgct acgtctcaa gggtcagatg atctacttac tgaagcaga tagcatcctt     960
tttctgtgtt caccaagtgt gatgaatctg gatgatctga caaggagagg tctgtatctg    1020
agcgacatcc ccctgcacga tgccacgcgt gacctcgttc ttttgggaga gcaattcaga    1080
gaggaataca aactgactca gaactggaa atcctcacag accggctgca gctcacgtta    1140
agagccttgg aagatctcga gggcagcggc ggttatattc ctgaagctcc aagagatggg    1200
caggcttacg ttcgtaaaga tggcgaatgg gtattacttt ctacctttt atga          1254
```

<210> SEQ ID NO 26
<211> LENGTH: 417
<212> TYPE: PRT
<213> ORGANISM: Artificial Sequence
<220> FEATURE:
<223> OTHER INFORMATION: Synthetic Construct

<400> SEQUENCE: 26

Met Tyr Gly Phe Val Asn His Ala Leu Glu Leu Leu Val Ile Arg Asn
1               5                   10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

```
Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Gly Asp Phe Tyr
            180                 185                 190

Glu Asp Leu Asp Arg Phe Glu Glu Asn Gly Thr Gln Glu Ser Arg Ile
        195                 200                 205

Ser Pro Tyr Thr Phe Cys Lys Ala Phe Pro Phe His Ile Ile Phe Asp
210                 215                 220

Arg Asp Leu Val Val Thr Gln Cys Gly Asn Ala Ile Tyr Arg Val Leu
225                 230                 235                 240

Pro Gln Leu Gln Pro Gly Asn Cys Ser Leu Leu Ser Val Phe Ser Leu
                245                 250                 255

Val Arg Pro His Ile Asp Ile Ser Phe His Gly Ile Leu Ser His Ile
            260                 265                 270

Asn Thr Val Phe Val Leu Arg Ser Lys Glu Gly Leu Leu Asp Val Glu
        275                 280                 285

Lys Leu Glu Cys Glu Asp Glu Leu Thr Gly Thr Glu Ile Ser Cys Leu
290                 295                 300

Arg Leu Lys Gly Gln Met Ile Tyr Leu Pro Glu Ala Asp Ser Ile Leu
305                 310                 315                 320

Phe Leu Cys Ser Pro Ser Val Met Asn Leu Asp Asp Leu Thr Arg Arg
                325                 330                 335

Gly Leu Tyr Leu Ser Asp Ile Pro Leu His Asp Ala Thr Arg Asp Leu
            340                 345                 350

Val Leu Leu Gly Glu Gln Phe Arg Glu Glu Tyr Lys Leu Thr Gln Glu
        355                 360                 365

Leu Glu Ile Leu Thr Asp Arg Leu Gln Leu Thr Leu Arg Ala Leu Glu
370                 375                 380

Asp Leu Glu Gly Ser Gly Gly Tyr Ile Pro Glu Ala Pro Arg Asp Gly
385                 390                 395                 400

Gln Ala Tyr Val Arg Lys Asp Gly Glu Trp Val Leu Leu Ser Thr Phe
                405                 410                 415

Leu

<210> SEQ ID NO 27
<211> LENGTH: 681
<212> TYPE: DNA
<213> ORGANISM: Artificial Sequence
<220> FEATURE:
<223> OTHER INFORMATION: Synthetic Construct

<400> SEQUENCE: 27
atgtacggat tcgtgaatca cgcgctggag ctgctggtga tccgcaacta cggccccgag      60
gtgtgggaag acatcaaaaa agaggcacag ttagatgaag aaggacaatt tcttgtcaga     120
ataatatatg atgattccaa aacttatgat tggtggctg ctgcaagcaa agtcctcaat      180
ctcaatgctg gggaaatcct ccaaatgttc gggaagatgt tttttgtctt ttgccaagag    240
```

```
tctggttatg atacaatctt gcgtgtcctg ggatctaatg tcagagaatt tctacagaac    300
cttgatgctc tacatgatca ccttgctacc atctacccag gcatgcgtgc tccttcgttt    360
aggtgcacgg atgcagaaaa gggcaaagga ctcattctgc actactactc cgagagagag    420
ggacttcagg atattgtcat cggaatcatc aaaactgttg ctcaacaaat acatggcacc    480
gaaatagaca tgaaggttat tcagcaaaga aatgaagaat gtgatcatac tcaatttcta    540
attgaggaaa agagtcaaa agaagaagat ttttatgaag atctcgaggg cagcggcggt    600
tatattcctg aagctccaag agatgggcag gcttacgttc gtaaagatgg cgaatgggta    660
ttactttcta ccttttatg a                                              681
```

<210> SEQ ID NO 28
<211> LENGTH: 226
<212> TYPE: PRT
<213> ORGANISM: Artificial Sequence
<220> FEATURE:
<223> OTHER INFORMATION: Synthetic Construct
<400> SEQUENCE: 28

```
Met Tyr Gly Phe Val Asn His Ala Leu Glu Leu Leu Val Ile Arg Asn
1               5                   10                  15

Tyr Gly Pro Glu Val Trp Glu Asp Ile Lys Lys Glu Ala Gln Leu Asp
            20                  25                  30

Glu Glu Gly Gln Phe Leu Val Arg Ile Ile Tyr Asp Asp Ser Lys Thr
        35                  40                  45

Tyr Asp Leu Val Ala Ala Ser Lys Val Leu Asn Leu Asn Ala Gly
    50                  55                  60

Glu Ile Leu Gln Met Phe Gly Lys Met Phe Phe Val Phe Cys Gln Glu
65                  70                  75                  80

Ser Gly Tyr Asp Thr Ile Leu Arg Val Leu Gly Ser Asn Val Arg Glu
                85                  90                  95

Phe Leu Gln Asn Leu Asp Ala Leu His Asp His Leu Ala Thr Ile Tyr
            100                 105                 110

Pro Gly Met Arg Ala Pro Ser Phe Arg Cys Thr Asp Ala Glu Lys Gly
        115                 120                 125

Lys Gly Leu Ile Leu His Tyr Tyr Ser Glu Arg Glu Gly Leu Gln Asp
    130                 135                 140

Ile Val Ile Gly Ile Ile Lys Thr Val Ala Gln Gln Ile His Gly Thr
145                 150                 155                 160

Glu Ile Asp Met Lys Val Ile Gln Gln Arg Asn Glu Glu Cys Asp His
                165                 170                 175

Thr Gln Phe Leu Ile Glu Glu Lys Glu Ser Lys Glu Glu Asp Phe Tyr
            180                 185                 190

Glu Asp Leu Glu Gly Ser Gly Gly Tyr Ile Pro Glu Ala Pro Arg Asp
        195                 200                 205

Gly Gln Ala Tyr Val Arg Lys Asp Gly Glu Trp Val Leu Leu Ser Thr
    210                 215                 220

Phe Leu
225
```

POLYMERIC FORMS OF H-NOX PROTEINS

CROSS-REFERENCE TO RELATED APPLICATIONS

This application is a divisional of U.S. patent application Ser. No. 16/450,913, filed Jun. 24, 2019, which is a continuation of U.S. patent application Ser. No. 14/759,635, now U.S. Pat. No. 10,385,116, which is a U.S. National Stage of International Patent Application No. PCT/US2013/020602, filed on Jan. 7, 2013. U.S. patent application Ser. No. 16/450,913 and U.S. patent application Ser. No. 14/759,635 are incorporated by reference herein in their entireties for all purposes.

STATEMENT REGARDING FEDERALLY SPONSORED RESEARCH OR DEVELOPMENT

This invention was made with government support under Grant No. 2 R44 CA138006-02 awarded by National Institutes of Health. The government has certain rights in the invention.

SEQUENCE LISTING

This application incorporates by reference a Sequence Listing submitted with this application as an ASCII text file entitled "14521-032-999_SEQ_LISTING.txt", created on Jul. 13, 2020 and having a size of 49,442 bytes.

TECHNICAL FIELD

This application pertains to polymeric H-NOX proteins and methods of using them to deliver oxygen. Polymeric H-NOX proteins provide a new therapeutic tool for delivering $O_2$ to humans and, for veterinary purposes, to animals.

BACKGROUND OF THE INVENTION

H-NOX proteins (named for Heme-Nitric oxide and OXygen binding domain) are members of a highly-conserved, well-characterized family of hemoproteins (Iyer, L M et al. (2003) *BMC Genomics* 4(1):5; Karow, D S et al. (2004) *Biochemistry* 43(31):10203-10211; Boon, E M et al. (2005) *Nature Chem. Biol.* 1:53-59; Boon, E M et al. (2005) *Curr. Opin. Chem. Biol.* 9(5):441-446; Boon, E M et al. (2005) *J. Inorg. Biochem.* 99(4):892-902; Cary, S P et al. (2005) *Proc Natl Acad Sci USA* 102(37):13064-9; Karow D S et al. (2005) *Biochemistry* 44(49):16266-74; Cary, S P et al. (2006) *Trends Biochem Sci* 31(4):231-9; Boon, E M et al. (2006) *J Biol Chem* 281(31):21892-902; Winger, J A et al. (2007) *J Biol Chem.* 282(2):897-907). H-NOX proteins are nitric-oxide-neutral, unlike previous hemoglobin-based oxygen carriers, H-NOX do not scavenge circulating nitric oxide, and thus are not associated with hypertensive or renal side effects. The intrinsic low NO reactivity (and high NO stability) makes wild-type and mutant H-NOX proteins desirable blood substitutes because of the lower probability of inactivation of H-NOX proteins by endogenous NO and the lower probability of scavenging of endogenous NO by H-NOX proteins. Importantly, the presence of a distal pocket tyrosine in some H-NOX proteins (Pellicena, P. et al. (2004) *Proc Natl. Acad Sci USA* 101(35):12854-12859) is suggestive of undesirable, high NO reactivity, contraindicating use as a blood substitute. For example, by analogy, a *Mycobacterium tuberculosis* hemoglobin protein, with a structurally analogous distal pocket tyrosine, reacts extremely rapidly with NO, and is used by the *Mycobacterium* to effectively scavenge and avoid defensive NO produced by an infected host (Ouellet, H. et al. (2002) *Proc. Natl. Acad. Sci. USA* 99(9):5902-5907). However, it was surprisingly discovered that H-NOX proteins actually have a much lower NO reactivity than that of hemoglobin making their use as blood substitutes possible.

It was discovered that H-NOX proteins that bind NO but not $O_2$ can be converted to H-NOX proteins that bind both NO and $O_2$ by the introduction of a single amino acid mutation (see WO 2007/139791 and WO 2007/139767). Thus, the affinity of H-NOX proteins for $O_2$ and NO and the ability of H-NOX proteins to discriminate between $O_2$ and NO ligands can be altered by the introduction of one or more amino acid mutations, allowing H-NOX proteins to be tailored to bind $O_2$ or NO with desired affinities. Additional mutations can be introduced to further alter the affinity for $O_2$ and/or NO. The H-NOX protein family can therefore be manipulated to exhibit improved or optimal kinetic and thermodynamic properties for $O_2$ delivery. For example, mutant H-NOX proteins have been generated with altered dissociation constants and/or off rates for $O_2$ binding that improve the usefulness of H-NOX proteins for a variety of clinical and industrial applications. The ability to tune H-NOX proteins to bind and deliver $O_2$ is a therapeutic avenue that addresses and overcomes the central shortcomings of current $O_2$ carriers.

H-NOX proteins are relatively small in size and may be filtered through the kidneys resulting in a short circulation half-life. What is needed for certain therapeutic uses is an H-NOX with a longer circulation half-life that can bind and deliver $O_2$ and/or NO to distal tissues for sufficient periods of time. Provided herein are polymeric H-NOX proteins with a longer circulation half-life. Additionally, H-NOX proteins extravasate into tumors where they accumulate at different rates. Polymeric H-NOX proteins are tuned to transport oxygen through normoxic regions of tumors and release oxygen deep within hypoxic zones within tumors. This combination of features represents a significant advance in the use of oxygen carriers as modifiers of the hypoxic niches of tumors to increase the efficacy of radiotherapy, chemotherapy and other anti-cancer treatments reliant on oxygenation of tumor cells.

All references cited herein, including patent applications and publications, are incorporated herein by reference in their entirety.

BRIEF SUMMARY OF THE INVENTION

In some aspects, the invention provides polymeric H-NOX protein comprising two or more H-NOX domains. In some embodiments, the two or more H-NOX domains are homologous H-NOX domains. In other embodiments, the H-NOX domains are heterologous H-NOX domains. In some embodiments, the polymeric H-NOX protein is a dimer, a trimer, a tetramer, or a pentamer. In some embodiments, the H-NOX domains are covalently linked.

In some embodiments of the invention, the polymeric H-NOX protein comprises monomers, wherein the monomers comprise an H-NOX domain and a polymerization domain. In some embodiments, the H-NOX domain is covalently linked to the polymerization domain. In some embodiments, the C-terminus of the H-NOX domain is covalently linked to the polymerization domain. In other embodiments, the N-terminus of the H-NOX domain is covalently linked to the polymerization domain. In some embodiments, monomers associate to form the polymeric H-NOX protein.

In some embodiments of the invention, the polymeric H-NOX protein is a trimeric H-NOX protein. In some embodiments, the trimeric H-NOX protein comprises one or more trimerization domains. In some embodiments, the trimeric H-NOX protein comprises three monomers, wherein the monomers comprise an H-NOX domain and a trimerization domain. In some embodiments, the trimerization domain is a bacteriophage T4 trimerization domain. In some embodiments, the trimerization domain is a foldon domain. In some embodiments, the foldon domain comprises the amino acid sequence of SEQ ID NO:4. In some embodiments, the H-NOX domain is covalently linked to the trimerization domain. In some embodiments, the C-terminus of the H-NOX domain is covalently linked to the N-terminus of the trimerization domain. In other embodiments, the N-termini of the H-NOX domains are covalently linked to the N-terminus of the trimerization domain.

In some embodiments of any of the above embodiments, the polymeric H-NOX protein does not comprise a guanylyl cyclase domain.

In some embodiments of the above embodiments, the polymeric H-NOX protein comprises at least one tag. In some embodiments, the polymeric H-NOX protein comprises at least one His$_6$ tag.

In some embodiments of any of the above embodiments, amino acid linkers are located between the H-NOX domain and/or the polymerization domain and/or the tag. In some embodiments, the amino acid linker is a Gly-Ser-Gly sequence of an Arg-Gly-Ser sequence.

In some embodiments of any of the above embodiments, at least one of the H-NOX domains is a *Thermoanaerobacter tengcongensis* H-NOX domain, a *L. pneumophilia* 2 H-NOX domain, a *Homo sapiens* β1 H-NOX domain, a *Canis lupus* H-NOX domain, a *Rattus norvegicus* β1 H-NOX domain, a *Drosophila melanogaster* β1 H-NOX domain, a *D. melanogaster* CG14885-PA H-NOX domain, a *Caenorhabdis elegans* GCY-35 H-NOX domain, a *Nostoc punctiforme* H-NOX domain, *Caulobacter crescentus* H-NOX domain, a *Shewanella oneidensis* H-NOX domain, or *Clostridium acetobutylicum* H-NOX domain. In some embodiments, the H-NOX domain corresponds to the H-NOX domain of *T. tengcongensis* set forth in SEQ ID NO:2.

In some embodiments of any of the above embodiments, at least one of the H-NOX domains comprises one or more distal pocket mutations. In some embodiments, the distal pocket mutation is an amino acid substitution at a site corresponding to L144 of *T. tengcongensis* H-NOX. In some embodiments, at least one of the H-NOX domains is a *T. tengcongensis* H-NOX domain and at least one of the *T. tengcongensis* H-NOX domains comprises an amino acid substitution at position 144. In some embodiments, the amino acid substitution at position 144 is an L144F substitution. In some embodiments, at least two of the H-NOX domains are *T. tengcongensis* H-NOX domains and at least two of the *T. tengcongensis* H-NOX domains comprises an amino acid substitution at position 144. In some embodiments, the amino acid substitution of at least one of the *T. tengcongensis* at position 144 is an L144F substitution. In some embodiments, at least one of the H-NOX domains comprises at least two distal pocket mutations. In some embodiments, the at least two distal pocket mutations are amino acid substitutions at sites corresponding to W9 and L144 of *T. tengcongensis* H-NOX. In some embodiments, at least one of the H-NOX domains is a *T. tengcongensis* H-NOX domain and at least one of the *T. tengcongensis* H-NOX domains comprises amino acid substitutions at positions 9 and 144. In some embodiments, the amino acid substitution at position 9 is a W9F substitution and the amino acid substitution at position 144 is an L144F substitution.

In some embodiments, the polymeric H-NOX protein comprises three wild type H-NOX domains of *T. tengcongensis*, each of the H-NOX domains is covalently linked at its C-terminus to the N-terminus of a T4 bacteriophage foldon domain by way of a Gly-Ser-Gly amino acid linker. In some embodiments, a His6 tag is linked to the C-terminus of the foldon domain via a Arg-Gly-Ser amino acid linker.

In some embodiments, the polymeric H-NOX protein comprises three L144F H-NOX domains of *T. tengcongensis*, each of the H-NOX domains is covalently linked at its C-terminus to the N-terminus of a T4 bacteriophage foldon domain by way of a Gly-Ser-Gly amino acid linker. In some embodiments, a His6 tag is linked to the C-terminus of the foldon domain via a Arg-Gly-Ser amino acid linker.

In some embodiments of any of the above embodiments, the $O_2$ dissociation constant of the polymeric H-NOX protein is within 2 orders of magnitude of that of hemoglobin, and wherein the NO reactivity of the H-NOX protein is at least 10-fold lower than that of hemoglobin. In some embodiments, the $O_2$ dissociation constant of the polymeric H-NOX protein is between about 1 nM and about 1000 nM at 20° C. In other embodiments, the $O^2$ dissociation constant of the polymeric H-NOX protein is between about 1 μM and about 10 μM at 20° C. In yet other embodiments, the $O_2$ dissociation constant of the H-NOX protein is between about 10 μM and about 50 μM at 20° C. In some embodiments, the NO reactivity of the polymeric H-NOX protein is less than about 700 $s^{-1}$ at 20° C. In some embodiments, the NO reactivity of the polymeric H-NOX protein is at least 100-fold lower than that of hemoglobin. In further embodiments, the NO reactivity of the polymeric H-NOX protein is at least 1,000-fold lower than that of hemoglobin. In some embodiments, the $k_{off}$ for oxygen of the polymeric H-NOX protein is less than or equal to about 0.65 $s^{-1}$ at 20° C. In some embodiments, the $k_{off}$ for oxygen of the polymeric H-NOX protein is between about 0.21 $s^{-1}$ and about 0.65 $s^{-1}$ at 20° C. In some embodiments, the $k_{off}$ for oxygen of the H-NOX protein is between about 1.35 $s^{-1}$ and about 2.9 $s^{-1}$ at 20° C. In some embodiments, the rate of heme autoxidation of the polymeric H-NOX protein is less than about 1 $h^{-1}$ at 37° C.

In some embodiments of the above embodiments, the polymeric H-NOX protein is greater than 50 kDal, greater than 100 kDal, or greater than 150 kDal. In some embodiments, the polymeric H-NOX protein preferentially accumulates in one or more tissues in a mammal compared to a corresponding monomeric H-NOX protein comprising a single H-NOX domain following administration of the H-NOX protein to the animal. In some embodiments, the polymeric H-NOX protein persists in a mammal for 1, 2, 3, 4, 6, 12 or 24 hours following administration of the H-NOX protein to the mammal. In some embodiments, less than 10% of the polymeric H-NOX is cleared from mammal by the kidneys within less than about 1 hour, 2 hours or 3 hours following administration of the H-NOX protein to the mammal.

In some embodiments, the polymeric H-NOX protein comprises the amino acid sequence set forth in SEQ ID NO:6, SEQ ID NO:8, SEQ ID NO:10, SEQ ID NO:12, SEQ ID NO:26 or SEQ ID NO:28.

In some aspects, the invention provides a recombinant H-NOX protein comprising an H-NOX domain and a polymerization domain. In some embodiments, the H-NOX domain is covalently linked to the polymerization domain. In some embodiments, the C-terminus of the H-NOX domain is linked to the polymerization domain. In other embodiments, the N-terminus of the H-NOX domain is linked to the polymerization domain. In some embodiments, the H-NOX domain is linked to the N-terminus of the polymerization domain. In other some embodiments, the H-NOX domain is linked to the C-terminus of the polymerization domain. In some embodiments, the polymerization domain is a trimerization domain. In further embodiments, the trimerization domain is a bacteriophage T4 trimerization domain. In yet further embodiments, the trimerization domain is a foldon domain. In some embodiments, the foldon domain comprises SEQ ID NO:4.

Is some embodiments of the above embodiments, the recombinant H-NOX protein does not comprise a guanylyl cyclase domain.

In some embodiments of the above embodiments, the recombinant H-NOX protein comprises a tag. In some embodiments, the recombinant H-NOX protein comprises a $His_6$ tag.

In some embodiments of the above aspect, amino acid linkers are located between the H-NOX domain and/or the polymerization domain and/or the tag. In some embodiments, the amino acid linker is a Gly-Ser-Gly sequence of an Arg-Gly-Ser sequence.

In some embodiments of the above embodiments, the H-NOX domain is a *Thermoanaerobacter tengcongensis* H-NOX domain, a *L. pneumophilia* 2 H-NOX domain, a *Homo sapiens* β1 H-NOX domain, a *Canis lupus* H-NOX domain, a *Rattus norvegicus* β1 H-NOX domain, a *Drosophila melanogaster* β1 H-NOX domain, a *D. melanogaster* CG14885-PA H-NOX domain, a *Caenorhabdis elegans* GCY-35 H-NOX domain, a *Nostoc* punctiforme H-NOX domain, *Caulobacter crescentus* H-NOX domain, a *Shewanella oneidensis* H-NOX domain, or *Clostridium acetobutylicum* H-NOX domain. In some embodiments, the H-NOX domain corresponds to the H-NOX domain of *T. tengcongensis* set forth in SEQ ID NO:2.

In some embodiments of the above embodiments, the H-NOX domain comprises one or more distal pocket mutations. In some embodiments, the distal pocket mutation is an amino acid substitution at a site corresponding to L144 of *T. tengcongensis* H-NOX. In some embodiments, at least one of the H-NOX domains is a *T. tengcongensis* H-NOX domain and at least one of the *T. tengcongensis* H-NOX domains comprises an amino acid substitution at position 144. In some embodiments, the amino acid substitution at position 144 is an L144F substitution. In some embodiments, at least one of the H-NOX domains comprises at least two distal pocket mutations. In some embodiments, the at least two distal pocket mutations are amino acid substitutions at sites corresponding to W9 and L144 of *T. tengcongensis* H-NOX. In some embodiments, at least one of the H-NOX domains is a *T. tengcongensis* H-NOX domain and at least one of the *T. tengcongensis* H-NOX domains comprises amino acid substitutions at positions 9 and 144. In some embodiments, the amino acid substitution at position 9 is a W9F substitution and the amino acid substitution at position 144 is an L144F substitution.

In some embodiments, the recombinant H-NOX protein comprises a wild type H-NOX domain of *T. tengcongensis* covalently linked at its C-terminus to the N-terminus of a T4 bacteriophage foldon domain by way of a Gly-Ser-Gly amino acid linker. In some embodiments, a $His_6$ tag is linked to the C-terminus of the foldon domain via a Arg-Gly-Ser amino acid linker.

In some embodiments, the recombinant H-NOX protein comprises a L144F H-NOX domain of *T. tengcongensis* covalently linked at its C-terminus to the N-terminus of a T4 bacteriophage foldon domain by way of a Gly-Ser-Gly amino acid linker. In some embodiments, a $His_6$ tag is linked to the C-terminus of the foldon domain via a Arg-Gly-Ser amino acid linker.

In some embodiments of the above embodiments, wherein the $O_2$ dissociation constant of the recombinant H-NOX protein is within 2 orders of magnitude of that of hemoglobin, and wherein the NO reactivity of the H-NOX protein is at least 10-fold lower than that of hemoglobin. In some embodiments, wherein the $O_2$ dissociation constant of the recombinant H-NOX protein is between about 1 nM and about 1000 nM at 20° C. In other embodiments, wherein the $O_2$ dissociation constant of the recombinant H-NOX protein is between about 1 µM and about 10 µM at 20° C. In yet other embodiments, the $O_2$ dissociation constant of the H-NOX protein is between about 10 µM and about 50 µM at 20° C. In some embodiments, the NO reactivity of the recombinant H-NOX protein is less than about 700 $s^{-1}$ at 20° C. In some embodiments, the NO reactivity of the recombinant H-NOX protein is at least 100-fold lower than that of hemoglobin. In further embodiments, the NO reactivity of the recombinant H-NOX protein is at least 1,000-fold lower than that of hemoglobin. In some embodiments, the $k_{off}$ for oxygen of the recombinant H-NOX protein is less than or equal to about 0.65 $s^{-1}$ at 20° C. In some embodiments, the $k_{off}$ for oxygen of the recombinant H-NOX protein is between about 0.21 $s^{-1}$ and about 0.65 $s^{-1}$ at 20° C. In some embodiments, the $k_{off}$ for oxygen of the H-NOX protein is between about 1.35 $s^{-1}$ and about 2.9 $s^{-1}$ at 20° C. In some embodiments, the rate of heme autoxidation of the recombinant H-NOX protein is less than about 1 $h^{-1}$ at 37° C.

In some embodiments of the above aspect, the recombinant H-NOX protein comprises the amino acid sequence set forth in SEQ ID NO:6, SEQ ID NO:8, SEQ ID NO:10, SEQ ID NO:12, SEQ ID NO:26 or SEQ ID NO:28.

In some aspects, the invention provides a pharmaceutical composition comprising a polymeric H-NOX protein comprising two or more H-NOX domains. In some embodiments, the pharmaceutical composition comprises a polymeric H-NOX protein of any one of the above embodiments. In some embodiments, the pharmaceutical composition further comprises a pharmaceutically acceptable excipient. In some embodiments, the pharmaceutical composition is sterile. In some embodiments, the pharmaceutical composition is essentially free of endotoxin. In some embodiments, the recombinant H-NOX protein comprises the amino acid sequence set forth in SEQ ID NO:6, SEQ ID NO:8, SEQ ID NO:10, SEQ ID NO:12, SEQ ID NO:26 or SEQ ID NO:28.

In some embodiments, the pharmaceutical composition comprises a polymeric H-NOX protein comprises three wild type H-NOX domains of *T. tengcongensis*, each of the H-NOX domains is covalently linked at its C-terminus to the N-terminus of a T4 bacteriophage foldon domain by way of a Gly-Ser-Gly amino acid linker. In some embodiments, a His6 tag is linked to the C-terminus of the foldon domain via a Arg-Gly-Ser amino acid linker.

In some embodiments, pharmaceutical composition comprises a polymeric H-NOX protein comprises three L144F H-NOX domains of *T. tengcongensis*, each of the H-NOX domains is covalently linked at its C-terminus to the N-terminus of a T4 bacteriophage foldon domain by way of a Gly-Ser-Gly amino acid linker. In some embodiments, a His6 tag is linked to the C-terminus of the foldon domain via a Arg-Gly-Ser amino acid linker.

In some aspects, the invention provides a pharmaceutical composition comprising a recombinant H-NOX protein comprising an H-NOX domain and a polymerization domain. In some embodiments, the pharmaceutical composition comprises a recombinant H-NOX protein comprising an H-NOX domain and a polymerization domain of any one of the above embodiments. In some embodiments, the pharmaceutical composition further comprises a pharmaceutically acceptable excipient. In some embodiments, the pharmaceutical composition is sterile. In some embodiments, the pharmaceutical composition is essentially free of endotoxin. In some embodiments, the recombinant H-NOX protein comprises the amino acid sequence set forth in SEQ ID NO:6, SEQ ID NO:8, SEQ ID NO:10, SEQ ID NO:12, SEQ ID NO:26 or SEQ ID NO:28.

In some aspects, the invention provides a method of delivering $O_2$ to a brain tumor in an individual with a brain cancer comprising administering an effective amount of an H-NOX protein to the individual. In some embodiments, the administration of the H-NOX protein is used in combination with radiation therapy or chemotherapy.

In some aspects, the invention provides a method of treating brain cancer in an individual with brain cancer comprising administering an effective amount of an H-NOX protein to the individual, and administering an effective amount of radiation to the individual.

In some aspects, the invention provides, a method of reducing brain tumor growth in an individual with brain cancer comprising administering an effective amount of an H-NOX protein to the individual, and administering an effective amount of radiation to the individual.

In some embodiments of the above aspects, the radiation or chemotherapy is administered to the individual 1, 2, 3, 4, 5 or 6 hours after the H-NOX is administered. In some embodiments, the radiation is X-radiation. In some embodiments, the X-radiation is administered at about 0.5 gray to about 75 gray. In some embodiments, the administration of the H-NOX protein and/or the administration of the radiation is repeated. In some embodiments, the administration is repeated two, three, or four times. In some embodiments, the administration is repeated after one week, two weeks, three weeks, or four weeks.

In some embodiments of the above aspects, the brain cancer is glioblastoma. In some embodiments, the individual is a mammal. In some embodiments, mammal is a human. In other embodiments, the mammal is a pet, a laboratory research animal, or a farm animal. In further embodiments, the pet, research animal or farm animal is a dog, a cat, a horse, a monkey, a rabbit, a rat, a mouse, a guinea pig, a hamster, a pig, or a cow.

In some embodiments of the above aspects, the administration of the H-NOX protein and the radiation is used in combination with another therapy.

In some embodiments of the above aspects, the H-NOX protein is a *T. tengcongensis* H-NOX, a *L. pneumophila* 2 H-NOX, a *H. sapiens* β1, a *R. norvegicus* β1, a *D. melanogaster* β1, a *D. melanogaster* CG14885-PA, a *C. elegans* GCY-35, a *N. punctiforme* H-NOX, *C. crescentus* H-NOX, a *S. oneidensis* H-NOX, or *C. acetobutylicum* H-NOX. In some aspects, the H-NOX protein comprises a H-NOX domain corresponding to the H-NOX domain of *T. tengcongensis* set forth in SEQ ID NO:2. In some embodiments, the H-NOX comprises one or more distal pocket mutations. In some embodiments, the distal pocket mutation is an amino acid substitution at a site corresponding to L144 of *T. tengcongensis* H-NOX. In some embodiments, the H-NOX is a *T. tengcongensis* H-NOX comprising an amino acid substitution at position 144. In some embodiments, the amino acid substitution at position 144 is an L144F substitution. In some embodiments, the H-NOX comprises at least two distal pocket mutations. In some embodiments, the at least two distal pocket mutations are amino acid substitutions at sites corresponding to W9 and L144 of *T. tengcongensis* H-NOX. In some embodiments, the H-NOX is a *T. tengcongensis* H-NOX comprising amino acid substitutions at positions 9 and 144. In some embodiments, the amino acid substitution at position 9 is a W9F substitution and the amino acid substitution at position 144 is an L144F substitution.

In some embodiments of the above aspects, the polymeric H-NOX protein does not comprise a guanylyl cyclase domain.

In some embodiments of the above aspects, the H-NOX protein comprises a tag. In some aspects, the tag is a $His_6$ tag.

In some embodiments of the above aspects, the $O_2$ dissociation constant of the H-NOX protein is within 2 orders of magnitude of that of hemoglobin, and wherein the NO reactivity of the H-NOX protein is at least 10-fold lower than that of hemoglobin. In some embodiments, the $O_2$ dissociation constant of the polymeric H-NOX protein is between about 1 nM and about 1000 nM at 20° C. In other embodiments, the $O_2$ dissociation constant of the H-NOX protein is between about 1 µM and about 10 µM at 20° C. In yet other embodiments, the $O_2$ dissociation constant of the H-NOX protein is between about 10 µM and about 50 µM at 20° C. In some embodiments, the NO reactivity of the H-NOX protein is less than about 700 $s^{-1}$ at 20° C. In some embodiments, the NO reactivity of the H-NOX protein is at least 100-fold lower than that of hemoglobin. In further embodiments, the NO reactivity of the H-NOX protein is at least 1,000-fold lower than that of hemoglobin. In some embodiments, the $k_{off}$ for oxygen of the H-NOX protein is less than or equal to about 0.65 $s^{-1}$ at 20° C. In some embodiments, the $k_{off}$ for oxygen of the H-NOX protein is between about 0.21 $s^{-1}$ and about 0.65 $s^{-1}$ at 20° C. In some embodiments, the $k_{off}$ for oxygen of the H-NOX protein is between about 1.35 $s^{-1}$ and about 2.9 $s^{-1}$ at 20° C. In some embodiments, the rate of heme autoxidation of the H-NOX protein is less than about 1 $h^{-1}$ at 37° C.

In some aspects, the invention provides a method to deliver oxygen to an individual in need thereof, said method comprising administering to the individual an effective amount of a polymeric H-NOX protein. In some embodiments, the administration of the H-NOX protein is used in combination with radiation therapy or chemotherapy.

In some aspects, the invention provides a method to treat cancer in an individual in need thereof comprising administering an effective amount of a polymeric H-NOX protein to the individual, and administering an effective amount of radiation to the individual.

In some aspects, the invention provides a method to reduce tumor growth in an individual in need thereof comprising administering an effective amount of an H-NOX protein to the individual, and administering an effective amount of radiation to the individual.

In some embodiments of the above aspects, the radiation or chemotherapy is administered to the individual 1, 2, 3, 4, 5 or 6 hours after the H-NOX is administered. In some embodiments, the radiation is X-radiation. In some embodiments, the X-radiation is administered at about 0.5 gray to about 75 gray. In some embodiments, the administration of the H-NOX protein and/or the administration of the radiation is repeated. In some embodiments, the administration is repeated two, three, or four times. In some embodiments, the administration is repeated after one week, two weeks, three weeks, or four weeks.

In some embodiments of the above embodiments, the cancer is brain cancer, lung cancer, colorectal cancer, or skin cancer. In some embodiments, the individual is a mammal. In further embodiments, the mammal is a human. In other further embodiments, the mammal is a pet, a laboratory research animal, or a farm animal. In yet further embodiments, the pet, research animal or farm animal is a dog, a cat, a horse, a monkey, a rabbit, a rat, a mouse, a guinea pig, a hamster, a pig, or a cow.

In some embodiments of the above aspects, the administration of the H-NOX protein and the radiation is used in combination with another therapy.

In some embodiments of the above aspects, the polymeric H-NOX protein comprises two or more H-NOX domains. In some embodiments, the two or more H-NOX domains are homologous H-NOX domains. In other embodiments, the H-NOX domains are heterologous H-NOX domains.

In some embodiments of the above aspects, the polymeric H-NOX protein is a dimer, a trimer, a tetramer, or a pentamer. In some embodiments, the H-NOX domains are covalently linked.

In some embodiments of the above aspects, the polymeric H-NOX protein comprises monomers, wherein the monomers comprise an H-NOX domain and a polymerization domain. In some embodiments, the H-NOX domain is covalently linked to the polymerization domain. In some embodiments, the C-terminus of the H-NOX domain is covalently linked to the polymerization domain. In other embodiments, the N-terminus of the H-NOX domain is covalently linked to the polymerization domain. In some embodiments, monomers associate to form the polymeric H-NOX protein.

In some embodiments of the above aspects, the polymeric H-NOX protein is a trimeric H-NOX protein. In some embodiments, the trimeric H-NOX protein comprises one or more trimerization domains. In some embodiments, the trimeric H-NOX protein comprises three monomers, wherein the monomers comprise an H-NOX domain and a trimerization domain. In some embodiments, the trimerization domain is a bacteriophage T4 trimerization domain. In some embodiments, the trimerization domain is a foldon domain. In some embodiments, the foldon domain comprises the amino acid sequence of SEQ ID NO:4. In some embodiments, the H-NOX domain is covalently linked to the trimerization domain. In other embodiments, the C-terminus of the H-NOX domain is covalently linked to the N-terminus of the trimerization domain. In some embodiments, the N-terminus of the H-NOX domain is covalently linked to the N-terminus of the trimerization domain.

In some embodiments of the above aspects, a tag is covalently linked to the C-terminus of the trimerization domain. In some embodiments, a His$_6$ tag is covalently linked to the C-terminus of the trimerization domain.

In some embodiments of the above aspects, amino acid linkers are located between the H-NOX domain and/or the polymerization domain and/or the tag. In some embodiments, the amino acid linker is a Gly-Ser-Gly sequence of an Arg-Gly-Ser sequence.

In some embodiments of the above aspects, the polymeric H-NOX protein does not comprise a guanylyl cyclase domain.

In some embodiments of the above aspects, at least one of the H-NOX domains is a *T. tengcongensis* H-NOX domain, a *L. pneumophilia* 2 H-NOX domain, a *H. sapiens* β1 H-NOX domain, a *C. lupus* H-NOX domain, a *R. norvegicus* β1 H-NOX domain, a *D. melanogaster* β1 H-NOX domain, a *D. melanogaster* CG14885-PA H-NOX domain, a *C. elegans* GCY-35 H-NOX domain, a *N. punctiforme* H-NOX domain, *C. crescentus* H-NOX domain, a *S. oneidensis* H-NOX domain, or *C. acetobutylicum* H-NOX domain. In some embodiments, the H-NOX domain corresponds to the H-NOX domain of *T. tengcongensis* set forth in SEQ ID NO:2. In some embodiments of the above aspects, the H-NOX protein is a *T. tengcongensis* H-NOX, a *L. pneumophilia* 2 H-NOX, a *H. sapiens* β1, a *R. norvegicus* β1, a *D. melanogaster* β1, a *D. melanogaster* CG14885-PA, a *C. elegans* GCY-35, a *N. punctiforme* H-NOX, *C. crescentus* H-NOX, a *S. oneidensis* H-NOX, or *C. acetobutylicum* H-NOX. In some embodiments, the H-NOX protein comprises a H-NOX domain corresponding to the H-NOX domain of *T. tengcongensis* set forth in SEQ ID NO:2. In some embodiments, the H-NOX comprises one or more distal pocket mutations. In some embodiments, the distal pocket mutation is an amino acid substitution at a site corresponding to L144 of *T. tengcongensis* H-NOX. In some embodiments, the H-NOX is a *T. tengcongensis* H-NOX comprising an amino acid substitution at position 144. In some embodiments, the amino acid substitution at position 144 is an L144F substitution. In some embodiments, the H-NOX comprises at least two distal pocket mutations. In some embodiments, the at least two distal pocket mutations are amino acid substitutions at sites corresponding to W9 and L144 of *T. tengcongensis* H-NOX. In some embodiments, the H-NOX is a *T. tengcongensis* H-NOX comprising amino acid substitutions at positions 9 and 144. In some embodiments, the amino acid substitution at position 9 is a W9F substitution and the amino acid substitution at position 144 is an L144F substitution.

In some embodiments, the polymeric H-NOX protein of the methods comprises three wild type H-NOX domains of *T. tengcongensis*, each of the H-NOX domains is covalently linked at its C-terminus to the N-terminus of a T4 bacteriophage foldon domain by way of a Gly-Ser-Gly amino acid linker. In some embodiments, a His6 tag is linked to the C-terminus of the foldon domain via a Arg-Gly-Ser amino acid linker.

In some embodiments, the polymeric H-NOX protein of the method comprises three L144F H-NOX domains of *T. tengcongensis*, each of the H-NOX domains is covalently linked at its C-terminus to the N-terminus of a T4 bacteriophage foldon domain by way of a Gly-Ser-Gly amino acid linker. In some embodiments, a His6 tag is linked to the C-terminus of the foldon domain via a Arg-Gly-Ser amino acid linker.

In some embodiments of the above aspects, the $O_2$ dissociation constant of the H-NOX protein is within 2 orders of magnitude of that of hemoglobin, and wherein the NO reactivity of the H-NOX protein is at least 10-fold lower than that of hemoglobin. In some embodiments, the $O_2$ dissociation constant of the polymeric H-NOX protein is between about 1 nM and about 1000 nM at 20° C. In other embodiments, the $O_2$ dissociation constant of the H-NOX protein is between about 1 μM and about 10 μM at 20° C. In yet other embodiments, the $O_2$ dissociation constant of the H-NOX protein is between about 10 μM and about 50 μM at 20° C. In some embodiments, the NO reactivity of the H-NOX protein is less than about 700 $s^{-1}$ at 20° C. In some embodiments, the NO reactivity of the H-NOX protein is at least 100-fold lower than that of hemoglobin. In further embodiments, the NO reactivity of the H-NOX protein is at least 1,000-fold lower than that of hemoglobin. In some embodiments, the $k_{off}$ for oxygen of the H-NOX protein is less than or equal to about 0.65 s$^{-1}$ at 20° C. In some embodiments, the $k_{off}$ for oxygen of the H-NOX protein is between about 0.21 s$^{-1}$ and about 0.65 s$^{-1}$ at 20° C. In some embodiments, the $k_{off}$ for oxygen of the H-NOX protein is between about 1.35 s$^{-1}$ and about 2.9 s$^{-1}$ at 20° C. In some embodiments, the rate of heme autoxidation of the H-NOX protein is less than about 1 h$^{-1}$ at 37° C.

In some embodiments of the above aspects, the polymeric H-NOX protein is greater than 50 kDal, greater than 100 kDal, or greater than 150 kDal. In some embodiments, the polymeric H-NOX protein preferentially accumulates in one or more tissues in a mammal compared to a corresponding monomeric H-NOX protein comprising a single H-NOX domain following administration of the H-NOX protein to the animal. In some embodiments, the polymeric H-NOX protein persists in a mammal for 1, 2, 3, 4, 6, 12 or 24 hours following administration of the H-NOX protein to the mammal. In some embodiments, less than 10% of the polymeric H-NOX is cleared from mammal by the kidneys within less than about 1 hour, 2 hours or 3 hours following administration of the H-NOX protein to the mammal.

In some embodiments, the polymeric H-NOX protein comprises the amino acid sequence set forth in SEQ ID NO:6, SEQ ID NO:8, SEQ ID NO:10, SEQ ID NO:12, SEQ ID NO:26 or SEQ ID NO:28.

In some aspects, the invention provides a recombinant nucleic acid encoding the polymeric H-NOX protein of any the embodiments described herein. In some embodiments, the nucleic acid is in a vector. The invention also provides a cell comprising a nucleic acid or vector encoding a polymeric H-NOX protein or monomeric H-NOX subunit described herein. In some embodiments, the nucleic acid comprises the nucleic acid sequence set forth in SEQ ID NO:5, SEQ ID NO:7, SEQ ID NO:9, SEQ ID NO:11, SEQ ID NO:25 or SEQ ID NO:27.

In some aspects, the invention provides a method of producing a polymeric H-NOX protein comprising culturing the cell comprising a nucleic acid encoding a polymeric H-NOS protein or a monomeric H-NOX subunit under conditions suitable for production of the polymeric H-NOX protein. In further embodiments the method includes a step of purifying the H-NOX protein.

In some aspects, the invention provides kits comprising a polymeric H-NOX protein comprising two or more H-NOX domains. In some embodiments, the kits further comprise instructions for use of the polymeric H-NOX protein. In some embodiments, the two or more H-NOX domains are homologous H-NOX domains. In other embodiments, the H-NOX domains are heterologous H-NOX domains. In some embodiments, the polymeric H-NOX protein is a dimer, a trimer, a tetramer, or a pentamer. In some embodiments, the H-NOX domains are covalently linked.

In some embodiments of the invention, the polymeric H-NOX protein of the kit comprises monomers, wherein the monomers comprise an H-NOX domain and a polymerization domain. In some embodiments, the H-NOX domain is covalently linked to the polymerization domain. In some embodiments, the C-terminus of the H-NOX domain is covalently linked to the polymerization domain. In other embodiments, the N-terminus of the H-NOX domain is covalently linked to the polymerization domain. In some embodiments, monomers associate to form the polymeric H-NOX protein.

In some embodiments of the invention, the polymeric H-NOX protein of the kit is a trimeric H-NOX protein. In some embodiments, the trimeric H-NOX protein comprises one or more trimerization domains. In some embodiments, the trimeric H-NOX protein comprises three monomers, wherein the monomers comprise an H-NOX domain and a trimerization domain. In some embodiments, the trimerization domain is a bacteriophage T4 trimerization domain. In some embodiments, the trimerization domain is a foldon domain. In some embodiments, the foldon domain comprises the amino acid sequence of SEQ ID NO:4. In some embodiments, the H-NOX domain is covalently linked to the trimerization domain. In some embodiments, the C-terminus of the H-NOX domain is covalently linked to the N-terminus of the trimerization domain. In other embodiments, the N-termini of the H-NOX domains are covalently linked to the N-terminus of the trimerization domain.

In some embodiments of any of the above embodiments, the polymeric H-NOX protein of the kit does not comprise a guanylyl cyclase domain.

In some embodiments of the above embodiments, the polymeric H-NOX protein of the kit comprises at least one tag. In some embodiments, the polymeric H-NOX protein comprises at least one His$_6$ tag.

In some embodiments of any of the above embodiments, amino acid linkers are located between the H-NOX domain and/or the polymerization domain and/or the tag. In some embodiments, the amino acid linker is a Gly-Ser-Gly sequence of an Arg-Gly-Ser sequence.

In some embodiments of any of the above embodiments, at least one of the H-NOX domain of the kit is a *Thermoanaerobacter tengcongensis* H-NOX domain, a *L. pneumophilia* 2 H-NOX domain, a *Homo sapiens* β1 H-NOX domain, a *Canis lupus* H-NOX domain, a *Rattus norvegicus* β1 H-NOX domain, a *Drosophila melanogaster* β1 H-NOX domain, a *D. melanogaster* CG14885-PA H-NOX domain, a *Caenorhabdis elegans* GCY-35 H-NOX domain, a *Nostoc punctiforme* H-NOX domain, *Caulobacter crescentus* H-NOX domain, a *Shewanella oneidensis* H-NOX domain, or *Clostridium acetobutylicum* H-NOX domain. In some embodiments, the H-NOX domain corresponds to the H-NOX domain of *T. tengcongensis* set forth in SEQ ID NO:2.

In some embodiments of any of the above embodiments, at least one of the H-NOX domain of the kit comprises one or more distal pocket mutations. In some embodiments, the distal pocket mutation is an amino acid substitution at a site corresponding to L144 of *T. tengcongensis* H-NOX. In some embodiments, at least one of the H-NOX domains is a *T. tengcongensis* H-NOX domain and at least one of the *T. tengcongensis* H-NOX domains comprises an amino acid substitution at position 144. In some embodiments, the amino acid substitution at position 144 is an L144F substitution. In some embodiments, at least two of the H-NOX domains are *T. tengcongensis* H-NOX domains and at least two of the *T. tengcongensis* H-NOX domains comprises an amino acid substitution at position 144. In some embodiments, the amino acid substitution of at least one of the *T. tengcongensis* at position 144 is an L144F substitution. In some embodiments, at least one of the H-NOX domains comprises at least two distal pocket mutations. In some embodiments, the at least two distal pocket mutations are amino acid substitutions at sites corresponding to W9 and L144 of *T. tengcongensis* H-NOX. In some embodiments, at least one of the H-NOX domains is a *T. tengcongensis* H-NOX domain and at least one of the *T. tengcongensis* H-NOX domains comprises amino acid substitutions at positions 9 and 144. In some embodiments, the amino acid substitution at position 9 is a W9F substitution and the amino acid substitution at position 144 is an L144F substitution.

In some embodiments, the polymeric H-NOX protein of the kit comprises three wild type H-NOX domains of *T. tengcongensis*, each of the H-NOX domains is covalently linked at its C-terminus to the N-terminus of a T4 bacteriophage foldon domain by way of a Gly-Ser-Gly amino acid linker. In some embodiments, a His6 tag is linked to the C-terminus of the foldon domain via a Arg-Gly-Ser amino acid linker.

In some embodiments, the polymeric H-NOX protein of the kit comprises three L144F H-NOX domains of *T. tengcongensis*, each of the H-NOX domains is covalently linked at its C-terminus to the N-terminus of a T4 bacteriophage foldon domain by way of a Gly-Ser-Gly amino acid linker. In some embodiments, a His6 tag is linked to the C-terminus of the foldon domain via a Arg-Gly-Ser amino acid linker.

In some embodiments of any of the above embodiments, the $O_2$ dissociation constant of the polymeric H-NOX protein of the kit is within 2 orders of magnitude of that of hemoglobin, and wherein the NO reactivity of the H-NOX protein is at least 10-fold lower than that of hemoglobin. In some embodiments, the $O_2$ dissociation constant of the polymeric H-NOX protein is between about 1 nM and about 1000 nM at 20° C. In other embodiments, the $O^2$ dissociation constant of the polymeric H-NOX protein is between about 1 µM and about 10 µM at 20° C. In yet other embodiments, the $O_2$ dissociation constant of the H-NOX protein is between about 10 µM and about 50 µM at 20° C. In some embodiments, the NO reactivity of the polymeric H-NOX protein is less than about 700 $s^{-1}$ at 20° C. In some embodiments, the NO reactivity of the polymeric H-NOX protein is at least 100-fold lower than that of hemoglobin. In further embodiments, the NO reactivity of the polymeric H-NOX protein is at least 1,000-fold lower than that of hemoglobin. In some embodiments, the $k_{off}$ for oxygen of the polymeric H-NOX protein is less than or equal to about 0.65 $s^{-1}$ at 20° C. In some embodiments, the $k_{off}$ for oxygen of the polymeric H-NOX protein is between about 0.21 $s^{-1}$ and about 0.65 $s^{-1}$ at 20° C. In some embodiments, the $k_{off}$ for oxygen of the H-NOX protein is between about 1.35 $s^{-1}$ and about 2.9 $s^{-1}$ at 20° C. In some embodiments, the rate of heme autoxidation of the polymeric H-NOX protein is less than about 1 $h^{-1}$ at 37° C.

In some embodiments of the above embodiments, the polymeric H-NOX protein of the kit is greater than 50 kDal, greater than 100 kDal, or greater than 150 kDal. In some embodiments, the polymeric H-NOX protein preferentially accumulates in one or more tissues in a mammal compared to a corresponding monomeric H-NOX protein comprising a single H-NOX domain following administration of the H-NOX protein to the animal. In some embodiments, the polymeric H-NOX protein persists in a mammal for 1, 2, 3, 4, 6, 12 or 24 hours following administration of the H-NOX protein to the mammal. In some embodiments, less than 10% of the polymeric H-NOX is cleared from mammal by the kidneys within less than about 1 hour, 2 hours or 3 hours following administration of the H-NOX protein to the mammal.

In some embodiments, the kit comprises any of the polymeric H-NOX proteins described herein. In some embodiments, the kit comprises any of the monomeric H-NOX subunits described herein. In some embodiments, the polymeric H-NOX protein of the kit comprises the amino acid sequence set forth in SEQ ID NO:6, SEQ ID NO:8, SEQ ID NO:10, SEQ ID NO:12, SEQ ID NO:26 or SEQ ID NO:28.

In some aspects, the invention provides an article of manufacture comprising a polymeric H-NOX protein as described herein. In some embodiments, the article of manufacture comprises a H-NOX protein and a bag. In some embodiments, the bag is an IV bag. In some embodiments, the H-NOX protein of the article of manufacture is for the delivery of $O_2$ to an individual in need thereof. In some embodiments, the individual has a brain tumor. In some embodiments, the brain tumor is a glioblastoma. In some embodiments, the polymeric H-NOX protein is used in conjunction with radiation therapy.

In some aspects, the invention provides a unit dose of a polymeric H-NOX protein as described herein. In some embodiments, the H-NOX protein of the unit dose is for the delivery of $O_2$ to an individual in need thereof. In some embodiments, the individual has a brain tumor. In some embodiments, the brain tumor is a glioblastoma. In some embodiments, the polymeric H-NOX protein is used in conjunction with radiation therapy.

BRIEF DESCRIPTION OF THE DRAWINGS

FIG. 1 shows the nucleic acid (SEQ ID NO:3) and amino acid sequence (SEQ ID NO:4) of the foldon domain of bacteriophage T4 fibritin.

FIG. 2A shows the nucleic acid (SEQ ID NO:5) and amino acid sequence (SEQ ID NO:6) of the foldon domain of bacteriophage T4 fibritin fused to the C-terminus of a *Thermoanaerobacter tengcongensis* L144F H-NOX sequence and including the $His_6$ tag. FIG. 2B shows the nucleic acid (SEQ ID NO:7) and amino acid sequence (SEQ ID NO:8) of the L144F H-NOX-foldon monomer without a $His_6$ tag.

FIG. 3A shows an alignment of the DNA sequence of the wild-type *Thermoanaerobacter tengcongensis* H-NOX-foldon-$His_6$ chimeric protein (top; SEQ ID NO:9) and the sequencing data from clone 3I-A (bottom; SEQ ID NO:5) encoding the L144F variant of H-NOX with the fused foldon and $His_6$ sequences. The L144F substitution and the Xho I and Hind III restriction sites used for the fusion are highlighted. FIG. 3B shows the amino acid sequence of the wild-type *Thermoanaerobacter tengcongensis* H-NOX-foldon-$His_6$ monomer (SEQ ID NO:10). FIG. 3C shows the nucleic acid (SEQ ID NO:11) and amino acid sequence (SEQ ID NO:12) of a wild-type H-NOX-foldon-monomer without a $His_6$ tag. FIG. 3D shows the nucleic acid (SEQ ID NO:25) and amino acid (SEQ ID NO:26) of *Canis lupus* H-NOX (1-385) fused at the C-terminus to the bacteriophage T4 foldon domain. FIG. 3E shows the nucleic acid (SEQ ID NO:27) and amino acid (SEQ ID NO:28) of *Canis lupus* H-NOX (1-194) fused at the C-terminus to the bacteriophage T4 foldon domain.

harvest supernatant; Lane 6: harvest pellet: Lane 7: post-lysis: Lane 8; post centrifugation: Lane 9: post-centrifugation pellet; Lane 10: NiNTA flowthrough; Lane 11: NiNTA pool; Lane 12: NiNTA no-good pool; Lane 13: pre-DEAE sample; Lane 14; Post-DEAE pool; Lane 15: final product.

Figure 5:
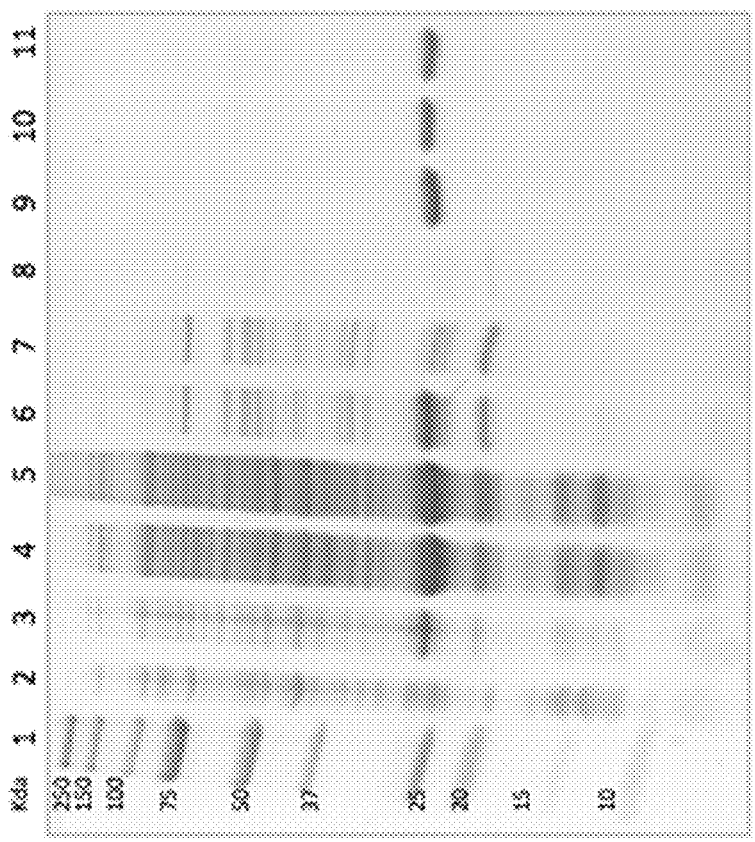

FIG. 5 shows an SDS PAGE gel of steps in the expression and purification of the H-NOX-foldon fusion protein. The H-NOX-foldon fusion protein is >95% pure after purification. The relative mobility on the SDS-PAGE gel is consistent with a 26.7 kDa monomer. Lane 1: Precision Plus Protein Dual Color Markers; Lane 2: Pre-induced; Lane 3: Induced; Lane 4: Post-lysis; Lane 5: Post-heat; Lane 6: Post-spin; Lane 7: Ni column flow-through; Lane 8: Ni column wash; Lane 9: Post-Ni column; Lane 10: Pre-DEAE column; Lane 11: Post DEAE column.

Figure 6:
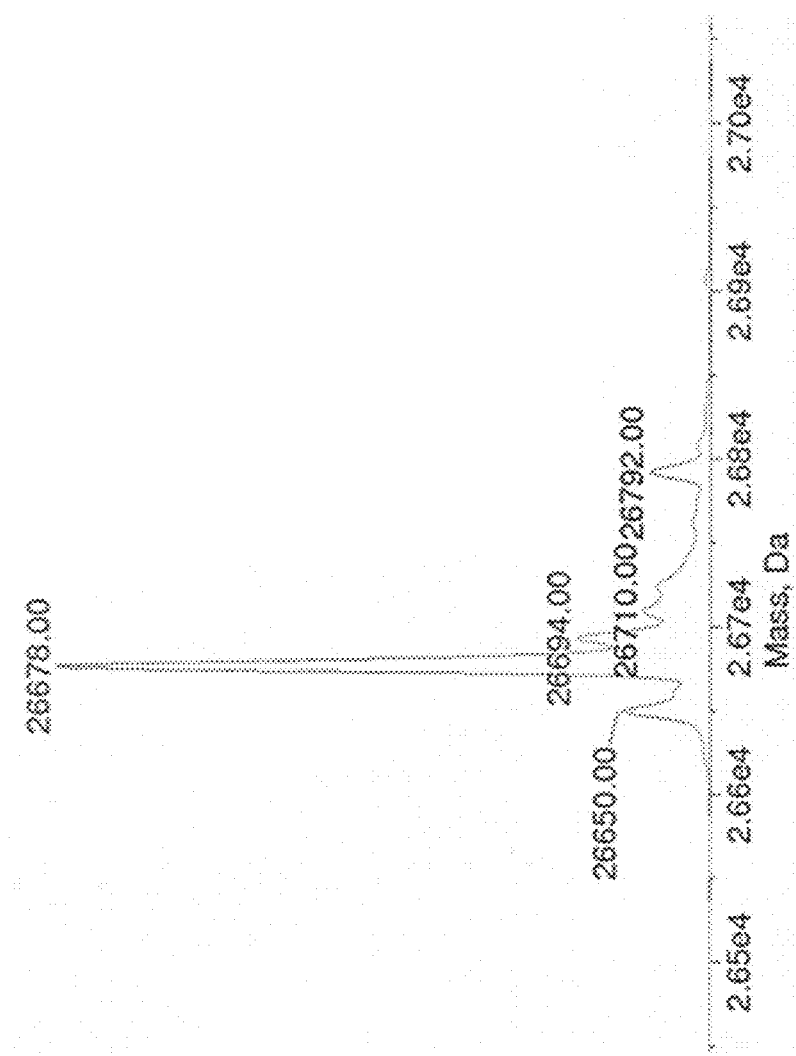

FIG. 6 is a graph showing deconvoluted LC-MS data from the analysis of H-NOX-foldon fusion protein. The final mass is consistent with the predicted molecular mass of 26,677 AMU for the H-NOX-foldon monomer unit.

Figure 7:
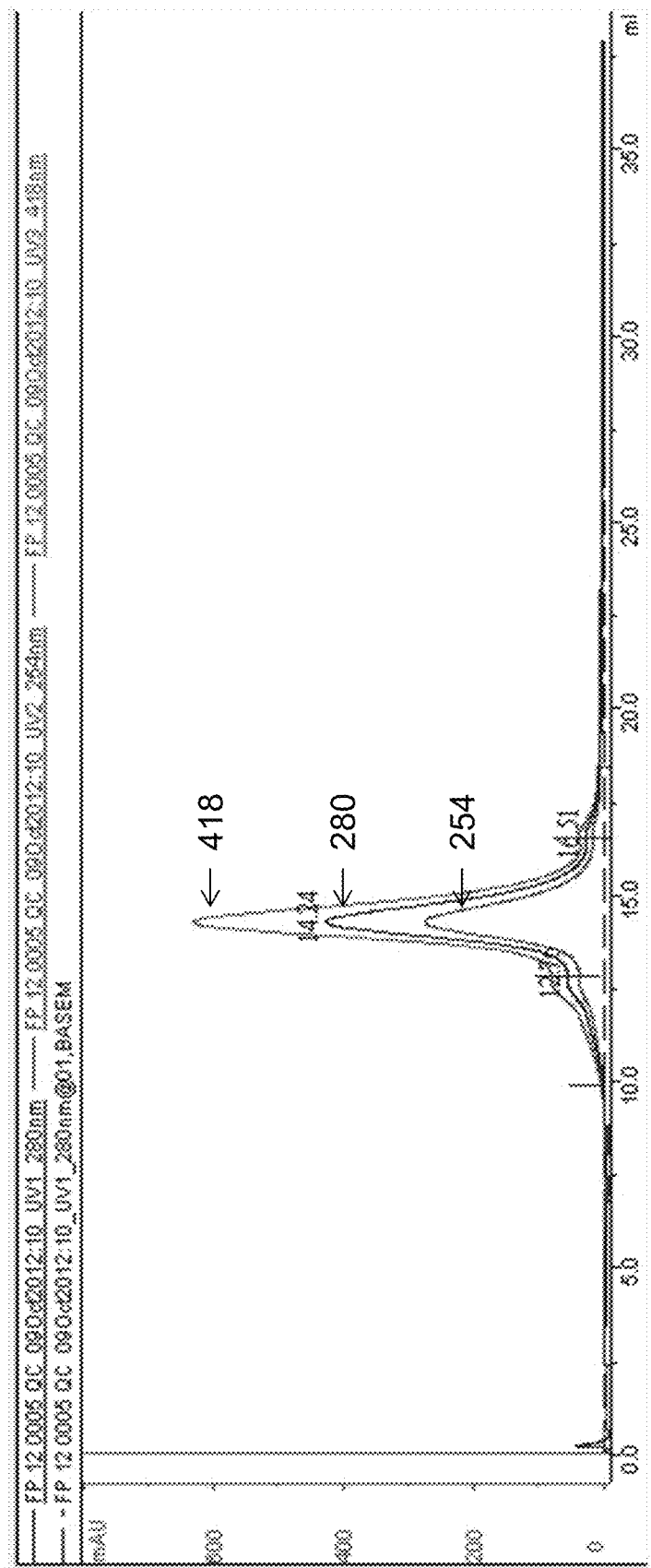

FIG. 7 shows a chromatogram from analytical size exclusion chromatography of the H-NOX-foldon protein. The chromatogram follows three wavelengths (254, 280, and 418 nm) to monitor both protein and heme constituents. The H-NOX-foldon protein elutes at 14.24 mL retention volume and an estimated molecular size of 75.6 kDa (similar to the 80.0 kDa predicted for a H-NOX-foldon trimer).

Figure 8:
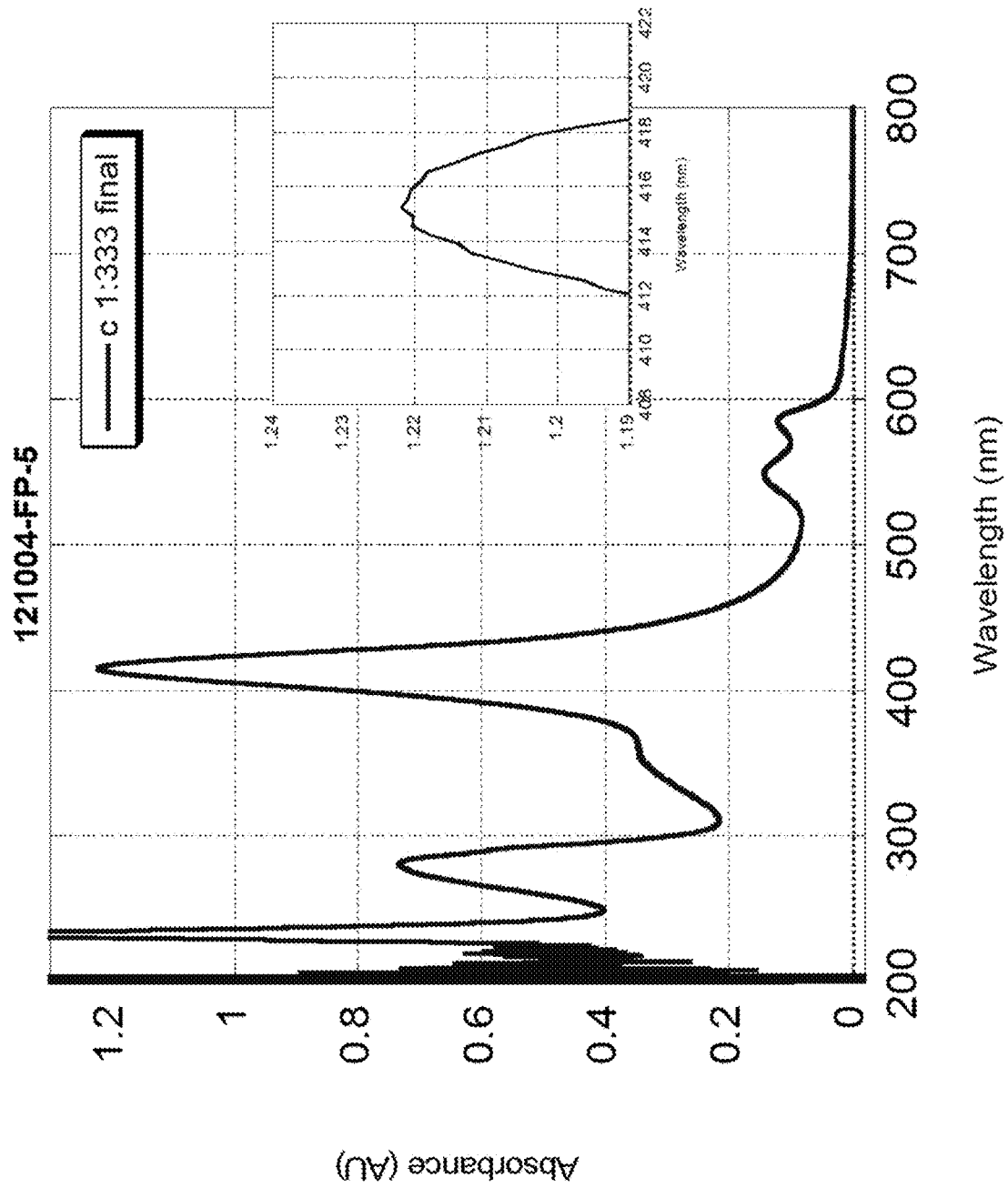

FIG. 8 shows spectroscopic analysis of the H-NOX-foldon protein. Fusion of the foldon domain does not interfere with the tertiary structure of the H-NOX domain, the binding of porphyrin IX with proper coordination, or the binding of oxygen to the porphyrin. Characteristic spectral peaks including the Soret peak (415 nm), and $\alpha/\beta$ peaks (550-600 nm) are all preserved between the H-NOX monomer and the H-NOX-foldon fusion protein.

Figure 9:

FIG. 9 is a model of the trimerized H-NOX protein with the trimerized foldon domain at the center. The porphyrin IX cofactor and bound oxygen are shown with spheres.

Figure 10:
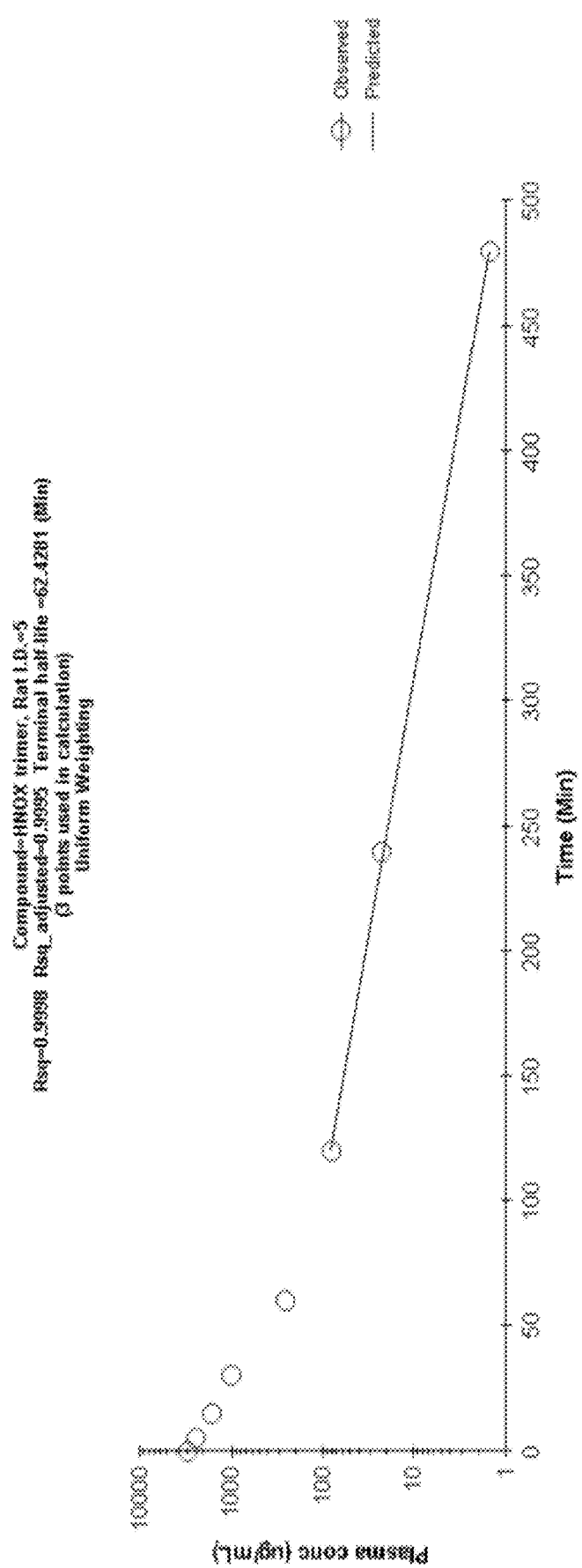
Figure 10:
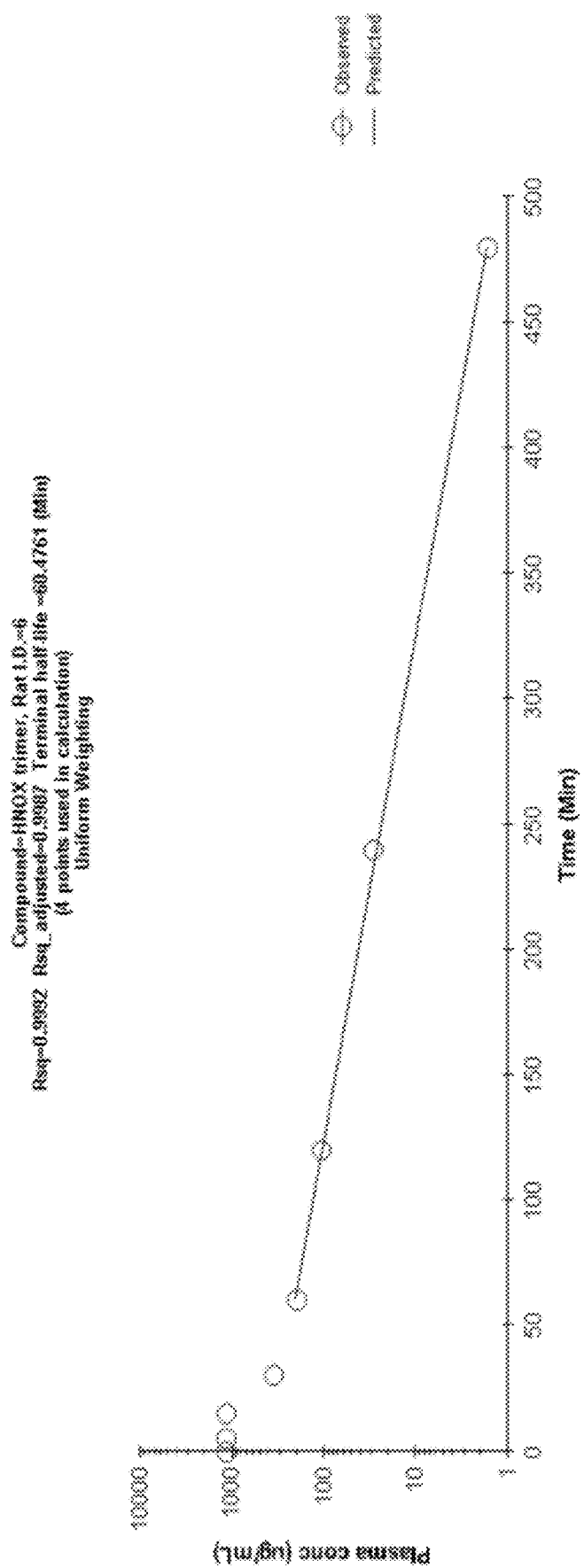

FIG. 10 shows plasma profiles of H-NOX trimer after intravenous bolus (100 mg/kg) in two different rats.

Figure 11:
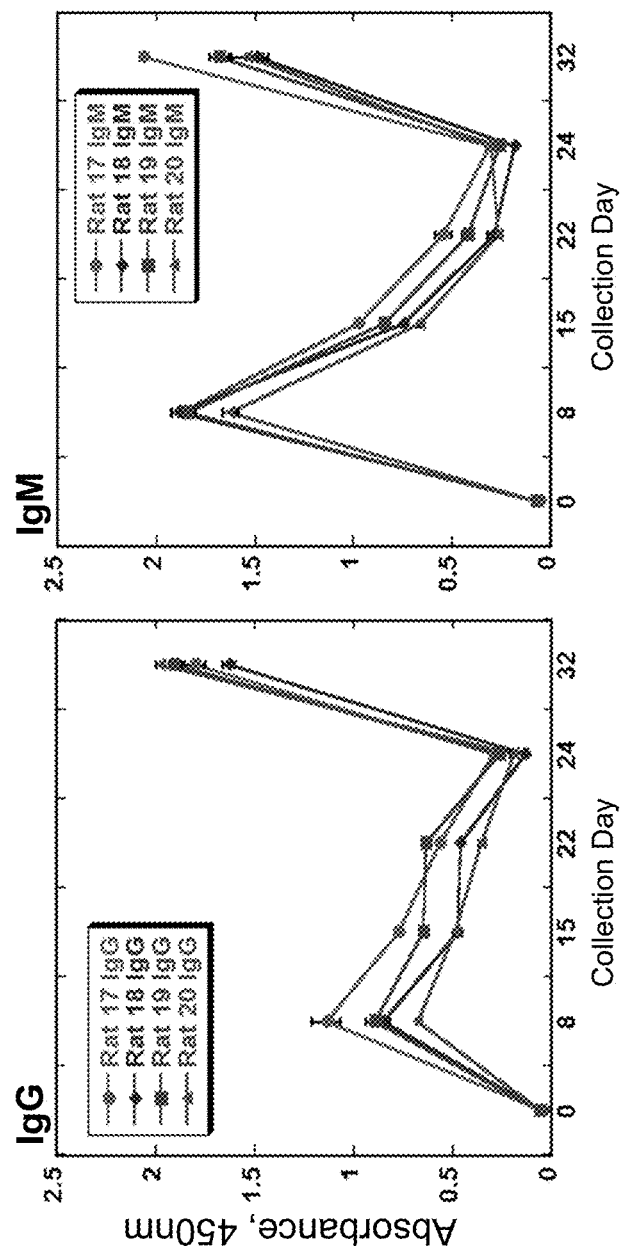

FIG. 11 shows IgG and IgM antibodies are produced in response to H-NOX trimer (50 mg/kg) dosing in rats. IgG or IgM antibodies in plasma (diluted 1:10,000) of rats (curves for individual rats are shown) dosed intravenously with 50 mg/kg H-NOX trimer on Days 1, 3, 5, and 22. Plasma samples were run on ELISA assay in triplicate. Average, +/−SEM.

Figure 12B:
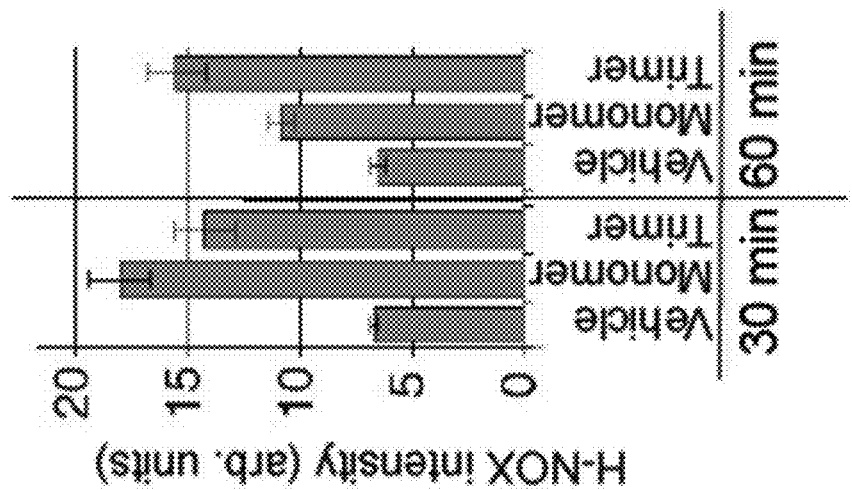
Figure 12A:
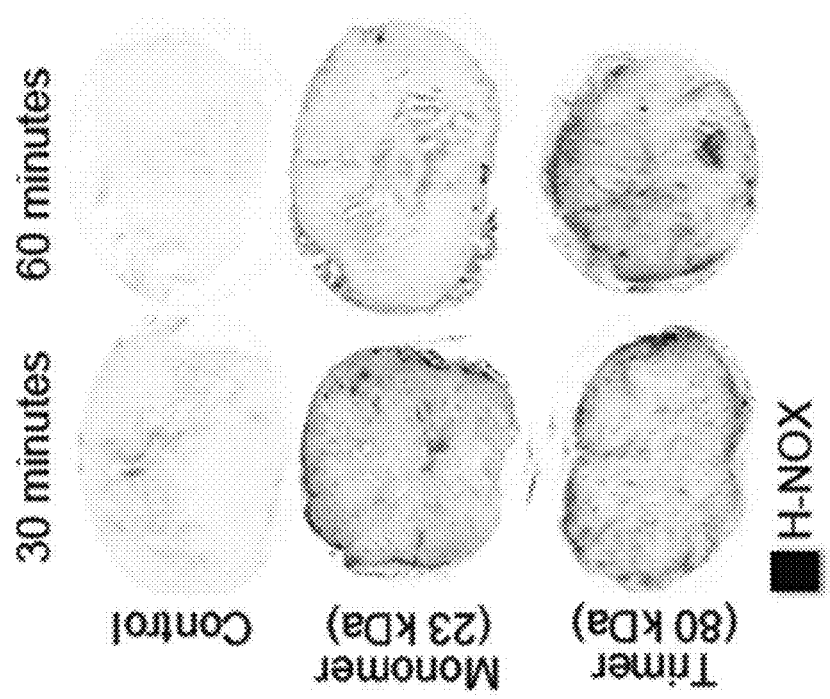
Figure 12C:
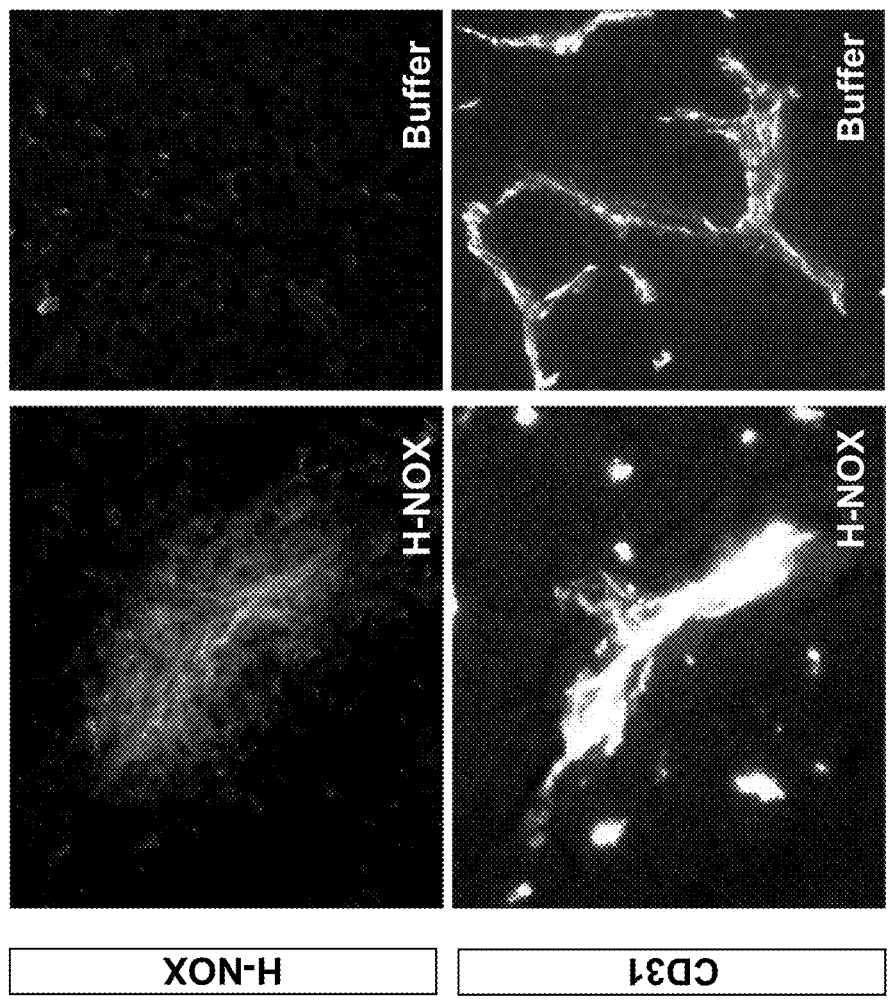

FIGS. 12A-12C show that H-NOX monomer and H-NOX trimer is distributed and retained in mice bearing HCT-116 colon-derived tumors. FIG. 12A) Immunohistochemistry staining of tumors with H-NOX protein antibody showed persistence of H-NOX trimer in tumors for 60 minutes as compared to H-NOX monomer which was partially cleared at 60 minutes. FIG. 12B) Quantification of H-NOX protein staining intensity in HCT-116 tumor sections. N=6, all groups. Mean values+/−SEM. FIG. 12C) Biodistribution of H-NOX in RIF1 syngeneic sarcoma tumors.

Figure 13A:
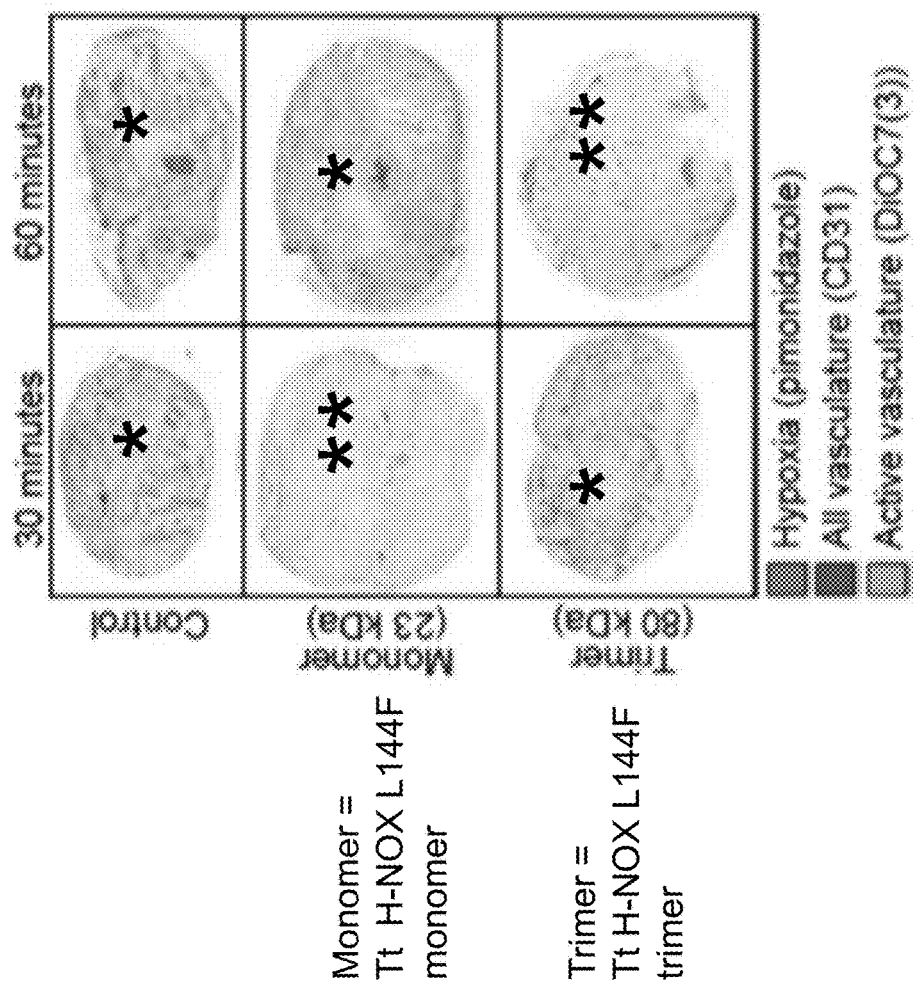
Figure 13B:
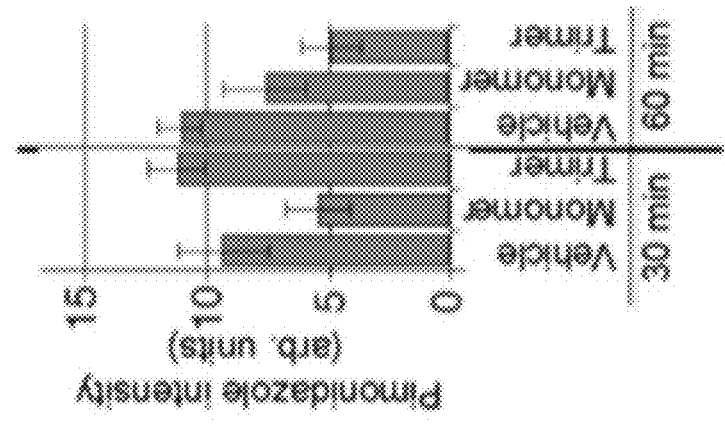

FIGS. 13A and 13B show that H-NOX monomer and H-NOX trimer reduced tumor hypoxia in mice bearing HCT-116 colon-derived tumors. FIG. 13A) Representative tumor section of a 125 mm$^3$ tumor isolated from mice treated with vehicle, H-NOX monomer, or H-NOX trimer. FIG. 13B) Quantification of an anti-pimonidazole antibody (Hypoxyprobe-1) intensity in tumor sections. N=6, all groups. Mean values+/−SEM. * indicates hypoxia throughout tumor, ** indicates no hypoxia in tumor.

FIGS. 14A-14C show tumor penetration and oxygenation by H-NOX monomer in mice bearing HCT-116 colon-derived tumors. FIG. 14A) Tumor sections stained with an anti-H-NOX protein antibody. FIG. 14B) Tumor sections stained with Hypoxyprobe-1. FIG. 14C) Quantification of the Hypoxyprobe-1 as a function of distance from the vasculature in the tumors from six mice per group. * indicates hypoxia throughout tumor, ¥ indicates no hypoxia in tumor.

Figure 15G:
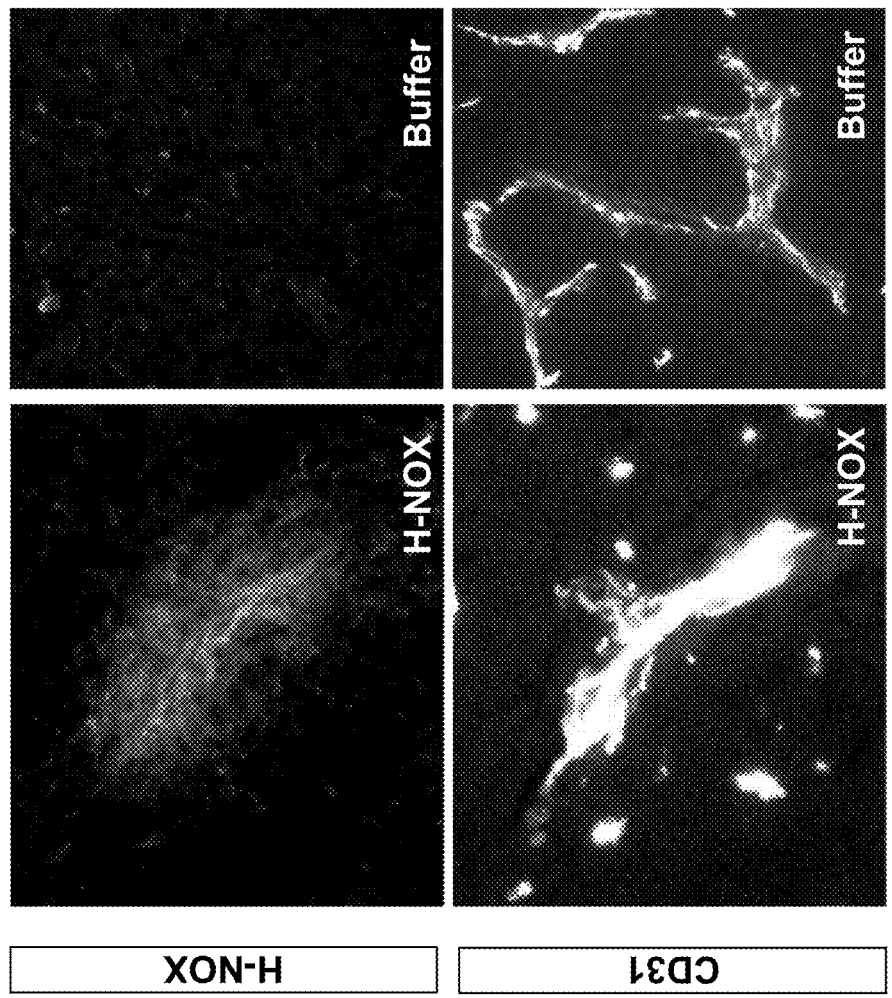

FIGS. 15A-15G show that H-NOX trimer was distributed and retained in mice bearing a RIF-1 syngeneic sarcoma tumor. Immunofluorescence images of a representative section from a 400 mm$^3$ tumor isolated from a mouse 120 minutes after administration of 750 mg/kg H-NOX trimer (FIG. 15A) or buffer (FIG. 15C), and of a 800 mm$^3$ tumor isolated from a mouse 120 minutes after administration of 750 mg/kg H-NOX trimer (FIG. 15B) or buffer (FIG. 15D). H-NOX protein staining was done with anti-H-NOX antibody. FIG. 15E and FIG. 15F show tumor oxygenation by H-NOX trimer in mice bearing a RIF-1 syngeneic sarcoma tumor. FIG. 15E) Tumor sections stained with an anti-pimonidazole antibody two hours after H-NOX or buffer control administration. Whole tumor picture is shown. FIG. 15F) Tumor sections stained with anti-pimonidazole antibody (Hypoxyprobe-1) and anti-CD31 antibody (BD Bioscience) two hours after H-NOX or buffer control administration. High magnification picture are shown. FIG. 15G) Biodistribution of H-NOX in RIF1 syngeneic sarcoma tumors. Two hours after intravenous injection, H-NOX trimer diffuses from the vasculature into the tumor tissue. Immunohistochemistry staining of tumor sections with H-NOX antibody and CD31 antibody (vasculature marker, BD Bioscience). No fluorescent staining is detected in mice injected with buffer.

Figure 16B:
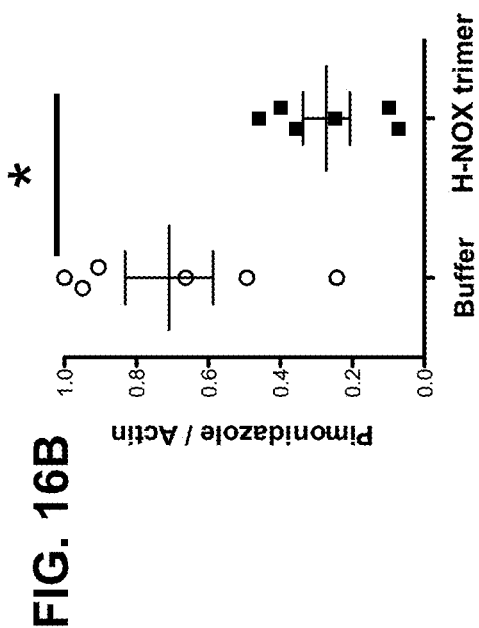
Figure 16C:
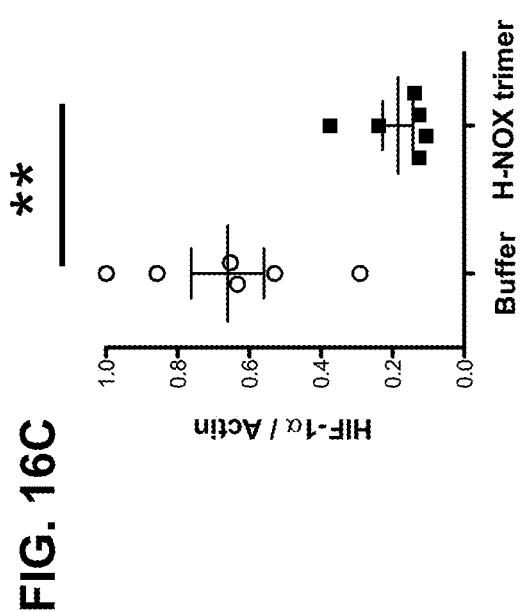
Figure 16A:
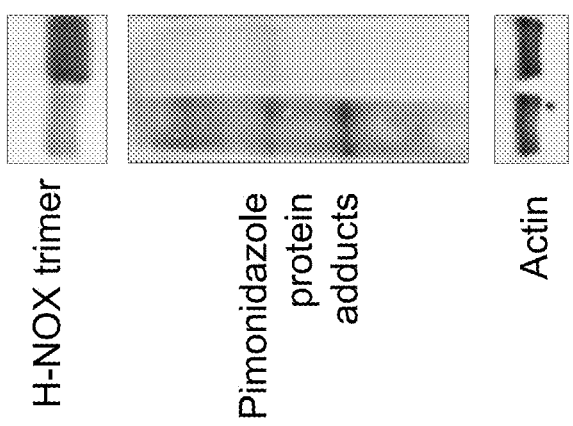

FIGS. 16A-16C show H-NOX trimer penetrated tumor in mice bearing a sarcoma derived tumor and reduced tumor hypoxia. FIG. 16A) Western blot membrane was probed with an anti-H-NOX antibody for detection of H-NOX trimer, with Hypoxyprobe-1 for detection of hypoxia-associated proteins, or with an anti-actin antibody for assessment of total protein levels. FIG. 16B) Quantification of pimonidazole staining intensity in tumor sections. FIG. 16C) Quantification of anti-HIF-1α staining intensity in tumor sections.

FIGS. 17A and 17B are panels of immunohistochemistry images showing tumor penetration by H-NOX trimer and reduced brain tumor hypoxia in mice bearing U251 orthotopic brain tumors. FIG. 17A) H-NOX trimer staining with an anti-H-NOX antibody in a U251 tumor two hours after administration with H-NOX trimer or saline (control). FIG. 17B) Hypoxyprobe-1 staining in U251 tumors two hours after administration with H-NOX trimer or saline (control). Enlarged images from a portion of the tumors are shown.

Figure 18A:
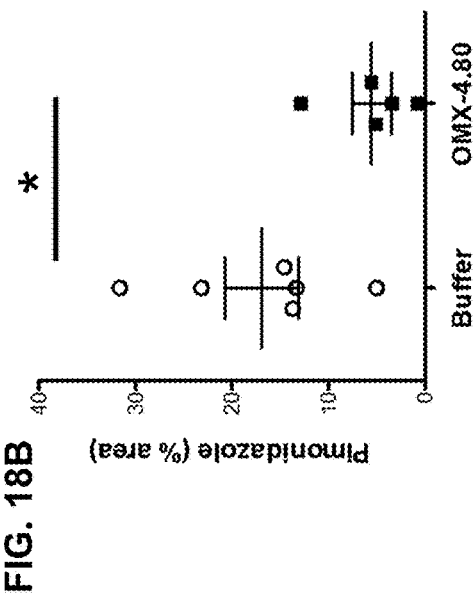
Figure 18B:
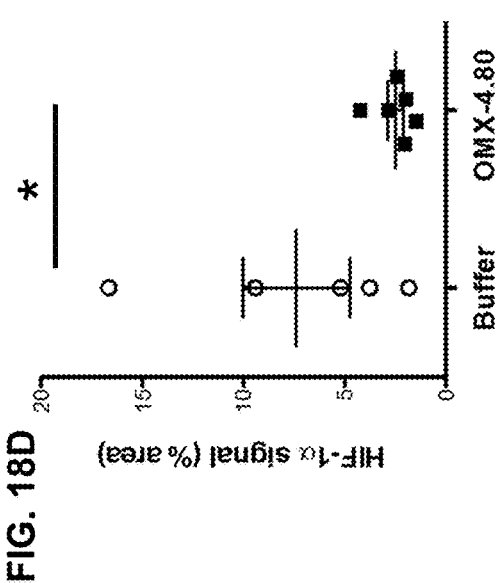
Figure 18C:
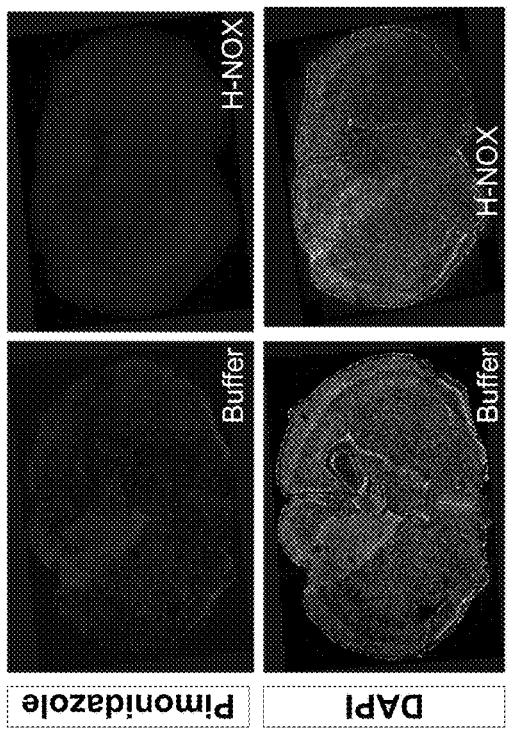
Figure 18D:
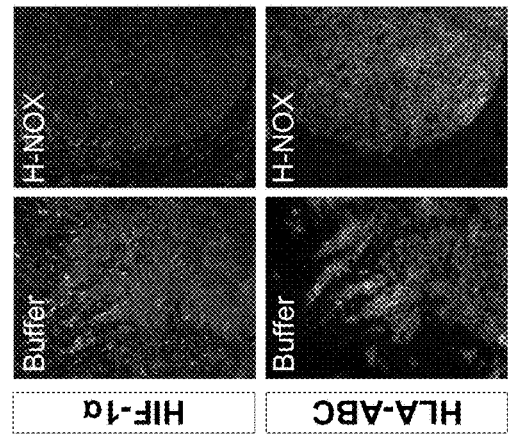

FIGS. 18A-18D show tumor penetration by H-NOX trimer and reduced brain tumor hypoxia in mice bearing U251 orthotopic brain tumors. FIG. 18A) Immunofluorescence images of Hypoxyprobe-1 staining in U251 tumors two hours after administration with H-NOX trimer (right panels) or saline (buffer, left panels). FIG. 18B) Quantification of Hypoxyprobe-1 staining from the immunofluorescence images (H-NOX trimer-right panels or saline-left panels). FIG. 18C) Immunofluorescence images of HIF-1α staining in U251 tumor two hours after administration with H-NOX trimer or saline (buffer). FIG. 18D) Quantification of HIF-1α staining from the immunofluorescence images.

FIGS. 19A-19E show the biodistribution of H-NOX trimer in U251 orthotopic brain tumor and healthy brain. FIG. 19A) H-NOX trimer staining with an anti-H-NOX antibody in a U251 tumor two hours after administration with H-NOX trimer. FIG. 19B) Nuclear DAPI staining in U251 tumors showing tumor localization in the brain. FIG. 19C) and FIG. 19D) Enlarged images from a portion of the tumors from FIG. 19A) show a diffused pattern of H-NOX inside the tumor and vascular-restricted pattern outside the tumor. FIG. 19E) H-NOX trimer staining with an anti-H-NOX antibody and vasculature staining with anti-CD31 antibody (BD Bioscience) in healthy mouse brain.

FIGS. 20A and 20B show real-time fluorescent images of H-NOX monomer or H-NOX trimer in mouse U251 orthotopic glioblastoma tumors. FIG. 20A) H-NOX monomer was cleared by two hours. FIG. 20B) H-NOX trimer persisted in tumors, peaking at 1-4 hours. Images acquired by IVIS; arrows indicate areas of fluorescence above a specific threshold; asterisks indicate peak level of fluorescence intensity.

FIGS. 21A-21D show ex vivo fluorescence images of H-NOX monomer or H-NOX trimer in mouse BT-12 orthotopic glioblastoma tumors. Brains bearing BT-12 tumors were resected 30 minutes after 750 mg/kg H-NOX monomer administration (FIG. 21A), 60 minutes after 750 mg/kg H-NOX monomer administration (FIG. 21B), 60 minutes after 750 mg/kg H-NOX trimer administration (FIG. 21C), or 60 minutes after vehicle administration (FIG. 21D).

FIGS. 22A-22D show real-time fluorescence images of H-NOX monomer in mouse U251 orthotopic glioblastoma tumors. Imaging was acquired at 30 minutes (FIG. 22A), 60 minutes (FIG. 22B), 120 minutes (FIG. 22C), and 240 minutes (FIG. 22D) after H-NOX monomer administration.

FIGS. 23A-23D show real-time fluorescence images of H-NOX trimer in mouse U251 orthotopic glioblastoma tumors. Imaging was acquired at 30 minutes (FIG. 23A), 60 minutes (FIG. 23B), 120 minutes (FIG. 23C), and 240 minutes (FIG. 23D) after H-NOX trimer administration. Arrows indicate areas of fluorescence; asterisks indicate peak level of fluorescence intensity.

Figures 24A, 24B:
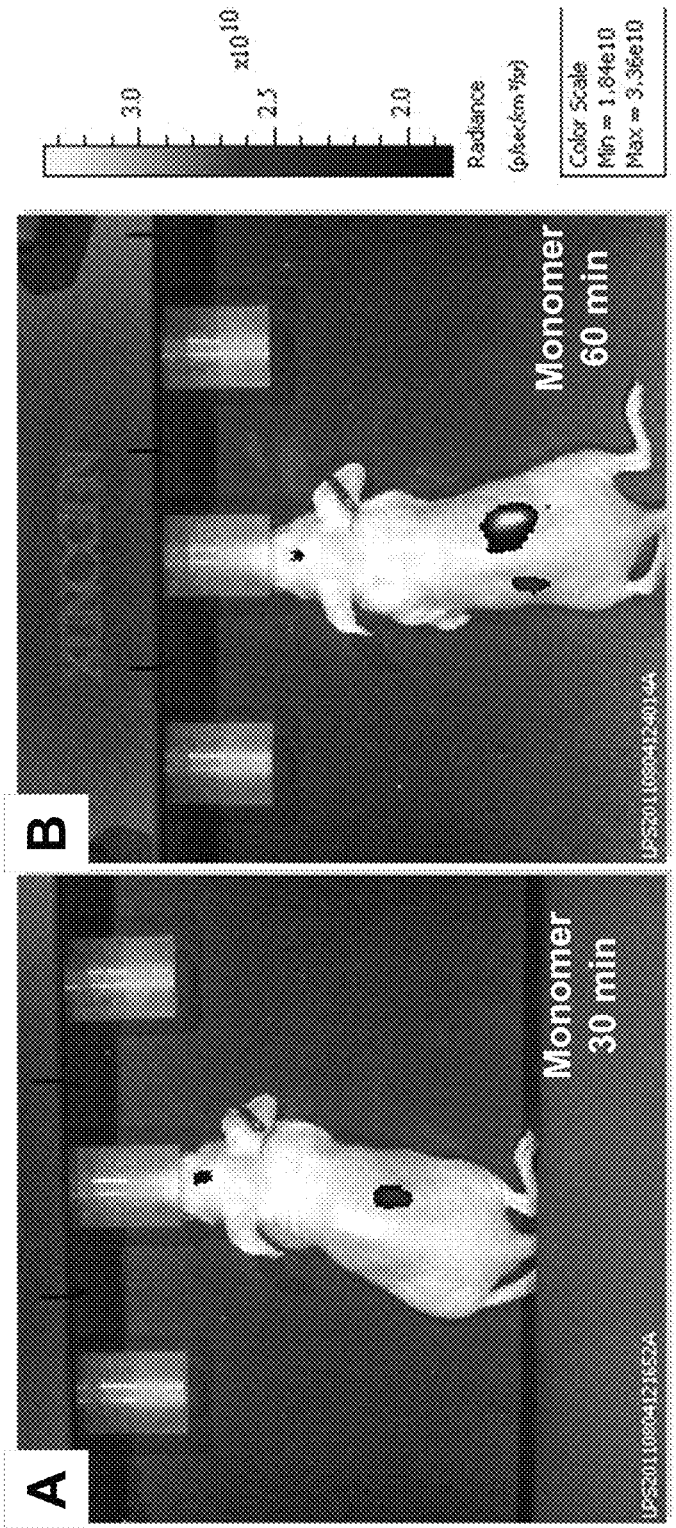

FIGS. 24A and 24B show real-time fluorescence images of H-NOX monomer in mouse U251 orthotopic glioblastoma tumors. Accumulation of H-NOX monomer in the kidney at 30 minutes (FIG. 24A) and 60 minutes (FIG. 24B) after H-NOX monomer administration.

FIGS. 25A-25F show real-time fluorescence images of H-NOX trimer in mouse GBM-43 orthotopic glioblastoma intracranial and spinal tumors. Distribution of H-NOX trimer in the spinal column prior to H-NOX trimer administration (FIG. 25A) and 0.5 hour (FIG. 25B), 1 hour (FIG. 25C), 2 hours (FIG. 25D), 4 hours (FIG. 25E), and 6 hours (FIG. 25F) after H-NOX trimer administration.

Figure 26:

FIG. 26 shows real-time fluorescence images of H-NOX trimer in mouse U251 orthotopic glioblastoma intracranial tumors. Top panel shows the distribution of H-NOX trimer in the brain prior to H-NOX trimer administration (0 minutes) and at 30 min, 1 hour, 2 hours, 4 hours, 6 hours, and 72 hours after H-NOX trimer administration. Bottom panel shows the distribution of H-NOX monomer.

FIGS. 27A-27F show real-time bioluminescence images of H-NOX trimer in mouse U251 orthotopic glioblastoma intracranial and spinal tumors. H-NOX trimer distribution prior to H-NOX trimer administration (FIG. 27A) and at 30 min (FIG. 27B), 1 hour (FIG. 27C), 2 hours FIG. 27D), 4 hours (FIG. 27E), and 6 hours (FIG. 27F) after H-NOX trimer administration at a dose of 295 mg/kg.

FIGS. 28A-28F show real-time fluorescence images of H-NOX trimer in mouse U251 orthotopic glioblastoma tumors. H-NOX trimer distribution prior to H-NOX trimer administration (FIG. 28A) and at 30 min (FIG. 28B), 1 hour (FIG. 28C), 2 hours (FIG. 28D), 4 hours (FIG. 28E), and 6 hours (FIG. 28F) after H-NOX trimer administration at a dose of 30 mg/kg.

FIGS. 29A-29F show real-time fluorescence images of H-NOX trimer L144F variant distribution in a U251 orthotopic glioblastoma mouse model containing small intracranial tumors. H-NOX trimer L144F variant distribution prior to H-NOX trimer administration (FIG. 29A) and at 30 min (FIG. 29B), 1 hour (FIG. 29C), 2 hours (FIG. 29D), 4 hours (FIG. 29E), and 6 hours (FIG. 29F) after H-NOX trimer L144F variant administration at a dose of 30 mg/kg. Small tumors were 1000× fold smaller than large tumors as determined by bioluminescence (BLI) score.

FIGS. 30A-30D show fluorescence images of H-NOX trimer distribution. Ex vivo fluorescence images of a GBM43 orthotopic glioblastoma mouse model administered 30 mg/kg H-NOX trimer (FIG. 30A) or 750 mg/kg H-NOX trimer (FIG. 30B). Real-time bioluminescence imaging in a U251 orthotopic glioblastoma mouse model containing large intracranial tumors (FIG. 30C) or small intracranial tumors (FIG. 30D) after administration of 295 mg/kg H-NOX trimer.

FIG. 31 shows real-time fluorescence images of H-NOX trimer distribution in two mouse models of orthotopic glioblastoma tumors (U251 and GBM-43) and one model of an atypical teratoid/rhabdoid tumor (AT/RT). Images were taken 60 minutes after H-NOX trimer administration and the color scale for each image was optimized FIGS. 32A-32E show ex vivo fluorescence images of H-NOX protein distribution in the tumor-bearing hemisphere of three mouse models of orthotopic glioblastoma tumors. FIG. 32A) H-NOX trimer distribution 60 minutes after administration in a GBM43 orthotopic glioblastoma mouse model, FIG. 32B) H-NOX trimer distribution 6 days after administration in a U251 orthotopic glioblastoma mouse model, FIG. 32C) H-NOX monomer distribution 30 minutes after administration in a BT-12 an atypical teratoid/rhabdoid tumor (AT/RT) mouse model, FIG. 32D) H-NOX trimer distribution 60 minutes after administration in a BT-12 orthotopic AT/RT mouse model, and FIG. 32E) lack of H-NOX protein signal 30 minutes after vehicle administration in a BT-12 orthotopic AT/RT mouse model.

Figure 33:
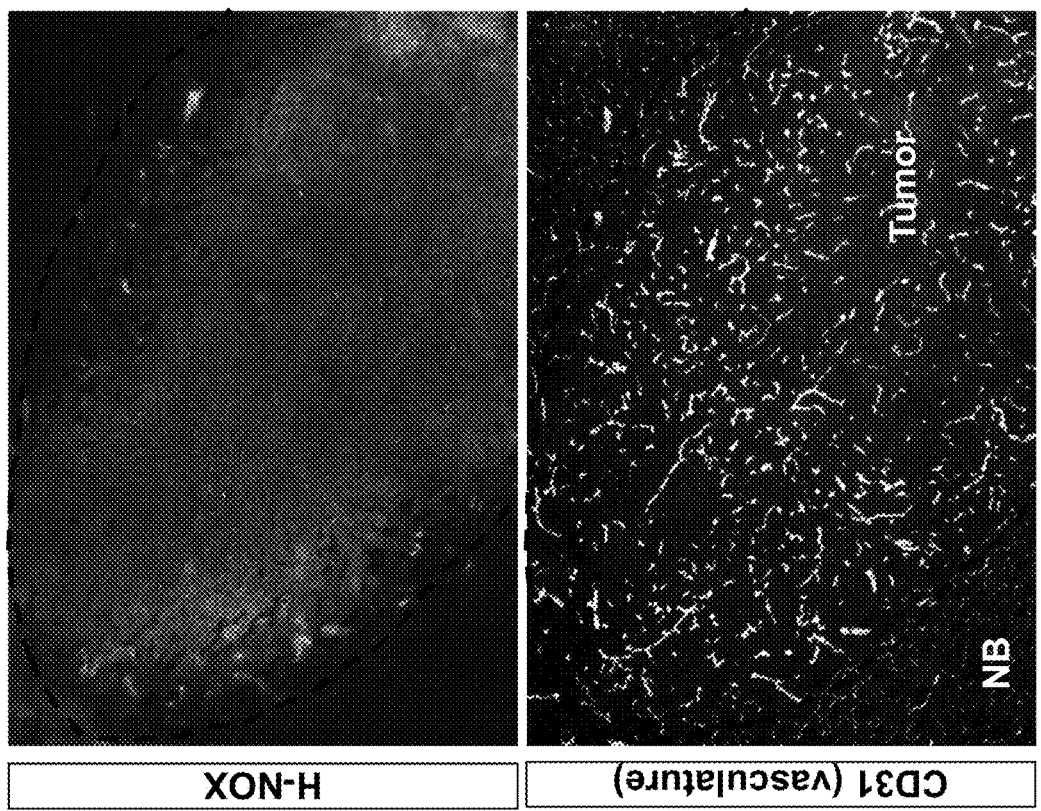

FIG. 33 is an immunofluorescence image showing escape of H-NOX trimer from the vasculature and diffusion throughout a U251 brain tumor in an orthotopic glioblastoma tumor mouse model. Tumor sections were stained with an anti-H-NOX antibody (top panel) and an anti-CD31 antibody (vasculature) (bottom panel).

Figure 34A:
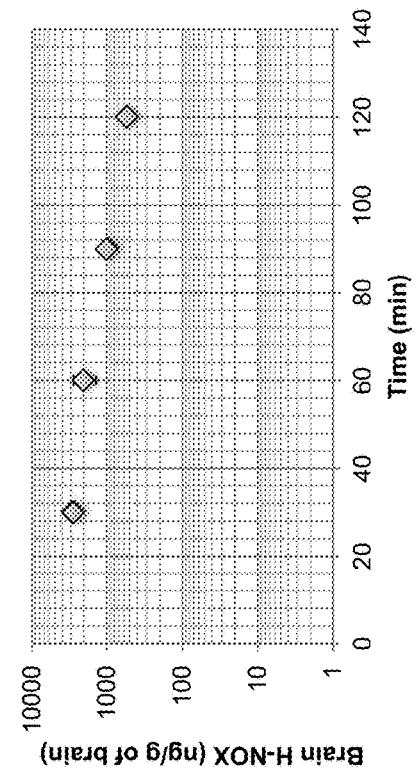
Figure 34B:
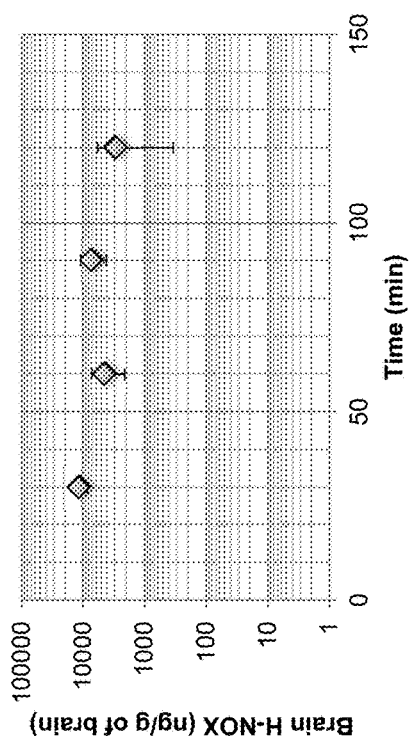
Figure 34C:
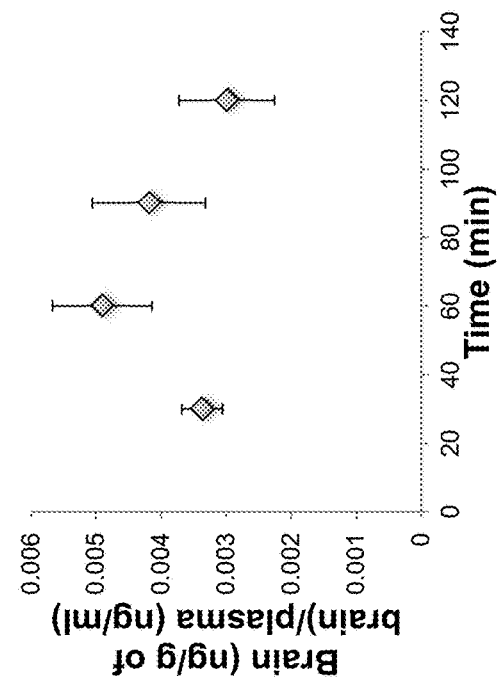
Figure 34D:
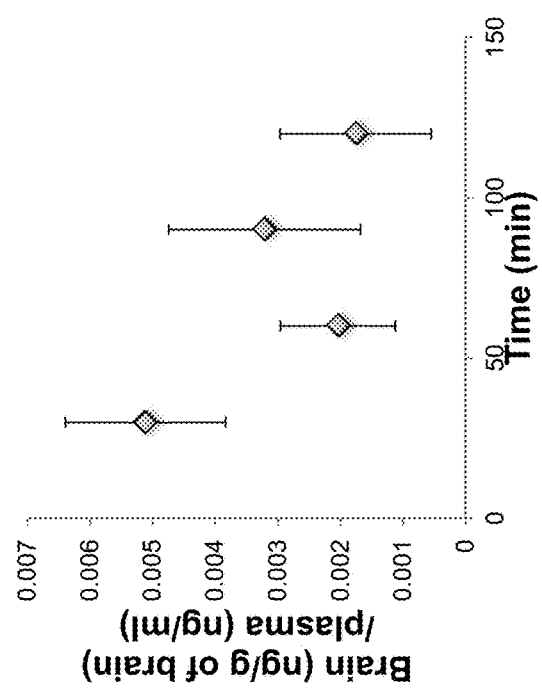

FIGS. 34A-34D show a sandwich ELISA assay of H-NOX trimer in the brain of healthy mice. FIG. 34A) ELISA assay on brain after intravenous injection of H-NOX trimer (750 mg/kg). FIG. 34B) ELISA assay on brain after intravenous injection of H-NOX trimer (200 mg/kg). FIG. 34C) Brain/plasma ratio of H-NOX trimer (750 mg/kg). FIG. 34D) Brain/plasma ratio of H-NOX trimer (200 mg/kg). Plasma and brain were collected at 30, 60, 90 and 120 min after H-NOX trimer administration. N=3, all groups. Mean values+/−SEM.

FIGS. 35A-35C are a series of graphs showing that H-NOX trimer sensitized intracranial xenografts to fractionated radiation therapy in a U251 mouse model of human glioblastoma. FIG. 35A) Mean bioluminescence imaging (BLI) scores+/−SEM from mice in both treatment groups, as well as an untreated control group (no H-NOX, no RT). N=9, all groups. FIG. 35B) Individual BLI scores for the RT and RT+H-NOX trimer groups on Day 29 (box in A). Line shows group mean, +\−SEM. The BLI scores of the RT+H-

NOX trimer mice were significantly lower than those from mice treated with RT alone (p=0.039, Student's t-test). FIG. 35C) H-NOX trimer group showed significantly enhanced survival, as compared to mice that received only radiotherapy (p=0.025, logrank test).

FIGS. 36A and 36B are a series of graphs showing that H-NOX trimer sensitized intracranial xenografts to fractionated radiation therapy in two mouse models of human glioblastoma. FIG. 36A) Percent survival in a U251 orthotopic glioblastoma mouse model administered 2 Gy radiation therapy (2 Gy), H-NOX trimer L144F variant (L144F Trimer), 2 Gy radiation therapy in combination with H-NOX trimer L144F variant (2 Gy+L144F Trimer), or treatment buffer (TB). Logrank p-values: 2 Gy versus 2 Gy+L144F Trimer (p=0.158), 2 Gy versus TB (p=0.0612), and L144F Trimer versus TB (p=0.326). FIG. 36B) Percent survival in a GBM43 orthotopic glioblastoma mouse model administered 2 Gy radiation therapy (2 Gy), 4 Gy radiation therapy (4 Gy), 8 Gy radiation therapy (8 Gy), 2 cycles of 4 Gy radiation therapy (4 Gy×2), 4 Gy radiation therapy in combination with H-NOX trimer (4 Gy+H-NOX), or treatment buffer (untreated). Logrank p-values: 4 Gy versus 4 Gy+H-NOX (p=0.597), 4 Gy versus 4 Gy×2 (p=0.038), and 4 Gy×2 versus 4 Gy+H-NOX (p=0.111).

FIGS. 37A-37G show the nucleic acid and amino acid sequences of H-NOX proteins. FIG. 37A) Wild-type *Thermoanaerobacter tengcongensis* H-NOX (SEQ ID NOs:1 and 2). FIG. 37B) Wildtype *Legionella pneumophilia* Orf2 H-NOX (SEQ ID NOs:13 and 14). FIG. 37C) Wildtype *Legionella pneumophilia* Orf1 H-NOX (SEQ ID NOs:15 and 16). FIG. 37D) *Homo sapiens* β1 (1-385) H-NOX (SEQ ID NOs:17 and 18). FIG. 37E) *Homo sapiens* β2 (1-217) H-NOX (SEQ ID NOs:19 and 20). FIG. 37F) *Rattus norvegicus* β1 H-NOX (SEQ ID NOs:21 and 22). FIG. 37G) *Rattus norvegicus* β2 H-NOX (SEQ ID NOs:23 and 24).

DETAILED DESCRIPTION OF THE INVENTION

The present invention is based in part on the surprising discovery that polymeric H-NOX proteins preferentially extravasate and accumulate in tissues such as the brain, thereby providing a longer oxygenation window and a longer circulation half-life compared to monomeric H-NOX proteins. A trimeric H-NOX protein comprising three H-NOX domains from *Thermoanaerobacter tengcongensis* and comprising a L144F mutation has been shown to be useful to deliver oxygen to hypoxic tumor tissue, such as glioblastoma tumor tissue, thereby enhancing radiation therapy of cancers. Accordingly, the present invention provides proteins, compositions, kits and methods for the delivery of oxygen; for example, as an adjuvant to radiation therapy.

Definitions

Unless defined otherwise, the meanings of all technical and scientific terms used herein are those commonly understood by one of skill in the art to which this invention belongs. One of skill in the art will also appreciate that any methods and materials similar or equivalent to those described herein can also be used to practice or test the invention.

For use herein, unless clearly indicated otherwise, use of the terms "a", "an," and the like refers to one or more.

In this application, the use of "or" means "and/or" unless expressly stated or understood by one skilled in the art. In the context of a multiple dependent claim, the use of "or" refers back to more than one preceding independent or dependent claim.

Reference to "about" a value or parameter herein includes (and describes) embodiments that are directed to that value or parameter per se. For example, description referring to "about X" includes description of "X."

It is understood that aspect and embodiments of the invention described herein include "comprising," "consisting," and "consisting essentially of" aspects and embodiments.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and polymers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification. As used herein, a protein may include two or more subunits, covalently or non-covalently associated; for example, a protein may include two or more associated monomers.

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

As used herein, an "H-NOX protein" means a protein that has an H-NOX domain (named for Heme-Nitric oxide and OXygen binding domain). An H-NOX protein may or may not contain one or more other domains in addition to the H-NOX domain. In some examples, an H-NOX protein does not comprise a guanylyl cyclase domain. An H-NOX protein may or may not comprise a polymerization domain.

As used herein, a "polymeric H-NOX protein" is an H-NOX protein comprising two or more H-NOX domains. The H-NOX domains may be covalently or non-covalently associated.

As used herein, an "H-NOX domain" is all or a portion of a protein that binds nitric oxide and/or oxygen by way of heme. The H-NOX domain may comprise heme or may be found as an apoproprotein that is capable of binding heme. In some examples, an H-NOX domain includes six alpha-helices, followed by two beta-strands, followed by one alpha-helix, followed by two beta strands. In some examples, an H-NOX domain corresponds to the H-NOX domain of *Thermoanaerobacter tengcongensis* H-NOX set forth in SEQ ID NO:2. For example, the H-NOX domain may be at least about 10%, 15%, 20%, 25%, 30%, 40%, 50%, 60%, 70%, 80%, 90%, 95%, or 99% identical to the H-NOX domain of *Thermoanaerobacter tengcongensis* H-NOX set forth in SEQ ID NO:2. In some embodiments, the H-NOX domain may be 10%-20%, 20%-30%, 30%-40%, 40%-50%, 50%-60%, 60%-70%, 70%-80%, 80%-

90%, 90%-95%, 95%-99% or 100% identical to the H-NOX domain of *Thermoanaerobacter tengcongensis* H-NOX set forth in SEQ ID NO:2.

As used herein, a "polymerization domain" is a domain (e.g. a polypeptide domain) that promotes the association of monomeric moieties to form a polymeric structure. For example, a polymerization domain may promote the association of monomeric H-NOX domains to generate a polymeric H-NOX protein. An exemplary polymerization domain is the foldon domain of T4 bacteriophage, which promotes the formation of trimeric polypeptides. Other examples of polymerization domains include, but are not limited to, Arc, POZ, coiled coil domains (including GCN4, leucine zippers, Velcro), uteroglobin, collagen, 3-stranded coiled colis (matrilin-1), thrombosporins, TRPV1-C, P53, Mnt, avadin, streptavidin, Bcr-Abl, COMP, verotoxin subunit B, CamKII, RCK, and domains from N ethylmaleimide-sensitive fusion protein, STM3548, KaiC, TyrR, Hcp1, CcmK4, GP41, anthrax protective antigen, aerolysin, a-hemolysin, C4b-binding protein, Mi-CK, arylsurfatase A, and viral capsid proteins.

As used herein, an "amino acid linker sequence" or an "amino acid spacer sequence" is a short polypeptide sequence that may be used to link two domains of a protein. In some embodiments, the amino acid linker sequence is one, two, three, four, five, six, seven, eight, nine, ten or more than ten amino acids in length. Exemplary amino acid linker sequences include but are not limited to a Gly-Ser-Gly sequence and an Arg-Gly-Ser sequence.

As used herein, a "His$_6$ tag" refers to a peptide comprising six His residues attached to a polypeptide. A His$_6$ tag may be used to facilitate protein purification; for example, using chromatography specific for the His$_6$ tag. Following purification, the His$_6$ tag may be cleaved using an exopeptidase.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

The phrase "substantially reduced," or "substantially different," as used herein, denotes a sufficiently high degree of difference between two numeric values such that one of skill in the art would consider the difference between the two values to be of statistical significance within the context of the biological characteristic measured by said values. In some embodiments, the two substantially different numeric values differ by greater than about any one of 10%, 20%, 25%, 30%, 35%, 40%, 45%, 50%, 60%, 70%, 80%, or 90%. In some embodiment, the two substantially different numeric values differ by about any one of 10%-20%, 20%-30%, 30%-40%, 40%-50%, 50%-60%, 60%-70%, 70%-80%, 80%-90%, 90%-95%, 95%-99% or 100%.

A "native sequence" polypeptide comprises a polypeptide having the same amino acid sequence as a polypeptide found in nature. Thus, a native sequence polypeptide can have the amino acid sequence of naturally occurring polypeptide from any organism. Such native sequence polypeptide can be isolated from nature or can be produced by recombinant or synthetic means. The term "native sequence" polypeptide specifically encompasses naturally occurring truncated or secreted forms of the polypeptide (e.g., an extracellular domain sequence), naturally occurring variant forms (e.g., alternatively spliced forms) and naturally occurring allelic variants of the polypeptide.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about any one of 80%, 90% or 95% amino acid sequence identity with the native sequence polypeptide. In some embodiments, a variant will have about any one of 80%-90%, 90%-95% or 95%-99% amino acid sequence identity with the native sequence polypeptide.

As used herein, a "mutant protein" means a protein with one or more mutations compared to a protein occurring in nature. In one embodiment, the mutant protein has a sequence that differs from that of all proteins occurring in nature. In various embodiments, the amino acid sequence of the mutant protein is at least about any of 10, 15, 20, 25, 30, 40, 50, 60, 70, 80, 90, 95, 97, 98, 99, or 99.5% identical to that of the corresponding region of a protein occurring in nature. In some embodiments, the amino acid sequence of the mutant protein is at least about any of 10%-20%, 20%-30%, 30%-40%, 40%-50%, 50%-60%, 60%-70%, 70%-80%, 80%-90%, 90%-95%, 95%-99% or 100% identical to that of the corresponding region of a protein occurring in nature. In some embodiments, the mutant protein is a protein fragment that contains at least about any of 25, 50, 75, 100, 150, 200, 300, or 400 contiguous amino acids from a full-length protein. In some embodiments, the mutant protein is a protein fragment that contains about any of 25-50, 50-75, 75-100, 100-150, 150-200, 200-300, or 300-400 contiguous amino acids from a full-length protein. Sequence identity can be measured, for example, using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various amino acids replacements, deletions, and other modifications.

As used herein, a "mutation" means an alteration in a reference nucleic acid or amino acid sequence occurring in nature. Exemplary nucleic acid mutations include an insertion, deletion, frameshift mutation, silent mutation, nonsense mutation, or missense mutation. In some embodiments, the nucleic acid mutation is not a silent mutation. Exemplary protein mutations include the insertion of one or more amino acids (e.g., the insertion of 2, 3, 4, 5, 6, 7, 8, 9, or 10 amino acids), the deletion of one or more amino acids (e.g., a deletion of N-terminal, C-terminal, and/or internal residues, such as the deletion of at least about any of 5, 10, 15, 25, 50, 75, 100, 150, 200, 300, or more amino acids or a deletion of about any of 5-10, 10-15, 15-25, 25-50, 50-75, 75-100, 100-150, 150-200, 200-300, or 300-400 amino acids), the replacement of one or more amino acids (e.g., the replacement of 1, 2, 3, 4, 5, 6, 7, 8, 9, or 10 amino acids), or combinations of two or more of the foregoing. The nomenclature used in referring to a particular amino acid mutation first identifies the wild-type amino acid, followed by the residue number and finally the substitute amino acid.

For example, Y140L means that tyrosine has been replaced by a leucine at residue number 140. Likewise, a variant H-NOX protein may be referred to by the amino acid variations of the H-NOX protein. For example, a *T. tengcongensis* Y140L H-NOX protein refers to a *T. tengcongensis* H-NOX protein in which the tyrosine residue at position number 140 has been replaced by a leucine residue and a *T. tengcongensis* W9F/Y140L H-NOX protein refers to a *T. tengcongensis* H-NOX protein in which the tryptophan residue at position 9 has been replaced by a phenylalanine residue and the tyrosine residue at position number 140 has been replaced by a leucine residue.

An "evolutionary conserved mutation" is the replacement of an amino acid in one protein by an amino acid in the corresponding position of another protein in the same protein family.

As used herein, "derived from" refers to the source of the protein into which one or more mutations is introduced. For example, a protein that is "derived from a mammalian protein" refers to protein of interest that results from introducing one or more mutations into the sequence of a wild-type (i.e., a sequence occurring in nature) mammalian protein.

As used herein, "Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

As used herein, a "$k_{off}$" refers to a dissociation rate, such as the rate of release of $O_2$ or NO from a protein. A lower numerical lower $k_{off}$ indicates a slower rate of dissociation.

As used herein, "$k_{on}$" refers to an association rate, such as the rate of binding of $O_2$ or NO to a protein. A lower numerical lower $k_{on}$ indicates a slower rate of association.

As used herein, "dissociation constant" refers to a "kinetic dissociation constant" or a "calculated dissociation constant." A "kinetic dissociation constant" or "$K_D$" is a ratio of kinetic off-rate ($k_{off}$) to kinetic on-rate ($k_{on}$), such as a $K_D$ value determined as an absolute value using standard methods (e.g., standard spectroscopic, stopped-flow, or flash-photolysis methods) including methods known to the skilled artisan and/or described herein. "Calculated dissociation constant" or "calculated $K_D$" refers to an approximation of the kinetic dissociation constant based on a measured $k_{off}$. A value for the $k_{on}$ is derived via the correlation between kinetic $K_D$ and $k_{off}$ as described herein.

As used herein, "oxygen affinity" is a qualitative term that refers to the strength of oxygen binding to the heme moiety of a protein. This affinity is affected by both the $k_{off}$ and $k_{on}$ for oxygen. A numerically lower oxygen $K_D$ value means a higher affinity.

As used herein, "NO affinity" is a qualitative term that refers to the strength of NO binding to a protein (such as binding to a heme group or to an oxygen bound to a heme group associated with a protein). This affinity is affected by both the $k_{off}$ and $k_{on}$ for NO. A numerically lower NO $K_D$ value means a higher affinity.

As used herein, "NO stability" refers to the stability or resistance of a protein to oxidation by NO in the presence of oxygen. For example, the ability of the protein to not be oxidized when bound to NO in the presence of oxygen is indicative of the protein's NO stability. In some embodiments, less than about any of 50, 40, 30, 10, or 5% of an H-NOX protein is oxidized after incubation for about any of 1, 2, 4, 6, 8, 10, 15, or 20 hours at 20° C.

As used herein, "NO reactivity" refers to the rate at which iron in the heme of a heme-binding protein is oxidized by NO in the presence of oxygen. A lower numerical value for NO reactivity in units of $s^{-1}$ indicates a lower NO reactivity As used herein, an "autoxidation rate" refers to the rate at which iron in the heme of a heme-binding protein is autoxidized. A lower numerical autoxidation rate in units of $s^{-1}$ indicates a lower autoxidation rate.

The term "vector" is used to describe a polynucleotide that may be engineered to contain a cloned polynucleotide or polynucleotides that may be propagated in a host cell. A vector may include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Exemplary prokaryotic cells include bacterial cells; for example, *E. coli* cells.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated".

The terms "individual" or "subject" are used interchangeably herein to refer to an animal; for example a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder.

A "disease" or "disorder" as used herein refers to a condition where treatment is needed.

The term "cancer" refers to a malignant proliferative disorder associated with uncontrolled cell proliferation, unrestrained cell growth, and decreased cell death via apoptosis.

The term "tumor" is used herein to refer to a group of cells that exhibit abnormally high levels of proliferation and growth. A tumor may be benign, pre-malignant, or malignant; malignant tumor cells are cancerous. Tumor cells may be solid tumor cells or leukemic tumor cells. The term "tumor growth" is used herein to refer to proliferation or growth by a cell or cells that comprise a tumor that leads to a corresponding increase in the size of the tumor.

As used herein, "treatment" is an approach for obtaining beneficial or desired clinical results. "Treatment" as used herein, covers any administration or application of a therapeutic for disease in a mammal, including a human. For purposes of this invention, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods of the invention contemplate any one or more of these aspects of treatment.

In the context of cancer, the term "treating" includes any or all of: inhibiting growth of tumor cells or cancer cells, inhibiting replication of tumor cells or cancer cells, lessening of overall tumor burden and ameliorating one or more symptoms associated with the disease.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In certain embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or 99%.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased on non-treated sample of a subject individual. In some examples, a reference is obtained from one or more healthy individuals who are not the subject or patient.

"Preventing," as used herein, includes providing prophylaxis with respect to the occurrence or recurrence of a disease in a subject that may be predisposed to the disease but has not yet been diagnosed with the disease.

An "effective amount" of an agent refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile and essentially free of endotoxins.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about 60 minutes, such as no more than about any of 30, 15, 10, 5, or 1 minutes.

The term "sequentially" is used herein to refer to administration of two or more therapeutic agents where the administration of one or more agent(s) continues after discontinuing the administration of one or more other agent(s). For example, administration of the two or more therapeutic agents are administered with a time separation of more than about 15 minutes, such as about any of 20, 30, 40, 50, or 60 minutes, 1 day, 2 days, 3 days, 1 week, 2 weeks, or 1 month.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In certain embodiments, the manufacture or kit is promoted, distributed, or sold as a unit for performing the methods described herein.

H-NOX Proteins

Overview of H-NOX Protein Family

Unless otherwise indicated, any wild-type or mutant H-NOX protein can be used in the compositions, kits, and methods as described herein. As used herein, an "H-NOX protein" means a protein that has an H-NOX domain (named for Heme-Nitric oxide and OXygen binding domain). An H-NOX protein may or may not contain one or more other domains in addition to the H-NOX domain. H-NOX proteins are members of a highly-conserved, well-characterized family of hemoproteins (Iyer, L. M. et al. (Feb. 3, 2003). *BMC Genomics* 4(1):5; Karow, D. S. et al. (Aug. 10, 2004). *Biochemistry* 43(31):10203-10211; Boon, E. M. et al. (2005). *Nature Chem. Biol.* 1:53-59; Boon, E. M. et al. (October 2005). *Curr. Opin. Chem. Biol.* 9(5):441-446; Boon, E. M. et al. (2005). *J. Inorg. Biochem.* 99(4):892-902). H-NOX proteins are also referred to as Pfam 07700 proteins or HNOB proteins (Pfam—A database of protein domain family alignments and Hidden Markov Models, Copyright (C) 1996-2006 The Pfam Consortium; GNU LGPL Free Software Foundation, Inc., 59 Temple Place— Suite 330, Boston, Mass. 02111-1307, USA). In some embodiments, an H-NOX protein has, or is predicted to have, a secondary structure that includes six alpha-helices, followed by two beta-strands, followed by one alpha-helix, followed by two beta-strands. An H-NOX protein can be an apoprotein that is capable of binding heme or a holoprotein with heme bound. An H-NOX protein can covalently or non-covalently bind a heme group. Some H-NOX proteins bind NO but not $O_2$, and others bind both NO and $O_2$. H-NOX domains from facultative aerobes that have been isolated bind NO but not $O_2$. H-NOX proteins from obligate aerobic prokaryotes, *C. elegans*, and *D. melanogaster* bind NO and $O_2$. Mammals have two H-NOX proteins: β1 and β2. An alignment of mouse, rat, cow, and human H-NOX sequences shows that these species share >99% identity. In some embodiments, the H-NOX domain of an H-NOX protein or the entire H-NOX protein is at least about any of 10, 15, 20, 25, 30, 40, 50, 60, 70, 80, 90, 95, 97, 98, 99, or 99.5% identical to that of the corresponding region of a naturally-occurring *Thermoanaerobacter tengcongensis* H-NOX protein (e.g. SEQ ID NO:2) or a naturally-occurring sGC protein (e.g., a naturally-occurring sGC β1 protein). In some embodiments, the H-NOX domain of an H-NOX protein or the entire H-NOX protein is at least about any of 10-20%, 20-30%, 30-40%, 40-50%, 50-60%, 60-70%, 70-80%, 80-90%, 90-95%, 95-99, or 99-99.9% identical to that of the corresponding region of a naturally-occurring *Thermoanaerobacter tengcongensis* H-NOX protein (e.g. SEQ ID NO:2) or a naturally-occurring sGC protein (e.g., a naturally-occurring sGC β1 protein). As discussed further herein, an H-NOX protein may optionally contain one or more mutations relative to the corresponding naturally-occurring H-NOX protein. In some embodiments, the H-NOX protein includes one or more domains in addition to the H-NOX domain. In particular embodiments, the H-NOX protein includes one or more domains or the entire sequence from another protein. For example, the H-NOX protein may be a fusion protein that includes an H-NOX domain and part or all of another protein, such as albumin (e.g., human serum albumin). In some embodiments, only the H-NOX domain is present. In some embodiments, the H-NOX protein does not comprise a guanylyl cyclase domain. In some embodiments, the H-NOX protein comprises a tag; for example, a $His_6$ tag.

Polymeric H-NOX Proteins

In some aspects, the invention provides polymeric H-NOX proteins comprising two or more H-NOX domains. The two or more H-NOX domains may be covalently linked or noncovalently linked. In some embodiments, the polymeric H-NOX protein is in the form of a dimer, a trimer, a tetramer, a pentamer, a hexamer, a heptamer, an octomer, a nanomer, or a decamer. In some embodiments, the polymeric H-NOX protein comprises homologous H-NOX domains. In some embodiments, the polymeric H-NOX protein comprises heterologous H-NOX domains; for example, the H-NOX domains may comprises amino acid variants of a particular species of H-NOX domain or may comprise H-NOX domains from different species. In some embodiments, at least one of the H-NOX domains of a polymeric H-NOX protein comprises a mutation corresponding to an L144F mutation of *T. tengcongensis* H-NOX. In some embodiments, at least one of the H-NOX domains of a polymeric H-NOX protein comprises a mutation corresponding to a W9F/L144F mutation of *T. tengcongensis* H-NOX. In some embodiments, the polymeric H-NOX proteins comprise one or more polymerization domains. In some embodiments, the polymeric H-NOX protein is a trimeric H-NOX protein. In some embodiments, the polymeric H-NOX protein comprises at least one trimerization domain. In some embodiments, the trimeric H-NOX protein comprises three *T. tengcongensis* H-NOX domains. In some embodiments the trimeric H-NOX domain comprises three *T. tengcongensis* L144F H-NOX domains. In some embodiments the trimeric H-NOX domain comprises three *T. tengcongensis* W9F/L144F H-NOX domains In some aspects of the invention, the polymeric H-NOX protein comprises two or more associated monomers. The monomers may be covalently linked or noncovalently linked. In some embodiments, monomeric subunits of a polymeric H-NOX protein are produced where the monomeric subunits associate in vitro or in vivo to form the polymeric H-NOX protein. In some embodiments, the monomers comprise an H-NOX domain and a polymerization domain. In some embodiments, the polymerization domain is covalently linked to the H-NOX domain; for example, the C-terminus of the H-NOX domain is covalently linked to the N-terminus or the C-terminus of the polymerization domain. In other embodiments, the N-terminus of the H-NOX domain is covalently linked to the N-terminus or the C-terminus of the polymerization domain. In some embodiments, an amino acid spacer is covalently linked between the H-NOX domain and the polymerization domain. An "amino acid spacer" and an "amino acid linker" are used interchangeably herein. In some embodiments, at least one of the monomeric subunits of a polymeric H-NOX protein comprises a mutation corresponding to an L144F mutation of *T. tengcongensis* H-NOX. In some embodiments, at least one of the monomeric subunits of a polymeric H-NOX protein comprises a mutation corresponding to a W9F/L144F mutation of *T. tengcongensis* H-NOX. In some embodiments the polymeric H-NOX protein is a trimeric H-NOX protein. In some embodiments, the monomer of a trimeric H-NOX protein comprises an H-NOX domain and a foldon domain of T4 bacteriophage. In some embodiments, the monomer of a trimeric H-NOX protein comprises a *T. tengcongensis* H-NOX domain and a foldon domain. In some embodiments, the monomer of a trimeric H-NOX protein comprises a *T. tengcongensis* L144F H-NOX domain and a foldon domain. In some embodiments, the monomer of a trimeric H-NOX protein comprises a *T. tengcongensis* W9F/L144F H-NOX domain and a foldon domain. In some embodiments, the trimer H-NOX protein comprises three monomers, each monomer comprising a *T. tengcongensis* L144F H-NOX domain and a foldon domain. In some embodiments, the H-NOX domain is linked to the foldon domain with an amino acid linker; for example a Gly-Ser-Gly linker. In some embodiments, at least one H-NOX domain comprises a tag. In some embodiments, at least one H-NOX domain comprises a $His_6$ tag. In some embodiments, the $His_6$ tag is linked to the foldon domain with an amino acid linker; for example an Arg-Gly-Ser linker. In some embodiments, all of the H-NOX domains comprise a $His_6$ tag. In some embodiments, the trimeric H-NOX protein comprises the amino acid sequence set forth in SEQ ID NO:6, SEQ ID NO:8, SEQ ID NO:10, SEQ ID NO:12, SEQ ID NO:26 or SEQ ID NO:28.

The exemplary H-NOX domain from *T. tengcongensis* is approximately 26.7 kDal. In some embodiments, the polymeric H-NOX protein has an atomic mass greater than any of about 50 kDal, 75 kDal, 100 kDal, 125 kDal, to about 150 kDal.

The invention provides polymeric H-NOX proteins that show greater accumulation in one or more tissues in an individual compared to a corresponding monomeric H-NOX protein comprising a single H-NOX domain following administration of the H-NOX protein to the individual. A corresponding H-NOX protein refers to a monomeric form of the H-NOX protein comprising at least one of the H-NOX domains of the polymeric H-NOX protein. Tissues of preferential polymeric H-NOX accumulation include, but are not limited to tumors and tissue with damaged vasculature. In some embodiments the polymeric H-NOX protein persists in a mammal for at least about 1, 2, 3, 4, 6, 12 or 24 hours following administration of the H-NOX protein to the individual. In some embodiments the polymeric H-NOX protein persists in a mammal for about 1-2, 2-3, 3-4, 4-6, 6-12 or 12-24 hours following administration of the H-NOX protein to the individual. In some embodiments, less than about 10% of the polymeric H-NOX is cleared from mammal by the kidneys within less than any of about 1 hour, 2 hours or 3 hours following administration of the H-NOX protein to the individual.

Sources of H-NOX Proteins and H-NOX Domains

H-NOX proteins and H-NOX domains from any genus or species can be used in the compositions, kits, and methods described herein. In various embodiments, the H-NOX protein or the H-NOX domains of a polymeric H-NOX protein is a protein or domain from a mammal (e.g., a primate (e.g., human, monkey, gorilla, ape, lemur, etc), a bovine, an equine, a porcine, a canine, or a feline), an insect, a yeast, or a bacteria or is derived from such a protein. Exemplary mammalian H-NOX proteins include wild-type human and rat soluble guanylate cyclase (such as the 131 subunit). Examples of H-NOX proteins include wild-type mammalian H-NOX proteins, e.g. *H. sapiens, M. musculus, C. familiaris, B. Taurus, C. lupus* and *R. norvegicus*; and wild-type non-mammalian vertebrate H-NOX proteins, e.g., *X. laevis, O. latipes, O. curivatus,* and *F. rubripes*. Examples of non-mammalian wild-type NO-binding H-NOX proteins include wild-type H-NOX proteins of *D. melanogaster, A. gambiae*, and *M. sexta*; examples of non-mammalian wild-type $O_2$-binding H-NOX proteins include wild-type H-NOX proteins of *C. elegans* gcy-31, gcy-32, gcy-33, gcy-34, gcy-35, gcy-36, and gcy-37; *D. melanogaster* CG14885, CG14886, and CG4154; and *M. sexta* beta-3; examples of prokaryotic wild-type H-NOX proteins include *T. tengcongensis, V. cholera, V. fischerii, N. punctiforme, D. desulfuricans, L. pneumophila* 1, *L. pneumophila* 2, and *C. acetobutylicum*.

NCBI Accession numbers for exemplary H-NOX proteins include the following: *Homo sapiens* β1 [gi:2746083], *Rattus norvegicus* β1 [gi:27127318], *Drosophila melanogaster* β1 [gi:861203], *Drosophila melanogaster* CG14885-PA [gi: 23171476], *Caenorhabditis elegans* GCY-35 [gi:52782806], *Nostoc punctiforme* [gi:23129606], *Caulobacter crescentus* [gi:16127222], *Shewanella oneidensis* [gi:24373702], *Legionella pneumophila* (ORF 2) [CUCGC_272624], *Clostridium acetobutylicum* [gi:15896488], and *Thermoanaerobacter tengcongensis* [gi:20807169]. *Canis lupus* H-NOX is provided by GenBank accession DQ008576. Nucleic acid and amino acid sequences of exemplary H-NOX proteins and domains are provided in FIGS. 37A-37G.

Exemplary H-NOX protein also include the following H-NOX proteins that are listed by their gene name, followed by their species abbreviation and Genbank Identifiers (such as the following protein sequences available as of May 21, 2006; May 22, 2006; May 21, 2007; or May 22, 2007, which are each hereby incorporated by reference in their entireties): Npun5905_Npu 23129606, alr2278_Ana_17229770, SO2144_Sone_24373702, Mdeg1343_Mde_23027521, VCA0720_Vch_15601476, CC2992_Ccr_16127222, Rsph2043_Rhsp_22958463 (gi:46192757), Mmc10739_Mcsp_22999020, Tar4_Tte_20807169, Ddes2822_Dde_23475919, CAC3243_Cac_15896488, gcy-31_Ce_17568389, CG14885_Dm_24647455, GUCY1B3_Hs_4504215, HpGCS-beta1_Hpul_14245738, Gycbeta100B_Dm_24651577, CG4154_Dm_24646993 (gi: NP_650424.2, gi:62484298), gcy-32_Ce_13539160, gcy-36_Ce_17568391 (gi:32566352, gi:86564713), gcy-35_Ce-17507861 (gi:71990146), gcy-37_Ce_17540904 (gi: 71985505), GCY1a3_Hs_20535603, GCY1a2-Hs_899477, or GYCa-99B_Dm_729270 (gi:68067738) (Lakshminarayan et al. (2003). *BMG Genomics* 4:5-13). The species abbreviations used in these names include Ana—*Anabaena* Sp; Ccr—*Caulobacter crescentus*; Cac—*Clostridium acetobutylicum*; Dde—*Desulfovibrio desulfuricans*; Mcsp—*Magnetococcus* sp.; Mde—*Microbulbifer degradans*; Npu—*Nostoc punctiforme*; Rhsp—*Rhodobacter sphaeroides*; Sone—*Shewanella oneidensis*; Tte—*Thermoanaerobacter tengcongensis*; Vch—*Vibrio cholerae*; Ce—*Caenorhabditis elegans*; Dm—*Drosophila melanogaster*; Hpul—*Hemicentrotus pulcherrimus*; Hs—*Homo sapiens*.

Other exemplary H-NOX proteins include the following H-NOX proteins that are listed by their organism name and Pfam database accession number (such as the following protein sequences available as of May 21, 2006; May 22, 2006; May 17, 2007; May 21, 2007; or May 22, 2007, which are each hereby incorporated by reference in their entireties): Caenorhabditis briggsae Q622M5_CAEBR, Caenorhabditis briggsae Q61P44_CAEBR, Caenorhabditis briggsae Q61R54_CAEBR, Caenorhabditis briggsae Q61V90_CAEBR, Caenorhabditis briggsae Q61A94_CAEBR, Caenorhabditis briggsae Q60TP4_CAEBR, Caenorhabditis briggsae Q60M10_CAEBR, Caenorhabditis elegans GCY37_CAEEL, Caenorhabditis elegans GCY31_CAEEL, Caenorhabditis elegans GCY36_CAEEL, Caenorhabditis elegans GCY32_CAEEL, Caenorhabditis elegans GCY35_CAEEL, Caenorhabditis elegans GCY34_CAEEL, Caenorhabditis elegans GCY33_CAEEL, Oryzias curvinotus Q7T040_ORYCU, Oryzias curvinotus Q75WF0_ORYCU, Oryzias latipes P79998_ORYLA, Oryzias latipes Q7ZSZ5_ORYLA, Tetraodon nigroviridis Q4SW38_TETNG, Tetraodon nigroviridis Q4RZ94_TETNG, Tetraodon nigroviridis Q4S6K5_TETNG, Fugu rubripes Q90VY5_FUGRU, Xenopus laevis Q6INK9_XENLA, Homo sapiens Q5T8J7_HUMAN, Homo sapiens GCYA2_HUMAN, Homo sapiens GCYB2_HUMAN, Homo sapiens GCYB1 HUMAN, Gorilla gorilla Q9N193_9PRIM, Pongo pygmaeus Q5RAN8_PONPY, Pan troglodytes Q9N192_PANTR, Macaca mulatta Q9N194_MACMU, Hylobates lar Q9N191_HYLLA, Mus musculus Q8BXH3_MOUSE, Mus musculus GCYB1_MOUSE, Mus musculus Q3UTI4_MOUSE, Mus musculus Q3UH83_MOUSE, Mus musculus Q6XE41_MOUSE, Mus musculus Q80YP4_MOUSE, Rattus norvegicus Q80WX7_RAT, Rattus norvegicus Q80WX8_RAT, Rattus norvegicus Q920Q1_RAT, Rattus norvegicus Q54A43_RAT, Rattus norvegicus Q80WY0_RAT, Rattus norvegicus Q80WY4_RAT, Rattus norvegicus Q8CH85_RAT, Rattus norvegicus Q80WY5_RAT, Rattus norvegicus GCYB1_RAT, Rattus norvegicus Q8CH90_RAT, Rattus norvegicus Q91XJ7_RAT, Rattus norvegicus Q80WX9_RAT, Rattus norvegicus GCYB2_RAT, Rattus norvegicus GCYA2_RAT, Canis familiaris Q4ZHR9_CANFA, Bos taurus GCYB1_BOVIN, Sus scrofa Q4ZHR7_PIG, Gryllus bimaculatus Q59HN5_GRYBI, Manduca sexta O77106_MANSE, Manduca sexta O76340_MANSE, Apis mellifera Q5UAF0_APIME, Apis mellifera Q5FAN0_APIME, Apis mellifera Q6L5L6 APIME, Anopheles gambiae str PEST Q7PYK9_ANOGA, Anopheles gambiae str PEST Q7Q9W6_ANOGA, Anopheles gambiae str PEST Q7QF31_ANOGA, Anopheles gambiae str PEST Q7PS01_ANOGA, Anopheles gambiae str PEST Q7PFY2_ANOGA, Anopheles gambiae Q7KQ93_ANOGA, Drosophila melanogaster Q24086_DROME, Drosophila melanogaster GCYH_DROME, Drosophila melanogaster GCY8E_DROME, Drosophila melanogaster GCYDA_DROME, Drosophila melanogaster GCYDB_DROME, Drosophila melanogaster Q9VA09_DROME, Drosophila pseudoobscura Q29CE1_DROPS, Drosophila pseudoobscura Q296C7_DROPS, Drosophila pseudoobscura Q296C8_DROPS, Drosophila pseudoobscura Q29BU7_DROPS, Aplysia californica Q7YWK7_APLCA, Hemicentrotus pulcherrimus Q95NK5_HEMPU, Chlamydomonas reinhardtii, Q5YLC2_CHLRE, Anabaena sp Q8YUQ7_ANASP, Flavobacteria bacterium BBFL7 Q26GR8_9BACT, Psychroflexus torquis ATCC 700755 Q1VQE5_9FLAO, marine gamma proteobacterium HTCC2207 Q1YPJ5_9GAMM, marine gamma proteobacterium HTCC2207 Q1YTK4_9GAMM, Caulobacter crescentus Q9A451_CAUCR, Acidiphilium cryptum JF-5 Q2DG60_ACICY, Rhodobacter sphaeroides Q3J0U9_RHOS4, Silicibacter pomeroyi Q5LPV1_SILPO, Paracoccus denitrificans PD1222, Q3PC67_PARDE, Silicibacter sp TM1040 Q3QNY2_9RHOB, Jannaschia sp Q28ML8_JANSC, Magnetococcus sp MC-1 Q3XT27_9PROT, Legionella pneumophila Q5WXP0_LEGPL, Legionella pneumophila Q5WTZ5_LEGPL, Legionella pneumophila Q5X268_LEGPA, Legionella pneumophila Q5X2R2_LEGPA, Legionella pneumophila subsp pneumophila Q5ZWM9_LEGPH, Legionella pneumophila subsp pneumophila Q5ZSQ8_LEGPH, Colwellia psychrerythraea Q47Y43_COLP3, Pseudoalteromonas atlantica T6c Q3CSZ5_ALTAT, Shewanella oneidensis Q8EF49_SHEON, Saccharophagus degradans Q21E20_SACD2, Saccharophagus degradans Q21ER7_SACD2, Vibrio angustum S14 Q1ZWE5_9 VIBR, Vibrio vulnificus Q8DAE2_VIBVU, Vibrio alginolyticus 12G01 Q1VCP6_VIBAL, Vibrio sp DAT722 Q2FA22_9VIBR, Vibrio parahaemolyticus Q87NJ1_VIBPA, Vibrio fischeri Q5E1F5_VIBF1, Vibrio vulnificus Q7MJS8_VIBVY, Photobacterium sp SKA34 Q2C6Z5_9GAMM, Hahella chejuensis Q2SFY7_HAHCH, Oceanospirillum sp MED92 Q2BKV0_9GAMM, Oceanobacter sp RED65 Q1N035_9GAMM, Desulfovibrio desulfuricans Q310U7 DESDG, Halothermothrix orenii H 168 Q2AIW5_9FIRM, Thermoanaerobacter tengcongensis Q8RBX6_THETN, Caldicellulosiruptor saccharolyticus DSM 8903 Q2ZH17_CALSA, Clostridium acetobutylicum Q97E73_CLOAB, Alkaliphilus metalliredigenes QYMF Q3C763_9CLOT, Clostridium tetani Q899J9_CLOTE, and Clostridium beijerincki NCIMB 8052 Q2WVN0_CLOBE. These sequences are predicted to encode H-NOX proteins based on the identification of these proteins as belonging to the H-NOX protein family using the Pfam database as described herein.

Additional H-NOX proteins, H-NOX domains of polymeric H-NOX proteins, and nucleic acids, which may be suitable for use in the pharmaceutical compositions and methods described herein, can be identified using standard methods. For example, standard sequence alignment and/or structure prediction programs can be used to identify additional H-NOX proteins and nucleic acids based on the similarity of their primary and/or predicted protein secondary structure with that of known H-NOX proteins and nucleic acids. For example, the Pfam database uses defined alignment algorithms and Hidden Markov Models (such as Pfam 21.0) to categorize proteins into families, such as the H-NOX protein family (Pfam—A database of protein domain family alignments and Hidden Markov Models, Copyright (C) 1996-2006 The Pfam Consortium; GNU LGPL Free Software Foundation, Inc., 59 Temple Place—Suite 330, Boston, Mass. 02111-1307, USA). Standard databases such as the swissprot-trembl database (world-wide web at "expasy.org", Swiss Institute of Bioinformatics Swiss-Prot group CMU—1 rue Michel Servet CH-1211 Geneva 4, Switzerland) can also be used to identify members of the H-NOX protein family. The secondary and/or tertiary structure of an H-NOX protein can be predicted using the default settings of standard structure prediction programs, such as PredictProtein (630 West, 168 Street, BB217, New York, N.Y. 10032, USA). Alternatively, the actual secondary and/or tertiary structure of an H-NOX protein can be determined using standard methods.

In some embodiments, the H-NOX domain has the same amino acid in the corresponding position as any of following distal pocket residues in *T. tengcongensis* H-NOX: Thr4, Ile5, Thr8, Trp9, Trp67, Asn74, Ile75, Phe78, Phe82, Tyr140, Leu144, or any combination of two or more of the foregoing. In some embodiments, the H-NOX domain has a proline or an arginine in a position corresponding to that of Pro115 or Arg135 of *T. tengcongensis* H-NOX, respectively, based on sequence alignment of their amino acid sequences. In some embodiments, the H-NOX domain has a histidine that corresponds to His105 of *R. norvegicus* β1 H-NOX. In some embodiments, the H-NOX domain has or is predicted to have a secondary structure that includes six alpha-helices, followed by two beta-strands, followed by one alpha-helix, followed by two beta-strands. This secondary structure has been reported for H-NOX proteins.

If desired, a newly identified H-NOX protein or H-NOX domain can be tested to determine whether it binds heme using standard methods. The ability of an H-NOX domain to function as an $O_2$ carrier can be tested by determining whether the H-NOX domain binds $O_2$ using standard methods, such as those described herein. If desired, one or more of the mutations described herein can be introduced into the H-NOX domain to optimize its characteristics as an $O_2$ carrier. For example, one or more mutations can be introduced to alter its $O_2$ dissociation constant, $k_{off}$ for oxygen, rate of heme autoxidation, NO reactivity, NO stability or any combination of two or more of the foregoing. Standard techniques such as those described herein can be used to measure these parameters.

Mutant H-NOX Proteins

As discussed further herein, an H-NOX protein or an H-NOX domain of a polymeric H-NOX protein may contain one or more mutations, such as a mutation that alters the $O_2$ dissociation constant, the $k_{off}$ for oxygen, the rate of heme autoxidation, the NO reactivity, the NO stability, or any combination of two or more of the foregoing compared to that of the corresponding wild-type protein. In some embodiments, the invention provides a polymeric H-NOX protein comprising one or more H-NOX domains that may contain one or more mutations, such as a mutation that alters the $O_2$ dissociation constant, the $k_{off}$ for oxygen, the rate of heme autoxidation, the NO reactivity, the NO stability, or any combination of two or more of the foregoing compared to that of the corresponding wild-type protein. Panels of engineered H-NOX domains may be generated by random mutagenesis followed by empirical screening for requisite or desired dissociation constants, dissociation rates, NO-reactivity, stability, physio-compatibility, or any combination of two or more of the foregoing in view of the teaching provided herein using techniques as described herein and, additionally, as known by the skilled artisan. Alternatively, mutagenesis can be selectively targeted to particular regions or residues such as distal pocket residues apparent from the experimentally determined or predicted three-dimensional structure of an H-NOX protein (see, for example, Boon, E. M. et al. (2005). *Nature Chemical Biology* 1:53-59, which is hereby incorporated by reference in its entirety, particularly with respect to the sequences of wild-type and mutant H-NOX proteins) or evolutionarily conserved residues identified from sequence alignments (see, for example, Boon E. M. et al. (2005). *Nature Chemical Biology* 1:53-59, which is hereby incorporated by reference in its entirety, particularly with respect to the sequences of wild-type and mutant H-NOX proteins).

In some embodiments of the invention, the mutant H-NOX protein or mutant H-NOX domain of a polymeric H-NOX protein has a sequence that differs from that of all H-NOX proteins or domains occurring in nature. In various embodiments, the amino acid sequence of the mutant protein is at least about any of 10, 15, 20, 25, 30, 40, 50, 60, 70, 80, 90, 95, 97, 98, 99, or 99.5% identical to that of the corresponding region of an H-NOX protein occurring in nature. In various embodiments, the amino acid sequence of the mutant protein is about 10-20%, 20-30%, 30-40%, 40-50%, 50-60%, 60-70%, 70-80%, 80-90%, 90-95%, 95-99%, or 99.5% identical to that of the corresponding region of an H-NOX protein occurring in nature. In some embodiments, the mutant protein is a protein fragment that contains at least about any of 25, 50, 75, 100, 150, 200, 300, or 400 contiguous amino acids from a full-length protein. In some embodiments, the mutant protein is a protein fragment that contains 25-50, 50-75, 75-100, 100-150, 150-200, 200-300, or 300-400 contiguous amino acids from a full-length protein. Sequence identity can be measured, for example, using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various amino acids replacements, deletions, and other modifications.

In some embodiments of the invention, the mutant H-NOX protein or mutant H-NOX domain of a polymeric H-NOX protein comprises the insertion of one or more amino acids (e.g., the insertion of 2, 3, 4, 5, 6, 7, 8, 9, or 10 amino acids). In some embodiments of the invention, the mutant H-NOX protein or mutant H-NOX domain comprises the deletion of one or more amino acids (e.g., a deletion of N-terminal, C-terminal, and/or internal residues, such as the deletion of at least about any of 5, 10, 15, 25, 50, 75, 100, 150, 200, 300, or more amino acids or a deletion of 5-10, 10-15, 15-25, 25-50, 50-75, 75-100, 100-150, 150-200, 200-300, or 300-400 amino acids). In some embodiments of the invention, the mutant H-NOX protein or mutant H-NOX domain comprises the replacement of one or more amino acids (e.g., the replacement of 1, 2, 3, 4, 5, 6, 7, 8, 9, or 10 amino acids), or combinations of two or more of the foregoing. In some embodiments, a mutant protein has at least one amino acid alteration compared to a protein occurring in nature. In some embodiments, a mutant nucleic acid sequence encodes a protein that has at least one amino acid alteration compared to a protein occurring in nature. In some embodiments, the nucleic acid is not a degenerate version of a nucleic acid occurring in nature that encodes a protein with an amino acid sequence identical to a protein occurring in nature.

In some embodiments the mutation in the H-NOX protein or H-NOX domain of a polymeric H-NOX protein is an evolutionary conserved mutations (also denoted class I mutations). Examples of class I mutations are listed in Table 1A. In Table 1A, mutations are numbered/annotated according to the sequence of human β1 H-NOX, but are analogous for all H-NOX sequences. Thus, the corresponding position in any other H-NOX protein can be mutated to the indicated residue. For example, Phe4 of human β1 H-NOX can be mutated to a tyrosine since other H-NOX proteins have a tyrosine in this position. The corresponding phenylalanine residue can be mutated to a tyrosine in any other H-NOX protein. In particular embodiments, the one or more mutations are confined to evolutionarily conserved residues. In some embodiments, the one or more mutations may include at least one evolutionarily conserved mutation and at least one non-evolutionarily conserved mutation. If desired, these mutant H-NOX proteins are subjected to empirical screening for NO/O$_2$ dissociation constants, NO-reactivity, stability, and physio-compatibility in view of the teaching provided herein.

TABLE IA

Exemplary Class I H-NOX mutations targeting evolutionary conserved residues

| | | |
|---|---|---|
| F4Y | Q30G | I145Y |
| F4L | E33P | I145H |
| H7G | N61G | K151E |
| A8E | C78H | I157F |
| L9W | A109F | E183F |

In some embodiments, the mutation is a distal pocket mutation, such as mutation of a residue in alpha-helix A, D, E, or G (Pellicena, P. et al. (Aug. 31, 2004). *Proc Natl. Acad Sci USA* 101(35):12854-12859). Exemplary distal pocket mutations (also denoted class II mutations) are listed in Table 1B. In Table 1B, mutations are numbered/annotated according to the sequence of human β1 H-NOX, but are analogous for all H-NOX sequences. Because several substitutions provide viable mutations at each recited residue, the residue at each indicated position can be changed to any other naturally or non-naturally-occurring amino acid (denoted "X"). Such mutations can produce H-NOX proteins with a variety of desired affinity, stability, and reactivity characteristics.

TABLE IB

Exemplary Class II H-NOX mutations targeting distal pocket residues

| | | |
|---|---|---|
| V8X | M73X | I145X |
| L9X | F77X | I149X |
| F70X | C78X | |

In particular embodiments, the mutation is a heme distal pocket mutation. As described herein, a crucial molecular determinant that prevents O$_2$ binding in NO-binding members of the H-NOX family is the lack of a H-bond donor in the distal pocket of the heme. Accordingly, in some embodiments, the mutation alters H-bonding between the H-NOX domain and the ligand within the distal pocket. In some embodiments, the mutation disrupts an H-bond donor of the distal pocket and/or imparts reduced O$_2$ ligand-binding relative to the corresponding wild-type H-NOX domain. Exemplary distal pocket residues include Thr4, Ile5, Thr8, Trp9, Trp67, Asn74, Ile75, Phe78, Phe82, Tyr140, and Leu144 of *T. tengcongensis* H-NOX and the corresponding residues in any other H-NOX protein. In some embodiments, the H-NOX protein or H-NOX domain of a polymeric H-NOX protein comprises one or more distal pocket mutations. In some embodiments, the H-NOX protein or H-NOX domain of a polymeric H-NOX protein comprises one, two, three, four, five, six, seven, eight, nine, ten or more than ten distal pocket mutations. In some embodiments, the distal pocket mutation corresponds to a L144F mutation of *T. tengcongensis* H-NOX. In some embodiments, the distal pocket mutation is a L144F mutation of *T. tengcongensis* H-NOX. In some embodiments, H-NOX protein or the H-NOX domain of a polymeric H-NOX protein comprises two distal pocket mutations. In some embodiments, the H-NOX protein or H-NOX domain of a polymeric H-NOX protein corresponds to a W9F/L144F mutation of *T. tengcongensis* H-NOX. In some embodiments, the H-NOX protein or H-NOX domain of a polymeric H-NOX protein is a W9F/L144F mutation of *T. tengcongensis* H-NOX.

Residues that are not in the distal pocket can also affect the three-dimensional structure of the heme group; this structure in turn affects the binding of O$_2$ and NO to iron in the heme group. Accordingly, in some embodiments, the H-NOX protein or H-NOX domain of a polymeric H-NOX protein has one or more mutations outside of the distal pocket. Examples of residues that can be mutated but are not in the distal pocket include Pro115 and Arg135 of *T. tengcongensis* H-NOX. In some embodiments, the mutation is in the proximal pocket which includes His105 as a residue that ligates to the heme iron.

In some embodiments when two or more mutations are present; at least one mutation is in the distal pocket, and at least one mutation is outside of the distal pocket (e.g., a mutation in the proximal pocket). In some embodiments, all the mutations are in the distal pocket.

To reduce the immunogenicity of H-NOX protein or H-NOX domains derived from sources other than humans, amino acids in an H-NOX protein or H-NOX domain can be mutated to the corresponding amino acids in a human H-NOX. For example, one or more amino acids on the surface of the tertiary structure of a non-human H-NOX protein or H-NOX domain can be mutated to the corresponding amino acid in a human H-NOX protein or H-NOX domain. In some variations, mutation of one or more surface amino acids may be combined with mutation of two or more distal pocket residues, mutation of one or more residues outside of the distal pocket (e.g., a mutation in the proximal pocket), or combinations of two or more of the foregoing.

The invention also relates to any combination of mutation described herein, such as double, triple, or higher multiple mutations. For example, combinations of any of the mutations described herein can be made in the same H-NOX protein. Note that mutations in equivalent positions in other mammalian or non-mammalian H-NOX proteins are also encompassed by this invention. Exemplary mutant H-NOX proteins or mutant H-NOX domains comprise one or more mutations that impart altered O$_2$ or NO ligand-binding relative to the corresponding wild-type H-NOX domain and are operative as a physiologically compatible mammalian O$_2$ blood gas carrier.

The residue number for a mutation indicates the position in the sequence of the particular H-NOX protein being described. For example, *T. tengcongensis* I5A refers to the replacement of isoleucine by alanine at the fifth position in *T. tengcongensis* H-NOX. The same isoleucine to alanine mutation can be made in the corresponding residue in any other H-NOX protein or H-NOX domain (this residue may or may not be the fifth residue in the sequence of other H-NOX proteins). Since the amino acid sequences of mammalian β1 H-NOX domains differ by at most two amino acids, mutations that produce desirable mutant H-NOX proteins or H-NOX domains when introduced into wild-type rat β1 H-NOX proteins are also expected to produce desirable mutant H-NOX proteins or H-NOX domains when introduced into wild-type β1 H-NOX proteins or H-NOX domains from other mammals, such as humans.

In some embodiments, the H-NOX protein is a trimer comprising three *T. tengcongensis* L144F H-NOX domains and three foldon domains. In some embodiments, the H-NOX protein is a trimer comprising three *T. tengcongensis* W9F/L144F H-NOX domains and three foldon domains. In some embodiments, the H-NOX protein is a trimer comprising three *T. tengcongensis* wildtype H-NOX domains and three foldon domains.

Modifications to H-NOX Proteins

Any of the wild-type or mutant H-NOX proteins, including polymeric H-NOX proteins, can be modified and/or formulated using standard methods to enhance therapeutic or industrial applications. For example, and particularly as applied to heterologous engineered H-NOX proteins, a variety of methods are known in the art for insulating such agents from immune surveillance, including crosslinking, PEGylation, carbohydrate decoration, etc. (e.g., Rohlfs, R. J. et al. (May 15, 1998). *J. Biol. Chem.* 273(20):12128-12134; Migita, R. et al. (June 1997). *J. Appl. Physiol.* 82(6):1995-2002; Vandegriff, K. D. et al. (Aug. 15, 2004). *Biochem J.* 382(Pt 1):183-189, which are each hereby incorporated by reference in their entireties, particularly with respect to the modification of proteins) as well as other techniques known to the skilled artisan. Fusing an H-NOX protein, including a polymeric H-NOX protein, with a human protein such as human serum albumin can increase the serum half-life, viscosity, and colloidal oncotic pressure. In some embodiments, an H-NOX protein is modified during or after its synthesis to decrease its immunogenicity and/or to increase its plasma retention time. H-NOX proteins can also be encapsulated (such as encapsulation within liposomes or nanoparticles).

In some embodiments, the H-NOX protein comprises one of more tags; e.g. to assist in purification of the H-NOX protein. Examples of tags include, but are not limited to $His_6$, FLAG, GST, and MBP. In some embodiments, the H-NOX protein comprises one of more $His_6$ tags. The one or more $His_6$ tags may be removed prior to use of the polymeric H-NOX protein; e.g. by treatment with an exopeptidase. In some embodiments, the H-NOX protein is a trimer comprising three *T. tengcongensis* L144F H-NOX domains, three foldon domains, and three $His_6$ tags. In some embodiments, the H-NOX protein is a trimer comprising three *T. tengcongensis* W9F/L144F H-NOX domains, three foldon domains, and three $His_6$ tags. In some embodiments, the H-NOX protein is a trimer comprising three *T. tengcongensis* wildtype H-NOX domains, three foldon domains, and three $His_6$ tags.

Polymerization Domains

In some aspects, the invention provides polymeric H-NOX proteins comprising two or more H-NOX domains and one or more polymerization domains. Polymerization domains are used to link two or more H-NOX domains to form a polymeric H-NOX protein. One or more polymerization domains may be used to produce dimers, trimers, tetramers, pentamers, etc. of H-NOX proteins. Polymerization domains are known in the art, such as: the foldon of T4 bacteriophage fibritin, Arc, POZ, coiled coil domains (including GCN4, leucine zippers, Velcro), uteroglobin, collagen, 3-stranded coiled colis (matrilin-1), thrombosporins, TRPV1-C, P53, Mnt, avadin, streptavidin, Bcr-Abl, COMP, verotoxin subunit B, CamKII, RCK, and domains from N ethylmaleimide-sensitive fusion protein, STM3548, KaiC, TyrR, Hcp1, CcmK4, GP41, anthrax protective antigen, aerolysin, a-hemolysin, C4b-binding protein, Mi-CK, arylsurfatase A, and viral capsid proteins. The polymerization domains may be covalently or non-covalently linked to the H-NOX domains. In some embodiments, a polymerization domain is linked to an H-NOX domain to form a monomer subunit such that the polymerization domains from a plurality of monomer subunits associate to form a polymeric H-NOX domain. In some embodiments, the C-terminus of an H-NOX domain is linked to the N-terminus of a polymerization domain. In other embodiments, the N-terminus of an H-NOX domain is linked to the N-terminus of a polymerization domain. In yet other embodiments, the C-terminus of an H-NOX domain is linked to the C-terminus of a polymerization domain. In some embodiments, the N-terminus of an H-NOX domain is linked to the C-terminus of a polymerization domain.

Linkers may be used to join a polymerization domain to an H-NOX domain; for example, for example, amino acid linkers. In some embodiments, a linker comprising any one of one, two, three, four, five, six, seven, eight, nine, ten or more than ten amino acids may be placed between the polymerization domain and the H-NOX domain. Exemplary linkers include but are not limited to Gly-Ser-Gly and Arg-Gly-Ser linkers.

Bacteriophage T4 Fibritin Trimerization Domain

An exemplary polymerization domain is the foldon domain of bacteriophage T4. The wac gene from the bacteriophage T4 encodes the fibritin protein, a 486 amino acid protein with a C-terminal trimerization domain (residues 457-483) (Efimov, V. P. et al. (1994) *J Mol Biol* 242:470-486). The domain is able to trimerize fibritin both in vitro and in vivo (Boudko, S. P. et al. (2002) *Eur J Biochem* 269:833-841; Letarov, A. V., et al., (1999) *Biochemistry* (Mosc)64:817-823; Tao, Y., et al., (1997) *Structure* 5:789-798). The isolated 27 residue trimerization domain, often referred to as the "foldon domain," has been used to construct chimeric trimers in a number of different proteins (including HIV envelope glycoproteins (Yang, X. et al., (2002) *J Virol* 76:4634-4642), adenoviral adhesins (Papanikolopoulou, K., et al., (2004) *J Biol Chem* 279:8991-8998; Papanikolopoulou, K. et al. (2004) *J Mol Biol* 342:219-227), collagen (Zhang, C., et al. (2009) *Biotechnol Prog* 25:1660-1668), phage P22 gp26 (Bhardwaj, A., et al. (2008) *Protein Sci* 17:1475-1485), and rabies virus glycoprotein (Sissoeff, L., et al. (2005) *J Gen Virol* 86:2543-2552). An exemplary sequence of the foldon domain is shown in FIG. 1 and provided by SEQ ID NO:4.

The isolated foldon domain folds into a single β-hairpin structure and trimerizes into a β-propeller structure involving three hairpins (Guthe, S. et al. (2004) *J Mol Biol* 337:905-915). The structure of the foldon domain alone has been determined by NMR (Guthe, S. et al. (2004) *J Mol Biol* 337:905-915) and the structures of several proteins trimerized with the foldon domain have been solved by X-ray crystallography (Papanikolopoulou, K., et al., (2004) *J Biol Chem* 279:8991-8998; Stetefeld, J. et al. (2003) *Structure* 11:339-346; Yokoi, N. et al. (2010) *Small* 6:1873-1879). The domain folds and trimerizes rapidly reducing the opportunity for misfolding intermediates or off-pathway oligomerization products (Guthe, S. et al. (2004) *J Mol Biol* 337:905-915). The foldon domain is very stable, able to maintain tertiary structure and oligomerization in >10% SDS, 6.0M guanidine hydrochloride, or 80° C. (Bhardwaj, A., et al. (2008) *Protein Sci* 17:1475-1485; Bhardwaj, A., et al. (2007) *J Mol Biol* 371:374-387) and can improve the stability of sequences fused to the foldon domain (Du, C. et al. (2008) *Appl Microbiol Biotechnol* 79:195-202.

In some embodiments, the C-terminus of an H-NOX domain is linked to the N-terminus of a foldon domain. In other embodiments, the N-terminus of an H-NOX domain is linked to the N-terminus of a foldon domain. In yet other embodiments, the C-terminus of an H-NOX domain is linked to the C-terminus of a foldon domain. In some embodiments, the N-terminus of an H-NOX domain is linked to the C-terminus of a foldon domain.

In some embodiments, linkers are be used to join a foldon domain to an H-NOX domain. In some embodiments, a linker comprising any one of one, two, three, four, five, six, seven, eight, nine, ten or more than ten amino acids may be placed between the polymerization domain and the H-NOX domain. Exemplary linkers include but are not limited to Gly-Ser-Gly and Arg-Gly-Ser linkers. In some embodiments, the invention provides a trimeric H-NOX protein comprising from N-terminus to C-terminus: a *T. tengcongensis* H-NOX domain, a Gly-Ser-Gly amino acid linker, and a foldon domain. In some embodiments, the invention provides a trimeric H-NOX protein comprising from N-terminus to C-terminus: a *T. tengcongensis* H-NOX domain, a Gly-Ser-Gly amino acid linker, a foldon domain, an Arg-Gly-Ser amino acid linker, and a His$_6$ tag. In some embodiments, the *T. tengcongensis* H-NOX domain comprises an L144F mutation. In some embodiments, the *T. tengcongensis* H-NOX domain comprises a W9F mutation and a L144F mutation. In some embodiments, the *T. tengcongensis* H-NOX domain is a wild-type H-NOX domain.

Monomeric H-NOX Domain Subunits

In one aspect, the invention provides recombinant monomeric H-NOX proteins (i.e. monomeric H-NOX subunits of polymeric H-NOX proteins) that can associate to form polymeric H-NOX proteins. In some embodiments, the invention provides recombinant H-NOX proteins comprising an H-NOX domain as described herein and a polymerization domain. The H-NOX domain and the polymerization domain may be covalently linked or noncovalently linked. In some embodiments, the C-terminus of an H-NOX domain of the recombinant monomeric H-NOX protein is linked to the N-terminus of a polymerization domain. In other embodiments, the N-terminus of an H-NOX domain of the recombinant monomeric H-NOX protein is linked to the N-terminus of a polymerization domain. In yet other embodiments, the C-terminus of an H-NOX domain of the recombinant monomeric H-NOX protein is linked to the C-terminus of a polymerization domain. In some embodiments, the N-terminus of an H-NOX domain of the recombinant monomeric H-NOX protein is linked to the C-terminus of a polymerization domain. In some embodiments, the recombinant monomeric H-NOX protein does not comprise a guanylyl cyclase domain.

In some embodiments, the monomeric H-NOX protein comprises a wild-type H-NOX domain. In some embodiments of the invention, the monomeric H-NOX protein comprises one of more mutations in the H-NOX domain. In some embodiments, the one or more mutations alter the O$_2$ dissociation constant, the k$_{off}$ for oxygen, the rate of heme autooxidation, the NO reactivity, the NO stability or any combination of two or more of the foregoing compared to that of the corresponding wild-type H-NOX domain. In some embodiments, the mutation is a distal pocket mutation. In some embodiments, the mutation comprises a mutation that is not in the distal pocket. In some embodiments, the distal pocket mutation corresponds to a L144 mutation of *T. tengcongensis* (e.g. a L144F mutation). In some embodiments, the recombinant monomeric H-NOX protein comprises two distal pocket mutations corresponding to a W9 and a L144 mutation of *T. tengcongensis* (e.g. a W9F/L144F mutation).

In some aspects, the invention provides recombinant monomeric H-NOX proteins that associate to form trimeric H-NOX proteins. In some embodiments, the recombinant H-NOX protein comprises an H-NOX domain and a trimerization domain. In some embodiments, the trimerization domain is a foldon domain as discussed herein. In some embodiments, the H-NOX domain is a *T. tengcongensis* H-NOX domain. In some embodiments the C-terminus of the *T. tengcongensis* H-NOX domain is covalently linked to the N-terminus of the foldon domain. In some embodiments the C-terminus of the *T. tengcongensis* H-NOX domain is covalently linked to the C-terminus of the foldon domain. In some embodiments, the *T. tengcongensis* domain is an L144F H-NOX domain. In some embodiments, the *T. tengcongensis* domain is a W9F/L144F H-NOX domain. In some embodiments, the *T. tengcongensis* domain is a wild-type H-NOX domain.

In some embodiments, the H-NOX domain is covalently linked to the polymerization domain using an amino acid linker sequence. In some embodiments, the amino acid linker sequence is one, two, three, four, five, six, seven, eight, nine, ten or more than ten amino acids in length. Exemplary amino acid linker sequences include but are not limited to a Gly-Ser-Gly sequence and an Arg-Gly-Ser sequence. In some embodiments, the polymeric H-NOX protein is a trimeric H-NOX protein comprising three H-NOX domains and three trimerization sequences wherein the H-NOX domain is covalently linked to the trimerization domain via an amino acid linker sequence. In some embodiments, the monomeric H-NOX protein comprises the following from the N-terminus to the C-terminus: an L144F *T. tengcongensis* H-NOX domain, a Gly-Ser-Gly amino acid linker sequence, and a foldon domain. In some embodiments, the monomeric H-NOX protein comprises the following from the N-terminus to the C-terminus: a W9F/L144F *T. tengcongensis* H-NOX domain, a Gly-Ser-Gly amino acid linker sequence, and a foldon domain. In some embodiments, the monomeric H-NOX protein comprises the following from the N-terminus to the C-terminus: a wild-type *T. tengcongensis* H-NOX domain, a Gly-Ser-Gly amino acid linker sequence, and a foldon domain.

In some embodiments, the recombinant monomeric H-NOX protein comprises a tag; e.g., a His$_6$, a FLAG, a GST, or an MBP tag. In some embodiments, the recombinant monomeric H-NOX protein comprises a His$_6$ tag. In some embodiments, the recombinant monomeric H-NOX protein does not comprise a tag. In some embodiments, the tag (e.g. a His$_6$ tag) is covalently linked to the polymerization domain using an amino acid spacer sequence. In some embodiments, the amino acid linker sequence is one, two, three, four, five, six, seven, eight, nine, ten or more than ten amino acids in length. Exemplary amino acid linker sequences include but are not limited to a Gly-Ser-Gly sequence and an Arg-Gly-Ser sequence. In some embodiments, the polymeric H-NOX protein is a trimeric H-NOX protein comprising three H-NOX domains, three trimerization sequences, and three His$_6$ tags, wherein the H-NOX domain is covalently linked to the trimerization domain via an amino acid linker sequence and the trimerization domain is covalently linked to the His$_6$ tag via an amino acid linker sequence. In some embodiments, the monomeric H-NOX protein comprises the following from the N-terminus to the C-terminus: an L144F *T. tengcongensis* H-NOX domain, a Gly-Ser-Gly amino acid linker sequence, a foldon domain, an Arg-Gly-Ser linker sequence, and a His$_6$ tag. In some embodiments, the monomeric H-NOX protein comprises the following from the N-terminus to the C-terminus: a W9F/L144F *T. tengcongensis* H-NOX domain, a Gly-Ser-Gly amino acid linker sequence, a foldon domain, an Arg-Gly-Ser linker sequence, and a His$_6$ tag. In some embodiments, the monomeric H-NOX protein comprises the following from the N-terminus to the C-terminus: a wild-type *T. tengcongensis* H-NOX domain, a Gly-Ser-Gly amino acid linker sequence, a foldon domain, an Arg-Gly-Ser linker sequence, and a His$_6$ tag.

In some embodiments the recombinant monomeric H-NOX protein comprises the amino acid sequence of SEQ ID NO:6, SEQ ID NO:8, SEQ ID NO:10 or SEQ ID NO:12.

Characteristics of Wild-Type and Mutant H-NOX Proteins

As described herein, a large number of diverse H-NOX mutant proteins, including polymeric H-NOX proteins, providing ranges of NO and $O_2$ dissociation constants, $O_2$ $k_{off}$, NO reactivity, and stability have been generated. To provide operative blood gas carriers, the H-NOX proteins may be used to functionally replace or supplement endogenous $O_2$ carriers, such as hemoglobin. In some embodiments, H-NOX proteins such as polymeric H-NOX proteins, are used to deliver $O_2$ to hypoxic tumor tissue (e.g. a glioblastoma) as an adjuvant to radiation therapy or chemotherapy. Accordingly, in some embodiments, an H-NOX protein has a similar or improved $O_2$ association rate, $O_2$ dissociation rate, dissociation constant for $O_2$ binding, NO stability, NO reactivity, autoxidation rate, plasma retention time, or any combination of two or more of the foregoing compared to an endogenous $O_2$ carrier, such as hemoglobin. In some embodiments, the H-NOX protein is a polymeric H-NOX protein. In some embodiments, the polymeric H-NOX protein is a trimeric H-NOX protein comprising three monomers, each monomer comprising a *T. tengcongensis* L144F H-NOX domain and a foldon domain. In some embodiments, the polymeric H-NOX protein is a trimeric H-NOX protein comprising three monomers, each monomer comprising a *T. tengcongensis* W9F/L144F H-NOX domain and a foldon domain. In some embodiments, the polymeric H-NOX protein is a trimeric H-NOX protein comprising three monomers, each monomer comprising a *T. tengcongensis* L144F H-NOX domain and a foldon domain.

In various embodiments, the $k_{off}$ for $O_2$ for an H-NOX protein, including a polymeric H-NOX protein, is between about 0.01 to about 200 $s^{-1}$ at 20° C., such as about 0.1 to about 200 $s^{-1}$, about 0.1 to 100 $s^{-1}$, about 1.0 to about 16.0 $s^{-1}$, about 1.35 to about 23.4 $s^{-1}$, about 1.34 to about 18 $s^{-1}$, about 1.35 to about 14.5 $s^{-1}$, about 0.21 to about 23.4 $s^{-1}$, about 1.35 to about 2.9 $s^{-1}$, about 2 to about 3 $s^{-1}$, about 5 to about 15 $s^{-1}$, or about 0.1 to about 1 $s^{-1}$. In some embodiments, the H-NOX protein has a $k_{off}$ for oxygen that is less than or equal to about 0.65 $s^{-1}$ at 20° C. (such as between about 0.21 $s^{-1}$ to about 0.65 $s^{-1}$ at 20° C.).

In various embodiments, the $k_o$ for $O_2$ for an H-NOX protein, including a polymeric H-NOX protein, is between about 0.14 to about 60 $\mu M^{-1}s^{-1}$ at 20° C., such as about 6 to about 60 $\mu M^{-1}s^{-1}$, about 6 to 12 $\mu M^{-1}s^{-1}$, about 15 to about 60 $\mu M^{-1}s^{-1}$, about 5 to about 18 $\mu M^{-1}s^{-1}$, or about 6 to about 15 $\mu M^{-1}s^{-1}$.

In various embodiments, the kinetic or calculated $K_D$ for $O_2$ binding by an H-NOX protein, including a polymeric H-NOX protein, is between about 1 nM to 1 mM, about 1 $\mu M$ to about 10 $\mu M$, or about 10 $\mu M$ to about 50 $\mu M$. In some embodiments the calculated $K_D$ for $O_2$ binding is any one of about 2 nM to about 2 $\mu M$, about 2$\mu$ M to about 1 mM, about 100 nM to about 1 $\mu M$, about 9 $\mu M$ to about 50 $\mu M$, about 100 $\mu M$ to about 1 mM, about 50 nM to about 10 $\mu M$, about 2 nM to about 50 $\mu M$, about 100 nM to about 1.9 $\mu M$, about 150 nM to about 1 $\mu M$, or about 100 nM to about 255 nM, about 20 nM to about 2 $\mu M$, 20 nM to about 75 nM, about 1 $\mu M$ to about 2 $\mu M$, about 2 $\mu M$ to about 10 $\mu M$, about 2 $\mu M$ to about 9 $\mu M$, or about 100 nM to 500 nM at 20° C. In some embodiments, the kinetic or calculated $K_D$ for $O_2$ binding is less than about any of 100 nM, 80 nM, 50 nM, 30 nM, 25 nM, 20 nM, or 10 nM at 20° C.

In various embodiments, the kinetic or calculated $K_D$ for $O_2$ binding by an H-NOX protein, including a polymeric H-NOX protein, is within about 0.01 to about 100-fold of that of hemoglobin under the same conditions (such as at 20° C.), such as between about 0.1 to about 10-fold or between about 0.5 to about 2-fold of that of hemoglobin under the same conditions (such as at 20° C.). In various embodiments, the kinetic or calculated $K_D$ for NO binding by an H-NOX protein is within about 0.01 to about 100-fold of that of hemoglobin under the same conditions (such as at 20° C.), such as between about 0.1 to about 10-fold or between about 0.5 to about 2-fold of that of hemoglobin under the same conditions (such as at 20° C.).

In some embodiments, less than about any of 50, 40, 30, 10, or 5% of an H-NOX protein, including a polymeric H-NOX protein, is oxidized after incubation for about any of 1, 2, 4, 6, 8, 10, 15, or 20 hours at 20° C.

In various embodiments, the NO reactivity of an H-NOX protein, including a polymeric H-NOX protein, is less than about 700 $s^{-1}$ at 20° C., such as less than about 600 $s^{-1}$, 500 $s^{-1}$, 400 $s^{-1}$, 300 $s^{-1}$, 200 $s^{-1}$, 100 $s^{-1}$, 75 $s^{-1}$, 50 $s^{-1}$, 25 $s^{-1}$, 20 $s^{-1}$, 10 $s^{-1}$, 50 $s^{-1}$, 3 $s^{-1}$ $s^{-1}$, 1.8 $s^{-1}$, 1.5 $s^{-1}$, 1.2 $s^{-1}$, 1.0 $s^{-1}$, 0.8 $s^{-1}$, 0.7 $s^{-1}$, or 0.6 $s^{-1}$ at 20° C. In various embodiments, the NO reactivity of an H-NOX protein is between about 0.1 to about 600 $s^{-1}$ at 20° C., such as between about 0.5 to about 400 $s^{-1}$, about 0.5 to about 100 $s^{-1}$, about 0.5 to about 50 $s^{-1}$, about 0.5 to about 10 $s^{-1}$, about 1 to about 5 $s^{-1}$, or about 0.5 to about 2.1 $s^{-1}$ at 20° C. In various embodiments, the reactivity of an H-NOX protein is at least about 10, 100, 1,000, or 10,000 fold lower than that of hemoglobin under the same conditions, such as at 20° C.

In various embodiments, the rate of heme autoxidation of an H-NOX protein, including a polymeric H-NOX protein, is less than about 1.0 $h^{-1}$ at 37° C., such as less than about any of 0.9 $h^{-1}$, 0.8 $h^{-1}$, 0.7 $h^{-1}$, 0.6 $h^{-1}$, 0.5 $h^{-1}$, 0.4 $h^{-1}$, 0.3 $h^{-1}$, 0.2 $h^{-1}$, 0.1 $h^{-1}$, or 0.05 $h^{-1}$ at 37° C. In various embodiments, the rate of heme autoxidation of an H-NOX protein is between about 0.006 to about 5.0 $h^{-1}$ at 37° C., such as about 0.006 to about 1.0 $h^{-1}$, 0.006 to about 0.9 $h^{-1}$, or about 0.06 to about 0.5 $h^{-1}$ at 37° C.

In various embodiments, a mutant H-NOX protein, including a polymeric H-NOX protein, has (a) an $O_2$ or NO dissociation constant, association rate ($k_{on}$ for $O_2$ or NO), or dissociation rate ($k_{off}$ for $O_2$ or NO) within 2 orders of magnitude of that of hemoglobin, (b) has an NO affinity weaker (e.g., at least about 10-fold, 100-fold, or 1000-fold weaker) than that of sGC β1, respectively, (c) an NO reactivity with bound $O_2$ at least 1000-fold less than hemoglobin, (d) an in vivo plasma retention time at least 2, 10, 100, or 1000-fold higher than that of hemoglobin, or (e) any combination of two or more of the foregoing.

Exemplary suitable $O_2$ carriers provide dissociation constants within two orders of magnitude of that of hemoglobin, i.e. between about 0.01 and 100-fold, such as between about 0.1 and 10-fold, or between about 0.5 and 2-fold of that of hemoglobin. A variety of established techniques may be used to quantify dissociation constants, such as the techniques described herein (Boon, E. M. et al. (2005). *Nature Chem. Biol.* 1:53-59; Boon, E. M. et al. (October 2005). *Curr. Opin. Chem. Biol.* 9(5):441-446; Boon, E. M. et al. (2005). *J. Inorg. Biochem.* 99(4):892-902), Vandegriff, K. D. et al. (Aug. 15, 2004). *Biochem J.* 382(Pt 1):183-189, which are each hereby incorporated by reference in their entireties, particularly with respect to the measurement of dissociation constants), as well as those known to the skilled artisan.

Exemplary $O_2$ carriers provide low or minimized NO reactivity of the H-NOX protein with bound $O_2$, such as an NO reactivity lower than that of hemoglobin. In some embodiments, the NO reactivity is much lower, such as at least about 10, 100, 1,000, or 10,000-fold lower than that of hemoglobin. A variety of established techniques may be used to quantify NO reactivity (Boon, E. M. et al. (2005). *Nature Chem. Biol.* 1:53-59; Boon, E. M. et al. (October 2005). *Curr. Opin. Chem. Biol.* 9(5):441-446; Boon, E. M. et al. (2005). *J. Inorg. Biochem.* 99(4):892-902), Vandegriff, K. D. et al. (Aug. 15, 2004). *Biochem J.* 382(Pt 1):183-189, which are each hereby incorporated by reference in their entireties, particularly with respect to the measurement of NO reactivity) as well as those known to the skilled artisan. Because wild-type *T. tengcongensis* H-NOX has such a low NO reactivity, other wild-type H-NOX proteins and mutant H-NOX proteins may have a similar low NO reactivity. For example, *T. tengcongensis* H-NOX Y140H has an NO reactivity similar to that of wild-type *T. tengcongensis* H-NOX.

In addition, suitable $O_2$ carriers provide high or maximized stability, particularly in vivo stability. A variety of stability metrics may be used, such as oxidative stability (e.g., stability to autoxidation or oxidation by NO), temperature stability, and in vivo stability. A variety of established techniques may be used to quantify stability, such as the techniques described herein (Boon, E. M. et al. (2005). *Nature Chem. Biol.* 1:53-59; Boon, E. M. et al. (October 2005). *Curr. Opin. Chem. Biol.* 9(5):441-446; Boon, E. M. et al. (2005). *J. Inorg. Biochem.* 99(4):892-902), as well as those known to the skilled artisan. For in vivo stability in plasma, blood, or tissue, exemplary metrics of stability include retention time, rate of clearance, and half-life. H-NOX proteins from thermophilic organisms are expected to be stable at high temperatures. In various embodiments, the plasma retention times are at least about 2-, 10-, 100-, or 1000-fold greater than that of hemoglobin (e.g. Bobofchak, K. M. et al. (August 2003). *Am. J. Physiol. Heart Circ. Physiol.* 285(2):H549-H561). As will be appreciated by the skilled artisan, hemoglobin-based blood substitutes are limited by the rapid clearance of cell-free hemoglobin from plasma due the presence of receptors for hemoglobin that remove cell-free hemoglobin from plasma. Since there are no receptors for H-NOX proteins in plasma, wild-type and mutant H-NOX proteins are expected to have a longer plasma retention time than that of hemoglobin. If desired, the plasma retention time can be increased by PEGylating or crosslinking an H-NOX protein or fusing an H-NOX protein with another protein using standard methods (such as those described herein and those known to the skilled artisan).

In various embodiments, the H-NOX protein, including a polymeric H-NOX protein, has an $O_2$ dissociation constant between about 1 nM to about 1 mM at 20° C. and a NO reactivity at least about 10-fold lower than that of hemoglobin under the same conditions, such as at 20° C. In some embodiments, the H-NOX protein has an $O_2$ dissociation constant between about 1 nM to about 1 mM at 20° C. and a NO reactivity less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the H-NOX protein has an $O_2$ dissociation constant within 2 orders of magnitude of that of hemoglobin and a NO reactivity at least about 10-fold lower than that of hemoglobin under the same conditions, such as at 20° C. In some embodiments, the H-NOX protein has a $k_{off}$ for oxygen between about 0.01 to about 200 $s^{-1}$ at 20° C. and an NO reactivity at least about 10-fold lower than that of hemoglobin under the same conditions, such as at 20° C. In some embodiments, the H-NOX protein has a $k_{off}$ for oxygen that is less than about 0.65 $s^{-1}$ at 20° C. (such as between about 0.21 $s^{-1}$ to about 0.64 $s^{-1}$ at 20° C.) and a NO reactivity at least about 10-fold lower than that of hemoglobin under the same conditions, such as at 20° C. In some embodiments of the invention, the $O_2$ dissociation constant of the H-NOX protein is between about 1 nM to about 1 µM (1000 nM), about 1 µM to about 10 µM, or about 10 µM to about 50 µM. In particular embodiments, the $O_2$ dissociation constant of the H-NOX protein is between about 2 nM to about 50 µM, about 50 nM to about 10 µM, about 100 nM to about 1.9 µM, about 150 nM to about 1 µM, or about 100 nM to about 255 nM at 20° C. In various embodiments, the $O_2$ dissociation constant of the H-NOX protein is less than about 80 nM at 20° C., such as between about 20 nM to about 75 nM at 20° C. In some embodiments, the NO reactivity of the H-NOX protein is at least about 100-fold lower or about 1,000 fold lower than that of hemoglobin, under the same conditions, such as at 20° C. In some embodiments, the NO reactivity of the H-NOX protein is less than about 700 $s^{-1}$ at 20° C., such as less than about 600 $s^{-1}$, 500 $s^{-1}$, 400 $s^{-1}$, 300 $s^{-1}$, 200 $s^{-1}$, 100 $s^{-1}$, 75 $s^{-1}$, 50 $s^{-1}$, 25 $s^{-1}$, 20 $s^{-1}$, 10 $s^{-1}$, 50 $s^{-1}$, 3 $s^{-1}$, 2 $s^{-1}$, 1.8 $s^{-1}$, 1.5 $s^{-1}$, 1.2 $s^{-1}$, 1.0 $s^{-1}$, 0.8 $s^{-1}$, 0.7 $s^{-1}$, or 0.6 $s^{-1}$ at 20° C. In some embodiments, the $k_{off}$ for oxygen of the H-NOX protein is between 0.01 to 200 $s^{-1}$ at 20° C., such as about 0.1 to about 200 $s^{-1}$, about 0.1 to 100 $s^{-1}$, about 1.35 to about 23.4 $s^{-1}$, about 1.34 to about 18 $s^{-1}$, about 1.35 to about 14.5 $s^{-1}$, about 0.21 to about 23.4 $s^{-1}$, about 2 to about 3 $s^{-1}$, about 5 to about 15 $s^{-1}$, or about 0.1 to about 1 $s^{-1}$. In some embodiments, the $O_2$ dissociation constant of the H-NOX protein is between about 100 nM to about 1.9 µM at 20° C., and the $k_{off}$ for oxygen of the H-NOX protein is between about 1.35 $s^{-1}$ to about 14.5 $s^{-1}$ at 20° C. In some embodiments, the rate of heme autoxidation of the H-NOX protein is less than about 1 $h^{-1}$ at 37° C., such as less than about any of 0.9 $h^{-1}$, 0.8 $h^{-1}$, 0.7 $h^{-1}$, 0.6 $h^{-1}$, 0.5 $h^{-1}$, 0.4 $h^{-1}$, 0.3 $h^{-1}$, 0.2 $h^{-1}$, or 0.1 $h^{-1}$. In some embodiments, the $k_{off}$ for oxygen of the H-NOX protein is between about 1.35 $s^{-1}$ to about 14.5 $s^{-1}$ at 20° C., and the rate of heme autoxidation of the H-NOX protein is less than about 1 $h^{-1}$ at 37° C. In some embodiments, the $k_{off}$ for oxygen of the H-NOX protein is between about 1.35 $s^{-1}$ to about 14.5 $s^{-1}$ at 20° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.). In some embodiments, the rate of heme autoxidation of the H-NOX protein is less than about 1 $h^{-1}$ at 37° C., and the NO reactivity of the H-NOX protein is less than about 700 $s^{-1}$ at 20° C. (e.g., less than about 600 $s^{-1}$, 500 $s^{-1}$, 100 $s^{-1}$, 20 $s^{-1}$, or 1.8 $s^{-1}$ at 20° C.).

In some embodiments, the viscosity of the H-NOX protein solution, including a polymeric H-NOX protein solution, is between 1 and 4 centipoise (cP). In some embodiments, the colloid oncotic pressure of the H-NOX protein solution is between 20 and 50 mm Hg.

Measurement of $O_2$ and/or NO Binding

One skilled in the art can readily determine the oxygen and nitric oxide binding characteristics of any H-NOX protein including a polymeric H-NOX protein such as a trimeric H-NOX protein by methods known in the art and by the non-limiting exemplary methods described below.

Kinetic KM: Ratio of $k_{off}$ to $k_{on}$

The kinetic $K_D$ value is determined for wild-type and mutant H-NOX proteins, including polymeric H-NOS proteins, essentially as described by Boon, E. M. et al. (2005). *Nature Chemical Biology* 1:53-59, which is hereby incorporated by reference in its entirety, particularly with respect to the measurement of $O_2$ association rates, $O_2$ dissociation rates, dissociation constants for $O_2$ binding, autoxidation rates, and NO dissociation rates.

$k_{on}$ ($O_2$ Association Rate)

$O_2$ association to the heme is measured using flash photolysis at 20° C. It is not possible to flash off the $Fe^{II}$-$O_2$ complex as a result of the very fast geminate recombination kinetics; thus, the $Fe^{II}$—CO complex is subjected to flash photolysis with laser light at 560 nm (Hewlett-Packard, Palo Alto, Calif.), producing the 5-coordinate $Fe^{II}$ intermediate, to which the binding of molecular $O_2$ is followed at various wavelengths. Protein samples are made by anaerobic reduction with 10 mM dithionite, followed by desalting on a PD-10 column (Millipore, Inc., Billerica, Mass.). The samples are then diluted to 20 µM heme in 50 mM TEA, 50 mM NaCl, pH 7.5 buffer in a controlled-atmosphere quartz cuvette, with a size of 100 µL to 1 mL and a path-length of 1-cm. CO gas is flowed over the headspace of this cuvette for 10 minutes to form the $Fe^{II}$—CO complex, the formation of which is verified by UV-visible spectroscopy (Soret maximum 423 nm). This sample is then either used to measure CO-rebinding kinetics after flash photolysis while still under 1 atmosphere of CO gas, or it is opened and stirred in air for 30 minutes to fully oxygenate the buffer before flash photolysis to watch $O_2$-rebinding events. $O_2$ association to the heme is monitored at multiple wavelengths versus time. These traces are fit with a single exponential using Igor Pro software (Wavemetrics, Inc., Oswego, Oreg.; latest 2005 version). This rate is independent of observation wavelength but dependent on $O_2$ concentration. UV-visible spectroscopy is used throughout to confirm all the complexes and intermediates (Cary 3K, Varian, Inc. Palo Alto, Calif.). Transient absorption data are collected using instruments described in Dmochowski, I. J. et al. (Aug. 31, 2000). *J Inorg Biochem.* 81(3):221-228, which is hereby incorporated by reference in its entirety, particularly with respect to instrumentation. The instrument has a response time of 20 ns, and the data are digitized at 200 megasamples $s^{-1}$.

$k_{off}$ ($O_2$ Dissociation Rate)

To measure the $k_{off}$, $Fe^{II}$—$O_2$ complexes of protein (5 µM heme), are diluted in anaerobic 50 mM TEA, 50 mM NaCl, pH 7.5 buffer, and are rapidly mixed with an equal volume of the same buffer (anaerobic) containing various concentrations of dithionite and/or saturating CO gas. Data are acquired on a HI-TECH Scientific SF-61 stopped-flow spectrophotometer equipped with a Neslab RTE-100 constant-temperature bath set to 20° C. (TGK Scientific LTD., Bradford On Avon, United Kingdom). The dissociation of $O_2$ from the heme is monitored as an increase in the absorbance at 437 nm, a maximum in the $Fe^{II}$—$Fe^{II}$-$O_2$ difference spectrum, or 425 nm, a maximum in the $Fe^{II}$—$Fe^{II}$-CO difference spectrum. The final traces are fit to a single exponential using the software that is part of the instrument. Each experiment is done a minimum of six times, and the resulting rates are averaged. The dissociation rates measured are independent of dithionite concentration and independent of saturating CO as a trap for the reduced species, both with and without 10 mM dithionite present.

Kinetic $K_D$

The kinetic $K_D$ is determined by calculating the ratio of $k_{off}$ to $k_{on}$ using the measurements of $k_{off}$ and $k_{on}$ described above.

Calculated $K_D$

To measure the calculated $K_D$, the values for the $k_{off}$ and kinetic $K_D$ that are obtained as described above are graphed. A linear relationship between $k_{off}$ and kinetic $K_D$ is defined by the equation (y=mx+b). $k_{off}$ values were then interpolated along the line to derive the calculated $K_D$ using Excel: MAC 2004 (Microsoft, Redmond, Wash.). In the absence of a measured $k_{on}$, this interpolation provides a way to relate $k_{off}$ to $K_D$.

Rate of Autoxidation

To measure the rate of autoxidation, the protein samples are anaerobically reduced, then diluted to 5 µM heme in aerobic 50 mM TEA, 50 mM NaCl, pH 7.5 buffer. These samples are then incubated in a Cary 3E spectrophotometer equipped with a Neslab RTE-100 constant-temperature bath set to 37° C. and scanned periodically (Cary 3E, Varian, Inc., Palo Alto, Calif.). The rate of autoxidation is determined from the difference between the maximum and minimum in the $Fe^{III}$—$Fe^{II}$ difference spectrum plotted versus time and fit with a single exponential using Excel: MAC 2004 (Microsoft, Redmond, Wash.).

Rate of Reaction with NO

NO reactivity is measured using purified proteins (H-NOX, polymeric H-NOX, *Homo sapiens* hemoglobin (Hs Hb) etc.) prepared at 2 µM in buffer A and NO prepared at 200 µM in Buffer A (Buffer A: 50 mM Hepes, pH 7.5, 50 mM NaCl). Data are acquired on a HI-TECH Scientific SF-61 stopped-flow spectrophotometer equipped with a Neslab RTE-100 constant-temperature bath set to 20° C. (TGK Scientific LTD., Bradford On Avon, United Kingdom). The protein is rapidly mixed with NO in a 1:1 ratio with an integration time of 0.00125 sec. The wavelengths of maximum change are fit to a single exponential using the software that is part of the spectrometer, essentially measuring the rate-limiting step of oxidation by NO. The end products of the reaction are ferric-NO for the HNOX proteins and ferric-aquo for Hs Hb.

p50 Measurements

If desired, the p50 value for mutant or wild-type H-NOX proteins can be measured as described by Guarnone, R. et al. (September/October 1995). *Haematologica* 80(5):426-430, which is hereby incorporated by reference in its entirety, particularly with respect to the measurement of p50 values. The p50 value is determined using a HemOx analyzer. The measurement chamber starts at 0% oxygen and slowly is raised, incrementally, towards 100% oxygen. An oxygen probe in the chamber measures the oxygen saturation %. A second probe (UV-Vis light) measures two wavelengths of absorption, tuned to the alpha and beta peaks of the hemoprotein's (e.g., a protein such as H-NOX complexed with heme) UV-Vis spectra. These absorption peaks increase linearly as hemoprotein binds oxygen. The percent change from unbound to 100% bound is then plotted against the % oxygen values to generate a curve. The p50 is the point on the curve where 50% of the hemoprotein is bound to oxygen.

Specifically, the Hemox-Analyzer (TCS Scientific Corporation, New Hope, Pa.) determines the oxyhemoprotein dissociation curve (ODC) by exposing 50 µL of blood or hemoprotein to an increasing partial pressure of oxygen and deoxygenating it with nitrogen gas. A Clark oxygen electrode detects the change in oxygen tension, which is recorded on the x-axis of an x-y recorder. The resulting increase in oxyhemoprotein fraction is simultaneously monitored by dual-wavelength spectrophotometry at 560 nm and 576 nm and displayed on the y-axis. Blood samples are taken from the antemedial vein, anticoagulated with heparin, and kept at 4° C. on wet ice until the assay. Fifty µL of whole blood are diluted in 5 µL of Hemox-solution, a manufacturer-provided buffer that keeps the pH of the solution at a value of 7.4±0.01. The sample-buffer is drawn into a cuvette that is part of the Hemox-Analyzer and the temperature of the mixture is equilibrated and brought to 37° C.; the sample is then oxygenated to 100% with air. After adjustment of the pO$_2$ value the sample is deoxygenated with nitrogen; during the deoxygenation process the curve is recorded on graph paper. The P50 value is extrapolated on the x-axis as the point at which O$_2$ saturation is 50% using the software that is part of the Hemox-Analyzer. The time required for a complete recording is approximately 30 minutes.

H-NOX Nucleic Acids

The invention also features nucleic acids encoding any of the mutant H-NOX proteins, polymeric H-NOX, or recombinant monomer H-NOX protein subunits as described herein.

In particular embodiments, the nucleic acid includes a segment of or the entire nucleic acid sequence of any of nucleic acids encoding an H-NOX protein or an H-NOX domain. In some embodiments, the nucleic acid includes at least about 50, 100, 150, 200, 300, 400, 500, 600, 700, 800, or more contiguous nucleotides from a H-NOX nucleic acid and contains one or more mutations (e.g., 1, 2, 3, 4, 5, 6, 7, 8, 9, or 10 mutations) compared to the H-NOX nucleic acid from which it was derived. In various embodiments, a mutant H-NOX nucleic acid contains less than about 20, 15, 12, 10, 9, 8, 7, 6, 5, 4, 3, or 2 mutations compared to the H-NOX nucleic acid from which it was derived. The invention also features degenerate variants of any nucleic acid encoding a mutant H-NOX protein.

In some embodiments, the nucleic acid includes nucleic acids encoding two or more H-NOX domains. In some embodiments, the nucleic acids including two or more H-NOX domains are linked such that a polymeric H-NOX protein is expressed from the nucleic acid. In further embodiments, the nucleic acid includes nucleic acids encoding one or more polymerization domains. In some embodiments, the nucleic acids including the two or more H-NOX domains and the one or more polymerization domains are linked such that a polymeric H-NOX protein is expressed from the nucleic acid.

In some embodiments, the nucleic acid includes a segment or the entire nucleic acid sequence of any nucleic acid encoding a polymerization domain. In some embodiments the nucleic acid comprises a nucleic acid encoding an H-NOX domain and a polymerization domain. In some embodiments, the nucleic acid encoding an H-NOX domain and the nucleic acid encoding a polymerization domain a linked such that the produced polypeptide is a fusion protein comprising an H-NOX domain and a polymerization domain.

In some embodiments, the nucleic acid comprises nucleic acid encoding one or more His$_6$ tags. In some embodiments the nucleic acid further comprised nucleic acids encoding linker sequences positioned between nucleic acids encoding the H-NOX domain, the polymerization domain and/or a His$_6$ tag.

In some embodiments, the invention provides a nucleic acid encoding an H-NOX domain and a foldon domain. In some embodiments, the H-NOX domain is a *T. thermoanaerobacter* H-NOX domain. In some embodiments, the H-NOX domain is a wild-type *T. thermoanaerobacter* H-NOX domain. In some embodiments, the H-NOX domain is a *T. thermoanaerobacter* L144F H-NOX domain. In some embodiments, the H-NOX domain is a *T. thermoanaerobacter* W9F/L144F H-NOX domain.

In some embodiments, the invention provides nucleic acids encoding the following 5' to 3': a L144F *T. tengcongensis* H-NOX domain, a Gly-Ser-Gly amino acid linker sequence, and a foldon domain. In some embodiments, the invention provides nucleic acids encoding the following 5' to 3': a W9F/L144F *T. tengcongensis* H-NOX domain, a Gly-Ser-Gly amino acid linker sequence, and a foldon domain. In some embodiments, the invention provides nucleic acids encoding the following 5' to 3': a wild-type *T. tengcongensis* H-NOX domain, a Gly-Ser-Gly amino acid linker sequence, and a foldon domain.

In some embodiments, the invention provides nucleic acids encoding the following 5' to 3': a L144F *T. tengcongensis* H-NOX domain, a Gly-Ser-Gly amino acid linker sequence, a foldon domain, an Arg-Gly-Ser linker sequence, and a His$_6$ tag. In some embodiments, the invention provides nucleic acids encoding the following 5' to 3': a W9F/L144F *T. tengcongensis* H-NOX domain, a Gly-Ser-Gly amino acid linker sequence, a foldon domain, an Arg-Gly-Ser linker sequence, and a His$_6$ tag. In some embodiments, the invention provides nucleic acids encoding the following 5' to 3': a wild-type *T. tengcongensis* H-NOX domain, a Gly-Ser-Gly amino acid linker sequence, a foldon domain, an Arg-Gly-Ser linker sequence, and a His$_6$ tag.

In some embodiments, the nucleic acid comprises the nucleic acid sequence set forth in SEQ ID NO:5, SEQ ID NO:7, SEQ ID NO:9 or SEQ ID NO:11.

The invention also includes a cell or population of cells containing at least one nucleic acid encoding a mutant H-NOX protein described herein. Exemplary cells include insect, plant, yeast, bacterial, and mammalian cells. These cells are useful for the production of mutant H-NOX proteins using standard methods, such as those described herein.

In some embodiments, the invention provides a cell comprising a nucleic acid encoding an H-NOX domain and a foldon domain. In some embodiments, the H-NOX domain is a *T. thermoanaerobacter* H-NOX domain. In some embodiments, the H-NOX domain is a wild-type *T. thermoanaerobacter* H-NOX domain. In some embodiments, the H-NOX domain is a *T. thermoanaerobacter* L144F H-NOX domain. In some embodiments, the H-NOX domain is a *T. thermoanaerobacter* W9F/L144F H-NOX domain. In some embodiments, the invention provides a cell comprising a nucleic acid comprising the nucleic acid sequence set forth in SEQ ID NO:5, SEQ ID NO:7, SEQ ID NO:9, or SEQ ID NO:11.

Formulations of H-NOX Proteins

Any wild-type or mutant H-NOX protein, including polymeric H-NOX proteins, described herein may be used for the formulation of pharmaceutical or non-pharmaceutical compositions. In some embodiments, the formulations comprise a monomeric H-NOX protein comprising an H-NOX domain and a polymerization domain such that the monomeric H-NOX proteins associate in vitro or in vivo to produce a polymeric H-NOX protein. As discussed further below, these formulations are useful in a variety of therapeutic and industrial applications.

In some embodiments, the pharmaceutical composition includes one or more wild-type or mutant H-NOX proteins described herein including polymeric H-NOX proteins and a pharmaceutically acceptable carrier or excipient. Examples of pharmaceutically acceptable carriers or excipients include, but are not limited to, any of the standard pharmaceutical carriers or excipients such as phosphate buffered saline solutions, water, emulsions such as oil/water emulsion, and various types of wetting agents. Exemplary diluents for aerosol or parenteral administration are phosphate buffered saline or normal (0.9%) saline. Compositions comprising such carriers are formulated by well-known conventional methods (see, for example, *Remington's Pharmaceutical Sciences*, 18th edition, A. Gennaro, ed., Mack Publishing Co., Easton, Pa., 1990; and *Remington, The*

Science and Practice of Pharmacy 20th Ed. Mack Publishing, 2000, which are each hereby incorporated by reference in their entireties, particularly with respect to formulations). In some embodiments, the formulations are sterile. In some embodiments, the formulations are essentially free of endotoxin.

While any suitable carrier known to those of ordinary skill in the art may be employed in the pharmaceutical compositions of this invention, the type of carrier will vary depending on the mode of administration. Compositions can be formulated for any appropriate manner of administration, including, for example, intravenous, intra-arterial, intravesicular, inhalation, intraperitoneal, intrapulmonary, intramuscular, subcutaneous, intra-tracheal, transmucosal, intraocular, intrathecal, or transdermal administration. For parenteral administration, such as subcutaneous injection, the carrier may include, e.g., water, saline, alcohol, a fat, a wax, or a buffer. For oral administration, any of the above carriers or a solid carrier, such as mannitol, lactose, starch, magnesium stearate, sodium saccharine, talcum, cellulose, glucose, sucrose, or magnesium carbonate, may be employed. Biodegradable microspheres (e.g., polylactate polyglycolate) may also be used as carriers.

In some embodiments, the pharmaceutical or non-pharmaceutical compositions include a buffer (e.g., neutral buffered saline, phosphate buffered saline, etc), a carbohydrate (e.g., glucose, mannose, sucrose, dextran, etc.), an antioxidant, a chelating agent (e.g., EDTA, glutathione, etc.), a preservative, another compound useful for binding and/or transporting oxygen, an inactive ingredient (e.g., a stabilizer, filler, etc.), or combinations of two or more of the foregoing. In some embodiments, the composition is formulated as a lyophilizate. H-NOX proteins may also be encapsulated within liposomes or nanoparticles using well known technology. Other exemplary formulations that can be used for H-NOX proteins are described by, e.g., U.S. Pat. Nos. 6,974,795, and 6,432,918, which are each hereby incorporated by reference in their entireties, particularly with respect to formulations of proteins.

The compositions described herein may be administered as part of a sustained release formulation (e.g., a formulation such as a capsule or sponge that produces a slow release of compound following administration). Such formulations may generally be prepared using well known technology and administered by, for example, oral, rectal or subcutaneous implantation, or by implantation at the desired target site. Sustained-release formulations may contain an H-NOX protein dispersed in a carrier matrix and/or contained within a reservoir surrounded by a rate controlling membrane. Carriers for use within such formulations are biocompatible, and may also be biodegradable. In some embodiments, the formulation provides a relatively constant level of H-NOX protein release. The amount of H-NOX protein contained within a sustained release formulation depends upon the site of implantation, the rate and expected duration of release, and the nature of the condition to be treated or prevented.

In some embodiments, the pharmaceutical composition contains an effective amount of a wild-type or mutant H-NOX protein. In some embodiments, the pharmaceutical composition contains an effective amount of a polymeric H-NOX protein comprising two or more wild-type or mutant H-NOX domains. In some embodiments, the pharmaceutical composition contains an effective amount of a recombinant monomeric H-NOX protein comprising a wild-type or mutant H-NOX domain and a polymerization domain as described herein. In some embodiments, the formulation comprises a trimeric H-NOX protein comprising three monomers, each monomer comprising a *T. tengcongensis* L144F H-NOX domain and a foldon domain. In some embodiments, the formulation comprises a trimeric H-NOX protein comprising three monomers, each monomer comprising a *T. tengcongensis* W9F/L144F H-NOX domain and a foldon domain. In some embodiments, the formulation comprises a trimeric H-NOX protein comprising three monomers, each monomer comprising a *T. tengcongensis* L144F H-NOX domain and a foldon domain.

An exemplary dose of hemoglobin as a blood substitute is from about 10 mg to about 5 grams or more of extracellular hemoglobin per kilogram of patient body weight. Thus, in some embodiments, an effective amount of an H-NOX protein for administration to a human is between a few grams to over about 350 grams. Other exemplary doses of an H-NOX protein include about any of 4.4, 5, 10, or 13 G/DL (where G/DL is the concentration of the H-NOX protein solution prior to infusion into the circulation) at an appropriate infusion rate, such as about 0.5 ml/min (see, for example, Winslow, R. Chapter 12 In *Blood Substitutes*). It will be appreciated that the unit content of active ingredients contained in an individual dose of each dosage form need not in itself constitute an effective amount since the necessary effective amount could be reached by the combined effect of a plurality of administrations. The selection of the amount of an H-NOX protein to include in a pharmaceutical composition depends upon the dosage form utilized, the condition being treated, and the particular purpose to be achieved according to the determination of the ordinarily skilled artisan in the field.

Exemplary compositions include genetically engineered, recombinant H-NOX proteins, which may be isolated or purified, comprising one or more mutations that collectively impart altered $O_2$ or NO ligand-binding relative to the corresponding wild-type H-NOX protein, and operative as a physiologically compatible mammalian blood gas carrier. For example, mutant H-NOX proteins as described herein. In some embodiments, the H-NOX protein is a polymeric H-NOX protein. In some embodiments, the H-NOX protein is a recombinant monomeric H-NOX protein comprising a wild-type or mutant H-NOX domain and a polymerization domain as described herein. In some embodiments, the composition comprises a trimeric H-NOX protein comprising three monomers, each monomer comprising a *T. tengcongensis* L144F H-NOX domain and a foldon domain. In some embodiments, the composition comprises a trimeric H-NOX protein comprising three monomers, each monomer comprising a *T. tengcongensis* W9F/L144F H-NOX domain and a foldon domain. In some embodiments, the composition comprises a trimeric H-NOX protein comprising three monomers, each monomer comprising a *T. tengcongensis* L144F H-NOX domain and a foldon domain.

To reduce or prevent an immune response in human subjects who are administered a pharmaceutical composition, human H-NOX proteins or domains (either wild-type human proteins or human proteins into which one or more mutations have been introduced) or other non-antigenic H-NOX proteins or domains (e.g., mammalian H-NOX proteins) can be used. To reduce or eliminate the immunogenicity of H-NOX proteins derived from sources other than humans, amino acids in an H-NOX protein or H-NOX domain can be mutated to the corresponding amino acids in a human H-NOX. For example, one or more amino acids on the surface of the tertiary structure of a non-human H-NOX protein can be mutated to the corresponding amino acid in a human H-NOX protein.

Therapeutic Applications of H-NOX Proteins Any of the wild-type or mutant H-NOX proteins, including polymeric H-NOX proteins, or pharmaceutical compositions described herein may be used in therapeutic applications.

Particular H-NOX proteins, including polymeric H-NOX proteins, can be selected for such applications based on the desired $O_2$ association rate, $O_2$ dissociation rate, dissociation constant for $O_2$ binding, NO stability, NO reactivity, autoxidation rate, plasma retention time, or any combination of two or more of the foregoing for the particular indication being treated. H-NOX proteins can be used to treat cardiovascular disease, neurological disease, tumor hypoxia, loss of blood, or wounds. For example, an $O_2$-binding H-NOX protein can be used in most situations where red blood cells or plasma expanders are currently utilized. Specifically, H-NOX protein can be used as red blood cell substitutes for the treatment of trauma (e.g., battlefield, disaster relief, or accidents), hemorrhages, hemorrhagic shock, surgery (e.g., abdominal aneurysm-surgery, orthopedic surgery such as hip replacement surgery, or any other surgery that produces high blood loss), hemodilution, blood extension uses (e.g., supplementing auto-donation), and any other situation where blood volume is lost or $O_2$ carrying capacity is reduced. Examples of wound repair applications include post-radiation wound repair (e.g., hyperbaric oxygen effect), post-surgical repair, diabetic ulcer repair, and burn wounds.

An oxygen-binging polymeric H-NOX can also be used to temporarily augment $O_2$ delivery during or after pre-donation of autologous blood prior to the return of the autologous blood to the individual (such as a replacement for blood that is removed during surgical procedures where the individual's blood is removed and saved for reinfusion at the end of surgery or during recovery). In some embodiments, the H-NOX proteins also function as simple volume expanders that provide oncotic pressure due to the presence of the large H-NOX protein molecule.

Because the distribution in the vasculature of extracellular H-NOX proteins is not limited by the size of the red blood cells, polymeric H-NOX proteins of the present invention can be used to deliver $O_2$ to areas that red blood cells cannot penetrate. These areas can include any tissue areas that are located downstream of obstructions to red blood cell flow, such as areas downstream of one or more thrombi, sickle cell occlusions, arterial occlusions, peripheral vascular occlusions, angioplasty balloons, surgical instruments, tissues that are suffering from oxygen starvation or are hypoxic, and the like. Additionally, all types of tissue ischemia can be treated using H-NOX proteins. Such tissue ischemias include, for example, perioperative ischemia, stroke, emerging stroke, transient ischemic attacks, myocardial stunning and hibernation, acute or unstable angina, emerging angina, and myocardial infarction (e.g., ST-segment elevation myocardial infarction). Other exemplary cardiovascular indications that can be treated using H-NOX proteins include cardioplegia and sickle cell anemia. Exemplary target indications include conditions of functional hemoglobin deficiency, such as where a blood substitute or $O_2$ carrier is indicated, including blood loss, hypoxia, etc.

H-NOX proteins, including polymeric H-NOX proteins, can also be used as an adjunct with radiation or chemotherapy for the treatment of cancer. In some embodiments, an H-NOX protein is used as a radiation therapy adjuvant in solid tumors (e.g., individuals with poor pre-metastatic prognoses) or as a PDT therapy adjuvant in surface tumors (e.g., colon, lung, or skin cancer, or cancer in another accessible surface or location). H-NOX proteins can be used to treat anemia by providing additional oxygen-carrying capacity in a patient who is suffering from anemia. Exemplary neurological indications include ischemic stroke, traumatic brain injury, and spinal cord injury. The methods and compositions are applicable to both acute (providing rapid oxygen to tissues or a specific site, e.g. acute myocardial infarction, acute local or systemic tissue oxygenation, or blood transfusion), and chronic situations (e.g. post-acute recovery from cardiac infarction).

In a particular aspect, the invention provides methods of using H-NOX proteins to deliver $O_2$ to brain tumors (e.g. a glioblastoma). In some embodiments, the administration of H-NOX is used as an adjunct to radiation therapy or chemotherapy. In some embodiments, the invention provides methods to treat a brain cancer (e.g. a glioblastoma) in an individual by administering an effective amount of an H-NOX protein and administering an effective amount of radiation to the individual. In some embodiments, the invention provides methods to reduce brain tumor growth (e.g. glioblastoma growth) in an individual by administering an effective amount of an H-NOX protein and administering an effective amount of radiation to the individual. In some embodiments, the H-NOX protein is a polymeric H-NOX protein (e.g. a trimeric H-NOX protein). In some embodiments, the polymeric H-NOX protein comprises one or more H-NOX domains comprising a mutation at a position corresponding to L144 of *T. tengcongensis* H-NOX. In some embodiments, the polymeric H-NOX protein comprises one or more H-NOX domains comprising a mutation corresponding to a L144F mutation of *T. tengcongensis* H-NOX. In some embodiments, the polymeric H-NOX protein comprises one or more H-NOX domains comprising a mutation at positions corresponding to W9 and L144 of *T. tengcongensis* H-NOX. In some embodiments, the polymeric H-NOX protein comprises one or more H-NOX domains comprising mutations corresponding to a W9F/L144F mutation of *T. tengcongensis* H-NOX. In some embodiments, the H-NOX domain is a human H-NOX domain. In some embodiments, the H-NOX domain is a canine H-NOX domain. In some embodiments, the polymeric H-NOX protein comprises a L144F *T. tengcongensis* H-NOX domain. In some embodiments, the polymeric H-NOX protein comprises a W9F/L144F *T. tengcongensis* H-NOX domain and a foldon domain.

In various embodiments, the invention features a method of delivering $O_2$ to an individual (e.g., a mammal, such as a primate (e.g., a human, a monkey, a gorilla, an ape, a lemur, etc.), a bovine, an equine, a porcine, a canine, or a feline) by administering to an individual in need thereof a wild-type or mutant H-NOX protein, including a polymeric H-NOX protein in an amount sufficient to deliver $O_2$ to the individual. In some embodiments, the invention provides methods of carrying or delivering blood gas to an individual such as a mammal, comprising the step of delivering (e.g., transfusing, etc.) to the blood of the individual (e.g., a mammal) one or more of H-NOX compositions. Methods for delivering $O_2$ carriers to blood or tissues (e.g., mammalian blood or tissues) are known in the art. In various embodiments, the H-NOX protein is an apoprotein that is capable of binding heme or is a holoprotein with heme bound. The H-NOX protein may or may not have heme bound prior to the administration of the H-NOX protein to the individual. In some embodiments, $O_2$ is bound to the H-NOX protein before it is delivered to the individual. In other embodiments, $O_2$ is not bound to the H-NOX protein prior to the administration of the protein to the individual, and the H-NOX protein transports $O_2$ from one location in the individual to another location in the individual.

Wild-type and mutant H-NOX proteins, including polymeric H-NOX proteins, with a relatively low $K_D$ for $O_2$ (such as less than about 80 nM or less than about 50 nM) are expected to be particularly useful to treat tissues with low oxygen tension (such as tumors, some wounds, or other areas where the oxygen tension is very low, such as a p50 below 1 mm Hg). The high affinity of such H-NOX proteins for $O_2$ may increase the length of time the $O_2$ remains bound to the H-NOX protein, thereby reducing the amount of $O_2$ that is released before the H-NOX protein reaches the tissue to be treated.

In some embodiments for the direct delivery of an H-NOX protein with bound $O_2$ to a particular site in the body (such as a glioblastoma), the $k_{off}$ for $O_2$ is more important than the $K_D$ value because $O_2$ is already bound to the protein (making the $k_{on}$ less important) and oxygen needs to be released at or near a particular site in the body (at a rate influenced by the $k_{off}$). In some embodiments, the $k_{off}$ may also be important when H-NOX proteins are in the presence of red cells in the circulation, where they facilitate diffusion of $O_2$ from red cells, and perhaps prolonging the ability of diluted red cells to transport $O_2$ to further points in the vasculature.

In some embodiments for the delivery of a H-NOX protein that circulates in the bloodstream of an individual, the H-NOX protein binds $O_2$ in the lungs and releases $O_2$ at one or more other sites in the body. For some of these applications, the $K_D$ value is more important than the $k_{off}$ since $O_2$ binding is at or near equilibrium. In some embodiments for extreme hemodilution, the $K_D$ more important than the $k_{off}$ when the H-NOX protein is the primary $O_2$ carrier because the H-NOX protein will bind and release $O_2$ continually as it travels through the circulation. Since hemoglobin has a p50 of 14 mm Hg, red cells (which act like capacitors) have a p50 of ~30 mm Hg, and HBOCs have been developed with ranges between 5 mm Hg and 90 mm Hg, the optimal $K_D$ range for H-NOX proteins may therefore be between ~2 mm Hg to ~100 mm Hg for some applications.

Polymeric H-NOX proteins can also be used for imaging. In particular, light imaging (e.g., optical coherence tomography; see, for example, Villard, J. W. (2002). *Circulation* 105:1843-1849, which is incorporated by reference in its entirety particularly with respect to optical coherence tomography) is obfuscated by erythrocytes. Perfusion with an H-NOX solution allows for clearer images of the circulation and vessel walls because the H-NOX protein is much smaller than erythrocytes.

H-NOX proteins, including polymeric H-NOX proteins, and pharmaceutical compositions of the invention can be administered to an individual by any conventional means such as by oral, topical, intraocular, intrathecal, intrapulmonary, intra-tracheal, or aerosol administration; by transdermal or mucus membrane adsorption; or by injection (e.g., subcutaneous, intravenous, intra-arterial, intravesicular, or intramuscular injection). H-NOX proteins may also be included in large volume parenteral solutions for use as blood substitutes. In exemplary embodiments, the H-NOX protein is administered to the blood (e.g., administration to a blood vessel such as a vein, artery, or capillary), a wound, a tumor, a hypoxic tissue, or a hypoxic organ of the individual.

In some embodiments, a sustained continuous release formulation of the composition is used. Administration of an H-NOX protein can occur, e.g., for a period of seconds to hours depending on the purpose of the administration. For example, as a blood delivery vehicle, an exemplary time course of administration is as rapid as possible. Other exemplary time courses include about any of 10, 20, 30, 40, 60, 90, or 120 minutes. Exemplary infusion rates for H-NOX solutions as blood replacements are from about 30 mL/hour to about 13,260 mL/hour, such as about 100 mL/hour to about 3,000 mL/hour. An exemplary total dose of H-NOX protein is about 900 mg/kg administered over 20 minutes at 13,260 mL/hour. An exemplary total dose of H-NOX protein for a swine is about 18.9 grams.

Exemplary dosing frequencies include, but are not limited to, at least 1, 2, 3, 4, 5, 6, or 7 times (i.e., daily) a week. In some embodiments, an H-NOX protein is administered at least 2, 3, 4, or 6 times a day. The H-NOX protein can be administered, e.g., over a period of a few days or weeks. In some embodiments, the H-NOX protein is administrated for a longer period, such as a few months or years. The dosing frequency of the composition may be adjusted over the course of the treatment based on the judgment of the administering physician.

In some embodiments of the invention, the H-NOX protein (e.g. a polymeric H-NOX protein) is used as an adjunct to radiation therapy or chemotherapy. For example, for the treatment of glioblastoma. In some embodiments, the H-NOX is administered to the individual any of at least 1, 2, 3, 4, 5 or 6 hours before administration of the radiation or chemotherapy. In some embodiments, the radiation is X irradiation. In some embodiments, the dose of X irradiation is any of about 0.5 gy to about 75 gy. In some embodiments, the cycle of H-NOX administration and radiation administration is repeated any one of one, two, three, four, five or six times. In some embodiments, the cycle of H-NOX administration and radiation administration is repeated after any one of about one week, two weeks, three weeks, four weeks, five weeks or six weeks. In some embodiments, the administration of H-NOX and radiation therapy is used in conjunction with another therapy; for example, a chemotherapy.

As noted above, the selection of dosage amounts for H-NOX proteins depends upon the dosage form utilized, the frequency and number of administrations, the condition being treated, and the particular purpose to be achieved according to the determination of the ordinarily skilled artisan in the field. In some embodiments, an effective amount of an H-NOX protein for administration to human is between a few grams to over 350 grams.

In some embodiments, two or more different H-NOX proteins are administered simultaneously, sequentially, or concurrently. In some embodiments, another compound or therapy useful for the delivery of $O_2$ is administered simultaneously, sequentially, or concurrently with the administration of one or more H-NOX proteins.

Other exemplary therapeutic applications for which H-NOX proteins can be used are described by, e.g., U.S. Pat. Nos. 6,974,795, and 6,432,918, which are each hereby incorporated by reference in their entireties, particularly with respect to therapeutic applications for $O_2$ carriers.

Kits with H-NOX Proteins

Also provided are articles of manufacture and kits that include any of the H-NOX proteins described herein including polymeric H-NOX proteins, and suitable packaging. In some embodiments, the invention includes a kit with (i) a H-NOX protein (such as a wild-type or mutant H-NOX protein described herein or formulations thereof as described herein) and (ii) instructions for using the kit to deliver $O_2$ to an individual. In various embodiments, the invention features a kit with (i) an H-NOX protein (such as a wild-type or mutant H-NOX protein described herein or formulations thereof as described herein) and (ii) instructions for using the kit for any of the industrial uses described herein (e.g., use of an H-NOX protein as a reference standard for analytical instrumentation needing such a reference standard, enhancement of cell growth in cell culture by maintaining or increasing $O_2$ levels in vitro, addition of $O_2$ to a solution, or removal of $O_2$ from a solution).

In some embodiments, kits are provided for use in the treatment of brain cancer (e.g. glioblastoma). In some embodiments, the kit comprises a polymeric H-NOX protein. In some embodiments, the kit comprises an effective amount of a polymeric H-NOX protein comprising two or more wild-type or mutant H-NOX domains. In some embodiments, the kit comprises an effective amount of a recombinant monomeric H-NOX protein comprising a wild-type or mutant H-NOX domain and a polymerization domain as described herein. In some embodiments, the kit comprises a trimeric H-NOX protein comprising three monomers, each monomer comprising a mutation corresponding to a *T. tengcongensis* L144F H-NOX mutation and a trimerization domain. In some embodiments, the kit comprises a trimeric H-NOX protein comprising three monomers, each monomer comprising a mutation corresponding to a *T. tengcongensis* W9F/L144F H-NOX mutation and a trimerization domain. In some embodiments, the trimeric H-NOX protein comprises human H-NOX domains. In some embodiments, the trimeric H-NOX protein comprises canine H-NOX domains. In some embodiments, the kit comprises a trimeric H-NOX protein comprising three monomers, each monomer comprising a *T. tengcongensis* L144F H-NOX domain and a foldon domain. In some embodiments, the kit comprises a trimeric H-NOX protein comprising three monomers, each monomer comprising a *T. tengcongensis* W9F/L144F H-NOX domain and a foldon domain. In some embodiments, the kit comprises a trimeric H-NOX protein comprising three monomers, each monomer comprising a *T. tengcongensis* L144F H-NOX domain and a foldon domain.

Suitable packaging for compositions described herein are known in the art, and include, for example, vials (e.g., sealed vials), vessels, ampules, bottles, jars, flexible packaging (e.g., sealed Mylar or plastic bags), and the like. These articles of manufacture may further be sterilized and/or sealed. Also provided are unit dosage forms comprising the compositions described herein. These unit dosage forms can be stored in a suitable packaging in single or multiple unit dosages and may also be further sterilized and sealed. Instructions supplied in the kits of the invention are typically written instructions on a label or package insert (e.g., a paper sheet included in the kit), but machine-readable instructions (e.g., instructions carried on a magnetic or optical storage disk) are also acceptable. The instructions relating to the use of H-NOX proteins generally include information as to dosage, dosing schedule, and route of administration for the intended treatment or industrial use. The kit may further comprise a description of selecting an individual suitable or treatment.

The containers may be unit doses, bulk packages (e.g., multi-dose packages) or subunit doses. For example, kits may also be provided that contain sufficient dosages of H-NOX proteins disclosed herein to provide effective treatment for an individual for an extended period, such as about any of a week, 2 weeks, 3 weeks, 4 weeks, 6 weeks, 8 weeks, 3 months, 4 months, 5 months, 6 months, 7 months, 8 months, 9 months, or more. Kits may also include multiple unit doses of H-NOX proteins and instructions for use and packaged in quantities sufficient for storage and use in pharmacies, for example, hospital pharmacies and compounding pharmacies. In some embodiments, the kit includes a dry (e.g., lyophilized) composition that can be reconstituted, resuspended, or rehydrated to form generally a stable aqueous suspension of H-NOX protein.

Exemplary Methods for Production of H-NOX Proteins

The present invention also provides methods for the production of any of the polymeric H-NOX proteins described herein. In some embodiments, the method involves culturing a cell that has a nucleic acid encoding a polymeric H-NOX protein under conditions suitable for production of the polymeric H-NOX protein. In various embodiments, the polymeric H-NOX is also purified (such as purification of the H-NOX protein from the cells or the culture medium). In some embodiments, the method involves culturing a cell that has a nucleic acid encoding a monomer H-NOX protein comprising an H-NOX domain and a polymerization domain. The monomers then associate in vivo or in vitro to form a polymeric H-NOX protein. A polymeric H-NOX protein comprising heterologous H-NOX domains may be generated by co-introducing two or more nucleic acids encoding monomeric H-NOX proteins with the desired H-NOX domains and where in the two or more monomeric H-NOX proteins comprise the same polymerization domain.

In some embodiments, a polymeric H-NOX protein comprising heterologous H-NOX domains is prepared by separately preparing polymeric H-NOX proteins comprising homologous monomeric H-NOX subunits comprising the desired H-NOX domains and a common polymerization domain. The different homologous H-NOX proteins are mixed at a desired ratio of heterologous H-NOX subunits, the homologous polymeric H-NOX proteins are dissociated (e.g. by heat, denaturant, high salt, etc.), then allowed to associate to form heterologous polymeric H-NOX proteins. The mixture of heterologous polymeric H-NOX proteins may be further purified by selecting for the presence of the desired subunits at the desired ratio. For example, each different H-NOX monomer may have a distinct tag to assist in purifying heterologous polymeric H-NOX proteins and identifying and quantifying the heterologous subunits.

As noted above, the sequences of several wild-type H-NOX proteins and nucleic acids are known and can be used to generate mutant H-NOX domains and nucleic acids of the present invention. Techniques for the mutation, expression, and purification of recombinant H-NOX proteins have been described by, e.g., Boon, E. M. et al. (2005). *Nature Chemical Biology* 1:53-59 and Karow, D. S. et al. (Aug. 10, 2004). *Biochemistry* 43(31):10203-10211, which is hereby incorporated by reference in its entirety, particularly with respect to the mutation, expression, and purification of recombinant H-NOX proteins. These techniques or other standard techniques can be used to generate any mutant H-NOX protein.

In particular, mutant H-NOX proteins described herein can be generated a number of methods that are known in the art. Mutation can occur at either the amino acid level by chemical modification of an amino acid or at the codon level by alteration of the nucleotide sequence that codes for a given amino acid. Substitution of an amino acid at any given position in a protein can be achieved by altering the codon that codes for that amino acid. This can be accomplished by site-directed mutagenesis using, for example: (i) the Amersham technique (Amersham mutagenesis kit, Amersham, Inc., Cleveland, Ohio) based on the methods of Taylor, J. W. et al. (Dec. 20, 1985). *Nucleic Acids Res.* 13(24):8749-8764;

Taylor, J. W. et al. (Dec. 20, 1985). *Nucleic Acids Res.* 13(24):8765-8785; Nakamaye, K. L. et al. (Dec. 22, 1986). *Nucleic Acids Res.* 14(24):9679-9698; and Dente et al. (1985). in *DNA Cloning, Glover, Ed.*, IRL Press, pages 791-802, (ii) the Promega kit (Promega Inc., Madison, Wis.), or (iii) the Biorad kit (Biorad Inc., Richmond, Calif.), based on the methods of Kunkel, T. A. (January 1985). *Proc. Natl. Acad. Sci. USA* 82(2):488-492; Kunkel, T. A. (1987). *Methods Enzymol.* 154:367-382; Kunkel, U.S. Pat. No. 4,873,192, which are each hereby incorporated by reference in their entireties, particularly with respect to the mutagenesis of proteins. Mutagenesis can also be accomplished by other commercially available or non-commercial means, such as those that utilize site-directed mutagenesis with mutant oligonucleotides.

Site-directed mutagenesis can also be accomplished using PCR-based mutagenesis such as that described in Zhengbin et al. (1992). pages 205-207 in PCR Methods and Applications, Cold Spring Harbor Laboratory Press, New York; Jones, D. H. et al. (February 1990). *Biotechniques* 8(2):178-183; Jones, D. H. et al. (January 1991). *Biotechniques* 10(1):62-66, which are each hereby incorporated by reference in their entireties, particularly with respect to the mutagenesis of proteins. Site-directed mutagenesis can also be accomplished using cassette mutagenesis with techniques that are known to those of skill in the art.

A mutant H-NOX nucleic acid and/or polymerization domain can be incorporated into a vector, such as an expression vector, using standard techniques. For example, restriction enzymes can be used to cleave the mutant H-NOX nucleic acid and the vector. Then, the compatible ends of the cleaved mutant H-NOX nucleic acid and the cleaved vector can be ligated. The resulting vector can be inserted into a cell (e.g., an insect cell, a plant cell, a yeast cell, or a bacterial cell) using standard techniques (e.g., electroporation) for expression of the encoded H-NOX protein.

In particular, heterologous proteins have been expressed in a number of biological expression systems, such as insect cells, plant cells, yeast cells, and bacterial cells. Thus, any suitable biological protein expression system can be utilized to produce large quantities of recombinant H-NOX protein. In some embodiments, the H-NOX protein (e.g., a mutant or wild-type H-NOX protein) is an isolated protein.

If desired, H-NOX proteins can be purified using standard techniques. In some embodiments, the protein is at least about 60%, by weight, free from other components that are present when the protein is produced. In various embodiments, the protein is at least about 75%, 90%, or 99%, by weight, pure. A purified protein can be obtained, for example, by purification (e.g., extraction) from a natural source, a recombinant expression system, or a reaction mixture for chemical synthesis. Exemplary methods of purification include immunoprecipitation, column chromatography such as immunoaffinity chromatography, magnetic bead immunoaffinity purification, and panning with a plate-bound antibody, as well as other techniques known to the skilled artisan. Purity can be assayed by any appropriate method, e.g., by column chromatography, polyacrylamide gel electrophoresis, or HPLC analysis. In some embodiments, the purified protein is incorporated into a pharmaceutical composition of the invention or used in a method of the invention. The pharmaceutical composition of the invention may have additives, carriers, or other components in addition to the purified protein.

In some embodiments, the polymeric H-NOX protein comprises one or more $His_6$ tags. An H-NOX protein comprising at least one $His_6$ tag may be purified using chromatography; for example, using $Ni^{2+}$-affinity chromatography. Following purification, the $His_6$ tag may be removed; for example, by using an exopeptidase. In some embodiments, the invention provides a purified polymeric H-NOX protein, wherein the polymeric H-NOX protein was purified through the use of a $His_6$ tag. In some embodiments, the purified H-NOX protein is treated with an exopeptidase to remove the $His_6$ tags.

EXAMPLES

The examples, which are intended to be purely exemplary of the invention and should therefore not be considered to limit the invention in any way, also describe and detail aspects and embodiments of the invention discussed above. The examples are not intended to represent that the experiments below are all or the only experiments performed. Unless indicated otherwise, temperature is in degrees Centigrade and pressure is at or near atmospheric.

Example 1. Creation and Expression of a Trimerized H-NOX Protein

To increase the circulation half-life of the H-NOX protein a chimeric fusion protein was designed to combine the *Thermoanaerobacter tengcongensis* H-NOX sequence with the trimerization domain from the bacteriophage T4 fibritin protein. This fusion strategy produces a more than 3 fold increase in the molecular weight and is completely modular (the trimerization domain could be added to any H-NOX sequence and even used to combine multiple H-NOX sequences in a single trimer molecule).

Fusion of the Foldon Domain to H-NOX

The foldon domain was genetically fused to the C-terminus of a *Thermoanaerobacter tengcongensis* H-NOX sequence using a three amino acid (Gly-Ser-Gly) linker between the Xho I restriction site at the C-terminus of the H-NOX sequence and the initial glycine of the foldon domain. A His6 protein purification tag was added to the C-terminus of the foldon domain using a three amino acid (Arg-Gly-Ser) linker between the foldon and $His_6$ tag. The DNA and amino acid sequence of the complete fusion protein is shown in FIGS. 2A and 2B. The full length fusion protein encodes a 229 amino acid protein with a molecular weight of 26,677 AMU (as a monomer).

Construction of the H-NOX-Foldon Fusion Protein Sequence

The construction of the H-NOX-foldon fusion sequence was designed to use restriction endonucleases to excise the DNA segment encoding the $His_6$ and stop codon from the parent H-NOX plasmid and replace it with a cassette encoding the foldon sequence, $His_6$ tag, and stop codon. DNA encoding the foldon domain, $His_6$ tag, and stop codon flanked by restriction enzyme sites (Xho I at the 5' end and Hind III at the 3' end after the $His_6$ tag and stop codon) was purchased from GenScript (Piscataway, N.J.). The sequence was delivered in the GenScript cloning vector pUC57.

Restriction enzymes Xho I and Hind III were used to digest the pUC57 plasmid to release the foldon-$His_6$ fragment (147 base pairs in length). The pCW vector encoding the L144F variant of *Thermoanaerobacter tengcongensis* H-NOX was also digested with Xho I and Hind III to remove the 48 base pair fragment encoding the $His_6$ tag and stop codon from the H-NOX sequence. The desired fragments from the restriction digestion reactions were isolated by preparative agarose gel electrophoresis and the DNA fragments were purified from the agarose. The fragments encoding the H-NOX sequence and foldon-His$_6$ tag were ligated using T4 ligase and the ligation reaction was used to transform competent E. coli cells. Sequencing with a pCW specific sequencing primer confirmed that one of the E. coli clones (clone 3I-A) matched the desired fusion sequence and encoded the complete H-NOX-foldon-His$_6$ chimeric protein (FIG. 3A shows the sequencing data aligned with the desired sequence). The clone 3I-A sequence was renamed v01-f002 to designate the pCW vector (v01) encoding the L144F H-NOX sequence (002) with the fused foldon domain (f). The sequences of wild-type T thermoanaerobacter H-NOX-foldon monomers with and without His6 tags and the sequence of C. lupus H-NOX-foldon monomers are presented in FIGS. 3A-3E.

Expression and Purification of the H-NOX-Foldon Fusion Protein

The v01-f002 plasmid derived from the pCW parent vector (Gegner, J A & Dahlquist, F W (1991) Proc Natl Acad Sci USA 88, 750-75; Muchmore, D C, et al. (1989) Methods Enzymol 177: 44-73) codes for expression of the f002 open reading frame by the multiple tac (hybrid trp-lac) promoters. Plasmid v01-f002 was transformed into competent E. coli strain RP523 (Li, J M, et al., (1988) J Bacteriol 170:1021-1025) for efficient expression of heme-bound H-NOX protein. Expression was tested at a range of induction temperatures (37° C., 30° C., 18° C.) and also in Rosetta2 cells (Merck Millipore, Darmstadt, Germany).

Robust expression of the v01-f002 plasmid was achieved in RP523 cells using an initial overnight starter culture of Luria Broth supplemented with 100 mg/L Ampicillin and 30 mg/L hemin grown at 30° C. The starter culture was then used to inoculate the 6 L expression culture of Terrific Broth supplemented with 100 mg/L Ampicillin, 30 mg/L hemin, and 1.5% glucose. The expression culture was grown at 30° C. to an OD$_{600}$ of ~0.5 and then protein expression was induced by the addition of IPTG to a final concentration of 0.1 mM. Expression was continued at 30° C. overnight (24.5 hours of induction) before cells were harvested by centrifugation and frozen at −80° C. for purification.

Figure 4:
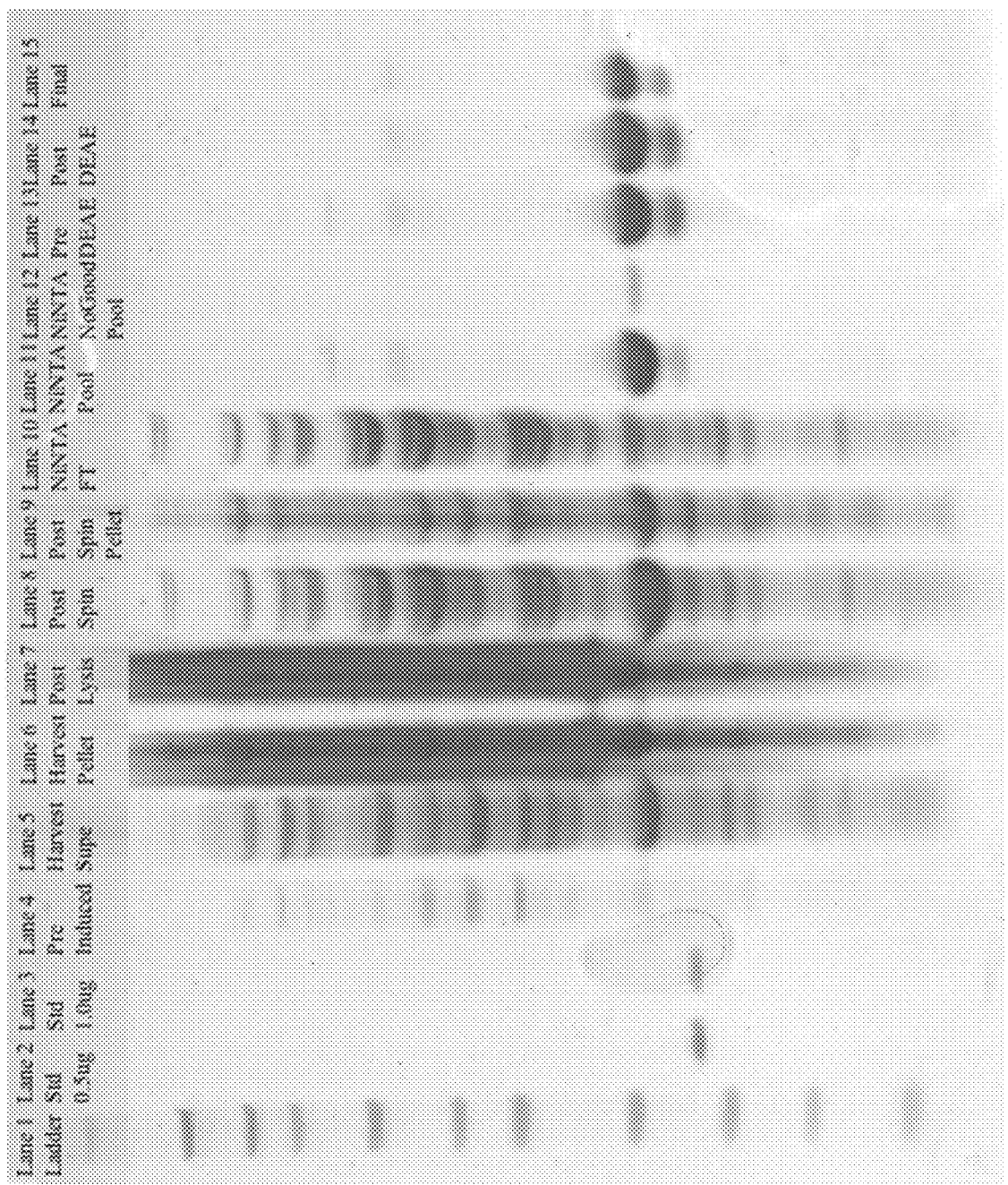
FIG. 4 shows SDS-PAGE gel of steps in the initial purification of the H-NOX-foldon fusion protein. The Ladder is the Novex Sharp Protein Standard (Invitrogen, Grand Island, N.Y.) with the 3.5 kDa band run off the bottom of the gel. The Std lanes are known amounts of $His_6$ tagged monomeric H-NOX protein (23 kDa). Induction of the H-NOX-foldon fusion can be seen by comparing lanes 4 and 5 (the fusion monomer has a molecular weight of 26.7 kDa). The double bands seen in lanes 11, 13, 14, and 15 result from insufficient DTT in the SDS-PAGE sample buffer for this quantity of protein. Lane 1: ladder; Lane 2: 0.5 µg standard; Lane 3: 1.0 µg standard; Lane 4: pre-induced; Lane 5.

Fusion protein was purified from the expressed cell pellet using a heat treatment step and two chromatography steps. First, the expressed cell pellet was resuspended in a 50 mM sodium phosphate, 500 mM NaCl, 20 mM imidazole, and 5% glycerol buffer at pH 7.9. The solution was homogenized using an EmulsiFlex C-50 homogenizer (Avestin, Ottawa, Canada) to lyse the bacterial cells. The cell lysate was heated for 15 minutes at 75° C. to precipitate non-thermostable proteins. The precipitate was removed by centrifugation at 27,000 g for 15 minutes to obtain a clarified supernatant. The clarified supernatant was applied to a HisTrap FastFlow column (GE, Piscataway, N.J.) to bind the His$_6$-tagged fusion protein. Bound protein was eluted with a buffer of 50 mM sodium phosphate, 500 mM NaCl, 250 mM imidazole, and 5% glycerol buffer at pH 7.9. Eluted protein was buffer exchanged into a 30 mM Triethanolamine, 50 mM NaCl, pH 7.4 buffer for application to a DEAE Sepharose FastFlow column (GE, Piscataway, N.J.). The H-NOX-foldon fusion protein flowed through the DEAE column while host cell contaminants and endotoxin were retained on the column. The H-NOX-foldon fusion protein could then be concentrated for storage at −80° C. An SDS-PAGE gel showing the H-NOX-foldon fusion protein at each stage of the purification process from the initial purification is shown in FIG. 4.

Characterization of Purified H-NOX-Foldon Fusion Protein

A number of techniques have been used to characterize the purified H-NOX-foldon protein. The purity of the final purified protein has been analyzed by SDS-PAGE (see FIGS. 4 and 5). Gel electrophoresis shows that the H-NOX-foldon fusion protein is >95% pure after the heat treatment and two chromatography steps. On the denaturing SDS-PAGE gel, the H-NOX-foldon fusion runs as a monomer with a mobility consistent with a monomeric molecular weight of 26.7 kDa.

More quantitative estimates of the size of the fusion protein have been obtained using both LC-MS to determine the exact mass of the monomeric unit and analytical size exclusion chromatography to estimate the size and dispersion of the trimer in the standard buffer solution. FIG. 6 shows LC-MS analysis of H-NOX-foldon fusion protein. The LC-MS derived mass of 26,678 AMU is consistent with the predicted mass of 26,677 AMU for the monomeric H-NOX-foldon fusion. FIG. 7 shows analytical size exclusion chromatography using a Superdex 200 10/300 GL (GE, Piscataway, N.J.) column and a 30 mM Triethanolamine, 50 mM NaCl, pH 7.4 buffer. Under the analytical SEC conditions, the H-NOX-foldon fusion should remain trimerized and the resulting retention volume is consistent with the predicted molecular weight of 80.0 kDa for the H-NOX-foldon trimer.

Spectroscopy of hemoproteins is used to characterize the nature of bound ligands and the oxidation state of the iron atom in the heme. UV-vis spectroscopic analysis of the H-NOX-foldon protein shows that the fusion of the foldon domain does not alter the characteristic H-NOX spectrum. Characteristic spectral peaks including the Soret peak (415 nm), and α/β peaks (550-600 nm) are all preserved between the H-NOX monomer and the H-NOX-foldon fusion protein and indicate that the H-NOX-foldon fusion binds the heme cofactor and diatomic oxygen gas in a manner similar to the original H-NOX monomer (FIG. 8).

A structural model of the H-NOX-foldon trimer has been constructed using the crystal structures of the foldon domain (1V1H) and the Thermoanaerobacter tengcongensis H-NOX monomer (1U4H) found in the RCSB Protein Data Bank (FIG. 9).

Example 2. Production of a Panel of H-NOX Trimers Demonstrating an Extended Half-Life and a Range of Oxygen Affinities Using structure-based computational design, H-NOX amino acids were systematically mutated to create a panel of H-NOX monomer variants that bind oxygen with a range of affinities. It was determined that small 23 kDa H-NOX monomers were cleared from the rat circulatory system with a half-life of 30 minutes. It was hypothesized that by raising the molecular weight above the renal filtration limit the circulation half-life of the H-NOX protein could possibly increase and therefore allow sustained oxygenation for longer durations. In order to determine if increased molecular weight could increase the circulation half-life of H-NOX protein, H-NOX variants with larger molecular weights were generated by trimerization of H-NOX monomers that had been successful at oxygenating hypoxic tissue. To generate a panel of trimerized variants, a small amino acid trimerization motif from the fibritin protein called a "foldon"

domain was genetically linked to the C-terminus of several H-NOX monomers with different oxygen affinities ranging from 1 to 20 mmHg. The panel included H-NOX trimers assembled with wild-type H-NOX, H-NOX variant L144F, H-NOX variant L144F with no His$_6$ tag at the C-terminus, H-NOX variant L144F/L189C, H-NOX variant L144F with no linker between H-NOX and foldon, H-NOX variant L144F with a three amino acid linker between H-NOX and foldon, H-NOX variant with a nine amino acid linker between H-NOX and foldon, or H-NOX variant W9F/L144F. The foldon domain consisted of 27 amino acid residues, GYIPEAPRDGQAYVRKDGEWVLLSTFL (SEQ ID NO:4), corresponding to amino acid residues 457 to 483 in fibritin and had a predicted mass of 3.08 kDa. As described above, the foldon domain has previously been shown to increase protein stability and has been widely used to trimerize proteins both in vitro and in vivo. Briefly, a plasmid containing the gene encoding the foldon domain with XhoI and HindIII restriction sites at the 5' and 3' ends, respectively, was digested with XhoI and HindIII restriction enzymes to clone the foldon domain gene into a plasmid encoding a H-NOX protein monomer. After expression of the plasmid in bacterial cells (*E. coli*), H-NOX+foldon protein was purified and tested to verify trimerization of the H-NOX+foldon monomers into H-NOX+foldon trimers (e.g., H-NOX trimer). For purification, bacterial cells were lysed with lysozyme and homogenized. The supernatant was collected and heat treated at 75° C. for 15 minutes prior to centrifugation at 14 krpm in a JA-17 rotor to remove insoluble protein. Soluble H-NOX+foldon was bound to a HisTrap (IMAC) column and eluted with imidazole, and the eluted samples were subjected to buffer exchange to provide a protein sample in a low salt buffer without imidazole. Additional contaminating proteins in the sample were removed by subjecting the protein sample to a DEAE ion exchange column and the eluted protein samples were concentrated prior to analysis. Mass spectroscopy and Size Exclusion Chromatography was used to verify the monomeric molecular weight (approximately 26.7 kDa) and trimeric molecular weight (approximately 80.1 kDa), respectively. Each trimerized variant, was tested to determine if it met biochemical parameters including: homogenous molecular weight, oxygen binding affinities between 1 and 20 mmHg as measured by $k_{off}$ and interpolating known $k_{on}$ values to arrive at $K_d$'s that correspond to mmHg. $K_{off}$ for homotrimers is essentially the same as for the corresponding monomers when measured by $k_{off}$, minimal nitric oxide (NO) reactivity, low autoxidation rates, and circulation persistence time of 3 hours or longer (Table 2). Spectroscopy was used to determine the nature of gas bound at STP and stopped flow spectroscopy was used to determine the kinetic rate constant for oxygen dissociation. From the analysis, H-NOX trimers were identified with oxygen affinities of 2 µM, an affinity that could possibly allow release of oxygen in tissues with low oxygen levels. The H-NOX trimers also demonstrated nitric oxide reactivity of about less than 1 $\mu M^{-1} s^{-1}$ which was considered minimal as compared to hemoglobin which has a nitric oxide reactivity of 58 $\mu M^{-1} s^{-1}$ that has previously been proven to be vasoactive and toxic.

TABLE 2

Biochemical and Clearance Properties of Polymerized H-NOX trimers

| Product parameter | Target Profile | Clinical Rationale |
|---|---|---|
| Molecular weight | 80 kDa | Persist in the circulation for clinically relevant period. Remain small enough to perfuse ischemic cerebral tissue. |
| Oxygen binding affinity | ~1 to ~20 mmHg | Release oxygen at normoxic levels to sustain neurological function and tissue survival. |
| Nitric oxide reactivity | $<7 \ s^{-1}$ | Avoid destruction of nitric oxide that is essential for multiple aspects of cardiovascular and neurological function. |
| Autoxidation rate | $k_{ox} < 0.1 \ h^{-1}$ | Commercially viable manufacturing and stability. |
| Circulation clearance rate | $T_{1/2} > 3$ hours | Reduce clearance through the kidneys and extravasation to other tissues to maximize efficacy and safety. |

Trimers were produced with high purity and low endotoxin levels for clearance studies in rats. H-NOX trimers were formulated for in vivo injection in a physiological buffer of 150 mM NaCl, 25 mM HEPES buffer (pH 7.4), and concentrated to 100 mg/mL for use in doses of up to 100 mg/kg. To verify extended circulation persistence times of the H-NOX trimers, trimer candidates were each tested using a group of four male Wister rats. Anesthesia was induced in an induction chamber with 2-3% isoflurane in N20:02 (2:1), and maintained with 1-1.5% isoflurane via nose cone. Adequate depth of anesthesia was assessed by lack of withdrawal to hind limb pinch and loss of eye blind reflex. Animals received 40 mg/kg of cefazolin sodium via intraperitoneal injection and 0.1 mg/kg of subcutaneous buprenorphine. One day prior to clearance testing, femoral vein and artery catheters were surgically implanted in each animal to allow for injection and blood removal, respectively. Candidate H-NOX trimers were injected at time 0 at a dose of 100 mg/kg by intravenous bolus injection into the venous catheter. About 250 µL of blood was collected from the arterial catheter of each rat at 5 min, 30 min, 1 hr, 1.5 hr, 2 hr, 3 hr, 4 hr, 6 hr, 8 hr, and 24 hr post injection of the candidate H-NOX trimer or buffer control. Collected blood was processed for serum and plasma and subsequently analyzed for the presence of H-NOX trimer using ELISA and SDS-PAGE assays with a polyclonal antibody against the H-NOX protein.

TABLE 3

Pharmacokinetic parameters of HNOX monomer and trimer when administered as an intravenous bolus (100 mg/kg) to rat

| Compound | Rat I.D. | Terminal $t_{1/2}$(min) | $AUC_{last}$ (μg*min/mL) | $AUC_\infty$ (μg*min/mL) | Cl (mL/min/kg) | $Cl_r$ (mL/min/kg) | $V_z$ (mL/kg) | $V_{ss}$ (mL/kg) |
|---|---|---|---|---|---|---|---|---|
| HNOX monomer | 1 | 24.7 | 53992.3 | 54006.9 | 1.85 | 0.04 | 66.05 | 31.04 |
|  | 2 | 49 | 6706.9 | 6722 | 14.88 | <0.01 | 1052.39 | 242.83 |
|  | 3 | 24.3 | 19774.8 | 19787.6 | 5.05 | <0.01 | 177.08 | 114.28 |
|  | Mean | 32.7 | 26824.7 | 26838.8 | 7.26 | ND | 431.84 | 129.38 |
|  | SD | 14.2 | 24418.3 | 24418.3 | 6.79 | ND | 540.27 | 106.7 |
| HNOX trimer | 5 | 62.4 | 84949.3 | 85081.5 | 1.18 | <0.01 | 105.86 | 49.95 |
|  | 6 | 60.5 | 52377.1 | 52516.9 | 1.9 | <0.01 | 166.13 | 121.99 |
|  | Mean | 61.5 | 68663.2 | 68799.2 | 1.54 | ND | 136 | 85.97 |
|  | SD | 1.4 | 23032 | 23026.7 | 0.52 | ND | 42.62 | 50.94 |

ND—not determined

In addition to measurement of clearance time for each trimer, preliminary safety in the animals was also monitored. A Good Laboratory Practice (GLP)-like safety study with H-NOX monomer showed no major adverse or immunological events at 48 hours, even at the maximal feasible dose of 1 g/kg. Candidate H-NOX trimers were similarly tested by monitoring gross toxicity, blood chemistry, and anti-therapeutic antibodies up to 4 weeks after the initial injection. For preliminary safety testing, groups of six mice were administered candidate H-NOX trimers or buffer control at time 0 at a dose of 750 mg/kg by intravenous bolus injection into the tail vein. Blood samples were collected from the jugular vein of each rat before administration of the H-NOX trimers and compared to blood collected each week for up to four weeks after administration the H-NOX trimers. Collected blood was processed for serum and plasma and subsequently subjected to clinical chemistry analysis and anti-therapeutic antibody production as detected by ELISA. All animals were observed daily to monitor for any evidence of gross toxicity.

Plasma profiles of H-NOX trimer after intravenous bolus (100 mg/kg) in two different rats are shown in FIG. 10. IgG and IgM antibody responses following H-NOX trimer administration is shown in FIG. 11.

Example 3. Identification of H-NOX Trimer Candidates Demonstrating Brain Tissue Penetration and Reduction of Hypoxia in In Vivo Mouse Models of Ischemia H-NOX trimer candidates with a circulation half-life of at least 3 hours were tested in a temporary MCA occlusion rodent model (tMCAO) of ischemic stroke for identification of H-NOX trimers that perfuse and persist in brain tissue. Lead H-NOX trimer candidates were each tested using a group of 24 male Wister rats. Anesthesia was induced in an induction chamber with 2-3% isoflurane in $N_2O:O_2$ (2:1), and maintained with 1-1.5% isoflurane via nose cone. Adequate depth of anesthesia was assessed by lack of withdrawal to hind limb pinch and loss of eye blind reflex. Animals received 40 mg/kg of cefazolin sodium via intraperitoneal injection and 0.1 mg/kg of subcutaneous buprenorphine. Temporary middle cerebral artery occlusion was initiated in Day 0 using a standard suture-based surgical technique. Briefly, a skin incision was made over the right common carotid artery (CCA) to allow temporary clamping of the CCA and ligation of a distal segment of the external carotid artery (ECA). A nylon suture was inserted through the proximal ECA and advanced into the internal carotid artery (ICA) to occlude blood flow to the brain. The CCA clip was removed and the skin incision was closed with surgical staples, and the animal was allowed to awaken. A 750 mg/kg dose of an H-NOX trimer candidate was infused by tail vein injection into rats 30 minutes after occlusion of the middle cerebral artery. In order to analyze tissue hypoxia, the hypoxia marker pimonidazole was injected intraperitoneally at 60 mg/kg about 15 minutes after H-NOX trimer injection to irreversibly label ischemic tissue. The occlusion was released 30 minutes after H-NOX trimer infusion by providing anesthesia to the rats, reopening the wound and removing the intravascular suture from the ECA before closing the wound again in order to provide a total of 1 hour of occlusion before reperfusion. To analyze tissue distribution of the H-NOX trimers and quantify reduction in hypoxia, rats were sacrificed at 2, 4, 12, and 24 hours after reperfusion (N=6 rats per H-NOX trimer per time point), and brain tissue and blood were collected. Brains from euthanized animals were sectioned and stained for H-NOX distribution and tissue hypoxia by using a polyclonal antibody to H-NOX and a Hydroxyprobe antibody to the pimonidazole hypoxia marker (Hydroxyprobe International), respectively, for subsequent immunohistochemical analysis. Images were taken using a microscope equipped with a camera and staining was quantified. Ischemia and reperfusion are known to trigger neuronal cell death and initiate inflammatory responses that result in post-ischemic damage. As secondary endpoints, apoptosis was measured in the brain tissue by TUNEL assay staining (Roche) and counting TUNEL positive cells, and by staining of apoptotic markers including Cleaved Caspase-1, -3, Bax, and Bcl-2. Blood chemistries were performed on samples taken at multiple time points to assess reduction of inflammatory markers, and any hematopoietic and systemic effects due to use of H-NOX trimer candidates. The upregulation of pro-inflammatory cytokines including TNFα, IL-1α, IL-1β IL-6, MCP-1, Rantes, and MIP were quantified from rat serum using ELISA (Signosis Rat Inflammation ELISA kit) and RT-PCR. H-NOX trimer candidates were identified that penetrated into ischemic tissue and that significantly reduced hypoxia.

Example 4: H-NOX Trimers Reduced Infarct Volume and Improved Neurological Outcomes in In Vivo Mouse Models of Ischemia H-NOX trimer candidates that demonstrated brain tissue penetration and reduced tissue hypoxia were further evaluated in the rat tMCAO stroke rodent model with a focus on clinically relevant assessments at extended time points after ischemia and reperfusion. Lead H-NOX trimer candidates were each tested using a group of 12 male Wister rats.

Anesthesia was induced in an induction chamber with 2-3% isoflurane in N20:02 (2:1), and maintained with 1-1.5% isoflurane via nose cone. Adequate depth of anesthesia was assessed by lack of withdrawal to hind limb pinch and loss of eye blind reflex. Animals received 40 mg/kg of cefazolin sodium via intraperitoneal injection and 0.1 mg/kg of subcutaneous buprenorphine. Temporary middle cerebral artery occlusion was initiated in Day 0 using a standard suture-based surgical technique. Briefly, a skin incision was made over the right common carotid artery (CCA) to allow temporary clamping of the CCA and ligation of a distal segment of the external carotid artery (ECA). A nylon suture was inserted through the proximal ECA and advanced into the internal carotid artery (ICA) to occlude blood flow to the brain. The CCA clip was removed and the skin incision was closed with surgical staples, and the animal was allowed to awaken. A 750 mg/kg dose of an H-NOX trimer candidate or a buffer control was infused by tail vein injection into rats 30 minutes after start of occlusion of the middle cerebral artery. The occlusion was released 30 minutes after H-NOX trimer infusion by providing anesthesia to the rats, reopening the wound and removing the intravascular suture from the ECA before closing the wound again in order to provide a total of 1 hour of occlusion before reperfusion. For neurological testing, each animal was evaluated at 72 hours, 1 week, 2 weeks, 3 weeks, and 4 weeks post reperfusion. Animals were assessed for neurological deficits by scoring on a 0-4 scale with 0 indicating no deficit, 1 indicating failure to extend a forelimb when placed, 2 indicating circling, 3 indicating unilateral weakness, and 4 indicating lack of spontaneous motor activity, as previously described. See Borlongan, C. V., et al., (1998) *Exp Neurol.*, 149:310-321, which is incorporated herein in its entirety by reference. At four weeks post reperfusion, animals were sacrificed and brain tissue was collected for H& E staining and subsequent histological analysis to assess infarct volume. For infarct volume measurements, seven sections from each animal brain (+4.7, +2.7, +0.7, −1.3, −3.3, −5.3, and −7.3, compared to bregma, respectively) were photographed by a digital camera. The infract area of each slice was quantified by Image J using the "indirect method" (area of the intact contralateral [left] hemisphere—area of intact regions of the ipsilateral [right] hemisphere) to correct for brain edema. Infarct areas were summed among slices and multiplied by slice thickness to give total infarct volume, which was expressed as a percentage of intact contralateral hemispheric volume. Infarction volume was measured for comparison with buffer control animals and scores for each group were compared by ANOVA and Newman-Keuls multiple range test with a 0.05 level of significance. Long-term assessments of up to 4 weeks after reperfusion insured that any improvement in neurological function or reduction in infarct volume resulted from a neuroprotective effect of the H-NOX protein and not simply a delay in the onset of neurological consequences due to the slow maturation of the infarct.

Example 5. H-NOX Proteins Demonstrated Tumor Penetration and Oxygenation in an in Vivo Mouse Model of Cancer Oxygen is a critical factor that enhances radiation-induced DNA damage and tumor killing. Low oxygen levels or hypoxia within solid tumors can blunt the therapeutic effects of tumor therapy. For example in hypoxic regions of the tumor, radiation therapy has been found to be three times less effective as compared to tumor regions with normal oxygen levels. As a result, many patients with tumors containing regions of hypoxia often show incomplete responses to conventional tumor therapy and have poor prognosis for survival. The correlation of hypoxia with poor patient outcomes has been observed in a wide range of tumors arising from, among others, prostate, sarcoma, pancreatic, head-and-neck, cervical, and brain cancers. See Moeller, B J et al. (2007) *Cancer Metastasis Rev* 26:241-248; Vaupel, P, (2004) *Semin Radiat Oncol*, 14:198-206; Varlotto, J, et al. (2005) *Int J Radiat Oncol Biol Phys*, 63:25-36; Rockwell, S, et al. (2009) *Curr Mol Med.* 9:442-458; which are all incorporated herein in their entirety by reference.

To determine the ability of H-NOX proteins to penetrate tumors, groups of 6 mice bearing subcutaneous HCT116 colon-derived tumors were injected via the tail vein with 750 mg/kg of a H-NOX monomer, 750 mg/kg of a *T. tengcongensis* L144F H-NOX trimer or saline control. The mice were subsequently sacrificed at 30 minutes or 60 minutes post-injection. The tumors were resected, sectioned, stained with an anti-H-NOX antibody, and imaged for H-NOX staining intensity (FIG. 12A). Quantification of the stained HCT-116 tumor sections demonstrated that the 23 kDa *T. tengcongensis* L144F H-NOX monomer accumulated in tumors by 30 minutes and exhibited partial clearance by 60 minutes (FIG. 12B). In comparison, the 80 kDa L144F H-NOX trimer accumulated in tumors by 30 minutes and continued to persist in the tumors at 60 minutes post-injection with accumulation peaking at 4 hours post-injection (FIG. 12B). Two hours after intravenous injection, H-NOX trimer diffuses from the vasculature into the tumor tissue (FIG. 12C). Immunohistochemistry staining of tumor sections with H-NOX antibody and CD31 antibody (vasculature marker, BD Bioscience). No fluorescent staining is detected in mice injected with buffer.

To determine if the H-NOX proteins reduced hypoxia in the tumors, groups of 6 mice bearing subcutaneous HCT116 colon-derived tumors were injected via the tail vein with 750 mg/kg of a L144F H-NOX monomer, 750 mg/kg of a L144F H-NOX trimer or saline control. Prior to euthanasia, mice were given hypoxia marker pimonidazole via intraperitoneal injection and active vasculature marker $DiOC7_3$ via intravenous injection. Tumors were harvested at either 30 minutes or 60 minutes after H-NOX protein injection, and assayed by immunohistochemistry for pimonidazole with Hydroxyprobe-1 monoclonal antibody and total vasculature with anti-CD31 antibody (FIG. 13A). Quantification of the stained HCT-116 tumor sections demonstrated that in contrast to control-treated mice the 23 kDa H-NOX monomer decreased hypoxia 30 minutes post-injection but that there was no recovery in hypoxia 60 minutes post-injection (FIG. 13B). In comparison, the 80 kDa L144F H-NOX trimer did not appear to reduce hypoxia at 30 minutes post-injection, but substantially reduced hypoxia at 60 minutes post-injection (FIG. 13B). Further experiments confirmed that in mice bearing subcutaneous HCT116 colon-derived tumors the H-NOX monomer distributed throughout the tumor tissue (FIG. 14A, bottom panel) and relieved tumor hypoxia at distances far from the vasculature as detected by anti-pimonidazole antibody (FIG. 14B, bottom panel). The Hypoxyprobe-1 (anti-pimonidazole antibody) stain was quantified in tumor tissue isolated from six mice by amount of staining as a function of distance from the vasculature. It was found that the average Hypoxyprobe-1 staining was reduced from about 13 μM in saline treated mice to 5 in H-NOX monomer treated mice at a distance of about 150 μm from the nearest blood vessel (FIG. 14C). These results were further confirmed in mice bearing murine RIF-1 sarcoma xenografts.

Mice bearing RIF-1 sarcoma tumors were injected via the tail vein with 750 mg/kg of *T. tengcongensis* L144F H-NOX trimer or saline control. Prior to euthanasia, mice were given hypoxia marker pimonidazole via intraperitoneal injection. Tumors were harvested at 120 minutes after L144F H-NOX trimer injection, and assayed by immunofluorescence imaging for H-NOX trimer distribution (FIGS. 15A-15G), or by western blot for pimonidazole with Hydroxyprobe-1 monoclonal antibody, hypoxia-inducible factor 1 (HIF-1α) with anti-HIF-1α antibody, H-NOX protein with an anti-H-NOX antibody, and total protein with anti-actin antibody (FIGS. 16A-16C). Immunofluorescence staining demonstrated distribution of L144F H-NOX trimer in tumor sections prepared from large isolated tumors approximately 400 mm$^3$ and 800 mm$^3$ in size (FIGS. 15A-15G). Western blot analysis of cell lysates from harvested tumors of treated mice demonstrated that the L144F H-NOX trimer localized to tumor tissue and that these tumors had decreased pimonidazole protein adducts as compared to untreated mice (FIG. 16A). Quantification of the western blots further confirmed low levels of pimonidazole protein adducts as well as low levels of HIF-1α protein in the tumors of treated mice as compared to saline treated mice (FIGS. 16B and 16C).

Example 6. H-NOX Proteins Demonstrated Tumor Penetration and Oxygenation in an in Vivo Mouse Model of Glioblastoma To further characterize the ability of H-NOX proteins to penetrate into tumor tissue, three mouse models of glioblastoma were used to assess the distribution of *T. tengcongensis* L144F H-NOX monomer and *T. tengcongensis* L144F H-NOX trimer in brain tumors. BT-12 cells, a childhood atypical teratoid/rhabdoid infant brain tumor line that is highly invasive into the spinal column, were used to generate a mouse model of child glioblastoma, GBM-43 cells were used for generating a radioresistant model of adult glioblastoma, and U251 cells were used to generate a hypoxic model of adult glioblastoma. The glioblastoma mouse models were generated as previous described. See Ozawa, T, et al., (2010) *J Vis Exp*, July 13; (41) which is incorporated in its entirety herein by reference. Briefly, BT-12 cells, U251 cells, or GBM-42 cells were harvested for intracranial injection and resuspended in Dulbecco's Modified Eagle Medium (DMEM) at a concentration of about 1×10$^8$ cells per mL. Mice were anesthetized by intraperitoneal (IP) injection of ketamine (100 mg/kg) and xylazine (10 mg/kg). The anesthetic depth was monitored prior to the first incision as well as at regular intervals through the procedure, using the pedal withdrawal reflex by pinching the foot pad on both feet. A 1 cm sagittal incision was made along the scalp, and the skull suture lines were exposed. A small hole was created by puncture with a 25 g needle, at 3 mm lateral and 0.5 mm anterior of the bregma. Using a sterile Hamilton syringe (Stoelting), 3×10$^5$ cells in 3 µl was injected at a depth of 3 mm over a 60 second period. After injection, the syringe was held in place for 1 minute and then slowly removed. The skull was cleaned with 3% hydrogen peroxide and then sealed with bone wax before closing the scalp using 7 mm surgical staples (Stoelting). Mice received a subcutaneous injection of 0.1 mg/kg buprenorphine, were placed on a heating pad and monitored until they regained mobility for use in these studies.

To determine if L144F H-NOX trimers could penetrate brain tissue, mice bearing U251 orthotopic brain tumors were injected via tail vein with either 750 mg/kg *T. tengcongensis* L144F H-NOX monomer or 750 mg/kg *T. tengcongensis* L144F H-NOX trimer. Prior to euthanasia, mice were given the hypoxia marker pimonidazole by intraperitoneal injection. For immunohistochemistry analysis, brains were isolated, sectioned and stained for pimonidazole with Hydroxyprobe-1 monoclonal antibody, hypoxia-inducible factor 1 (HIF-1α) with anti-HIF-1α antibody, H-NOX protein with an anti-H-NOX antibody, and HLA-ABC protein with an anti-HLA-ABC antibody (NvusBiological rat monoclonal antibody clone #YTH862.2) about two hours after H-NOX protein administration. A set of brain tissue samples was further stained with secondary antibodies conjugated to anti-rabbit antibody conjugated with FITC (green channel) manufactured by Jackson ImmunoResearch and DAPI for immunofluorescence imaging. Mice treated with H-NOX trimer demonstrated increased staining for H-NOX as compared to control treated mice indicating that the H-NOX trimer penetrated brain tissue (FIG. 17A). In addition, decreased staining for pimonidazole with Hydroxyprobe-1 monoclonal antibody showed that H-NOX trimer administration substantially reduced hypoxia at 60 minutes post-injection (FIG. 17B). Decreased staining for pimonidazole and HIF-1α protein was further observed in immunofluorescence images (FIGS. 18A and 18C). Quantification of the immunofluorescence images demonstrated low levels of pimonidazole staining as well as low levels of HIF-1α protein staining in the tumors of L144F H-NOX trimer treated mice as compared to saline treated mice (FIGS. 18B and 18D).

FIGS. 19A-19E show the biodistribution of H-NOX trimer in U251 orthotopic brain tumor and healthy brain. Fluorescent imaging of H-NOX trimer at high magnification shows weak diffusion outside vessels in healthy brain.

To compare penetration and retention times between *T. tengcongensis* L144F H-NOX monomer and *T. tengcongensis* L144F H-NOX trimer, mice bearing orthotopic brain tumors were injected via tail vein with either 750 mg/kg Alexa-647 labeled H-NOX monomer or 750 mg/kg Alexa-647 labeled H-NOX trimer and subjected to bioluminescence imaging at various time points. Alexa-647 labeled H-NOX proteins were generated to confirm fluorescence excitation and emission spectra of fluorescently labeled H-NOX proteins as follows.

Purified protein, H-NOX monomer protein, H-NOX trimer, or BSA (Sigma, used as a control), was thawed on ice and buffer exchanged into endotoxin-free Labeling Buffer (50 mM HEPES, 50 mM NaCl, pH 8.0) using endotoxin-free dialysis cassettes (Pierce Slide-A-Lyzer, 7 kDa MWCO). Protein concentration after dialysis into Labeling Buffer was determined by UV-vis spectroscopy. Alexa 647 dye (Alexa Fluor® 647 carboxylic acid, succinimidyl ester, Invitrogen #A-20006) was prepared immediately before addition to the labeling reactions. Dye was warmed to room temperature and then dissolved in DMSO at a final concentration of 10 mg/mL. The mixture was vortexed for 10 seconds and then dye was added to each labeling reaction. Labeling reactions used a range of protein:dye ratios to control the extent of Alexa labeling. Reactions consisted of protein (in Labeling Buffer) and dye for a final DMSO concentration of 5-10%. Reactions were incubated for 1 hour at room temperature (protected from light) with moderate shaking. After the reaction, free Alexa dye was removed by extensive dialysis into endotoxin-free formulation buffer (30 mM Triethanolamine, 50 mM NaCl, pH 7.4) using endotoxin-free dialysis cassettes (Pierce Slide-A-Lyzer, 7 kDa MWCO cutoff).

After dialysis into formulation buffer, the protein concentration and extent of labeling was determined by UV-vis spectroscopy using the intrinsic absorbance of H-NOX (at 280 and 415 nm) and Alexa dye (653 nm) to determine the molar ratio of dye to protein after labeling. Fluorescence of the labeled protein was analyzed by excitation at 647 nm to collect an emission spectrum. The emission spectrum of the labeled protein was consistent with published data and Invitrogen data. Labeled protein was further analyzed by size exclusion chromatography to ensure that labeling did not affect the oligomerization state of the protein. Final endotoxin contamination in the labeled protein was determined using the Charles River LAL Gel Clot assay (0.03 EU/mL sensitivity).

For bioluminescence imaging, mice were anesthetized by IP injection of ketamine (100 mg/kg) and xylazine (10 mg/kg), and then injected by IP with 33.3 mg of D-luciferin (potassium salt, Gold Biotechnology, St. Louis, Mo., USA) dissolved in sterile saline. Tumor bioluminescence was determined 10 minutes after luciferin injection, using the IVIS Lumina System (Caliper Life Sciences, Alameda, Calif., USA) and LivingImage software, as the sum of photon counts per second in regions of interest defined by a lower threshold value of 25% of peak pixel intensity. Imaging acquisition was non-invasive, and animal body temperature was maintained using a heated imaging platform. For BT-12 mice treated with H-NOX monomer or H-NOX trimer, imaging was performed at 0, 0.5, 1, 2, and 4 hrs post injection. For GBM-41 mice treated with H-NOX monomers or H-NOX trimers, imaging was performed at 0, 0.5, 1, 2, 4, and 6 hrs post injection. For U251 mice treated with H-NOX monomers or H-NOX trimers, imaging was performed at 0, 0.5, 1, 2, 4, 6, and 72 hrs post injection. Tumor bioluminescence has previously been shown to be directly proportional to tumor volume in mice bearing orthotopic GB xenografts. See Moeller, B J et al., (2007) *Cancer Metastasis Rev*, 26:241-248, which is incorporated herein in its entirety by reference. Comparison of H-NOX monomer and trimer biodistribution demonstrated that in the BT-12 mouse model of glioblastoma, both L144F H-NOX monomer (FIG. 20A) and L144F H-NOX trimers (FIG. 20B) penetrated brain tumors. H-NOX trimer had a significantly longer retention time in tumors as compared to H-NOX monomers. Whereas HNOX monomer was largely eliminated from tumors by 2 hours (FIG. 20A), H-NOX trimer continued to accumulate in tumors for several hours (FIG. 20B). H-NOX intracranial localization was confirmed by ex vivo imaging of brain tissue isolated from mice 30 and 60 minutes post injection with the H-NOX monomer (FIGS. 21A and 18B) and 60 minutes post injection with the H-NOX trimer (FIG. 21C). Further visualization by bioluminescence at 30, 60, 120, and 240 minutes post injection demonstrated that the H-NOX monomer (FIGS. 22A-22D) and H-NOX trimer (FIGS. 23A-23D) also localized to metastatic colonies in the spinal column. Whereas H-NOX monomer substantially accumulated in the spinal column at 30 minutes (FIG. 22A) as compared to H-NOX trimer (FIG. 23A), it was largely eliminated by 2 hours (FIG. 22B-D) while the H-NOX trimer continued to accumulate in the spinal column for several hours (FIG. 23B-D). By using a smaller amount of labeled protein and increasing the signal intensity, it was revealed that H-NOX monomer accumulated in the kidneys over time suggesting a route of elimination (FIGS. 24A-24B).

The accumulation of L144F H-NOX trimers in the brain and spinal column was confirmed in the GBM-43 (FIGS. 25A-25F) and U251 mouse models (FIG. 26). Localization of L144F H-NOX trimers was further investigated in U251 mice that were injected with a higher H-NOX trimer dose of 295 mg/kg and a lower dose of 30 mg/kg. Bioluminescence imaging at 0, 0.5, 1, 2, 4, and 6 hr post-injection demonstrated that the L144F H-NOX trimer accumulated in brain tumors of the mice at both the high and low concentrations of H-NOX trimer administration (FIGS. 27A-27F and 28A-28F, respectively). In comparison, localization of an H-NOX trimer assembled from a H-NOX monomer L144F variant did not accumulate in small brain tumors as evidenced by bioluminescence images 0, 0.5, 1, 2, 4, and 6 hr post-injection with 30 mg/kg (FIGS. 29A-29F). Ex vivo bioluminescence imaging of isolated brain from mice treated with 30 mg/kg L144F H-NOX trimer (FIG. 30A) or 750 mg/kg L144F trimer (FIG. 30B) showed that the amount of H-NOX protein in a single dose had little effect on H-NOX localization to intracranial tumors. Furthermore, real-time bioluminescence imaging of mice bearing large (FIG. 30C) or small tumors (FIG. 30D) showed that after administration of 295 mg/kg of L144F H-NOX trimer, the trimer distributed to intracranial tumors regardless of tumor size (FIG. 30B). Real-time and ex vivo bioluminescence imaging of three mouse models of glioblastoma, GBM, U251, and BT-12, demonstrated that L144F H-NOX trimer distributed to intracranial tumors and spinal tumors in all three models (FIGS. 31 and 32A-32E). Immunofluorescence imaging of a tumor section stained with antibodies to H-NOX protein and the vasculature showed that L144F H-NOX trimer left the vasculature and diffused throughout the brain tumor (FIG. 33). Overall, these data identified H-NOX proteins with clinically relevant tumor biodistribution profiles.

To verify the partition of H-NOX trimers between plasma and brain, L144F trimer was tested using a group of three female FVB mice (FIGS. 34A-34D). Candidate H-NOX trimers were injected at time 0 at a dose of 200 and 750 mg/kg by intravenous bolus injection into the tail vein. At 30 min, 1 hr, 1.5 hr and 2 hr post injection of the candidate H-NOX trimer or buffer control, mice were sacrificed. About one ml of blood was collected by intracardiac puncture and brain were harvested. Collected blood was processed for plasma and brain samples were lyzed to extract proteins. Plasma and brain were subsequently analyzed for the presence of H-NOX trimer using an ELISA assay with a polyclonal antibody against the H-NOX protein.

Example 7. H-NOX Trimers Enhanced Effects of Radiation in In Vivo Mouse Models of Glioblastoma To determine if oxygenation of hypoxic tumors due to H-NOX penetration could enhance radiation-induced tumor killing, studies were conducted in groups of 10 athymic U251 mice bearing intracranial glioblastoma tumors to evaluate the effects of radiation therapy (RT) in the presence of H-NOX trimer. Mice were treated with three fractions of radiation therapy at 2 Gy per fraction on days 15, 17, and 20 post-tumor implantation either with or without administration of 750 mg/kg Alexa-647 labeled *T. tengcongensis* L144F H-NOX trimer delivered by intravenous injection. Mice were monitored up to day 29 and subjected to bioluminescence imaging at days 15, 17, 20, 22, 24, and 29. Mean bioluminescence imaging (BLI) scores determined for each treatment group demonstrated that multiple doses of L144F H-NOX trimer resulted in statistically significant delays in tumor growth (FIGS. 35A and 35B) and despite the aggressive and mildly hypoxic nature of the treated U251 orthotopic tumors, animal survival was also significantly enhanced in L144F H-NOX treated groups (FIG. 35C). Tumors were also harvested for immunohistochemistry staining and analysis.

The effect of *T. tengcongensis* L144F H-NOX trimer on radiation therapy of human glioblastoma was further investigated in two mouse models bearing intracranial glioblastoma tumors, U251 and GBM43. In one study, groups of 10 female athymic U251 mice bearing intracranial glioblastoma tumors were treated with either 1) treatment buffer alone, 2) treatment buffer in combination with a single dose of 2 Gy radiation (irradiator set up=0.81; dose rate of Cesium irradiator was 247 CGy/min), 3) 750 mg/kg L144F H-NOX trimer by IV alone, or 4) L144F H-NOX trimer in combination with a single dose of 2 Gy radiation (irradiator set up=0.81; dose rate of Cesium irradiator was 247 CGy/min). Mice receiving the combination treatment were irradiated 2 hours post L144F H-NOX trimer delivery at the supratentorial portion of the brain. Treatment for all mice began 14 days after intracranial injection of mice with $3.0 \times 10^5$ U251 cells. It was found that animal survival increased in cohorts receiving the combination treatment of L144F H-NOX trimer and 2 Gy radiation (FIG. 36A). In another study, groups of 10 GBM43 mice bearing intracranial glioblastoma tumors were treated with either 1) 2 Gy radiation therapy; 2) 4 Gy radiation therapy; 3) 8 Gy radiation therapy; 4) 2 cycles of 4 Gy radiation therapy; 5) 4 Gy radiation therapy in combination with L144F H-NOX trimer; or 6) treatment buffer. Mice receiving the combination treatment were irradiated 1 to 1.5 hours post H-NOX trimer delivery and mice receiving multiple doses of RT had administration of RT separated by 4 days. Radiation treatment was administered at the supratentorial portion of the brain for all RT groups. Treatment for all mice began 7 days post-tumor implantation. It was found that animal survival in cohorts receiving the combination treatment of L144F H-NOX trimer and 4 Gy radiation was similar to animal survival in cohorts receiving 4 Gy treatment alone (FIG. 36B).

Example 8. Toxicology Testing of H-NOX Proteins

To assess the safety profile of H-NOX monomers in anticipation of IND-enabling toxicology studies, a preliminary GLP-like toxicology study in Sprague-Dawley rats was conducted at an FDA-accredited independent Contract Research Organization (MPI Research Laboratories). No adverse events or differences from control were detected at the 100 and 300 mg/kg doses of *T. tengcongensis* L144F H-NOX monomer at 48 hours post-injection (IV). At the 1000 mg/kg maximum feasible dose, some mild signs of toxicity were noted (Table 4). The elevated white blood cell counts at 48 hours were likely due to trace amounts of endotoxin present in the protein formulation and these levels were reduced 100-fold in production runs for further studies. In a separate study, rats were injected with either 50 mg/kg L144F H-NOX monomer or L144F H-NOX trimer and followed out to Day 32. Both IgM and IgG anti-therapeutic antibodies were generated, however, there were no cases of anaphylactic shock, regardless of H-NOX variant or number of doses (up to 4 doses tested).

TABLE 4

H-NOX monomer was well tolerated in rats.

| Unaffected toxicity parameters at 1000 mg/kg | Affected toxicity parameters at 1000 mg/kg |
|---|---|
| Most hematology measures RBCs, Hb, HCT, Platelets, Neutrophils, Eosinophils | Decreased reticulocytes $120 \pm 60$ [$300\pm$ for control] × $10^3$ cells/µl |
| All kidney and liver function tests BUN, Creatine, ALT, AST | Elevated White Blood Cells (× $10^3$ cells/µl) Lymphocytes: $11.2 \pm 2.2$ [$5.8 \pm 0.3$ for control] Leukocytes: $14.2 \pm 0.9$ [$7.3 \pm 0.7$ for control] Monocytes: $0.4 \pm 0.2$ [$0.145 \pm 0.007$ for control] |
| Urinalysis Volume, specific gravity, pH | Kidney Histology Mild inclusions and necrosis |
| Major organ histology Heart, lung, liver, small and large intestines, pancreas | |

Example 9. Characterization of Minimal H-NOX Trimer Dosing Schedules in In Vivo Animal Models of Glioblastoma To best inform the design of IND-enabling toxicity studies and clinical studies, the dose levels and schedules of a lead H-NOX trimer is characterized using a U251 glioblastoma mouse model. Results from these studies are validated in additional animal models of glioblastoma to best inform patient selection.

Identify the Minimum Effective Dose of Lead H-NOX Trimer that Enhances RT

To minimize adverse events in patients receiving the lead H-NOX trimer and to quantify the pharmacodynamics (PD) of the lead H-NOX trimer in oxygenating and radiosensitizing tumors, the minimum effective dose (MED) of the H-NOX trimer is identified in the U251 glioblastoma mouse model. Preliminary studies demonstrated that at a dose of 750 mg/kg H-NOX trimer resulted in substantial reduction in tumor hypoxia two hours after administration (FIGS. 17A and 17B) and that this effect was sufficient to significantly enhance tumor responses to RT (FIGS. 35A-35C). Other xenograft tumor studies demonstrated that H-NOX trimer accumulated in tumors at doses as low as 10 mg/kg, establishing a wide potential range for an efficacious dose. To identify a MED of H-NOX trimer, dosages ranging from 7.5 mg/kg to 750 mg/kg are used for enhancing tumor responses to RT.

To identify H-NOX trimer MED, the radiosensitizing effects of 75 mg/kg and 7.5 mg/kg doses against the previously established efficacious dose of 750 mg/kg is compared (Table 5). Efficacy is tested against an orthotopic mouse model of GB, using the luciferase modified U251 human GB cell line. One cohort of 10 mice is used to follow tumor growth by bioluminescence imaging and to follow survival. Three additional cohorts of 3 mice each are used to examine molecular mechanisms behind H-NOX trimer action, including H-NOX trimer localization by immunohistochemistry and quantitative ELISA, tumor oxygenation by immunohistochemistry using EF5 as a marker for hypoxia, and assessment of DNA damage by immunohistochemistry using γH2AX staining (Table 5).

For these studies, U251 cells are resuspended in Dulbecco's Modified Eagle Medium (DMEM) at a concentration of about $1 \times 10^8$ cells per mL. Athymic mice are anesthetized by intraperitoneal (IP) injection of ketamine (100 mg/kg) and xylazine (10 mg/kg). A 1 cm sagittal incision is made along the scalp and a small hole is created by puncture with a 25 g needle, at 3 mm lateral and 0.5 mm anterior of the bregma. Using a sterile Hamilton syringe (Stoelting), $3 \times 10^5$ cells in a 3 µl volume is injected at a depth of 3 mm over a 60 second period. After injection, the syringe is removed and the skull is sealed with bone wax before closing the scalp using 7 mm surgical staples (Stoelting). See Ozawa, T et al., (2010) *J Vis Exp*, July 13; (41). The mice receive a subcutaneous injection of 0.1 mg/kg buprenorphin and are monitored until they regain mobility. Between 21 and 25 days post-tumor implantation, H-NOX trimer at the indicated dosage for each cohort is administered by tail vein injection two hours before RT, which is administered at 2 Gy/dose to the entire supratentorial brain (Table 6). For whole brain RT administration, a $^{137}$Cs source that delivers a dose rate of approximately 280 cGy/min is used and mice are irradiated for a length of time that results in 2 Gy.

t-tests and a change at $P \leq 0.05$ is considered statistically significant. For survival analysis, the logrank test is used with a two-tailed alpha equal to 0.05 for 88% power to detect an effect size of 1.5. The effect size is defined as the difference in mean survival divided by the within treatment standard deviation.

Correlate Residence Time of Lead H-NOX Trimer and Oxygenation in Tumors with Radiosensitization To better inform the target clinical profile of H-NOX trimers, the longevity of the H-NOX trimer oxygenating effects in tumors that results in radiosensitization is investigated. RT is administered at a range of time points based on the peak intracranial tumor localization timeframe of H-NOX trimer (FIG. 26), and using the MED of H-NOX trimer, the length of time between H-NOX trimer administration and RT is varied (Table 6). Similar to the studies for determining the MED of H-NOX trimer, several pharmacodynamic parameters are evaluated such as H-NOX trimer distribution in tumor tissue, hypoxia reduction, DNA damage, tumor growth delay, and enhanced overall survival.

TABLE 5

Cohorts for H-NOX trimer dose de-escalation studies

| Study Cohort | H-NOX trimer dosage | $N_{efficacy}$ | $N_{hypoxia\ and\ H\text{-}NOX\ trimer\ IHC}$ | $N_{H\text{-}NOX\ trimer\ ELISA}$ | $N_{DNA\ Damage\ IHC}$ |
|---|---|---|---|---|---|
| Vehicle | N/A | 10 | 3 | 3 | 3 |
| Radiation therapy | N/A | 10 | 3 | 3 | 3 |
| Radiation therapy + H-NOX trimer | 7.5 mg/kg | 10 | 3 | 3 | 3 |
| Radiation therapy + H-NOX trimer | 75 mg/kg | 10 | 3 | 3 | 3 |
| Radiation therapy + H-NOX trimer | 750 mg/kg | 10 | 3 | 3 | 3 |
| H-NOX trimer | 7.5 mg/kg | 10 | 3 | 3 | 3 |
| H-NOX trimer | 75 mg/kg | 10 | 3 | 3 | 3 |
| H-NOX trimer | 750 mg/kg | 10 | 3 | 3 | 3 |

All RT schedules consist of 3 doses weekly of 2 Gy/dose

Non-invasive tumor growth is monitored by bioluminescence imaging throughout the course of the study. For bioluminescence imaging, mice are anesthetized by IP injection of ketamine (100 mg/kg) and xylazine (10 mg/kg), and then injected by IP with 33.3 mg of D-luciferin (potassium salt, Gold Biotechnology, St. Louis, Mo., USA) dissolved in sterile saline. Tumor bioluminescence is determined 10 minutes after luciferin injection, using the IVIS Lumina System (Caliper Life Sciences, Alameda, Calif., USA) and LivingImage software, as the sum of photon counts per second in regions of interest defined by a lower threshold value of 25% of peak pixel intensity. For survival analysis, mice are euthanized when body weight decreases by more than 15% or when neurological deficits are observed ($N_{efficacy}$, Table 5).

To investigate tumor oxygenation, or hypoxia reduction, and H-NOX trimer localization in the tumor, three mice from each dosage group are injected with 10 mM EF5, a clinical biomarker for hypoxia, by IV and sacrificed immediately after RT for IHC analysis on whole brain sections ($N_{hypoxia\ and\ H\text{-}NOX\ trimer\ IHC}$, Table 5). An additional cohort of three mice are sacrificed immediately after RT and tumors are resected for analysis of H-NOX trimer content by quantitative ELISA (NH-NOX trimer ELISA, Table 5). Two hours after the completion of RT, an additional cohort of three mice are sacrificed for analysis of DNA damage by γH2AX IHC on whole brain sections ($N_{DNA\ Damage\ IHC}$, Table 5). For RT efficacy analysis and molecular analysis of hypoxia, tumor localization, and DNA damage, statistical analyses is performed by ANOVA with subsequent paired

TABLE 6

Cohorts for length of radiosensitization studies

| Study Cohort | Time between H-NOX trimer and RT | $N_{efficacy}$ | $N_{hypoxia\ and\ H\text{-}NOX\ trimer\ IHC}$ | $N_{H\text{-}NOX\ trimer\ ELISA}$ | $N_{DNA\ Damage\ IHC}$ |
|---|---|---|---|---|---|
| Vehicle | N/A | 10 | 3 | 3 | 3 |
| Radiation therapy | N/A | 10 | 3 | 3 | 3 |
| Radiation therapy + H-NOX trimer | 1 hour | 10 | 3 | 3 | 3 |
| Radiation therapy + H-NOX trimer | 2 hour | 10 | 3 | 3 | 3 |
| Radiation therapy + H-NOX trimer | 4 hour | 10 | 3 | 3 | 3 |
| Radiation therapy + H-NOX trimer | 6 hour | 10 | 3 | 3 | 3 |

All RT schedules consist of 3 doses weekly of 2 Gy/dose

H-NOX Trimer-Mediated Radiosensitization Reproducibility in Additional Classes of GB Three molecularly-defined clinical GB subclasses are studied for H-NOX trimer mediated radiosensitization. Xenograft models derived from cell lines (GBM43, GBM6, and GBM14) of these three subclasses are established as previously described. See Verhaak et al., (2010) *Cancer Cell,* 17:98-110 and Phillips et al., (2006) *Cancer Cell,* 9:157-173. Briefly, for production of the these three mouse models, subcutaneous tumors of these three cancer types are minced with a scalpel and are subjected to three rounds of passage through a 40 μm pore filter, with centrifugation after each round of filtering with increasing speed of 158×g, 355×g, 631×g at 10 minutes each. After the final round of centrifugation, the cells are resuspended in 1 mL of sterile DMEM media, counted and diluted to $1 \times 10^8$ cells/mL for intracranial injection. Additionally, H-NOX trimer mediated radiosensitization is studied in an immunocompetent model of GB (GL261), which replicates the intact immune system in GB patients. For production of the GL261 mouse model, tumor cell harvest and injection is conducted similarly to the U251 model using a mouse GB cell line that is syngeneic with C57BL/6 mice. See Newcomb et al., (2006) *Cell Cycle,* (5):93-99. For efficacy testing four experimental groups for each tumor model are used (Table 7). As with the U251 model, initiation of treatment occurs when the tumor model is 75% complete, with average day of survival reflecting 100% completion. Similar to the studies for determining the MED of H-NOX trimer, pharmacodynamic parameters are evaluated such as H-NOX trimer distribution in tumor tissue, hypoxia reduction, DNA damage, tumor growth delay, and enhanced overall survival.

TABLE 7

Cohorts for studies in additional GB models

| Study Cohort | GB Model | $N_{efficacy}$ | $N_{hypoxia}$ and H-NOX trimer IHC | $N_{H\text{-}NOX}$ trimer ELISA | $N_{DNA}$ Damage IHC |
|---|---|---|---|---|---|
| Vehicle | GBM43 | 10 | 3 | 3 | 3 |
| Radiation therapy | GBM43 | 10 | 3 | 3 | 3 |
| Radiation therapy + H-NOX trimer | GBM43 | 10 | 3 | 3 | 3 |
| H-NOX trimer | GBM43 | 10 | 3 | 3 | 3 |
| Vehicle | GBM6 | 10 | 3 | 3 | 3 |
| Radiation therapy | GBM6 | 10 | 3 | 3 | 3 |
| Radiation therapy + H-NOX trimer | GBM6 | 10 | 3 | 3 | 3 |
| H-NOX trimer | GBM6 | 10 | 3 | 3 | 3 |
| Vehicle | GBM14 | 10 | 3 | 3 | 3 |
| Radiation therapy | GBM14 | 10 | 3 | 3 | 3 |
| Radiation therapy + H-NOX trimer | GBM14 | 10 | 3 | 3 | 3 |
| H-NOX trimer | GBM14 | 10 | 3 | 3 | 3 |
| Vehicle | GL261 | 10 | 3 | 3 | 3 |
| Radiation therapy | GL261 | 10 | 3 | 3 | 3 |
| Radiation therapy + H-NOX trimer | GL261 | 10 | 3 | 3 | 3 |
| H-NOX trimer | GL261 | 10 | 3 | 3 | 3 |

All RT schedules consist of 3 doses weekly of 2 Gy/dose

Example 10. Pharmacodynamic Characterization of H-NOX Trimer Single Dose Toxicity in In Vivo Animal Models of Glioblastoma To justify species selection for IND-enabling GLP toxicity studies and to inform Phase 1b clinical trials, exploratory non-GLP toxicity and GB PD studies are performed in rats (rodent) and dogs (non-rodent). As H-NOX trimer does not bind to or react with a human-specific target, non-primate species are acceptable to the FDA.

Non-GLP Single Dose-Ranging Toxicity Study in Rats

To identify the maximum tolerated dose (MTD) and characterize the toxicity and toxicokinetic (TK) profile of H-NOX trimer, a non-GLP single dose study in Sprague-Dawley (SD) rats is conducted.

Male and female SD rats of at least 6 to 8 weeks of age are assigned to 5 study groups (Table 8). Each animal receives vehicle or H-NOX trimer by slow IV bolus (4-5 minutes) administration in the tail vein at volumes of up to 10 mL/kg. The animals are dosed one group at a time with 3 days between each dose. The H-NOX trimer dose levels range from the approximate MED to the maximum feasible dose. Plasma samples are taken at regular intervals post-dosing to evaluate the plasma pharmacokinetics (PK) of H-NOX trimer. Time points for toxicokinetic analyses are based on the PK results. Doses are administered volumetrically, based on the most recent body weight of the animal. Clinical observations, body weights, food consumption, and clinical pathology are reviewed before selection of the next dose (Table 9). A recovery period of up to 14 days allows assessment of the persistence, delayed occurrence, and recovery of any toxicity events.

TABLE 8

Cohorts for single dose toxicity study in rats

| Study Cohort | H-NOX trimer dosage | $N_{males}$ | $N_{females}$ | $N_{Toxicokinetic\ males}$ | $N_{Toxicokinetic\ females}$ |
|---|---|---|---|---|---|
| 1 | Vehicle | 2 | 2 | 3 | 3 |
| 2 | Low dose | 3 | 3 | 6 | 6 |
| 3 | Mid dose | 3 | 3 | 6 | 6 |
| 4 | High dose | 3 | 3 | 6 | 6 |
| 5 | Higher dose | 3 | 3 | 6 | 6 |

TABLE 9

Measurements and observations for single dose toxicity study in rats

| Observation | Time/Frequency |
| --- | --- |
| Dosing schedule | Single dose on Day 1 (IV bolus) |
| Daily Observations | Twice daily. |
| Body Weights | Pre-dose, Day 1, and Day 3. Weekly during recovery (up to Day 14). |
| Detailed Observations | Once pre-dose, before and after dosing on Day 1, and on Day 3 and Day 14. |
| Food Consumption | Quantitative, once pre-dose and daily for Days 1 through 3. Weekly recovery (up to Day 14). |
| Hematology (including coagulation) | 48 hours post dose (Day 3). |
| Clinical Chemistry | 48 hours post dose (Day 3). |
| Dose analysis verification | At each dose preparation. |
| Toxicokinetics | Yes, 6 time points. |
| Anti-therapeutic antibodies | Yes, pre-dose, Day 3, Day 7, and Day 14. |
| Necropsy | Only on unscheduled euthanasia and deaths. |

Evaluate H-NOX Trimer Tumor Distribution and PD in a Rat Model of GB

To verify that H-NOX tumor distribution and hypoxia reduction is similar in rats and mice, tumor distribution and PD of H-NOX trimer in the rat 9 L glioma model is evaluated. To produce the rat 9 L glioma model, 9 L glioma cells are implanted intracranially in Wistar rats as previously described. See Stojiljkovic et al., (2003) *J. Neurooncol*, (63):1-7. Briefly, 9 L cells, a rat glioma cell line, is harvested for intracranial injection by monolayer trypsinization and resuspended in DMEM at a concentration of $4 \times 10^4$ cell in 5 µL. Anesthesia is induced by IP injection of 10 mM ketamine and 7.5 mg/kg xylazine. A 2 cm sagittal incision is made along the scalp and a burr hole is created using a small dental drill at 3 mm lateral and 0.5 mm anterior of the bregma. Using a sterile Hamilton syringe (Stoelting), $5 \times 10^5$ cells in 10 µl is injected at a depth of 4.5 mm over a 60 second period. After injection, the syringe is removed and the skull is sealed with bone wax before closing the scalp using 7 mm surgical staples (Stoelting). H-NOX trimer is administered to the rats by tail vein injection using a 27 g needle in a dosing volume not exceeding 10 mL/kg. One hour after H-NOX trimer administration, rats receive a 10 mM dose of the hypoxia marker EF5 by IV. Two hours after H-NOX administration, rats are euthanized and tumor-bearing brains are harvested for H-NOX trimer localization and hypoxia quantification by immunohistochemistry analysis or for H-NOX trimer quantification by ELISA (Table 10).

TABLE 10

Cohorts for H-NOX trimer biodistribution and oxygenation studies in rats.

| Study Cohort | $N_{hypoxia\ and\ H\text{-}NOX\ trimer\ IHC}$ | $N_{H\text{-}NOX\ trimer\ ELISA}$ |
| --- | --- | --- |
| Vehicle | 3 | 3 |
| H-NOX trimer - low dose | 3 | 3 |
| H-NOX trimer - medium dose | 3 | 3 |
| H-NOX trimer - maximum tolerated dose | 3 | 3 |

Non-GLP Single Dose-Ranging Toxicity Study in Canines

The toxicity and toxicokinetics of H-NOX trimer is investigated in Beagle dogs. Briefly, male and female Beagle dogs at least 5 months of age are assigned to 4 dosing groups (Table 11). The H-NOX trimer dose levels range from the approximate MED, as the calculated equivalent in this species, to the maximum feasible dose. Each animal receives H-NOX trimer by a slow IV bolus via the cephalic vein. Plasma samples are taken at regular intervals post-dosing to evaluate the plasma pharmacokinetics (PK) of H-NOX trimer. Time points for toxicokinetic analyses are based on the PK results. Doses are administered volumetrically, based on the most recent body weight of the animal. Clinical observations, body weights, food consumption, and clinical pathology are reviewed before selection of the next dose (Table 12). A recovery period of up to 14 days allows assessment of the persistence, delayed occurrence, and recovery of any toxicity events. Statistical analyses is performed using Graph Pad Prism (Version 4.03). Comparisons are made between the vehicle and H-NOX trimer study groups at each corresponding data analysis time point using either parametric (e.g., repeated measures analysis of variance followed by Dunnett's multiple comparison t-test) or non-parametric (e.g., Friedman Test and Dunn's post-hoc Test) statistical procedures. The choice of parametric or non-parametric statistics is based on whether the compared groups satisfy the homogeneity of variance criterion. Differences between the vehicle and H-NOX trimer treatment are noted as $p < 0.05$.

TABLE 11

Cohorts for single dose toxicity study in canines

| Study Cohort | H-NOX trimer dosage | $N_{males}$ | $N_{females}$ |
| --- | --- | --- | --- |
| 1 | Low dose | 2 | 2 |
| 2 | Mid dose | 2 | 2 |
| 3 | High dose | 2 | 2 |
| 4 | Higher dose (if needed) | 2 | 2 |

TABLE 12

Measurements and observations for single dose toxicity study in canines

| Observation | Time/Frequency |
| --- | --- |
| Dosing schedule | Single dose on Day 1. |
| Daily Observations | Twice daily. |
| Body Weights | Pre-dose, Day 1, Day 3, Day 5, and Day 7, Day 9, Day 11, Day 14. |
| Detailed Observations | Once pre-dose, before dosing on Day 1, and on Day 7 and Day 14. |
| Food Consumption | Quantitative, once pre-dose and daily for Days 1 through 3. Weekly during recovery (up to Day 14). |
| Hematology (including coagulation) | Twice pre-dose, Day 3, Day 7, Day 11, Day 14. |
| Clinical Chemistry | Twice pre-dose, Day 3, Day 7, Day 11, Day 14. |
| Dose analysis verification | At each dose preparation. |
| Pharmacokinetic/Toxicokinetic time points | Yes, 6 time points. |
| Anti-therapeutic antibodies | Yes, pre-dose, Day 3, Day 7, and Day 14. |
| Necropsy | Only on unscheduled euthanasia and deaths. |

Evaluate H-NOX Trimer Tumor Distribution and PD in a Canine Model of GB

To confirm that tumor distribution and oxygenation seen in rodent GB models is representative of tumors similar to human tumors, a Phase 1b-like trial in canines with GB is conducted to measure H-NOX trimer accumulation in spontaneous brain tumors, and to quantify changes in hypoxia using a clinically relevant real-time PET probe for hypoxia (and PET probe may be used; for example, $^{18}$F-EF5 of $^{18}$F-MISO). Ten client-owned dogs (herein referred to as "canine patients") with spontaneous GB are enrolled in the study. Overall, canine patients receive a single dose of H-NOX trimer accompanied by pre- and post-$^{18}$F-EF5 PET scans to evaluate any change in tumor hypoxia resulting from H-NOX trimer treatment. Dogs that do not have hypoxic tumors (defined as a tumor:normal brain ratio 2.0) are removed from the study prior to H-NOX trimer administration. Canine patients with sufficiently hypoxic tumors are scheduled for treatment with H-NOX trimer no fewer than 72 hours after the initial PET scan. H-NOX trimer is administered as a bolus IV injection in a dosing volume not exceeding 10 mL/kg. H-NOX trimer dosage levels begin at MED and escalate according to a 3+3 dose escalation design. Dose escalation is stopped after 3 dose levels or when dose limiting toxicity is reached in 1 or more dogs. Two hours after the H-NOX-trimer administration, canine patients undergo a second PET scan and tumor hypoxia is scored. For the PET scans, food is withheld for 12 hours prior to anesthesia. An intravenous catheter is placed in each canine patient and anesthesia is induced with 10-25 mg/kg thiopental or 6 mg/kg propofol and maintained with 1-5% isoflurane in oxygen. $^{18}$F-EF5 is administered shortly after anesthesia is induced, and the PET/CT scan is initiated one hour after $^{18}$F-EF5 administration. For canine patients that undergo surgery as part of standard of care, a portion of the resected tumor is reserved for analysis of H-NOX trimer content. To evaluate H-NOX trimer tumor localization, resected tumors are evaluated by quantitative IHC or ELISA using antibodies to H-NOX protein and pimonidazole. Small amounts of whole blood are obtained pre-dose and at 24 hours, 48 hours, and 14 days after H-NOX trimer administration for analysis of safety parameters such as maximum tolerated dose and to assay for the presence of anti-therapeutic antibodies. Safety data is taken pre-dosing and 14 days post-dosing. Additional hypoxia biomarkers are used in this study such as copper (II) (diacetyl-bis (N4-methylthiosemicarbazone)) ($^{64}$Cu-ATSM).

H-NOX Trimer-Mediated Radiosensitization in Canines

Utilizing the information from the single dose toxicity studies in canines, H-NOX trimer mediated radiosensitization is further studied in these animals. Male and female Beagle dogs at least 5 months of age are assigned to dosing groups consisting of H-NOX trimer or vehicle treatment with or without high dose radiation therapy at 8 Gy single fraction. Tumors are resected in these canine patients for analysis of H-NOX trimer content. For H-NOX trimer tumor localization, resected tumors are evaluated by quantitative IHC or ELISA using antibodies to H-NOX protein and pimonidazole. Additional hypoxia biomarkers are used in this study such as $^{64}$Cu-ATSM.

Example 11. GMP Production of H-NOX Trimers

The development of H-NOX trimer, including cGMP production, GLP safety testing, and regulatory preparation necessary to obtain FDA approval for initiation of clinical trials is investigated.

GMP Manufacturing of Candidate H-NOX Trimer

Large amounts (e.g., kilogram quantities) of GMP protein to support toxicology testing, rat and canine PD studies, and clinical trials is produced. Cell lines, plasmids, and culture growth conditions necessary to grow cells and create the GMP cell banks are provided herein. Methods for production of H-NOX trimer from 4 L fermentation with ODs reaching as high as 115 are also provided herein. Methods for protein purification of H-NOX trimer which can generate up to 1 g of purified H-NOX trimer protein from 12 L of cell culture are further provided herein. Also provided herein, are quality control assays for H-NOX trimer, including but not limited to, SDS-PAGE, UV/Vis spectral analysis, LC-MS, analytical SEC, SEC-HPLC, endotoxin testing, filtration testing for particulates, viral contamination testing, and oxygen release rates for efficacy. Further provided herein are systems for the production of H-NOX trimer including but not limited to microreactor systems, process scale equipment, pumps and filters. H-NOX trimer undergoes QC/QA testing and validation before release for preclinical and clinical studies.

GLP Toxicity Testing of H-NOX Trimer in Rats and Dogs

GLP toxicity studies are performed in accordance with ICH Guidelines S6(R1) and S9. As per the ICH guidelines, toxicology testing is performed in a rodent (Sprague-Dawley rat) and non-rodent (Beagle dog) species. For the rat 7-day repeat-dose study, male and female Sprague-Dawley rats are assigned to four treatment groups (Table 14). H-NOX trimer dose levels range from the approximate MED to the maximum feasible dose or the maximum tolerated dose. Each animal receives vehicle or H-NOX trimer by slow IV bolus administration in the tail vein at volumes up to 10 mL/kg. Doses are administered volumetrically based on the most recent body weight of the animal. Animals are dosed once per day for 7 consecutive days. Animals designated for terminal necropsy (up to the first 10 rats/sex/group) are necropsied on Day 8. Animals designated for recovery necropsy (up to the last 5 rats/sex/group) undergo 7 days of dosing followed by 7 days of recovery and are necropsied on Day 15 in order to evaluate the toxicity and toxicokinetics of H-NOX trimer. Standard toxicity parameters, including the assessment of vital organs (respiratory, cardiovascular, and central nervous systems) are monitored (Table 15).

TABLE 14

Cohorts for GLP toxicity study in rats

| Study Cohort | H-NOX trimer dosage | $N_{males}$ | $N_{females}$ |
|---|---|---|---|
| Toxicity Animals | | | |
| 1 | Vehicle | 15 | 15 |
| 2 | Low dose | 15 | 15 |
| 3 | Mid dose | 15 | 15 |
| 4 | High dose | 15 | 15 |
| Toxicokinetic Animals | | | |
| 5 | Vehicle | 3 | 3 |
| 6 | Low dose | 9 | 9 |
| 7 | Mid dose | 9 | 9 |
| 8 | High dose | 9 | 9 |

TABLE 15

Measurements and observations for GLP toxicity study in rats

| Observation | Time/Frequency |
|---|---|
| Dosing schedule | Once daily for 7 days (IV bolus) |
| Daily Observations | Twice daily. |
| Body Weights | Pre-dose, Day 1, 3, 7, 8, 15. |
| Detailed Observations | Once pre-dose, before dosing on Day 1, and weekly thereafter. |
| Food Consumption | Quantitative, weekly. |
| Hematology (including coagulation) | Day 8 and Day 15 |
| Clinical Chemistry | Day 8 and Day 15 |
| Urinalysis | Day 8 and Day 15 |
| Formulation method validation (includes stability) | Yes |
| Dose Solution Analysis | Day 1 and Day 7 |
| Functional observational battery (FOB) & Motor Activity | Last 10 rats/sex/group - pre-dose and Day 7. Then remaining 5 rats/sex/group-last day of recovery |
| Bioanalytical method development and validation includes ATAs | Yes |
| Pharmacokinetic/Toxicokinetic time points | Yes, 6 time points. |
| Anti-therapeutic antibodies time points | Yes, 3 time points. |
| Ophthalmology | Once pre-dose, once on Week 1 |
| Necropsy | Day 8 and Day 15 |
| Histopathology | All organs (standard) |

For the dog 7-day repeat-dose study, male and female purebred beagle dogs at least 5 months of age are assigned to 4 groups (Table 16). H-NOX trimer dose levels range from the approximate MED to the maximum feasible dose or the maximum tolerated dose. Each animal receives vehicle or H-NOX trimer by slow IV bolus administration in the cephalic vein at volumes up to 10 mL/kg. Animals are given vehicle or H-NOX trimer once a day for 7 consecutive days. Animals designated for terminal necropsy (up to the first 3 canines/sex/group) are necropsied on Day 8. Animals designated for recovery necropsy (up to the last 2 canines/sex/group) undergo 7 days of dosing followed by 7 days of recovery and are necropsied on Day 15 in order to evaluate the toxicity and toxicokinetics of H-NOX trimer. Standard toxicity parameters, including the assessment of vital organs (respiratory, cardiovascular, and central nervous systems) are monitored (Table 17). Cardiac safety is evaluated as part of this study by monitoring electrocardiograms (ECGs) during the dosing phase.

TABLE 16

Cohorts for GLP toxicity study in canines

| Study Cohort | H-NOX trimer dosage | $N_{males}$ | $N_{females}$ |
|---|---|---|---|
| 1 | Vehicle | 5 | 5 |
| 2 | Low dose | 5 | 5 |
| 3 | Mid dose | 5 | 5 |
| 4 | High dose | 5 | 5 |

TABLE 17

Measurements and observations for GLP toxicity study in canines

| Observation | Time/Frequency |
|---|---|
| Dosing schedule | Once daily for 7 days (IV bolus) |
| Daily Observations | Twice daily. |
| Body Weights | Pre-dose, Day 1, 4, 7, 8, 11, 15. |
| Detailed Observations | Once pre-dose, before dosing on Day 1, and weekly thereafter. |
| Physical Examinations and Vital Signs (body temperature, respiratory rate, heart rate, and pulse oximetry) | Pre-dose, Day 7 and 14. |
| Food Consumption | Quantitative, every 3-4 days. |
| Hematology (including coagulation) | Pre-dose, Day 8 and Day 15 |
| Clinical Chemistry | Pre-dose, Day 8 and Day 15 |
| Urinalysis | Day 8 and Day 15 (cystocentisis) |
| Formulation method validation (includes stability) | Yes |
| Dose Solution Analysis | Day 1 and Day 7 |
| Bioanalytical method development and validation includes ATAs | Yes |
| Pharmacokinetic/Toxicokinetic time points | Yes, 6 time points. |
| Anti-therapeutic antibodies time points | Yes, 3 time points. |
| ECGs | Pre-dose, Day 1 and Day 7 (Tmax) |
| Ophthalmology | Once pre-dose, once on Day 7 |
| Necropsy | Day 8 and Day 15 |
| Histopathology | All organs (standard) |

Furthermore, since H-NOX trimer is a novel protein therapeutic, a stand-alone cardiac safety study is performed in canines to monitor effects on heart function and vasoactivity. Four non-naïve, male Beagle dogs (9 to 18 kg), previously implanted with radiotelemetry devices (DSI: TL11M2-D70-PCT) are dosed by IV bolus injection. The canines are administered vehicle and 3 dose levels of H-NOX trimer using an ascending or Latin Square dosing regimen (Table 18). Each animal receives 1 of 4 doses (in a pre-determined order) once-weekly (Days 1, 8, 15 and 22 of the dosing phase). The doses are elected based on the previously conducted studies in canines. All animals are observed frequently for clinically relevant signs of reactions to H-NOX trimer or vehicle on the day of dosing, and then observed cage side at least once daily during the in-life phase of the study. Hemodynamic parameters (arterial blood pressure, heart rate, and lead II electrocardiogram [ECG]) are recorded. Recording commences at least 1 hour prior to dosing and continues for at least 24 hours post dosing. Parameters evaluated include; systolic, diastolic, and mean arterial pressure, heart rate, PR, QRS, QT, and RR intervals, QRS duration, and QTcVW and QTcI corrected QT intervals (Table 19). Data is visually inspected for accuracy, and values tabulated at 10 pre-determined time points based on test article pharmacokinetics. A visual inspection of all ECG waveforms for disturbances in rhythm and waveform morphology is added. Statistical analysis of hemodynamic and ECG data is performed using Graph Pad Prism (Version 4.03). Comparisons are made between the vehicle and H-NOX trimer treatment groups at each corresponding data analysis time point using either parametric (e.g., repeated measures analysis of variance followed by Dunnett's multiple comparison t-test) or non-parametric (e.g., Friedman Test and Dunn's post-hoc Test) statistical procedures. The choice of parametric or non-parametric statistics is based on whether the compared groups satisfy the homogeneity of variance criterion. Differences between the vehicle and H-NOX trimer treatment are noted as $p<0.05$.

TABLE 18

Cohorts for cardiovascular telemetry study in canines

| Animal ID | H-NOX trimer Dosage on Specified Dosing Days | | | |
|---|---|---|---|---|
| Male | Day 1 | Day 8 | Day 15 | Day 22 |
| 1 | Low dose | Vehicle | High dose | Mid dose |
| 2 | Mid dose | High dose | Vehicle | Low dose |
| 3 | High dose | Low dose | Mid dose | Vehicle |
| 4 | Vehicle | Mid dose | Low dose | High dose |

TABLE 19

Measurements and observations for cardiovascular telemetry study in canines

| Observation/Examination | Time/Frequency | Comments |
|---|---|---|
| Dose preparation | Weekly | N/A |
| Dose analysis | Yes, weekly. Concentration verification once at all dose levels at each interval. | Method validation and stability performed under a validation protocol. |
| Clinical signs-mortality check | Twice daily. | N/A |
| Clinical observations | Cageside observation once pre-dose and once daily throughout the study. Detailed observation once weekly prior to each dose. | N/A |
| Food Consumption | Qualitative, daily. | N/A |
| Body Weights | Weekly and last day in-life. | N/A |
| Telemetry Collection/Data analysis | One hour baseline collection on each day of dosing. 2 post-dose analysis blocks within 4 time points in each block. ECGs, hemodynamic measurements (heart rate, systolic, diastolic, mean arterial blood pressures) and pulse pressures, and body temperature. | ECGs evaluated by a veterinarian trained in electrocardiography. |
| Necropsy | None | Animals to be returned to stock colony. |

Example 11. Phase 1 Clinical Trials for Use of H-NOX Trimer in Glioblastoma Patents A Phase 1b study is conducted to assess H-NOX trimer safety, biodistribution in tumors, and hypoxia reduction in patients with recurrent GB. A second Phase 1b study is conducted to assess H-NOX trimer safety in patients newly diagnosed with GB.

Phase 1b Trial in Recurrent GB Patients

The first Phase 1b trial is a single dose targeted endpoint escalation study for patients with recurrent GB who are candidates for a second resection. This study provides direction in terms of selecting a dose level and route of administration in a clinically relevant population. Twenty patients with recurrent GB meeting the inclusion and exclusion criteria are included in the study.

Inclusion Criteria:

1. Patients with imaging evidence of recurrent GB who plan to have a repeat resection as part of standard of care are eligible.

2. Patients are eligible if the original histological diagnosis was low-grade glioma and a subsequent histological diagnosis is GB.

3. All patients must sign an informed consent indicating that they are aware of the investigational nature of this study. Patients must have signed an authorization for the release of their protected health information. Patients must register in a database prior to treatment with study drug.

4. Patients must be 18 years or older, and with a life expectancy >8 weeks.

5. Patients must have a Karnofsky performance status of >60.

6. At the time of registration: patients must have recovered from the toxic effects of prior therapy: >28 days from any investigational agent, >28 days from prior cytotoxic therapy, >14 days from vincristine, >42 days from nitrosoureas, >21 days from procarbazine administration, and >7 days for non-cytotoxic agents, e.g., interferon, tamoxifen, thalidomide, cis-retinoic acid, etc. Any questions related to the definition of non-cytotoxic agents should be directed to the Study Chair.

7. Patients must have adequate bone marrow function (WBC>3,000/µl, ANC>1,500/mm$^3$, platelet count of >100,000/mm$^3$, and hemoglobin >10 gm/dl), adequate liver function (SGOT and bilirubin <2 times ULN), and adequate renal function (creatinine <1.5 mg/dL) before starting therapy. These tests must be performed within 14 days prior to registration. Eligibility level for hemoglobin may not be reached by transfusion.

8. Patients must have shown unequivocal radiographic evidence for tumor progression by MRI or CT. A scan should be performed within 14 days prior to registration and on a steroid dose that has been stable for at least 5 days. If the steroid dose is increased between the date of imaging and registration a new baseline MR/CT is required. The same type of scan, i.e., MRI or CT must be used throughout the period of protocol treatment for tumor measurement.

9. Patients may have had treatment for any number of prior relapses.

10. Women of childbearing potential must have a negative B-HCG pregnancy test documented within 14 days prior to registration.

Exclusion Criteria:

1. Patients must not have received prior therapy with bevacizumab (Avastin), other VEGF or VEGFR agents, or other agents considered to be anti-angiogenic agents.

2. Any patient with PET evidence of low hypoxic fraction ($SUV_{tumor}$/$SUV_{cerebellum}$ ratio 2.0) is excluded.

3. Any patient on anti-hypertensive drug therapy is excluded.

4. Patients must not have any significant medical illnesses that in the investigator's opinion cannot be adequately controlled with appropriate therapy or would compromise the patient's ability to tolerate this therapy.

5. Patients with a history of any other cancer (except non-melanoma skin cancer or carcinoma in situ of the cervix), unless in complete remission and off of all therapy for that disease for a minimum of 3 years, are ineligible.

6. Patients must not have an active infection or serious intercurrent medical illness.

7. Patients must not have any disease that will obscure toxicity or dangerously alter drug metabolism.

Patients in this study receive H-NOX trimer alone, with no other concurrent therapy. There are four dose levels with exact dosing levels determined from levels identified as well-tolerated in preclinical toxicology studies, and are escalated according to a 3+3 design. Stopping points and dose escalations are primarily based on hypoxia reduction, due to the expected low toxicity of a single dose of H-NOX trimer. Based on preliminary toxicity testing of the H-NOX protein, little or no toxicity is expected to be associated with H-NOX trimer. However, if dose limiting toxicity (DLT) is observed the criteria for escalation is immediately changed to be based on DLT and escalation rules based on a standard 3+3 design. DLTs for the study is defined as any of the following events that can be attributable to H-NOX trimer:
1. Grade 3 thrombocytopenia
2. Grade 4 anemia and/or grade 4 neutropenia
3. Any non-hematologic grade 3 toxicity, excluding alopecia.

To evaluate biologic activity of H-NOX trimer, patients receive a $^{18}$F-EF5 PET scan 72 hours prior to H-NOX trimer dosing. The PET scan allows for quantification of the hypoxic fraction, characterized as the ratio of the standard uptake value (SUV) of the tumor to the SUV of the cerebellum (normal brain) and establishes baseline levels of tumor hypoxia prior to surgery. Patients with low levels of hypoxia (as defined by a tumor:normal brain ratio below 2.0) are excluded. Patients with sufficiently hypoxic tumors receive a single dose of H-NOX intravenously and a second $^{18}$F-EF5 PET scan two hours after H-NOX trimer dosing to assess changes in hypoxic fraction. The second PET scan is scored and any change from the baseline scan is recorded. A change in hypoxic fraction of at least 15% is deemed as clinically promising and constitutes a 'positive' change whereas a change less than 15% is declared a 'negative' change. Planned surgical resections proceed within 24 hours of H-NOX trimer dosing. Resected tumors are examined via quantitative immunohistochemistry (IHC) for H-NOX trimer penetration, as well as quantitative IHC for EF5 staining to confirm PET results. H-NOX trimer distribution data is confirmed by quantitative ELISA, using homogenized tissue samples, when possible. All routine clinical laboratory tests for safety (e.g. liver function, kidney function, CBC) are performed pre-dosing and 24 hours, 48 hours, and 14 days post-dosing. Blood samples from each of these time points are used to determine plasma pharmacokinetics (PK), as well as to assay for the presence of anti-therapeutic antibodies (ATAs). The primary endpoint includes single agent safety and secondary endpoints include tumor PK, hypoxia reduction, and time to ATA production.

Phase 1b Trial in Newly Diagnosed GB Patients

The second Phase 1b trial is a classical 3+3 dose escalation study combining H-NOX trimer with current standard of care therapy for newly diagnosed GB. After diagnosis and an initial resection, GB patients currently receive approximately 60 Gy in fractioned RT in conjunction with temozolomide (TMZ), an oral DNA alkylating chemotherapy. Since the mechanism of action of H-NOX trimer involves reducing hypoxia in solid tumors, only patients with partial (i.e. sub-total) resections are enrolled in the study. Twenty patients with newly diagnosed GB meeting the inclusion and exclusion criteria are included in the study.

Inclusion Criteria:
1. Patients with histologically proven, newly diagnosed intracranial GB will be eligible for this protocol.
2. Patients must have significant hypoxic fraction on $^{18}$F-EF5 PET imaging to be done before starting therapy.
3 Residual and evaluable disease following resection of newly diagnosed GB is mandated for eligibility into the study. To best assess the extent of residual disease postoperatively, a CT/MRI should be done no later than 96 hours in the immediate post-operative period or at least 4 weeks post-operatively, within 14 days prior to registration. If the 96-hour scan is more than 14 days before registration, the scan needs to be repeated. If the steroid dose is increased between the date of imaging and registration, a new baseline MRI/CT is required on a stable steroid dosage for at least 5 days.
4. Biopsy or resection must have been performed no more than 5 weeks prior to treatment.
5. All patients must sign an informed consent indicating that they are aware of the investigational nature of this study. Patients must have signed an authorization for the release of their protected health information. Patients must be register in a database prior to treatment with study drug.
6. Patients must be 18 years or older, and with a life expectancy >8 weeks.
7. Patients must have a Karnofsky performance status of >60.
8. Patients must have adequate bone marrow function (WBC>3,000/µl, ANC>1,500/mm$^3$, platelet count of >100,000/mm$^3$, and hemoglobin >10 gm/dl), adequate liver function (SGOT and bilirubin <2 times ULN), and adequate renal function (creatinine <1.5 mg/dL) before starting therapy. These tests must be performed within 14 days prior to registration. Eligibility level for hemoglobin may NOT be reached by transfusion.
9. Women of childbearing potential must have a negative B-HCG pregnancy test documented within 14 days prior to registration.
10. Patients must not have received prior cytotoxic drug therapy, non-cytotoxic drug therapy, or experimental drug therapy for brain tumors. Patients who received polifespan 20 with carmustine implant (Gliadel) wafers at the time of original resection will be excluded.
11. Patients must plan to begin partial brain radiotherapy the following day after starting H-NOX trimer and temozolomide. Radiotherapy must be at an affiliated site such that a radiation oncologist can provide assurance that radiation can be performed as specified in this protocol. Radiotherapy must be given by external beam to a partial brain field in daily fractions of 1.8 to 2.0 Gy, to a planned total dose to the tumor of 59.4 to 61.0 Gy. Stereotactic radiosurgery (for example, Gamma-Knife treatment) and brachytherapy will not be allowed.
12. Patients must be willing to forego other cytotoxic and noncytotoxic drug therapy against the tumor while being treated with H-NOX trimer and temozolomide.
13. Male and female patients with reproductive potential must use an approved contraceptive method, if appropriate (for example, intrauterine device [IUD], birth control pills, or barrier device) during and for 3 months after discontinuation of study treatment. Women of childbearing potential must have a negative beta-HCG pregnancy test documented within 14 days prior to treatment. If condoms are used as a barrier contraceptive, a spermicidal agent should be added to ensure that pregnancy does not occur. Should a woman become pregnant or suspect she is pregnant while participating in this study, she should inform her treating physician immediately.

Exclusion Criteria:
1. Patients must not have received prior on concurrent therapy with bevacizumab (Avastin), other VEGF or VEGFR agents, or other agents considered to anti-angiogenic agents.
2. $^{18}$F-EF5 PET evidence of low hypoxic fraction will result in exclusion.
3. Any patient on anti-hypertensive drug therapy is excluded.
4. Patients must not have any significant medical illnesses that in the investigator's opinion cannot be adequately controlled with appropriate therapy or would compromise the patient's ability to tolerate this therapy.

5. Patients with a history of any other cancer (except non-melanoma skin cancer or carcinoma in situ of the cervix), unless in complete remission and off of all therapy for that disease for a minimum of 3 years, are ineligible.

6. Patients must not have an active infection or serious intercurrent medical illness.

7. Patients must not have any disease that will obscure toxicity or dangerously alter drug metabolism.

8. Those patients with a gross total resection are excluded.

9. Patient must not have had prior cranial radiation therapy.

A baseline $^{18}$F-EF5-PET scan is performed, and patients with normoxic tumors (defined as a tumor:normal brain ratio <2.0) are removed from the study. Starting with the first day of RT therapy, patients receive a dose of H-NOX trimer by IV two hours prior to RT. To minimize the chances of an allergic reaction to the H-NOX trimer protein, dosing is limited to the first 5 days of RT, when residual tumor is the largest. This regimen continues on a daily basis for 5 days, with dose levels escalating according to a 3+3 design. Toxicities are graded as described in the first Phase 1b study with modifications to the DLT definition. DLT is defined as any of the following events occurring Week 10 of the study and attributable to H-NOX trimer alone or H-NOX trimer dosed in combination with TMZ and RT:

1. Any grade 3 or 4 thrombocytopenia, grade 4 anemia, or grade 4 neutropenia lasting more than 7 days.

2. Any febrile neutropenia.

3. Any non-hematologic grade 3 or greater toxicity, excluding alopecia, despite maximal medical therapy. Non-hematologic toxicity such as rash, nausea, vomiting and diarrhea, will only be considered a DLT if it remains grade 3 or greater despite maximal medical therapy.

4. Any grade 4 radiation-induced skin changes.

The current standard of care therapy for GB consisting of concurrent RT and temozolomide, elicits dose limiting toxicities in approximately 1 out of 6 patients. H-NOX trimer dose escalation by cohort continues as long as the dose produces a DLT in ≤1 out of 3 patients or ≤2 out of 6 patients if cohort size is increased. The cohort size is slightly higher than the more conventional size of 3 patients due to the relatively high frequency of known and expected toxicities during treatment with RT and temozolomide. If a dosing cohort does not have 3 evaluable patients enrolled due to dropouts or if 3 out of 6 patients experience a DLT, then up to 3 additional patients are enrolled in the cohort one at a time (Table 20).

TABLE 20

Dose escalation ruled for second Phase 1b study

| Frequency of DLT | Action |
|---|---|
| 0/3, 1/3 | Escalate to next dosing level |
| 2/3 | Increase evaluable cohort up to 6 patients |

TABLE 20-continued

Dose escalation ruled for second Phase 1b study

| Frequency of DLT | Action |
|---|---|
| 3/3 | MTD is surpassed and the dose is decreased to the next lower level |
| Dose escalation rules if cohort is increased to 6 patients | |
| ≤3/6 | Escalate to next dosing level |
| >3/6 | MTD is surpassed and the dose is decreased to the next lower level |

After completion of H-NOX trimer dosing, patients are evaluated for adverse events weekly for the duration of the concurrent radiation/TMZ phase (generally a six week period). Patients will be followed for 12 months, with progression-free survival determined at 6 months and 12 months after treatment. The MTD of H-NOX trimer is a dose at which less than or equal to one-third of patients experience DLTs. The MTD is based on DLTs observed during the course of concurrent radiation and TMZ, and is defined for use in subsequent Phase 2 studies. The primary endpoint includes safety in combination with standard care treatment and the secondary endpoint includes time to ATA production and PFS-12.

Due to the expected low toxicity of H-NOX trimer, the first Phase 1b study is able to find a biologically adequate dose, i.e. a dose that yields a 80% response rate. A Proportion [4/6] design will be implemented with a binary response of positive/negative hypoxic fraction change. See Brown et al., (2010) *Int Radiat Oncol Biol Phys* 78:323-327. This design ensures that if the true response rate associated with a dose is low (defined here as 0.3) there is a high probability of escalating to the next dose; whereas a high true response rate (defined as 0.8) results in a low probability of escalating further. Cohorts of 3 are used for escalation as long as ≤1/3 responses are observed. When ≥2/3 responses are observed the cohort will be expanded to 6. Escalation are continued if ≤3/6 responses are observed. The dose recommended for the second Phase 1b trial is the dose that achieves ≥4/6 responses or the maximum dose level, i.e. 100 mg/kg. If the starting dose of 5 mg/kg achieves ≥4/6 responses lower doses are investigated for sufficient activity. In contrast to standard toxicity designs, if it is clear that the response criteria for stopping at a certain dose are not met (i.e. 0/2 or 2/5 responses have been observed) early escalation to a higher dose will occur. The probability of escalating when the true rate=0.3 is 0.94 while the probability of escalating when the true rate is 0.8 is 0.15. A minimum of 9 and a maximum of 24 patients are used given the four dose levels.

If toxicities are observed, the trials are switched from a target endpoint escalation study to one based on DLTs. As such, the MTD is based on the assessment of DLT during the two weeks after treatment with H-NOX trimer and are defined as the dose at which fewer than one-third of patients experience a DLT; that is, the MTD is the dose level at which 0/3 or 1/6 patients experience DLT with the next higher dose having at least 2/3 or 2/6 patients encountering DLT. If DLT, as defined above, is not achieved in any cohort up to a dose level of 100 mg/kg there is no further escalation.

What is claimed is:

1. A recombinant nucleic acid encoding a fusion H-NOX protein comprising a *Thermoanaerobacter tengcongensis* ("*T. tengcongensis*") H-NOX domain and a trimerization domain, wherein the H-NOX domain comprises an L144F substitution; and wherein the trimerization domain is a foldon domain of bacteriophage T4 fibritin.

2. The recombinant nucleic acid of claim 1, wherein the C-terminus of the H-NOX domain is covalently linked to the trimerization domain in the encoded protein.

3. The recombinant nucleic acid of claim 1, wherein the H-NOX domain is fused via an amino acid linker to the foldon domain of T4 bacteriophage fibritin in the encoded protein.

4. The recombinant nucleic acid of claim 2, wherein the H-NOX domain is fused via an amino acid linker to the foldon domain of T4 bacteriophage fibritin in the encoded protein.

5. The recombinant nucleic acid of claim 3, wherein the amino acid linker of the encoded protein is three, four; five; six, seven, eight, nine, or ten amino acids in length.

6. The recombinant nucleic acid of claim 5, wherein the amino acid linker of the encoded protein is three amino acids in length.

7. The recombinant nucleic acid of claim 6, wherein the amino acid linker of the encoded protein comprises Gly-Ser-Gly.

8. The recombinant nucleic acid of claim 1, wherein the *T. tengcongensis* H-NOX domain comprises the amino acid sequence of SEQ ID NO:2, except for a L144F amino acid substitution in SEQ ID NO:2.

9. The recombinant nucleic acid of claim 4, wherein the *T. tengcongensis* H-NOX domain comprises the amino acid sequence of SEQ ID NO:2, except for a L144F amino acid substitution in SEQ ID NO:2.

10. The recombinant nucleic acid of claim 1, wherein the fusion protein comprises the amino acid sequence of SEQ ID NO:8.

11. A recombinant nucleic acid comprising the nucleotide sequence of SEQ ID NO:7.

12. A vector comprising the recombinant nucleic acid of claim 1.

13. A host cell comprising the vector of claim 12.

14. The host cell of claim 13, wherein the host cell is a bacterial cell.

15. A method of producing a trimeric H-NOX protein comprising culturing the host cell of claim 13 under conditions wherein the fusion H-NOX protein is expressed and associates to form a trimeric H-NOX protein.

16. The method of claim 15, further comprising the step of purifying the trimeric H-NOX protein.

17. A host cell comprising the recombinant nucleic acid of claim 1.

18. A method of producing a trimeric H-NOX protein comprising culturing the host cell of claim 17 under conditions wherein the fusion H-NOX protein is expressed and associates to form a trimeric H-NOX protein.

19. The method of claim 18, further comprising the step of purifying the trimeric H-NOX protein.

20. A host cell comprising the recombinant nucleic acid of claim 8.

21. A method of producing a trimeric H-NOX protein comprising culturing the host cell of claim 20 under conditions wherein the fusion H-NOX protein is expressed and associates to form a trimeric protein.

22. The method of claim 21, further comprising the step of purifying the trimeric H-NOX protein.

23. A host cell comprising the recombinant nucleic acid of claim 10.

24. A method of producing a trimeric H-NOX protein comprising culturing the host cell of claim 23 under conditions wherein the fusion H-NOX protein is expressed and associates to form a trimeric H-NOX protein.

25. The method of claim 24, further comprising the step of purifying the trimeric H-NOX protein.

* * * * *